US010172856B2

(12) United States Patent
Bacani et al.

(10) Patent No.: US 10,172,856 B2
(45) Date of Patent: Jan. 8, 2019

(54) 2,4-DIAMINOPYRIMIDINE DERIVATIVES AS HISTAMINE H4 MODULATORS

(71) Applicant: Janssen Pharmaceutica NV, Beerse (BE)

(72) Inventors: Genesis M. Bacani, San Diego, CA (US); Wenying Chai, San Diego, CA (US); James P. Edwards, Ambler, PA (US); Russell C. Smith, San Diego, CA (US); Mark S. Tichenor, San Diego, CA (US); Jennifer D. Venable, Solana Beach, CA (US); Jianmei Wei, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/947,077

(22) Filed: Apr. 6, 2018

(65) Prior Publication Data

US 2018/0289706 A1 Oct. 11, 2018

Related U.S. Application Data

(60) Provisional application No. 62/557,967, filed on Sep. 13, 2017, provisional application No. 62/500,284, filed on May 2, 2017, provisional application No. 62/482,553, filed on Apr. 6, 2017.

(51) Int. Cl.
*A61K 31/506* (2006.01)
*A61P 37/02* (2006.01)
*A61P 29/00* (2006.01)

(52) U.S. Cl.
CPC ............ *A61K 31/506* (2013.01); *A61P 29/00* (2018.01); *A61P 37/02* (2018.01)

(58) Field of Classification Search
CPC ......... A61K 31/506; A61P 37/02; A61P 29/00
See application file for complete search history.

(56) References Cited

U.S. PATENT DOCUMENTS

| 5,280,009 | A | 1/1994 | Hamprecht et al. |
| 6,107,301 | A | 8/2000 | Aldrich et al. |
| 2012/0202806 | A1 | 8/2012 | Dürrenberger et al. |
| 2013/0296327 | A1* | 11/2013 | Zhuo .................... C07D 239/48 514/249 |

FOREIGN PATENT DOCUMENTS

| AU | 198773642 A | 12/1987 |
| EP | 0248349 A2 | 12/1987 |
| EP | 0373891 A2 | 6/1990 |
| EP | 0945443 B9 | 9/1999 |
| GB | 2230527 B | 10/1990 |
| WO | 199118887 A1 | 12/1991 |
| WO | 199510506 A1 | 4/1995 |
| WO | 200122938 A1 | 4/2001 |
| WO | 200162233 A2 | 8/2001 |
| WO | WO 2007031529 A1 | 3/2007 |

OTHER PUBLICATIONS

Altenbach, et al., Structure-Activity Studies on a Series of a 2-Aminopyrimidine-Containing Histamine $H_4$ Receptor Ligands, Journal of Medicinal Chemistry, 2008, pp. 6571-6580, vol. 51 Issue 20.
Amin, et al., Inflammation and Structural Changes in the Airways of Patients with Atopic and Nonatopic Asthma, American Journal of Respiratory and Critical Care Medicine, 2000, pp. 2295-2301, vol. 162.
Bell, et al., Involvement of histamine $H_4$ and $H_1$ receptors in scratching induced by histamine receptor agonists in BalbC mice, British Journal of Pharmacology, 2004, pp. 374-380, vol. 142.
Benoist, et al., Mast cells in autoimmune disease, Nature, 2002, pp. 875-878, vol. 420.
Berge, et al., Pharmaceutical Salts, Journal of Pharmaceutical Sciences, 1977, pp. 1-19, vol. 66, No. 1.
Bradford, Marion M., A Rapid and Sensitive Method for the Quantitation of Microgram Quantities of Protein Utilizing the Principle of Protein-Dye Binding, Analytical Biochemistry, 1976, pp. 248-254, vol. 72.
Buckland, et al., Histamine induces cytoskeletal changes in human eosinophils via the $H_4$ receptor, British Journal of Pharmacology, 2003, pp. 1117-1127, vol. 140 Issue 6.
Bull, et al., Total Synthesis of Potent Antifungal Marine Bisoxazole Natural Products Bengazoles A and B, Chem. Eur. J., 2007, pp. 5515-5538, vol. 13.
Cheng, et al., Relationship between the inhibition Constant ($K_1$) and the Concentration of inhibitor which causes 50 per cent Inhibition ($I_{50}$) of an enzymatic reaction, Biochemical Pharmacology, 1973, pp. 3099-3108, vol. 22.
Coge, et al., Structure and Expression of the Human Histamine $H_4$-Receptor Gene, Biochemical and Biophysical Research Communication, 2001, pp. 301-309, vol. 284 Issue 2.
Cohen, Jonathan, The immunopathogenesis of sepsis, Nature, 2002, pp. 885-891, vol. 420.
Coussens, et al., Inflammation and cancer, Nature, 2002, pp. 860-867, vol. 420.
Crimi, et al., Increased Numbers of Mast Cells in Bronchial Mucosa after the Late-Phase Asthmatic Response to Allergen[1-3], Am Rev Respir Dis, 1991, pp. 1282-1286, vol. 144.
De Esch, et al., The histamine $H_4$ receptor as a new therapeutic target for inflammation, Trends in Pharmacological Sciences, 2005, pp. 462-469, vol. 26 Issue 9.
Fokkens, et al., Dynamics of mast cells in the nasal mucosa of patients with allergic rhinitis and non-allergic controls: a biopsy study, Clinical and Experimetal Allergy, 1992, pp. 701-710, vol. 22.
Fung-Leung, et al., Histamine $H_4$ receptor antagonists: The new antihistamines?, Current Opinion in Investigational Drugs, 2004, pp. 1174-1183, vol. 5 Issue 11.

(Continued)

*Primary Examiner* — Timothy R Rozof

(57) ABSTRACT

The present invention relates to 2,4-diaminopyrimidines and pharmaceutically acceptable salts thereof, purification methods for the same, pharmaceutical compositions containing them, methods of obtaining and using them for the treatment of disease states, disorders, and conditions mediated by the histamine $H_4$ receptor activity.

22 Claims, No Drawings

(56) References Cited

OTHER PUBLICATIONS

Gantner, et al., Histamine $H_4$ and $H_2$ Receptors Control Histamine-Induced Interleukin-16 Release from Human CD8+ T Cells, The Journal of Pharmacology and Experimental Therapeutics, 2002, pp. 300-307, vol. 303.
Gauvreau, et al., Increased Numbers of both Airway Basophils and Mast Cells in Sputum after Allergen Inhalation Challenge of Atopic Asthmatics, Am J Respir Crit Care Med, 2000, pp. 1473-1478, vol. 161.
Gutzmer, et al., Histamine H4 Receptor Stimulation Suppresses IL-12p70 Production and Mediates Chemotaxis in Human Monocyte-Derived Dendritic Cells[1], The Journal of Immunology, 2005, pp. 5224-5232, vol. 174.
Hofstra, et al., Histamine $H_4$ Receptor Mediates Chemotaxis and Calcium Mobilization of Mast Cells, The Journal of Pharmacology and Experimental Therapeutics, 2003, pp. 1212-1221, vol. 305 Issue 3.
Ikawa, et al., Histamine H4 Receptor Expression in Human Synovial Cells Obtained from Patients Suffering from Rheumatoid Arthritis, Biol. Pharm. Bull, 2005, pp. 2016-2018, vol. 28 Issue 10.
Istyastono, et al., Molecular Determinants of Selective Agonist and Antagonist Binding to the Histamine $H_4$ Receptor, Current Topics in Medicinal Chemistry, 2011, pp. 661-679, vol. 11 Issue 6.
Kassel, et al., Local increase in the number of mast cells and expression of nerve growth factor in the bronchus of asthmatic patients after repeated inhalation of allergen at low-dose, Clinical and Experimental Allergy, 2001, pp. 1432-1440, vol. 31.
Kirby, et al., Bronchoalveolar Cell Profiles of Asthmatic and Nonasthmatic Subjects[1-3], Am Rev Respir Dis, 1987, pp. 379-383, vol. 136.
Kiss, et al., Histamine H4 receptor ligands and their potential therapeutic applications, Expert Opin. Ther. Patents, 2009, pp. 119-135, vol. 19 Issue 2.
Kiss, et al., Histamine H4 receptor ligands and their potential therapeutic applications: an update, Expert Opin. Ther. Patents, 2012, pp. 205-221, vol. 22 Issue 3.
Kiss, et al., Novel histamine $H_4$ receptor ligands and their potential therapeutic applications: an update, Expert Opin. Ther. Patents, 2014, pp. 1185-1197, vol. 24 Issue 11.
Krug, et al., Interleukin 16 and T-cell Chemoattractant Activity in Bronchoalveolar Lavage 24 Hours after Allergen Challenge in Asthma, Am J Respir Crit Care Med, 2000, pp. 105-111, vol. 162.
Lazewska, et al., Azines as histamine $H_4$ receptor antagonists, Frontiers in Bioscience, 2012, pp. 967-987, S4.
Libby, Peter, Inflammation in atherosclerosis, Nature, 2002, pp. 868-874, vol. 420.
Ling, et al., Histamine $H_4$ receptor mediates eosinophil chemotaxis with cell shape change and adhesion molecule upregulation, British Journal of Pharmacology, 2004, pp. 161-171, vol. 142.
Lippert, et al., Human Skin Mast Cells Express H2 and H4, but not H3 Receptors, J Invest Dermatol, 2004, pp. 116-123, vol. 123.
Liu, et al., Cloning and Pharmacological Characterization of a Fourth Histamine Receptor ($H_4$) Expressed in Bone Marrow, Molecular Pharmacology, 2001, pp. 420-426, vol. 59 Issue 3.
Mashikian, et al., Identification of IL-16 as the lymphocyte chemotactic activity in the bronchoalveolar lavage fluid of histamine-challenged asthmatic patients, J Allergy Clin Immunol, 1998, pp. 786-792, vol. 101 No. 6 Part 1.
Morse, et al., Cloning and Characterization of a Novel Human Histamine Receptor, The Journal of Pharmacology and Experimental Therapeutics, 2001, pp. 1058-1066, vol. 296 Issue 3.
Nathan, Carl, Points of Control in Inflammation, Nature, 2002, pp. 846-852, vol. 420.
O'Reilly, et al., Identification of a Histamine $H_4$ Receptor on Human Eosinophils-Role in Eosinophil Chemotaxis, Journal of Receptors and Signal Transduction, 2002, pp. 431-448, vol. 22 Issue 1-4.
Schreeb, et al., Histamine $H_4$ Receptor Ligands, Histamine $H_4$ Receptor: A Novel Drug Target for Immunoregulation and Inflammation, 2014, pp. 21-62, Chapter 2.
Slater, et al., Increase in epithelial mast cell numbers in the nasal mucosa of patients with perennial allergic rhinitis, The Journal of Laryngology and Otology, 1996, pp. 929-933, vol. 110.
Smits, et al., Major advances in the development of histamine $H_4$ receptor ligands, Drug Discovery Today, 2009, pp. 745-753, vol. 14 Issue 15/16.
Steinberg, Daniel, Atherogenesis in perspective: Hypercholesterolemia and inflammation as partners in crime, Nature Medicine, 2002, pp. 1211-1217, vol. 8 Issue 11.
Takeshita, et al., Critical Role of Histamine $H_4$ Receptor in Leukotriene $B_4$ Production and Mast Cell-Dependent Neutrophil Recruitment Induced by Zymosan in Vivo, The Journal of Pharmacology and Experimental Therapeutics, 2003, pp. 1072-1078, vol. 307 Issue 3.
Thurmond, et al., A Potent and Selective Histamine $H_4$ Receptor Antagonist with Anti-Inflammatory Properties, The Journal of Pharmacology and Experimental Therapeutics, 2004, pp. 404-413, vol. 309 Issue 1.
Tracey, Kevin J., The inflammatory reflex, Nature, 2002, pp. 853-859, vol. 420.
Varga, et al., Inhibitory effects of histamine $H_4$ receptor antagonists on experimental colitis in the rat, European Journal of Pharmacology, 2005, pp. 130-138, vol. 522.
Voehringer, et al., Type 2 Immunity Reflects Orchestrated Recruitment of Cells Committed to IL-4 Production, Immunity, 2004, pp. 267-277, vol. 20.
Weiner, et al., Inflammation and therapeutic vaccination in CNS diseases, Nature, 2002, pp. 879-884, vol. 420.
Corrêa, et al., Histamine H4 Receptor Ligands: Future Applications and State of Art, Chem Biol Drug Des, 2015, pp. 461-480, vol. 85.
Engelhardt, et al., Bispyrimidines as Potent Histamine H4 Receptor Ligands: Delineation of Structure-Activity Relationships and Detailed H4 Receptor Binding Mode, Journal of Medicinal Chemistry, 2013, pp. 4264-4276, vol. 56.
International Search Report and Written Opinion dated Jun. 25, 2018, for International Application No. PCT/US2018/026397.

* cited by examiner

2,4-DIAMINOPYRIMIDINE DERIVATIVES AS HISTAMINE H4 MODULATORS

This application claims the benefit of U.S. Provisional Application 62/482,553, filed on Apr. 6, 2017, U.S. Provisional Application 62/500,284, filed on May 2, 2017, and U.S. Provisional Application 62/557,967 filed on Sep. 13, 2017, all of which are hereby incorporated by reference in their entirety.

FIELD OF THE INVENTION

The present invention relates to 2,4-diaminopyrimidines and pharmaceutically acceptable salts thereof, purification methods for the same, pharmaceutical compositions containing them, methods of obtaining and using them for the treatment of disease states, disorders, and conditions mediated by histamine $H_4$ receptor activity.

BACKGROUND OF THE INVENTION

The histamine $H_4$ receptor ($H_4R$) is one of the identified receptors for histamine (for reviews, see: Fung-Leung, W.-P., et al., Curr. Opin. Invest. Drugs 2004, 5(11), 1174-1183; de Esch, I. J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; Morse, K. L., et al., J. Pharmacol. Exp. Ther. 2001, 296(3), 1058-1066; Hofstra, C. L., et al., J. Pharmacol. Exp. Ther. 2003, 305(3), 1212-1221; Lippert, U., et al., J. Invest. Dermatol. 2004, 123(1), 116-123; Voehringer, D., et al., Immunity 2004, 20(3), 267-277), $CD8^+$ T cells (Gantner, F., et al., J. Pharmacol. Exp. Ther. 2002, 303(1), 300-307), dendritic cells, and human synovial cells from rheumatoid arthritis patients (Ikawa, Y., et al., Biol. Pharm. Bull. 2005, 28(10), 2016-2018). However, expression in neutrophils and monocytes is less well defined (Ling, P., et al., Br. J. Pharmacol. 2004, 142(1), 161-171). Receptor expression is at least in part controlled by various inflammatory stimuli (Coge, F., et al., Biochem. Biophys. Res. Commun. 2001, 284(2), 301-309; Morse, et al., 2001), thus supporting that $H_4R$ activation influences inflammatory responses. Because of its preferential expression on immunocompetent cells, $H_4R$ is closely related with the regulatory functions of histamine during the immune response.

A biological activity of histamine in the context of immunology and autoimmune diseases is closely related with the allergic response and its deleterious effects, such as inflammation. Events that elicit the inflammatory response include physical stimulation (including trauma), chemical stimulation, infection, and invasion by a foreign body. The inflammatory response is characterized by pain, increased temperature, redness, swelling, reduced function, or a combination of these.

Mast cell degranulation (exocytosis) releases histamine and leads to an inflammatory response that may be initially characterized by a histamine-modulated wheal and flare reaction. A wide variety of immunological stimuli (e.g., allergens or antibodies) and non-immunological (e.g., chemical) stimuli may cause the activation, recruitment, and de-granulation of mast cells. Mast cell activation initiates allergic inflammatory responses, which in turn cause the recruitment of other effector cells that further contribute to the inflammatory response. It has been shown that histamine induces chemotaxis of mouse mast cells (Hofstra, et al., 2003). Chemotaxis does not occur using mast cells derived from $H_4R$ knockout mice. Furthermore, the response is blocked by an $H_4$-specific antagonist, but not by $H_1$, $H_2$ or $H_3$ receptor antagonists (Hofstra, et al., 2003; Thurmond, R. L., et al., J. Pharmacol. Exp. Ther. 2004, 309(1), 404-413). The in vivo migration of mast cells to histamine has also been investigated and shown to be $H_4R$ dependent (Thurmond, et al., 2004). The migration of mast cells may play a role in allergic rhinitis and allergy where increases in mast cell number are found (Kirby, J. G., et al., Am. Rev. Respir. Dis. 1987, 136(2), 379-383; Crimi, E., et al., Am. Rev. Respir. Dis. 1991, 144(6), 1282-1286; Amin, K., et al., Am. J. Resp. Crit. Care Med. 2000, 162(6), 2295-2301; Gauvreau, G. M., et al., Am. J. Resp. Crit. Care Med. 2000, 161(5), 1473-1478; Kassel, O., et al., Clin. Exp. Allergy 2001, 31(9), 1432-1440). In addition, it is known that in response to allergens there is a redistribution of mast cells to the epithelial lining of the nasal mucosa (Fokkens, W. J., et al., Clin. Exp. Allergy 1992, 22(7), 701-710; Slater, A., et al., J. Laryngol. Otol. 1996, 110, 929-933). These results show that the chemotactic response of mast cells is mediated by $H_4R$.

It has been shown that eosinophils can chemotax towards histamine (O'Reilly, M., et al., J. Recept. Signal Transduction 2002, 22(1-4), 431-448; Buckland, K. F., et al., Br. J. Pharmacol. 2003, 140(6), 1117-1127; Ling et al., 2004). Using $H_4$ selective ligands, it has been shown that histamine-induced chemotaxis of eosinophils is mediated through the $H_4R$ (Buckland, et al., 2003; Ling et al., 2004). Cell surface expression of adhesion molecules CD11b/CD18 (LFA-1) and CD54 (ICAM-1) on eosinophils increases after histamine treatment (Ling, et al., 2004). This increase is blocked by $H_4R$ antagonists but not by $H_1$, $H_2$, or $H_3$ receptor antagonists.

$H_4R$ also plays a role in dendritic cells and T cells. In human monocyte-derived dendritic cells, $H_4R$ stimulation suppresses IL-12p70 production and drives histamine-mediated chemotaxis (Gutzmer, R., et al., J. Immunol. 2005, 174(9), 5224-5232). A role for the $H_4R$ in CD8 T cells has also been reported. Gantner, et al., (2002) showed that both $H_4$ and $H_2$ receptors control histamine-induced IL-16 release from human $CD8^+$ T cells. IL-16 is found in the bronchoalveolar fluid of allergen- or histamine-challenged asthmatics (Mashikian, V. M., et al., J. Allergy Clin. Immunol. 1998, 101 (6, Part 1), 786-792; Krug, N., et al., Am. J. Resp. Crit. Care Med. 2000, 162(1), 105-111) and is considered important in $CD4^+$ cell migration. The activity of the receptor in these cell types indicates an important role in adaptive immune responses such as those active in autoimmune diseases.

In vivo $H_4R$ antagonists were able to block neutrophillia in zymosan-induced peritonitis or pleurisy models (Takeshita, K., et al., J. Pharmacol. Exp. Ther. 2003, 307(3), 1072-1078; Thurmond, R., et al., 2004). In addition, $H_4R$ antagonists have activity in a widely used and well-characterized model of colitis (Varga, C., et al., Eur. J. Pharmacol. 2005, 522(1-3), 130-138). These results support the conclusion that $H_4R$ antagonists have the capacity to be anti-inflammatory in vivo.

Another physiological role of histamine is as a mediator of itch and $H_1$ receptor antagonists are not completely effective in the clinic. Recently, $H_4R$ has also been implicated in histamine-induced scratching in mice (Bell, J. K., et al., Br. J. Pharmacol. 2004, 142(2), 374-380). The effects of histamine could be blocked by $H_4R$ antagonists. These results support the hypothesis that $H_4R$ is involved in histamine-induced itch and that $H_4R$ antagonists will therefore have positive effects in treating pruritus.

Modulation of H₄R controls the release of inflammatory mediators and inhibits leukocyte recruitment, thus providing the ability to prevent and/or treat H₄-mediated diseases and conditions, including the deleterious effects of allergic responses such as inflammation. Compounds according to the present invention have H₄R-modulating properties. Compounds according to the present invention have leukocyte recruitment inhibiting properties. Compounds according to the present invention have anti-inflammatory properties.

Examples of textbooks on the subject of inflammation include: Gallin, J. I.; Snyderman, R., *Inflammation: Basic Principles and Clinical Correlates,* 3rd ed.; Lippincott Williams & Wilkins: Philadelphia, 1999; Stvrtinova, V., et al., Inflammation and Fever. *Pathophysiology Principles of Diseases* (Textbook for Medical Students); Academic Press: New York, 1995; Cecil; et al. *Textbook Of Medicine,* 18th ed.; W.B. Saunders Co., 1988; and Stedman's Medical Dictionary.

Background and review material on inflammation and conditions related with inflammation can be found in articles such as the following: Nathan, C., Nature 2002, 420(6917), 846-852; Tracey, K. J., Nature 2002, 420(6917), 853-859; Coussens, L. M., et al., Nature 2002, 420(6917), 860-867; Libby, P., Nature 2002, 420, 868-874; Benoist, C., et al., Nature 2002, 420(6917), 875-878; Weiner, H. L., et al., Nature 2002, 420(6917), 879-884; Cohen, J., Nature 2002, 420(6917), 885-891; Steinberg, D., Nature Med. 2002, 8(11), 1211-1217.

Thus, small-molecule histamine H₄R modulators according to this invention control the release of inflammatory mediators and inhibit leukocyte recruitment, and may be useful in treating inflammation of various etiologies, including the following conditions and diseases: inflammatory disorders, allergic disorders, dermatological disorders, autoimmune disease, lymphatic disorders, pruritus, and immunodeficiency disorders. Diseases, disorders and medical conditions that are mediated by histamine H₄R activity include those referred to herein.

SUMMARY OF THE INVENTION

The invention relates to 2,4-diaminopyrimidines and pharmaceutically acceptable salts thereof, purification methods for the same, pharmaceutical compositions containing them, methods of obtaining and using them for the treatment of disease states, disorders, and conditions mediated by the histamine H₄ receptor activity. The 2,4-diaminopyrimidines are compounds of Formula I

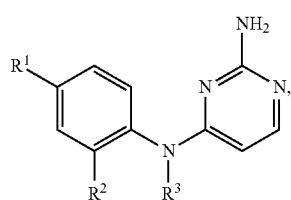

Formula I wherein
R¹ is S(O)ₙR⁴ or SF₅;
  n is 1 or 2;
  R⁴ is selected from the group consisting of C₁-C₄ alkyl, C₁-C₂ perhaloalkyl, C₃-C₄ cycloalkyl and NR⁵R⁶;

each of R⁵ and R⁶ is independently C₁-C₄ alkyl or R⁵ and R⁶ together with the nitrogen to which they are attached form a 5-6 membered heterocyclic ring;
  or
R¹ is selected from the group consisting of halo, CF₃, OCF₃, C(OH)(CF₃)₂, CN, and C(O)NH₂;
R² is selected from the group consisting of C₁-C₅ alkyl, C₂-C₅ alkenyl, C₃-C₅ cycloalkyl, C₁-C₂ perhaloalkyl, OC₁-C₄ alkyl, and OC₁-C₃ perhaloalkyl;
R³ is selected from the group consisting of

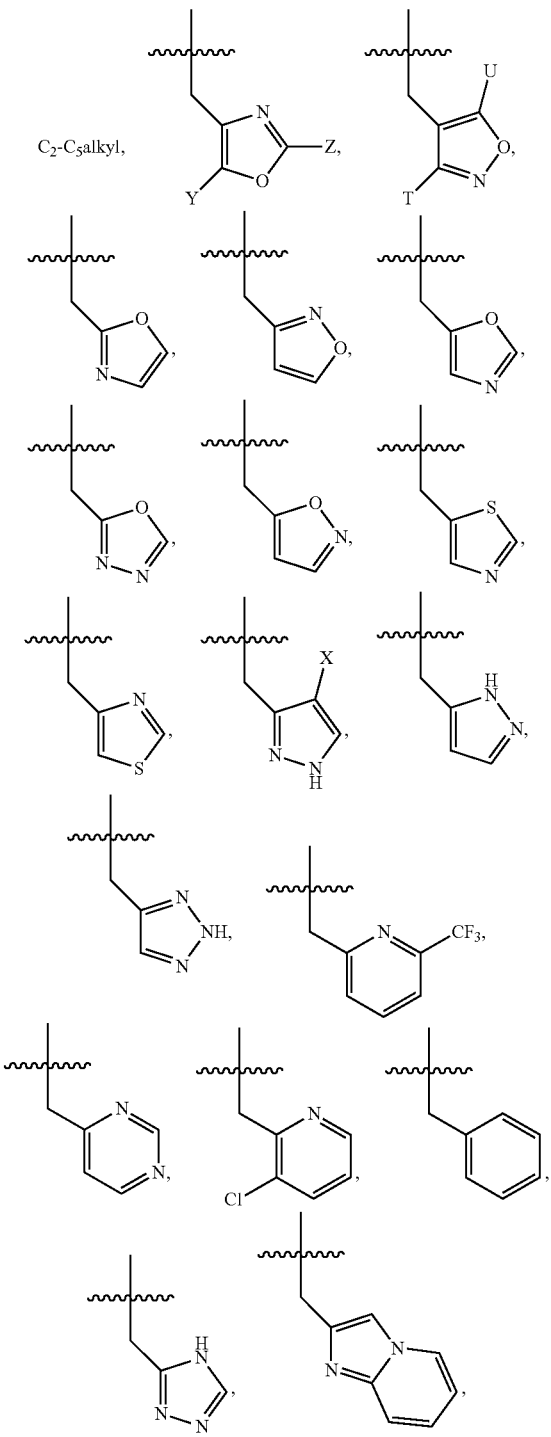

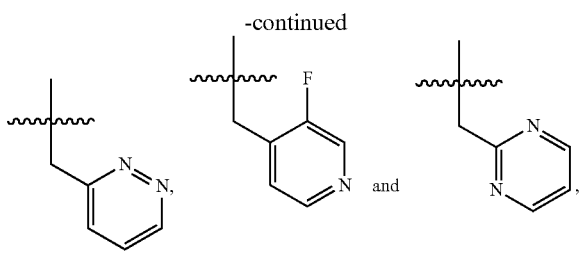

wherein
said C$_2$-C$_5$ alkyl is optionally substituted with one OCH$_3$ group;
each of Y, U, T and Z is independently H or CH$_3$; and
X is selected from the group consisting of H, Cl, and F.

DETAILED DESCRIPTION OF THE INVENTION

As used herein, the terms "including", "containing" and "comprising" are used in their open, non-limiting sense.

Unless qualified specifically in particular instances of use, the term "alkyl" refers to a straight- or branched-chain alkyl group having from 1 to 8 carbon atoms in the chain. Examples of alkyl groups include methyl (Me), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. "C$_1$-C$_4$ alkyl" refers to straight- or branched-chain alkyl group having from 1 to 4 carbon atoms in the chain.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

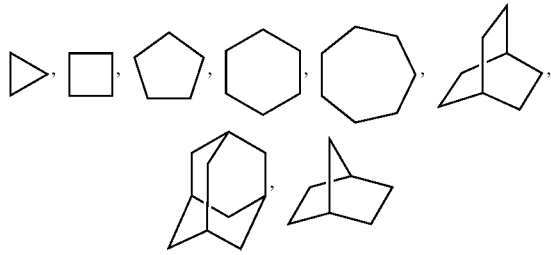

The term "halogen" represents chlorine, fluorine, bromine, or iodine.

The term "perhaloalkyl" or "haloalkyl" refers to a straight- or branched-chain alkyl group having from 1 to 6 carbon atoms in the chain optionally substituting hydrogens with halogens. The term "C$_1$-C$_4$ haloalkyl" as used here refers to a straight- or branched-chain alkyl group having from 1 to 4 carbon atoms in the chain, optionally substituting hydrogens with halogens. Examples of "perhaloalkyl", "haloalkyl" groups include trifluoromethyl (CF$_3$), difluoromethyl (CF$_2$H), monofluoromethyl (CH$_2$F), pentafluoroethyl (CF$_2$CF$_3$), tetrafluoroethyl (CHFCF$_3$), monofluoroethyl (CH$_2$CH$_2$F), trifluoroethyl (CH$_2$CF$_3$), tetrafluorotrifluoromethylethyl (CF(CF$_3$)$_2$), and groups that in light of the ordinary skill in the art and the teachings provided herein would be considered equivalent to any one of the foregoing examples.

Those of ordinary skill in the art will recognize that the species of cycloalkyl, and heterocyclic ring groups listed or illustrated above are not exhaustive, and that additional species within the scope of these defined terms may also be selected.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Any formula given herein is intended to represent compounds having structures depicted by the structural formula as well as certain variations or forms. Furthermore, certain structures may exist as geometric isomers (i.e., cis and trans isomers), or as tautomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number in an enriched form. Examples of isotopes that can be incorporated into compounds of the invention in a form that exceeds natural abundances include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for such variable appearing elsewhere. In other words, where a variable appears more than once, the choice of the species from a specified list is independent of the choice of the species for the same variable elsewhere in the formula, unless stated otherwise.

The nomenclature "C$_i$-C$_j$" with j>i, when applied herein to a class of substituents, is meant to refer to embodiments of this invention for which each and every one of the number of carbon members, from i to j including i and j, is independently realized. By way of example, the term C$_1$-C$_3$ refers independently to embodiments that have one carbon member (C$_1$), embodiments that have two carbon members (C$_2$), and embodiments that have three carbon members (C$_3$). The term C$_{n-m}$ alkyl refers to an aliphatic chain, whether straight or branched, with a total number N of carbon members in the chain that satisfies n≤N≤m, with m>n.

When the same plurality of substituents is assigned to various groups, the specific individual substituent assignment to each of such groups is meant to be independently made with respect to the specific individual substituent assignments to the remaining groups. By way of illustration, but not as a limitation, if each of groups Q and R can be H or F, the choice of H or F for Q is made independently of the choice of H or F for R, so the choice of assignment for Q does not determine or condition the choice of assignment for R, or vice-versa, unless it is expressly indicated otherwise. Illustrative claim recitation in this regard would read as "each of Q and R is independently H or F", or "each of Q and R is independently selected form the group consisting of H and F".

"Tautomers" refer to compounds that are interchangeable forms of a particular compound structure, and that vary in the displacement of hydrogen atoms and electrons. Thus, two structures that have an H member in different positions may be in equilibrium while satisfying valency rules. For example, enols and ketones are tautomers because they are rapidly interconverted by treatment with either acid or base.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound would be encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent assignments described herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S^1$, $S^2$, and $S^3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

Compounds of Formula I contain at least one nitrogen of basic character, so desired pharmaceutically acceptable salts may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

Illustrative embodiments of this invention are given by compounds of Formula I

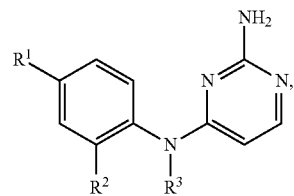

wherein
$R^1$ is $S(O)_nR^4$ or $SF_5$;
n is 1 or 2;
$R^4$ is selected from the group consisting of $C_1$-$C_4$ alkyl, $C_1$-$C_2$ perhaloalkyl, $C_3$-$C_4$ cycloalkyl and $NR^5R^6$;
each of $R^5$ and $R^6$ is independently $C_1$-$C_4$ alkyl, or $R^5$ and $R^6$ together with the nitrogen to which they are attached form a 5-6 membered heterocyclic ring;
or
$R^1$ is selected from the group consisting of halo, $CF_3$, $OCF_3$, $C(OH)(CF_3)_2$, CN, and $C(O)NH_2$;
$R^2$ is selected from the group consisting of $C_1$-$C_5$ alkyl, $C_2$-$C_5$ alkenyl, $C_3$-$C_5$ cycloalkyl, $C_1$-$C_2$ perhaloalkyl, $OC_1$-$C_4$ alkyl, and $OC_1$-$C_3$ perhaloalkyl;
$R^3$ is selected from the group consisting of

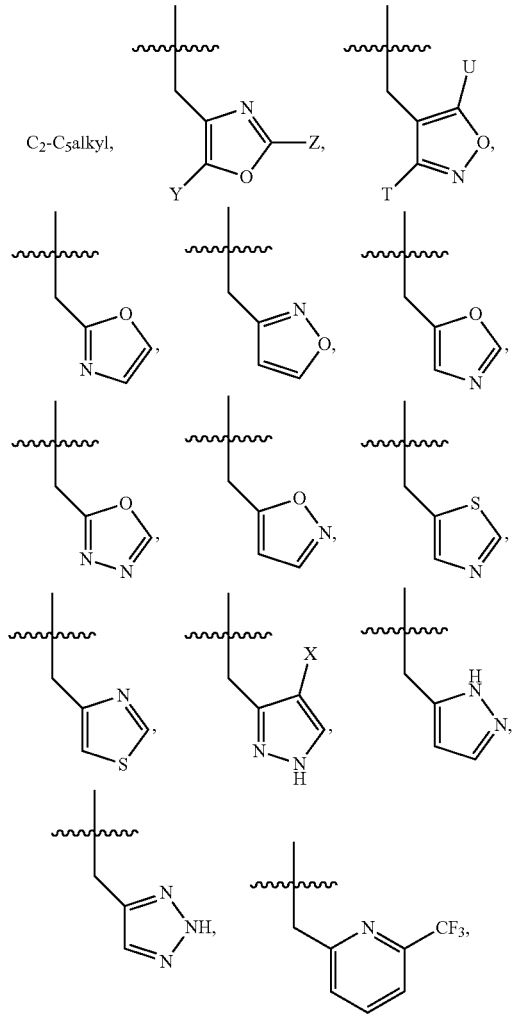

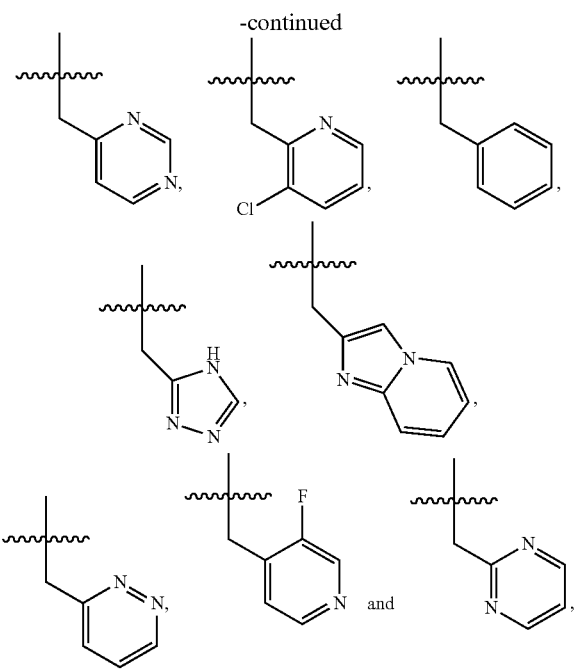

wherein
said $C_2-C_5$ alkyl is optionally substituted with one $OCH_3$ group;
each of Y, U, T and Z are independently H or $CH_3$; and
X is selected from the group consisting of H, Cl, and F.

An additional illustrative embodiment of the invention is a compound of Formula I, wherein $R^1$ is $S(O)_nR^4$ or $SF_5$.

An additional illustrative embodiment of the invention is a compound of Formula I, wherein $R^1$ is $S(O)_nR^4$, $R^4$ is $C_1-C_4$ alkyl, and n is 2.

An additional illustrative embodiment of the invention is a compound of Formula I, wherein $R^1$ is $S(O)_nR^4$, $R^4$ is $CH_3$, and n is 2.

An additional illustrative embodiment of the invention is a compound of Formula I, wherein $R^1$ is $SF_5$.

An additional illustrative embodiment of the invention is a compound of Formula I, wherein $R^1$ is selected from the group consisting of halo, $CF_3$, $OCF_3$, $C(OH)(CF_3)_2$, CN, and $C(O)NH_2$.

An additional illustrative embodiment of the invention is a compound of Formula I, wherein $R^1$ is selected from the group consisting of $SO_2CH_3$, $SO_2CF_3$, $SF_5$, F, and $OCF_3$.

An additional illustrative embodiment of the invention is a compound of Formula I, wherein $R^1$ is selected from the group consisting of $SO_2CH_3$, $SO_2CF_3$, $SF_5$, and $OCF_3$.

An additional illustrative embodiment of the invention is a compound of Formula I, wherein $R^1$ is selected from the group consisting of $SO_2CH_3$, $SO_2CF_3$, and $SF_5$.

An additional illustrative embodiment of the invention is a compound of Formula I, wherein $R^1$ is selected from the group consisting of $SO_2CH_3$ and $SF_5$.

An additional illustrative embodiment of the invention is a compound of Formula I, wherein $R^1$ is $SO_2CH_3$.

An additional illustrative embodiment of the invention is a compound of Formula I, wherein $R^1$ is $SO_2CF_3$.

An additional illustrative embodiment of the invention is a compound of Formula I, wherein $R^1$ is $SF_5$.

An additional illustrative embodiment of the invention is a compound of Formula I, wherein $R^1$ is halo.

An additional illustrative embodiment of the invention is a compound of Formula I, wherein $R^1$ is F or Cl.

An additional illustrative embodiment of the invention is a compound of Formula I, wherein $R^1$ is F.

An additional illustrative embodiment of the invention is a compound of Formula I, wherein $R^1$ is $OCF_3$.

An additional illustrative embodiment of the invention is a compound of Formula I, wherein $R^2$ is selected from the group consisting of $C_1-C_5$ alkyl, $C_2-C_5$ alkenyl, $C_3-C_5$ cycloalkyl, $C_1-C_2$ perhaloalkyl, $OC_1-C_4$ alkyl, and $OC_1-C_3$ perhaloalkyl.

An additional illustrative embodiment of the invention is a compound of Formula I, wherein $R^2$ is selected from the group consisting of $C_1-C_5$ alkyl, $C_3-C_5$ cycloalkyl, $C_1-C_2$ perhaloalkyl, $OC_1-C_4$ alkyl, and $OC_1-C_3$ perhaloalkyl.

An additional illustrative embodiment of the invention is a compound of Formula I, wherein $R^2$ is selected from the group consisting of $C_1-C_5$ alkyl, $C_3-C_5$ cycloalkyl, $C_1-C_2$ perhaloalkyl, and $OC_1-C_4$ alkyl.

An additional illustrative embodiment of the invention is a compound of Formula I, wherein $R^2$ is selected from the group consisting of $C_1-C_5$ alkyl, $C_3-C_5$ cycloalkyl, and $OC_1-C_4$ alkyl.

An additional illustrative embodiment of the invention is a compound of Formula I, wherein $R^2$ is $OC_1-C_4$ alkyl.

An additional illustrative embodiment of the invention is a compound of Formula I, wherein $R^2$ is $OC_1-C_3$ alkyl.

An additional illustrative embodiment of the invention is a compound of Formula I, wherein $R^2$ is $OC_1-C_2$ alkyl.

An additional illustrative embodiment of the invention is a compound of Formula I, wherein $R^2$ is $OCH_2CH_3$.

An additional illustrative embodiment of the invention is a compound of Formula I, wherein $R^2$ is selected from the group consisting of $C_1-C_5$ alkyl and $C_3-C_5$ cycloalkyl.

An additional illustrative embodiment of the invention is a compound of Formula I, wherein $R^2$ is $C_1-C_5$ alkyl.

An additional illustrative embodiment of the invention is a compound of Formula I, wherein $R^2$ is $C_1-C_3$ alkyl.

An additional illustrative embodiment of the invention is a compound of Formula I, wherein $R^2$ is $C_1-C_2$ alkyl.

An additional illustrative embodiment of the invention is a compound of Formula I, wherein $R^2$ is $CH_3$.

An additional illustrative embodiment of the invention is a compound of Formula I, wherein $R^2$ is $CH_2CH_3$.

An additional illustrative embodiment of the invention is a compound of Formula I, wherein $R^2$ is $C_3-C_5$ cycloalkyl.

An additional illustrative embodiment of the invention is a compound of Formula I, wherein $R^2$ is $C_3-C_4$ cycloalkyl.

An additional illustrative embodiment of the invention is a compound of Formula I, wherein $R^2$ is cyclopropyl.

An additional illustrative embodiment of the invention is a compound of Formula I, wherein $R^2$ is cyclobutyl.

An additional illustrative embodiment of the invention is a compound of Formula I, wherein $R^3$ is selected from the group consisting of

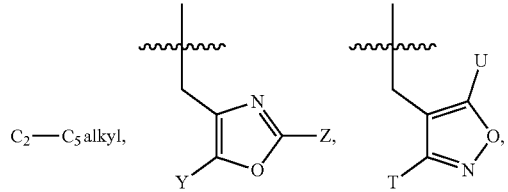

-continued

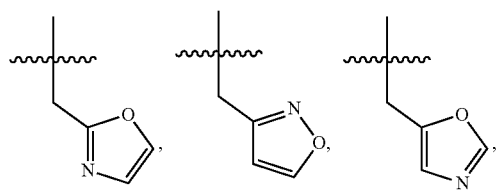

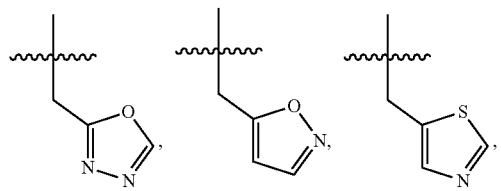

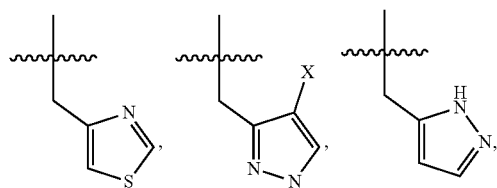

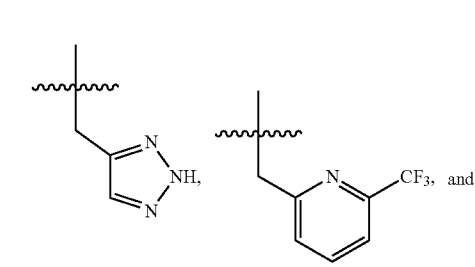

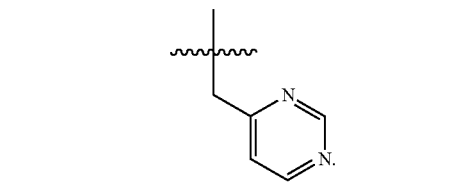

An additional illustrative embodiment of the invention is a compound of Formula I, wherein R³ is selected from the group consisting of
C₂-C₅alkyl,

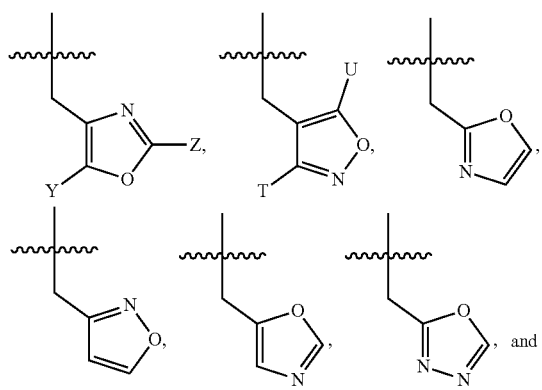

-continued

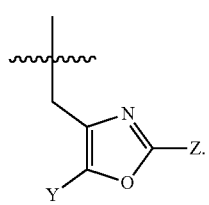

An additional illustrative embodiment of the invention is a compound of Formula I, wherein R³ is selected from the group consisting of
C₂-C₅ alkyl,

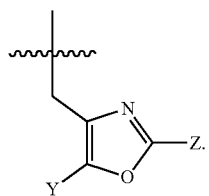

An additional illustrative embodiment of the invention is a compound of Formula I, wherein R³ is selected from the group consisting of An additional illustrative embodiment of the invention is a compound of Formula I, wherein R³ is An additional illustrative embodiment of the invention is a compound of Formula I, wherein each of Y and Z is H, and R³ is An additional illustrative embodiment of the invention is a compound of Formula I, wherein R³ is C₂-C₅ alkyl.

An additional illustrative embodiment of the invention is a compound of Formula I, wherein R³ is C₂-C₃ alkyl.

An additional illustrative embodiment of the invention is a compound of Formula I, wherein $R^3$ is selected from the group consisting of ethyl, n-propyl, and isopropyl.

An additional illustrative embodiment of the invention is a compound of Formula I, wherein $R^3$ is ethyl.

An additional illustrative embodiment of the invention is a compound of Formula I, wherein $R^3$ is isopropyl.

An additional illustrative embodiment of the invention is a compound of Formula I, wherein $R^1$ is $SO_2CH_3$, $R^2$ is cyclobutyl, and $R^3$ is ethyl.

An additional illustrative embodiment of the invention is a compound of Formula I, wherein $R^1$ is $SF_5$, $R^2$ is $CH_3$, and $R^3$ is

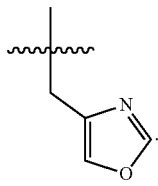 [SMILES: *Cc1cocn1]

An additional illustrative embodiment of the invention is a compound of Formula I, wherein $R^1$ is $SO_2CF_3$, $R^2$ is cyclobutyl, and $R^3$ is

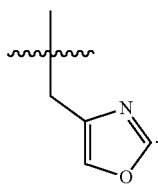 [SMILES: *Cc1cocn1]

An additional illustrative embodiment of the invention is a compound of Formula I, wherein $R^1$ is F, $R^2$ is $OCH_2CH_3$, and $R^3$ is isopropyl.

Additional illustrative embodiments of this invention are compounds or a pharmaceutically acceptable salt thereof selected from the group consisting of (2-Ethoxy-4-fluorophenyl)-$N^4$-isopropylpyrimidine-2,4-diamine;
$N^4$-((1H-Pyrazol-5-yl)methyl)-$N^4$-(4-fluoro-2-methylphenyl)pyrimidine-2,4-diamine;
$N^4$-(2-Ethoxy-4-fluorophenyl)-$N^4$-(isoxazol-4-ylmethyl)pyrimidine-2,4-diamine;
$N^4$-Benzyl-$N^4$-(2-ethoxy-4-fluorophenyl)pyrimidine-2,4-diamine;
$N^4$-(Oxazol-4-ylmethyl)-$N^4$-(2-propyl-4-(trifluoromethoxy)phenyl)pyrimidine-2,4-diamine;
$N^4$-(2-Cyclobutyl-4-(trifluoromethoxy)phenyl)-$N^4$-(oxazol-4-ylmethyl)pyrimidine-2,4-diamine;
$N^4$-(2-Methyl-4-(trifluoromethoxy)phenyl)-$N^4$-(oxazol-4-ylmethyl)pyrimidine-2,4-diamine;
$N^4$-(2-Isobutyl-4-(trifluoromethoxy)phenyl)-$N^4$-(oxazol-4-ylmethyl)pyrimidine-2,4-diamine;
2-(4-((2-Aminopyrimidin-4-yl)(oxazol-4-ylmethyl)amino)-3-ethylphenyl)-1,1,1,3,3,3-hexafluoropropan-2-ol;
$N^4$-(2-Ethoxy-4-fluorophenyl)-$N^4$-(oxazol-2-ylmethyl)pyrimidine-2,4-diamine;
$N^4$-((1H-Pyrazol-3-yl)methyl)-$N^4$-(2-ethoxy-4-fluorophenyl)pyrimidine-2,4-diamine;
$N^4$-(2-Ethoxy-4-fluorophenyl)-$N^4$-(oxazol-4-ylmethyl)pyrimidine-2,4-diamine;
$N^4$-((4-Chloro-1H-pyrazol-3-yl)methyl)-$N^4$-(2-ethoxy-4-fluorophenyl)pyrimidine-2,4-diamine;
$N^4$-(2-Ethoxy-4-fluorophenyl)-$N^4$-(isoxazol-3-ylmethyl)pyrimidine-2,4-diamine;
$N^4$-(2-Ethoxy-4-fluorophenyl)-$N^4$-(thiazol-5-ylmethyl)pyrimidine-2,4-diamine;
$N^4$-(2-Ethoxy-4-fluorophenyl)-$N^4$-(oxazol-5-ylmethyl)pyrimidine-2,4-diamine;
$N^4$-(2-Ethoxy-4-fluorophenyl)-$N^4$-(thiazol-4-ylmethyl)pyrimidine-2,4-diamine;
$N^4$-((1H-Pyrazol-3-yl)methyl)-$N^4$-(4-fluoro-2-(2,2,2-trifluoroethoxy)phenyl)pyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(4-Bromo-2-(trifluoromethyl)phenyl)-$N^4$-isopropylpyrimidine-2,4-diamine;
$N^4$-(2-Cyclobutyl-4-(methylsulfonyl)phenyl)-$N^4$-ethylpyrimidine-2,4-diamine;
$N^4$-Ethyl-$N^4$-(2-methyl-4-(pentafluorosulfanyl)phenyl)pyrimidine-2,4-diamine;
$N^4$-[2-Ethyl-4-(pentafluorosulfanyl)phenyl]-$N^4$-(oxazol-4-ylmethyl)pyrimidine-2,4-diamine;
$N^4$-(2-Methyl-4-(pentafluorosulfanyl)phenyl)-$N^4$-(pyridazin-3-ylmethyl)pyrimidine-2,4-diamine;
$N^4$-[2-Ethyl-4-(pentafluorosulfanyl)phenyl]-$N^4$-(1H-pyrazol-5-ylmethyl)pyrimidine-2,4-diamine;
$N^4$-[2-Ethyl-4-(pentafluorosulfanyl)phenyl]-$N^4$-(1,3,4-oxadiazol-2-ylmethyl)pyrimidine-2,4-diamine;
$N^4$-Isopropyl-$N^4$-(2-(2-methylprop-1-en-1-yl)-4-(pyrrolidin-1-ylsulfonyl)phenyl)pyrimidine-2,4-diamine;
$N^4$-(2-Cyclobutyl-4-(pyrrolidin-1-ylsulfonyl)phenyl)-$N^4$-isopropylpyrimidine-2,4-diamine;
$N^4$-(4-((Difluoromethyl)sulfonyl)-2-ethylphenyl)-$N^4$-(oxazol-4-ylmethyl)pyrimidine-2,4-diamine;
$N^4$-Isopropyl-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(2-methoxyethyl)pyrimidine-2,4-diamine;
$N^4$-(2-Methyl-4-(pentafluorosulfanyl)phenyl)-$N^4$-(pyrimidin-2-ylmethyl)pyrimidine-2,4-diamine;
$N^4$-[(5-Methyloxazol-4-yl)methyl]-$N^4$-[2-methyl-4-(pentafluorosulfanyl)phenyl]pyrimidine-2,4-diamine;
$N^4$-(Isoxazol-3-ylmethyl)-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(oxazol-5-ylmethyl)pyrimidine-2,4-diamine;
$N^4$-(2-Methyl-4-(pentafluorosulfanyl)phenyl)-$N^4$-(oxazol-2-ylmethyl)pyrimidine-2,4-diamine;
$N^4$-[(3-Chloro-2-pyridyl)methyl]-$N^4$-[2-methyl-4-(pentafluorosulfanyl)phenyl]pyrimidine-2,4-diamine;
$N^4$-(2-Methyl-4-(pentafluorosulfanyl)phenyl)-$N^4$-(thiazol-4-ylmethyl)pyrimidine-2,4-diamine;
$N^4$-[(4-Fluoro-1H-pyrazol-3-yl)methyl]-$N^4$-[2-methyl-4-(pentafluorosulfanyl)phenyl]pyrimidine-2,4-diamine;
$N^4$-((4-Chloro-1H-pyrazol-3-yl)methyl)-$N^4$-(2-methyl-4-(pentafluorosulfanyl)phenyl)pyrimidine-2,4-diamine;
$N^4$-[2-Methyl-4-(pentafluorosulfanyl)phenyl]-$N^4$-(1H-pyrazol-3-ylmethyl)pyrimidine-2,4-diamine;
$N^4$-Ethyl-$N^4$-(2-ethyl-4-((trifluoromethyl)sulfonyl)phenyl)pyrimidine-2,4-diamine;
$N^4$-(2-Cyclobutyl-4-((trifluoromethyl)sulfonyl)phenyl)-$N^4$-ethylpyrimidine-2,4-diamine;
$N^4$-(2-Cyclobutyl-4-((trifluoromethyl)sulfonyl)phenyl)-$N^4$-(oxazol-4-ylmethyl)pyrimidine-2,4-diamine;
$N^4$-(2-Cyclobutyl-4-(methylsulfonyl)phenyl)-$N^4$-isopropylpyrimidine-2,4-diamine;

$N^4$-(2-Ethyl-4-((trifluoromethyl)sulfonyl)phenyl)-$N^4$-(oxazol-2-ylmethyl)pyrimidine-2,4-diamine;
$N^4$-(2-Ethyl-4-((trifluoromethyl)sulfonyl)phenyl)-$N^4$-((3-fluoropyridin-2-yl)methyl)pyrimidine-2,4-diamine;
$N^4$-(2-Gyclobutyl-4-(methylsulfonyl)phenyl)-$N^4$-((6-(trifluoromethyl)pyridin-2-yl)methyl)pyrimidine-2,4-diamine;
$N^4$-((3,5-Dimethylisoxazol-4-yl)methyl)-$N^4$-(2-ethyl-4-((trifluoromethyl)sulfonyl)phenyl)pyrimidine-2,4-diamine;
$N^4$-(2-Ethyl-4-((trifluoromethyl)sulfonyl)phenyl)-$N^4$-(pyrimidin-2-ylmethyl)pyrimidine-2,4-diamine;
$N^4$-(2-Cyclobutyl-4-((trifluoromethyl)sulfonyl)phenyl)-$N^4$-isopropylpyrimidine-2,4-diamine;
$N^4$-Isopropyl-$N^4$-(2-methyl-4-(trifluoromethoxy)phenyl)pyrimidine-2,4-diamine;
$N^4$-(2-Ethyl-4-(trifluoromethoxy)phenyl)-$N^4$-(oxazol-4-ylmethyl)pyrimidine-2,4-diamine;
$N^4$-(2-Cyclobutyl-4-(methylsulfonyl)phenyl)-$N^4$-propylpyrimidine-2,4-diamine;
$N^4$-(2-Cyclopropyl-4-(methylsulfonyl)phenyl)-$N^4$-ethylpyrimidine-2,4-diamine;
$N^4$-(2-Cyclopropyl-4-(methylsulfonyl)phenyl)-$N^4$-propylpyrimidine-2,4-diamine;
$N^4$-(2-Cyclopropyl-4-(ethylsulfonyl)phenyl)-$N^4$-ethylpyrimidine-2,4-diamine;
$N^4$-Ethyl-$N^4$-(2-isobutyl-4-(methylsulfonyl)phenyl)pyrimidine-2,4-diamine;
$N^4$-(2-Cyclobutyl-4-methylsulfonylphenyl)-$N^4$-(oxazol-4-ylmethyl)pyrimidine-2,4-diamine;
$N^4$-(2-Gyclobutyl-4-methylsulfonylphenyl)-$N^4$-(2-methoxyethyl)pyrimidine-2,4-diamine;
$N^4$-Ethyl-$N^4$-(2-ethyl-4-(methylsulfonyl)phenyl)pyrimidine-2,4-diamine;
$N^4$-(2-Isobutyl-4-((trifluoromethyl)sulfonyl)phenyl)-$N^4$-(oxazol-4-ylmethyl)pyrimidine-2,4-diamine;
$N^4$-(2-Ethyl-4-((trifluoromethyl)sulfonyl)phenyl)-$N^4$-isopropylpyrimidine-2,4-diamine;
$N^4$-(2-Ethyl-4-((trifluoromethyl)sulfonyl)phenyl)-$N^4$-(oxazol-4-ylmethyl)pyrimidine-2,4-diamine;
$N^4$-(2-Ethyl-4-(methylsulfonyl)phenyl)-$N^4$-((6-(trifluoromethyl)pyridin-2-yl)methyl)pyrimidine-2,4-diamine;
$N^4$-(2-Ethyl-4-(methylsulfonyl)phenyl)-$N^4$-(2-methoxyethyl)pyrimidine-2,4-diamine;
$N^4$-(2-Ethyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-(oxazol-4-ylmethyl)pyrimidine-2,4-diamine;
$N^4$-((1H-Pyrazol-5-yl)methyl)-$N^4$-(2-cyclobutyl-4-(methylsulfonyl)phenyl)pyrimidine-2,4-diamine;
$N^4$-(2-Cyclobutyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-isopropylpyrimidine-2,4-diamine;
$N^4$-(2-Isobutyl-4-(methylsulfonyl)phenyl)-$N^4$-propylpyrimidine-2,4-diamine;
$N^4$-(2-Ethyl-4-((trifluoromethyl)sulfonyl)phenyl)-$N^4$-((6-(trifluoromethyl)pyridin-2-yl)methyl)pyrimidine-2,4-diamine;
$N^4$-(2-Ethyl-4-((trifluoromethyl)sulfonyl)phenyl)-$N^4$-(pyrimidin-4-ylmethyl)pyrimidine-2,4-diamine;
$N^4$-(2-Ethyl-4-((trifluoromethyl)sulfonyl)phenyl)-$N^4$-(2-methoxyethyl)pyrimidine-2,4-diamine;
$N^4$-(4-((Difluoromethyl)sulfonyl)-2-ethylphenyl)-$N^4$-ethylpyrimidine-2,4-diamine;
$N^4$-(2-Cyclobutyl-4-(ethylsulfonyl)phenyl)-$N^4$-ethylpyrimidine-2,4-diamine;

$N^4$-(2-Ethoxy-4-fluorophenyl)-$N^4$-(imidazo[1,2-a]pyridin-2-ylmethyl)pyrimidine-2,4-diamine;
$N^4$-(2-Ethoxy-4-fluorophenyl)-$N^4$-((2-methyloxazol-4-yl)methyl)pyrimidine-2,4-diamine;
4-((2-Aminopyrimidin-4-yl)(ethyl)amino)-3-cyclobutyl-N-ethyl-N-methylbenzenesulfonamide;
4-((2-Aminopyrimidin-4-yl)(propyl)amino)-3-cyclobutyl-N-methyl-N-propylbenzenesulfonamide;
$N^4$-(4-Bromo-2-(trifluoromethoxy)phenyl)-$N^4$-(oxazol-4-ylmethyl)pyrimidine-2,4-diamine;
$N^4$-Ethyl-$N^4$-(4-(methylsulfonyl)-2-(prop-1-en-2-yl)phenyl)pyrimidine-2,4-diamine;
$N^4$-Ethyl-$N^4$-(2-isopropyl-4-(methylsulfonyl)phenyl)pyrimidine-2,4-diamine;
$N^4$-(4-Bromo-2-(trifluoromethoxy)phenyl)-$N^4$-isopropylpyrimidine-2,4-diamine;
$N^4$-(4-Bromo-2-isopropoxyphenyl)-$N^4$-isopropylpyrimidine-2,4-diamine;
$N^4$-(4-Bromo-2-(2,2,2-trifluoroethoxy)phenyl)-$N^4$-isopropylpyrimidine-2,4-diamine;
$N^4$-(4-Bromo-2-methylphenyl)-$N^4$-isopropylpyrimidine-2,4-diamine;
4-((2-Aminopyrimidin-4-yl)(isopropyl)amino)-3-(trifluoromethoxy)benzonitrile;
$N^4$-(4-(Ethylsulfonyl)-2-(trifluoromethoxy)phenyl)-$N^4$-isopropylpyrimidine-2,4-diamine;
$N^4$-(4-Bromo-2-methylphenyl)-$N^4$-(oxazol-4-ylmethyl)pyrimidine-2,4-diamine;
$N^4$-(4-(Ethylsulfonyl)-2-methylphenyl)-$N^4$-(oxazol-4-ylmethyl)pyrimidine-2,4-diamine;
$N^4$-Isopropyl-$N^4$-(4-(methylsulfonyl)-2-(trifluoromethyl)phenyl)pyrimidine-2,4-diamine;
$N^4$-Isopropyl-$N^4$-(4-(isopropylsulfonyl)-2-(trifluoromethyl)phenyl)pyrimidine-2,4-diamine;
$N^4$-(2-Ethoxy-4-fluorophenyl)-$N^4$-(isoxazol-5-ylmethyl)pyrimidine-2,4-diamine;
$N^4$-((1,3,4-Oxadiazol-2-yl)methyl)-$N^4$-(2-ethoxy-4-fluorophenyl)pyrimidine-2,4-diamine;
4-((2-Aminopyrimidin-4-yl)(isopropyl)amino)-3-propylbenzonitrile;
(E)-4-((2-Aminopyrimidin-4-yl)(oxazol-4-ylmethyl)amino)-3-(prop-1-en-1-yl)benzamide;
(E)-4-((2-Aminopyrimidin-4-yl)(isopropyl)amino)-3-(prop-1-en-1-yl)benzonitrile;
(E)-4-((2-Aminopyrimidin-4-yl)(isopropyl)amino)-3-(prop-1-en-1-yl)benzamide;
(E)-$N^4$-(4-Chloro-2-(prop-1-en-1-yl)phenyl)-$N^4$-(oxazol-4-ylmethyl)pyrimidine-2,4-diamine;
$N^4$-(2-Cyclobutyl-4-(isopropylsulfonyl)phenyl)-$N^4$-isopropylpyrimidine-2,4-diamine;
$N^4$-(4-Fluoro-2-(trifluoromethoxy)phenyl)-$N^4$-isopropylpyrimidine-2,4-diamine;
$N^4$-((2H-1,2,3-Triazol-4-yl)methyl)-$N^4$-(2-ethoxy-4-fluorophenyl)pyrimidine-2,4-diamine.
$N^4$-Ethyl-$N^4$-(4-(methylsulfonyl)-2-propylphenyl)pyrimidine-2,4-diamine;
$N^4$-(2-Cyclobutyl-4-(cyclopropylsulfonyl)phenyl)-$N^4$-ethylpyrimidine-2,4-diamine;
$N^4$-(2-Cyclobutyl-4-(cyclopropylsulfonyl)phenyl)-$N^4$-propylpyrimidine-2,4-diamine;
$N^4$-((4H-1,2,4-Triazol-3-yl)methyl)-$N^4$-(2-ethoxy-4-fluorophenyl)pyrimidine-2,4-diamine;
$N^4$-(2-Ethyl-4-(trifluoromethyl)phenyl)-$N^4$-(oxazol-4-ylmethyl)pyrimidine-2,4-diamine;
$N^4$-(Oxazol-4-ylmethyl)-$N^4$-(4-(trifluoromethyl)phenyl)pyrimidine-2,4-diamine;

4-((2-Aminopyrimidin-4-yl)(ethyl)amino)-3-cyclobutylbenzamide;
4-((2-Aminopyrimidin-4-yl)(isopropyl)amino)-3-cyclobutylbenzamide;
4-((2-Aminopyrimidin-4-yl)(ethyl)amino)-3-isobutylbenzamide;
(E)-$N^4$-Isopropyl-$N^4$-(2-(prop-1-en-1-yl)-4-(trifluoromethyl)phenyl)pyrimidine-2,4-diamine;
$N^4$-Isopropyl-$N^4$-(2-propyl-4-(trifluoromethyl)phenyl)pyrimidine-2,4-diamine;
$N^4$-Isopropyl-$N^4$-(2-methyl-4-(trifluoromethyl)phenyl)pyrimidine-2,4-diamine;
4-((2-Aminopyrimidin-4-yl)(oxazol-4-ylmethyl)amino)-3-propylbenzonitrile;
(E)-$N^4$-(4-Fluoro-2-(prop-1-en-1-yl)phenyl)-$N^4$-isopropylpyrimidine-2,4-diamine;
$N^4$-(4-Fluoro-2-propylphenyl)-$N^4$-isopropylpyrimidine-2,4-diamine;
$N^4$-(4-Fluoro-2-(prop-1-en-2-yl)phenyl)-$N^4$-isopropylpyrimidine-2,4-diamine;
$N^4$-(4-Fluoro-2-isopropylphenyl)-$N^4$-isopropylpyrimidine-2,4-diamine; and
(E)-4-((2-Aminopyrimidin-4-yl)(oxazol-4-ylmethyl)amino)-3-(prop-1-en-1-yl)benzonitrile.

Additional illustrative embodiments of this invention are compounds or a pharmaceutically acceptable salt thereof selected from the group consisting of:
$N^4$-(2-Cyclobutyl-4-(methylsulfonyl)phenyl)-$N^4$-ethylpyrimidine-2,4-diamine;
$N^4$-Isopropyl-$N^4$-(2-(2-methylprop-1-en-1-yl)-4-(pyrrolidin-1-ylsulfonyl)phenyl)pyrimidine-2,4-diamine;
$N^4$-(2-Cyclobutyl-4-(pyrrolidin-1-ylsulfonyl)phenyl)-$N^4$-isopropylpyrimidine-2,4-diamine;
$N^4$-(4-((Difluoromethyl)sulfonyl)-2-ethylphenyl)-$N^4$-(oxazol-4-ylmethyl)pyrimidine-2,4-diamine;
$N^4$-Ethyl-$N^4$-(2-ethyl-4-((trifluoromethyl)sulfonyl)phenyl)pyrimidine-2,4-diamine;
$N^4$-(2-Cyclobutyl-4-((trifluoromethyl)sulfonyl)phenyl)-$N^4$-ethylpyrimidine-2,4-diamine;
$N^4$-(2-Cyclobutyl-4-((trifluoromethyl)sulfonyl)phenyl)-$N^4$-(oxazol-4-ylmethyl)pyrimidine-2,4-diamine;
$N^4$-(2-Cyclobutyl-4-(methylsulfonyl)phenyl)-$N^4$-isopropylpyrimidine-2,4-diamine;
$N^4$-(2-Ethyl-4-((trifluoromethyl)sulfonyl)phenyl)-$N^4$-(oxazol-2-ylmethyl)pyrimidine-2,4-diamine;
$N^4$-(2-Ethyl-4-((trifluoromethyl)sulfonyl)phenyl)-$N^4$-((3-fluoropyridin-4-yl)methyl)pyrimidine-2,4-diamine;
$N^4$-(2-Cyclobutyl-4-(methylsulfonyl)phenyl)-$N^4$-((6-(trifluoromethyl)pyridin-2-yl)methyl)pyrimidine-2,4-diamine;
$N^4$-((3,5-Dimethylisoxazol-4-yl)methyl)-$N^4$-(2-ethyl-4-((trifluoromethyl)sulfonyl)phenyl)pyrimidine-2,4-diamine;
$N^4$-(2-Ethyl-4-((trifluoromethyl)sulfonyl)phenyl)-$N^4$-(pyrimidin-2-ylmethyl)pyrimidine-2,4-diamine;
$N^4$-(2-Cyclobutyl-4-((trifluoromethyl)sulfonyl)phenyl)-$N^4$-isopropylpyrimidine-2,4-diamine;
$N^4$-(2-Cyclobutyl-4-(methylsulfonyl)phenyl)-$N^4$-propylpyrimidine-2,4-diamine;
$N^4$-(2-Cyclopropyl-4-(methylsulfonyl)phenyl)-$N^4$-ethylpyrimidine-2,4-diamine;
$N^4$-(2-Cyclopropyl-4-(methylsulfonyl)phenyl)-$N^4$-propylpyrimidine-2,4-diamine;
$N^4$-(2-Cyclopropyl-4-(ethylsulfonyl)phenyl)-$N^4$-ethylpyrimidine-2,4-diamine;
$N^4$-Ethyl-$N^4$-(2-isobutyl-4-(methylsulfonyl)phenyl)pyrimidine-2,4-diamine;
$N^4$-(2-Cyclobutyl-4-methylsulfonylphenyl)-$N^4$-(oxazol-4-ylmethyl)pyrimidine-2,4-diamine;
$N^4$-(2-Cyclobutyl-4-methylsulfonylphenyl)-$N^4$-(2-methoxyethyl)pyrimidine-2,4-diamine;
$N^4$-Ethyl-$N^4$-(2-ethyl-4-(methylsulfonyl)phenyl)pyrimidine-2,4-diamine;
$N^4$-(2-Isobutyl-4-((trifluoromethyl)sulfonyl)phenyl)-$N^4$-(oxazol-4-ylmethyl)pyrimidine-2,4-diamine;
$N^4$-(2-Ethyl-4-((trifluoromethyl)sulfonyl)phenyl)-$N^4$-isopropylpyrimidine-2,4-diamine;
$N^4$-(2-Ethyl-4-((trifluoromethyl)sulfonyl)phenyl)-$N^4$-(oxazol-4-ylmethyl)pyrimidine-2,4-diamine;
$N^4$-(2-Ethyl-4-(methylsulfonyl)phenyl)-$N^4$-((6-(trifluoromethyl)pyridin-2-yl)methyl)pyrimidine-2,4-diamine;
$N^4$-(2-Ethyl-4-(methylsulfonyl)phenyl)-$N^4$-(2-methoxyethyl)pyrimidine-2,4-diamine;
$N^4$-(2-Ethyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-(oxazol-4-ylmethyl)pyrimidine-2,4-diamine;
$N^4$-((1H-Pyrazol-5-yl)methyl)-$N^4$-(2-cyclobutyl-4-(methylsulfonyl)phenyl)pyrimidine-2,4-diamine;
$N^4$-(2-Cyclobutyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-isopropylpyrimidine-2,4-diamine;
$N^4$-(2-Isobutyl-4-(methylsulfonyl)phenyl)-$N^4$-propylpyrimidine-2,4-diamine;
$N^4$-(2-Ethyl-4-((trifluoromethyl)sulfonyl)phenyl)-$N^4$-((6-(trifluoromethyl)pyridin-2-yl)methyl)pyrimidine-2,4-diamine;
$N^4$-(2-Ethyl-4-((trifluoromethyl)sulfonyl)phenyl)-$N^4$-(pyrimidin-4-ylmethyl)pyrimidine-2,4-diamine;
$N^4$-(2-Ethyl-4-((trifluoromethyl)sulfonyl)phenyl)-$N^4$-(2-methoxyethyl)pyrimidine-2,4-diamine;
$N^4$-(4-((Difluoromethyl)sulfonyl)-2-ethylphenyl)-$N^4$-ethylpyrimidine-2,4-diamine;
$N^4$-(2-Cyclobutyl-4-(ethylsulfonyl)phenyl)-$N^4$-ethylpyrimidine-2,4-diamine;
4-((2-Aminopyrimidin-4-yl)(ethyl)amino)-3-cyclobutyl-N-ethyl-N-methylbenzenesulfonamide;
4-((2-Aminopyrimidin-4-yl)(propyl)amino)-3-cyclobutyl-N-methyl-N-propylbenzenesulfonamide;
$N^4$-Ethyl-$N^4$-(4-(methylsulfonyl)-2-(prop-1-en-2-yl)phenyl)pyrimidine-2,4-diamine;
$N^4$-Ethyl-$N^4$-(2-isopropyl-4-(methylsulfonyl)phenyl)pyrimidine-2,4-diamine;
$N^4$-(4-(Ethylsulfonyl)-2-(trifluoromethoxy)phenyl)-$N^4$-isopropylpyrimidine-2,4-diamine;
$N^4$-(4-(Ethylsulfonyl)-2-methylphenyl)-$N^4$-(oxazol-4-ylmethyl)pyrimidine-2,4-diamine;
$N^4$-Isopropyl-$N^4$-(4-(methylsulfonyl)-2-(trifluoromethyl)phenyl)pyrimidine-2,4-diamine;
$N^4$-Isopropyl-$N^4$-(4-(isopropylsulfonyl)-2-(trifluoromethyl)phenyl)pyrimidine-2,4-diamine;
$N^4$-(2-Cyclobutyl-4-(isopropylsulfonyl)phenyl)-$N^4$-isopropylpyrimidine-2,4-diamine;
$N^4$-Ethyl-$N^4$-(4-(methylsulfonyl)-2-propylphenyl)pyrimidine-2,4-diamine;
$N^4$-(2-Cyclobutyl-4-(cyclopropylsulfonyl)phenyl)-$N^4$-ethylpyrimidine-2,4-diamine; and
$N^4$-(2-Cyclobutyl-4-(cyclopropylsulfonyl)phenyl)-$N^4$-propylpyrimidine-2,4-diamine.

Additional illustrative embodiments of this invention are compounds selected from the group consisting of:
$N^4$-(2-Methyl-4-(pentafluorosulfanyl)phenyl)-$N^4$-(oxazol-4-ylmethyl)pyrimidine-2,4-diamine;

$N^4$-Ethyl-$N^4$-(2-methyl-4-(pentafluorosulfanyl)phenyl)pyrimidine-2,4-diamine;
$N^4$-[2-Ethyl-4-(pentafluorosulfanyl)phenyl]-$N^4$-(oxazol-4-ylmethyl)pyrimidine-2,4-diamine;
$N^4$-(2-Methyl-4-(pentafluorosulfanyl)phenyl)-$N^4$-(pyridazin-3-ylmethyl)pyrimidine-2,4-diamine;
$N^4$-[2-Ethyl-4-(pentafluorosulfanyl)phenyl]-$N^4$-(1H-pyrazol-5-ylmethyl)pyrimidine-2,4-diamine;
$N^4$-[2-Ethyl-4-(pentafluorosulfanyl)phenyl]-$N^4$-(1,3,4-oxadiazol-2-ylmethyl)pyrimidine-2,4-diamine;
$N^4$-Isopropyl-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(2-methoxyethyl)pyrimidine-2,4-diamine;
$N^4$-(2-Methyl-4-(pentafluorosulfanyl)phenyl)-$N^4$-(pyrimidin-2-ylmethyl)pyrimidine-2,4-diamine;
$N^4$-[(5-Methyloxazol-4-yl)methyl]-$N^4$-[2-methyl-4-(pentafluorosulfanyl)phenyl]pyrimidine-2,4-diamine;
$N^4$-(Isoxazol-3-ylmethyl)-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(oxazol-5-ylmethyl)pyrimidine-2,4-diamine;
$N^4$-(2-Methyl-4-(pentafluorosulfanyl)phenyl)-$N^4$-(oxazol-2-ylmethyl)pyrimidine-2,4-diamine;
$N^4$-[(3-Chloro-2-pyridyl)methyl]-$N^4$-[2-methyl-4-(pentafluorosulfanyl)phenyl]pyrimidine-2,4-diamine;
$N^4$-(2-Methyl-4-(pentafluorosulfanyl)phenyl)-$N^4$-(thiazol-4-ylmethyl)pyrimidine-2,4-diamine;
$N^4$-[(4-Fluoro-1H-pyrazol-3-yl)methyl]-$N^4$-[2-methyl-4-(pentafluorosulfanyl)phenyl]pyrimidine-2,4-diamine; and
$N^4$-((4-Chloro-1H-pyrazol-3-yl)methyl)-$N^4$-(2-methyl-4-(pentafluorosulfanyl)phenyl)pyrimidine-2,4-diamine; and
$N^4$-[2-Methyl-4-(pentafluorosulfanyl)phenyl]-$N^4$-(1H-pyrazol-3-ylmethyl)pyrimidine-2,4-diamine.

An embodiment of the invention are compounds or a pharmaceutically acceptable salt thereof selected from the group consisting of:
(2-Ethoxy-4-fluorophenyl)-$N^4$-isopropylpyrimidine-2,4-diamine;
$N^4$-(2-Cyclobutyl-4-(trifluoromethoxy)phenyl)-$N^4$-(oxazol-4-ylmethyl)pyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(2-Cyclobutyl-4-(((trifluoromethyl)sulfonyl)phenyl)-$N^4$-(oxazol-4-ylmethyl)pyrimidine-2,4-diamine and
$N^4$-(2-Cyclobutyl-4-(methylsulfonyl)phenyl)-$N^4$-ethylpyrimidine-2,4-diamine.

Additional illustrative embodiments of this invention are compounds or a pharmaceutically acceptable salt thereof selected from the group consisting of
$N^4$-(2-Cyclobutyl-4-(methylsulfonyl)phenyl)-$N^4$-ethylpyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(2-Cyclobutyl-4-(((trifluoromethyl)sulfonyl)phenyl)-$N^4$-(oxazol-4-ylmethyl)pyrimidine-2,4-diamine;
$N^4$-(2-Cyclobutyl-4-(trifluoromethoxy)phenyl)-$N^4$-(oxazol-4-ylmethyl)pyrimidine-2,4-diamine; and
(2-Ethoxy-4-fluorophenyl)-$N^4$-isopropylpyrimidine-2,4-diamine.

Additional embodiments of this invention are pharmaceutical compositions each comprising an effective amount of at least one of the compounds illustratively given above.

An additional embodiment of the invention is directed to a method of treating a subject suffering from or diagnosed with a disease, disorder, or medical condition mediated by $H_4R$ activity, comprising administering to the subject in need of such treatment an effective amount of at least one of the above compounds or a pharmaceutically acceptable salt thereof, pharmaceutically acceptable prodrug, or pharmaceutically active metabolite of such compounds. In certain embodiments of the inventive method, the disease, disorder, or medical condition is inflammation. Inflammation herein refers to the response that develops as a consequence of histamine release, which in turn is caused by at least one stimulus. Examples of such stimuli are immunological stimuli and non-immunological stimuli.

An additional embodiment of the invention is directed to a method for modulating $H_4R$ activity, comprising exposing a $H_4R$ to an effective amount of at least one of the above compounds.

An additional embodiment of the invention is a method of treating a subject suffering from or diagnosed with a disease, disorder, or medical condition mediated by $H_4R$ activity, comprising administering to a subject in need of such treatment an effective amount of at least one compound of Formula I, or a pharmaceutically acceptable salt thereof.

An additional illustrative embodiment of the invention is a method, wherein the disease, disorder, or medical condition is inflammation.

An additional illustrative embodiment of the invention is a method, wherein the disease, disorder, or medical condition is selected from the group consisting of: inflammatory disorders, allergic disorders, dermatological disorders, autoimmune disease, lymphatic disorders, and immunodeficiency disorders.

An additional illustrative embodiment of the invention is a method, wherein the disease, disorder, or medical condition is selected from allergy, asthma, eosinophilic asthma, dry eye, chronic obstructive pulmonary disease (COPD), atherosclerosis, rheumatoid arthritis, multiple sclerosis, inflammatory bowel diseases, psoriasis, pruritus, itchy skin, atopic dermatitis, urticaria, ocular inflammation, conjunctivitis, nasal polyps, allergic rhinitis, nasal itch, parasitic or fungal infections, hidradenitis suppurativa, malignancy, such as lymphoma, jaundice, polycythemia, punctate palmoplantar keratoderma, thyroid illness/hyperparathyroidism, diabetes, chicken pox, iron deficiency anemia, psychiatric diseases, medication-induced itch; cholestasis; pregnancy-related itch, xerosis, sunburn, dandruff, scab/scars, insect bites, poison ivy, poison oak, hemorrhoids, contact dermatitis, age associated itch, itch associated with dialysis, scleroderma, autoimmune thyroid diseases, immune-mediated diabetes mellitus, lupus, myasthenia gravis, autoimmune neuropathies, autoimmune uveitis, autoimmune hemolytic anemia, pernicious anemia, autoimmune thrombocytopenia, temporal arteritis, anti-phospholipid syndrome, vasculitides, Behcet's disease, dermatitis herpetiformis, pemphigus vulgaris, vitiligo, primary biliary cirrhosis, autoimmune hepatitis, autoimmune oophoritis and orchitis, autoimmune disease of the adrenal gland, polymyositis, dermatomyositis, spondyloarthropathy, Sjogren's syndrome, pruritus, and diabetic nephropathy.

An additional illustrative embodiment of the invention is a method, wherein the disease, disorder, or medical condition is selected from allergy, asthma, autoimmune diseases, and pruritus.

An additional illustrative embodiment of the invention is a method, wherein said inflammatory bowel disease is one of colitis, Crohn's disease, and ulcerative colitis.

An additional illustrative embodiment of the invention is a method, wherein said parasitic or fungal infections is a parasitic infection.

An additional illustrative embodiment of the invention is a method, wherein said parasitic or fungal infections is a fungal infection.

An additional illustrative embodiment of the invention is a method, wherein said parasitic or fungal infections is one of lice infection, scabies, swimmer's itch, jock itch, athlete's foot.

An additional illustrative embodiment of the invention is a method, wherein said malignancy is lymphoma.

An additional illustrative embodiment of the invention is a method, wherein said malignancy is Hodgkin's disease.

An additional illustrative embodiment of the invention is a method, wherein said medication-induced itch is one of photodermatitis, morphine-induced itch, opiate-induced itch, and chloroquine-induced itch).

An additional illustrative embodiment of the invention is a method, wherein said pregnancy-related itch is one of obstetric cholestasis, pruritic urticarial, papules and plaques of pregnancy, and gestational pemphigoid.

An additional illustrative embodiment of the invention is a method, wherein said autoimmune neuropathy is Guillain-Barré neuropathy.

An additional illustrative embodiment of the invention is a method, wherein said vasculitides is Wegener's granulomatosis.

An additional illustrative embodiment of the invention is a method, wherein said spondyloarthropathy is ankylosing spondylitis.

An embodiment of the invention is directed to the making, including purifying the above compounds.

Additional embodiments, features, and advantages of the invention will be apparent from the following detailed description and through practice of the invention.

TABLE 1

Table of abbreviations and acronyms used herein include those listed in the following table.

| Acronym | Term |
| --- | --- |
| ACN | Acetonitrile |
| aq | Aqueous |
| atm | Atmosphere |
| n-BuOH | n-Butanol |
| br | Broad |
| Celite ® | Diatomaceous Earth |
| dba | dibenzylideneacetone |
| tBuBrettPhos | 2-(Di-tert-butylphosphino)-2',4',6'-triisopropyl-3,6-dimethoxy-1,1'-biphenyl |
| DCM | Dichloromethane |
| DMA | Dimethylacetamide |
| DME | 1,2-Dimethoxyethane |
| DMF | N,N-Dimethylformamide |
| DMS | Dimethylsulfide |
| DMSO | Dimethylsulfoxide |
| EtOAc, or EA | Ethyl Acetate |
| EtOH | Ethanol |
| ESI | Electrospray ionization |
| dppf | 1,1'-Ferrocenediyl-bis(diphenylphosphine), |
| FCC | Normal-phase silica gel chromatography |
| g | Grams |
| h | Hours |
| HATU | 1-[Bis(dimethylamino)methylene]-1H-1,2,3-triazolo[4,5-b]pyridinium 3-oxid hexafluorophosphate |
| HPLC | High-pressure liquid chromatography |
| Hz | Hertz |
| iPrOH, IPA | Isopropyl alcohol |
| LCMS | Liquid chromatography and mass spectrometry |
| M | Molar |
| m/z | Mass to charge ratio |

TABLE 1-continued

Table of abbreviations and acronyms used herein include those listed in the following table.

| Acronym | Term |
| --- | --- |
| mCPBA | meta-Chloroperoxybenzoic acid |
| MeOH | Methanol |
| mg | Milligrams |
| min | Minute |
| mL | Milliliter |
| μL | Microliter |
| mmol | Millimoles |
| MS | Mass spectrometry |
| MTBE | Methyl tert-butyl ether |
| NBS | N-Bromosuccinimide |
| NCS | N-Chlorosuccinimide |
| NMR | Nuclear magnetic resonance |
| Pd(PPh$_3$)$_2$Cl$_2$ | Palladium(II)bis(triphenylphosphine) dichloride |
| Pd(PPh$_3$)$_4$ | Tetrakis(triphenylphosphine)palladium(0) |
| PdCl$_2$(dppf) or Pd(dppf)Cl$_2$ | [1,1'-Bis(diphenylphosphino)ferrocene]dichloropalladium(II) |
| ppm | Parts per million |
| ppt | Precipitate |
| Rt, RT or rt | Room temperature |
| Na(OAC)$_3$BH | Sodium triacetoxyborohydride |
| tBu$_3$P | Tributylphosphine |
| TEA | Triethylamine |
| TFA | Trifluoroacetic acid |
| THF | Tetrahydrofuran |
| TLC | Thin layer chromatography |
| TsOH | p-Toluenesulfonic Acid |
| XPhos | 2-Dicyclohexylphosphino-2',4',6'-triisopropylbiphenyl |

Illustrative compounds useful in methods of this invention are be described below by reference to the illustrative synthetic schemes ("Schemes") and specific examples for their preparation. One of ordinary skill in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula I. If no temperature or temperature range is stated, it is to be understood that the reaction is to be run at room temperature. Schemes given below describe general preparation procedures.

Scheme 1

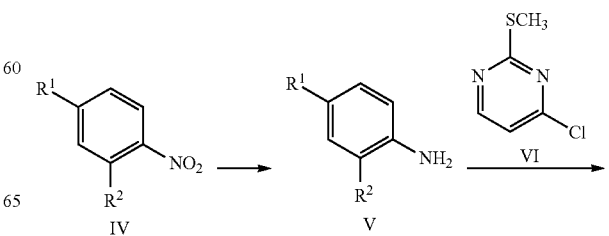

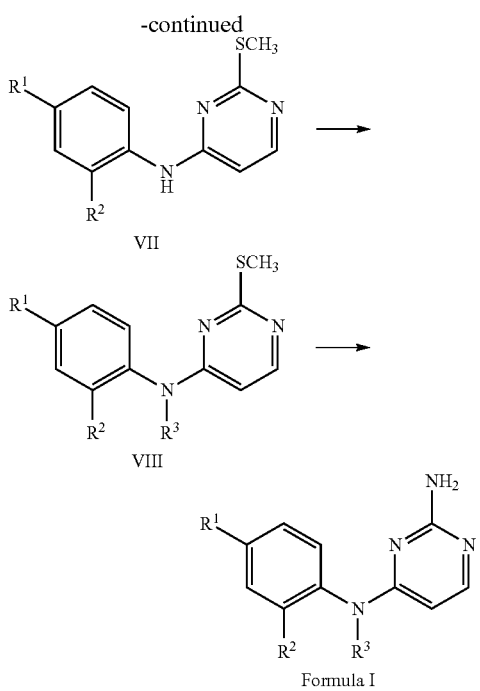

Formula I

Compound IV is converted to compound V through the reduction of the nitro group. One of ordinary skill in the art will realize that this reduction is accomplished through a variety of methods. Some methods include catalytic hydrogenation conditions such as $H_2$ gas and a catalytic amount of a metal catalyst such as Pd or Pt, wherein the Pd and Pt catalyst used may be 5-10% Pd on carbon and 5-10% Pt on carbon, respectively. This reduction may be conventionally run in a flask wherein the atmosphere above the reaction mixture is $H_2$ gas or wherein $H_2$ gas is bubbled through the solution. Alternatively, the reaction may be run through a continuous hydrogenation flow reactor. The nitro group can also be reduced with, Fe, Zn or $SnCl_2$ in solvents such as methanol, ethanol, isopropanol, THF or mixtures of some of such solvents.

Depending on specific substituent assignments for $R^1$ and $R^2$, starting compound IV in the foregoing transformation is available commercially or it is prepared from commercially available forms through known transformations such as those illustratively described in processes (a)-(c) below.

(a) When compound IV is desired in the form in which $R^2$ is $OC_1$-$C_4$ alkyl, then compound IV in the form in which $R^2$ is OH is reacted with $C_1$-$C_4$ alkyl-LG, wherein LG is a leaving group such as Cl, Br, I, mesylate or tosylate, with a base such as $K_2CO_3$ or $Cs_2CO_3$ in a solvent such as acetone or THF.

(b) When compound IV is desired in the form in which $R^2$ is $OC_1$-$C_3$ perhaloalkyl, then compound IV in the form in which $R^2$ is F is reacted with $HOC_1$-$C_3$ perhaloalkyl and NaH in a solvent such as toluene at a temperature ranging from −20° C. to 0° C.

(c) When compound IV is desired in the form in which $R^1$ is $NO_2$, then compound IV in the form in which $R^1$ is H is treated with $H_2SO_4$, fuming $HNO_3$ at a temperature of about −10° C.

Compound V with certain $R^1$ and/or $R^2$ assignments are transformed to other forms of compound V that have different $R^1$ and/or $R^2$ assignments as illustratively described in processes (d)-(i) below.

(d) When compound V is desired in the form in which $R^2$ is $C_1$-$C_4$ alkyl or $C_3$-$C_4$ cycloalkyl, then compound V in which $R^2$ is Cl, Br or I is treated with an alkyl or cycloalkyl boronic acid, a trialkyl or tricycloalkylborane, or an alkyl 1,3,5,2,4,6-trioxatriborinane, a metal catalyst such as $Pd(Ph_3)_4$, $Pd(dppf)Cl_2$, 2-dicyclohexylphosphino-2',6'-diisopropoxybiphenyl, palladium(II) phenethylamine chloride (1:1 MTBE solvate), $Pd(dppf)Cl_2$—$CH_2Cl_2$ or chloro-(2-dicyclohexylphosphino-2',6'-diisopropoxy-1,1'-biphenyl)[2-(2-aminoethyl)phenyl]palladium(II)-methyl-t-butyl ether adduct and a base such as $Cs_2CO_3$ or $K_2CO_3$ in a solvent such as MeOH, DMF, benzene, toluene or mixtures thereof at a temperature of about 60° C.-125° C. for a time from about 1 hour to 24 hours. An alternative method to convert compound V ($R^2$ is Cl, Br or I) to compound V ($R^2$ is $C_1$-$C_4$ alkyl or $C_3$-$C_4$ cycloalkyl) is treating compound V ($R^2$ is Cl, Br or I) with a palladium catalyst such as $Pd(t$-$Bu_3P)_2$ or bis(tri-tert-butylphosphine)palladium(0) and $C_1$-$C_4$ alkyl-zinc bromide or $C_3$-$C_4$ cycloalkylzinc bromide in a solvent such as THF at a temperature of about 50° C. for a time from about 1 hour to 24 hours.

(e) When compound V is desired in the form in which $R^2$ is $C_1$-$C_4$ alkyl, then compound V in which $R^2$ is OH is treated with $C_1$-$C_4$ alkyl-LG, wherein LG is a leaving group such as Cl, Br, I, mesylate or tosylate, with a base such as $K_2CO_3$ or $Cs_2CO_3$ in a solvent such as acetone or THF at a temperature of about rt to the reflux temperature of the solvent.

(f) When compound V is desired in the form in which $R^2$ is O $C_1$-$C_4$ alkyl, then compound V in which $R^2$ is F is treated with $C_1$-$C_4$ alkyl-OH and NaH in a solvent such as toluene wherein the reaction is run at a temperature between 0° C. and 45° C. for a time of about 15 h.

(g) When compound V is desired in the form in which $R^2$ is Br, then compound V in which $R^2$ is H) is treated with a brominating agent such as 1,3-dibromo-5,5-dimethylhydantoin or NBS in a solvent such as dichloromethane at a temperature of about 0° C. to rt for a time of approximately 15 minutes to 1 hour.

(h) When compound V is desired in the form in which $R^2$ is Cl, then compound V in which $R^2$ is H is treated with a chlorinating agent such as NCS in a solvent such as acetonitrile at a temperature of about 50° C. to 75° C. for a time ranging from 1 hour to 22 hours.

(i) When compound V is desired in the form in which $R^1$ is —$SO_2$-cyclopropyl and $R^2$ is H, then compound V in which $R^1$ is I and $R^2$ is H is treated with sodium cyclopropanesulfinate, trifluoromethanesulfonate benzene complex, and dimethylethylenediamine in a solvent such as DMSO with heating to a temperature of about 120° C. for approximately 16 h.

Reacting compound V with compound VI and an acid, such as concentrated HCl or p-toluene sulfonic acid hydrate, in a solvent such as iPrOH at a temperature of about 50-80° C. for about 15-22 hours yields compound VII.

Furthermore, reacting compound VII with a base such as NaH in a solvent such as DMF, ACN or THF, and a compound such as $R^3$-LG, wherein LG is a leaving group such as Cl, Br, I, mesylate or tosylate at a temperature of about 0-50° C. for a time ranging from 15 minutes to 22 hours yields compound VIII.

Compound VIII with certain $R^1$ or $R^2$ assignments is transformed to other forms of compound VIII that have different $R^1$ or $R^2$ assignments as illustratively described in processes (j), (k) and (m) below.

(j) When compound VIII is desired in the form in which $R^1$ is CN, then compound VIII in which $R^1$ is Br is cyanized through a palladium catalyzed cyanation. Typical conditions include treatment with a cyanide source such as $Zn(CN)_2$, NaCN or KCN, a metal such as zinc powder, ligands such as X-Phos and tBuBrettPhos, a palladium source such as $Pd_2dba_3$ in a solvent such as DMSO or DMA with heating to a temperature of about 120° C.

(k) When compound VIII is desired in the form in which $R^2$ is (E)-prop-1-en-1-yl, then compound VIII in which $R^2$ is I is treated with [(E)-prop-1-enyl]boronic acid, chloro-(2-dicyclohexylphosphino-2',6'-diisopropoxy-1,1'-biphenyl)[2-(2-aminoethyl)phenyl]palladium(II)-methyl-t-butyl ether adduct, and degassed 0.5M phosphate solution in a solvent such as dioxane with heating to a temperature of about 120° C. This reaction may be heated in a microwave reactor or may be heated in the conventional manner.

(m) When compound VIII is desired in the form in which $R^1$ is S-iPr, then compound VIII in which $R^1$ is Br is treated with n-butyllithium (2.5M in hexanes) in a solvent such as THF at −73° C. followed by treatment with isopropyl disulfide at a temperature from −73 C to rt for a time from about 15 minutes to 24 hours.

Compound VIII is converted to compound of formula I through a two-step process wherein in the first step the —$SCH_3$ group is initially oxidized to a —$SO_2CH_3$ group upon treatment with an oxidizing agent such as a monopersulfate, for example potassium monopersulfate, sometimes available in the form of a triple salt combination, and found under the tradename oxone, in methanol and water at a temperature of about 0° C. to rt or MCPBA. The second step of the two-step process comprises treatment of the —$SO_2CH_3$ intermediate (structure not shown) with $NH_4OH$ in iPrOH at a temperature of about 140° C. for about 40 minutes. The reaction may be run in a microwave reactor or may be heated in the conventional manner.

Compound of formula I with certain $R^1$ or $R^2$ assignments are transformed to other forms of compound of formula I that have different $R^1$ or $R^2$ assignments as illustratively described in processes (n)-(w) below.

(n) When compound of formula I is desired in the form in which $R^1$ is $SO_2R^4$, where $R^4$ is $C_1$-$C_4$ alkyl, $C_1$-$C_2$ perhaloalkyl or $C_3$-$C_4$ cycloalkyl, then compound of formula I in which $R^1$ is Br is treated with $NaSO_2R^4$, a catalyst such as CuI or $(CF_3SO_3Cu)_2C_6H_6$, in a solvent or mixtures thereof such as DMA and DMSO, with heating to a temperature of about 120-140° C.

(o) When compound of formula I is desired in the form in which $R^1$ is —CH═CH—$CH_3$ then compound of formula I in which $R^1$ is Br is treated with prop-1-enylboronic acid, $Cs_2CO_3$, $Pd(Ph_3)_4$ in a solvent mixture such as dioxane and water at a temperature of about 100° C. for approximately 15 minutes.

(p) When compound of formula I is desired in the form in which $R^1$ is propyl then compound of formula I in which $R^1$ is —CH═CH—$CH_3$ is subjected to hydrogenation conditions which include catalytic hydrogenation conditions such as $H_2$ gas and a catalytic amount of a metal catalyst such as Pd or Pt, wherein the Pd and Pt used may be 5-10% Pd on carbon and 5-10% Pt on carbon, respectively. This reduction may be run in the conventional manner in a flask wherein the atmosphere above the reaction mixture is $H_2$ gas or wherein $H_2$ gas is bubbled through the solution. Alternatively, the reaction may be run through a continuous hydrogenation flow reactor.

(q) When compound of formula I is desired in the form in which $R^1$ is —CH═CH—$CH_3$ (trans)) then compound of formula I in which $R^1$ is Cl is treated with trans-1-propen-1-ylboronic acid, $K_3PO_4$ solution (0.5M), and 2-dicyclohexylphosphino-2',6'-diisopropoxybiphenyl, palladium(II) phenethylamine chloride in a solvent mixture such as dioxane and water at a temperature of about 140° C. for approximately 20 minutes.

(r) When compound of formula I is desired in the form in which $R^1$—$C(CH_3)$═$CH_2$ then compound of formula I in which $R^1$ is Cl is treated with isopropenylboronic acid pinacol ester, $K_3PO_4$ solution (0.5M), and 2-dicyclohexylphosphino-2',6'-diisopropoxybiphenyl, palladium(II) phenethylamine chloride in a solvent mixture such as dioxane and water at a temperature of about 140° C. for approximately 20 minutes.

(s) When compound of formula I is desired in the form in which $R^1$ is isopropyl then compound of formula I in which $R^1$ is —$C(CH_3)$═$CH_2$ is subjected to hydrogenation conditions which include catalytic hydrogenation conditions such as $H_2$ gas and a catalytic amount of a metal catalyst such as Pd or Pt, wherein the Pd and Pt used may be 5-10% Pd on carbon and 5-10% Pt on carbon, respectively. This reduction may be run in the conventional manner in a flask wherein the atmosphere above the reaction mixture is $H_2$ gas or wherein $H_2$ gas is bubbled through the solution. Alternatively, the reaction may be run through a continuous hydrogenation flow reactor.

(t) When compound of formula I is desired in the form in which $R^1$ is —CH═$CH_2$ then compound of formula I in which $R^1$ is Br is treated with chloro-(2-dicyclohexylphosphino-2',6'-diisopropoxy-1,1'-biphenyl)[2-(2-aminoethyl)phenyl]palladium(II)-methyl-t-butyl ether adduct, $K_3PO_4$ (0.5M in $H_2O$), and 4,4,5,5-tetramethyl-2-vinyl-1,3,2-dioxaborolane in a solvent such as dioxane at a temperature of about 120° C. for 1 h in a microwave reactor.

(u) When compound of formula I is desired in the form in which $R^1$ is ethyl then compound of formula I in which $R^1$ is —CH═$CH_2$ is subjected to hydrogenation conditions which include catalytic hydrogenation conditions such as $H_2$ gas and a catalytic amount of a metal catalyst such as Pd or Pt, wherein the Pd and Pt used may be 5-10% Pd on carbon and 5-10% Pt on carbon, respectively. This reduction may be run in the conventional manner in a flask wherein the atmosphere above the reaction mixture is $H_2$ gas or wherein $H_2$ gas is bubbled through the solution. Alternatively, the reaction may be run through a continuous hydrogenation flow reactor.

(v) When compound of formula I is desired in the form in which $R^1$ is $CH_3$ then compound of formula I in which $R^1$ is Cl is treated with 2,4,6-trimethyl-1,3,5,2,4,6-trioxatriborinane, 1,1'-bis(diphenylphosphino)ferrocene-palladium(II) dichloride dichloromethane complex, a 0.5M degassed phosphate solution at a temperature of about 140° C. for approximately 30 min in a microwave reactor.

(w) When compound of formula I is desired in the form in which $R^1$ is CN then compound of formula I in which $R^1$ is Cl is treated with zinc cyanide, 2-dicyclohexylphosphino-2',4',6'-triisopropylbiphenyl, Zn powder, and $Pd_2(dba)_3$ in a solvent such as DMA at a temperature of about 120° C. for approximately 1 h.

Scheme 2

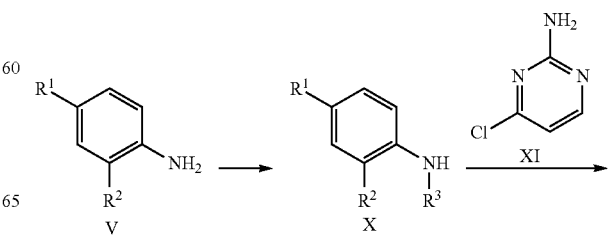

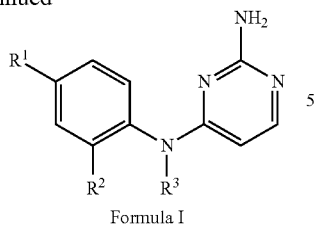

Formula I

Compound V is converted to compound X through a variety of methods. Reductive amination of the aniline is accomplished through treatment with an appropriately substituted aldehyde, a reducing agent such as NaBH(OAc)$_3$, NaCNBH$_3$, and NaBH$_4$, in a suitable solvent such as DCM and DCE, for a period of 1-24 h, optionally an acid, such as acetic acid, may be added.

Alternatively, compound V is converted to compound X through a two-step procedure (not expressly shown in Scheme 2) wherein compound V is coupled first with a carboxylic acid using amide bond coupling conditions. The resulting amide is then fully reduced by using reduction conditions such as LiAlH$_4$ in ether and BH$_3$-THF or BH$_3$-DMS in a solvent such as THF at a temperature of about 40° C.

Compound X is converted to compound of formula I through treatment with compound XI and an acid such as p-toluenesulfonic acid in a solvent such as dioxane and water or mixtures thereof at a temperature of about 60° C.

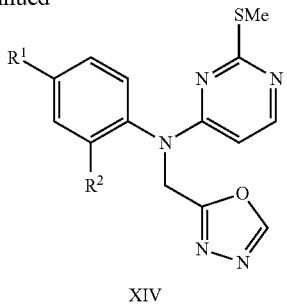

XIV

Compound VII is converted to compound XII by treating it with 2-bromoacetate and NaH in a solvent such as DMF wherein the reaction in conducted at a temperature between 0° C. and room temperature. Compound XII is then converted to compound XIII by treating it with NH$_2$NH$_2$—H$_2$O in a solvent such as ethanol at a temperature of about 80° C. Compound XIII is converted to compound XIV by treating it with TsOH and trimethoxymethane at a temperature at or close to the reflux temperature. Compound XIV then is converted to compound of formula I using the conditions described to convert compound VIII to compound of formula I in Scheme 1.

Scheme 4

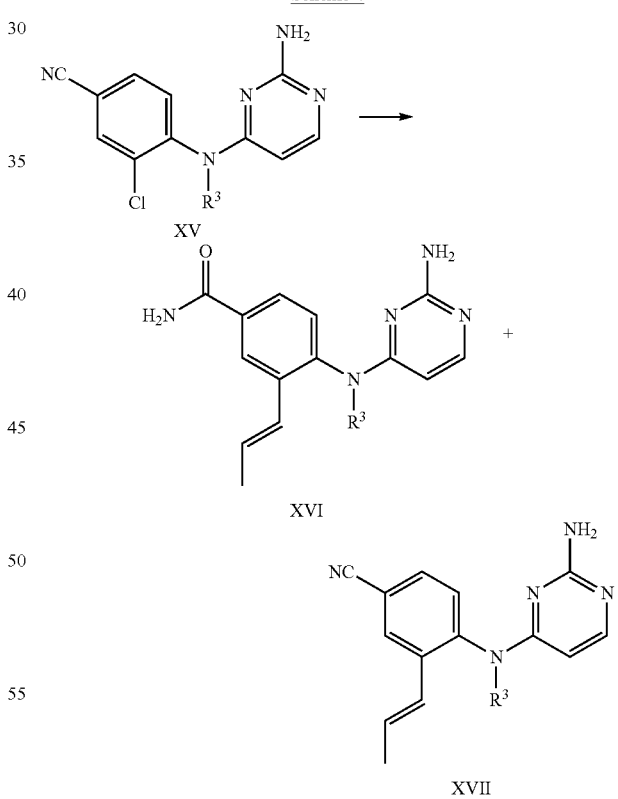

Compound XV is converted to compounds XVI and XVII by treating it with [(E)-prop-1-enyl]boronic acid, 2-dicyclohexylphosphino-2',6'-diisopropoxybiphenyl and a palladium (II) phenethylamine chloride, and degassed 0.5M phosphate solution in a solvent such as dioxane. Compounds XVI and XVII are compounds of formula I. The mixture of compounds XVI and XVII is separated into individual constitu- Scheme 3

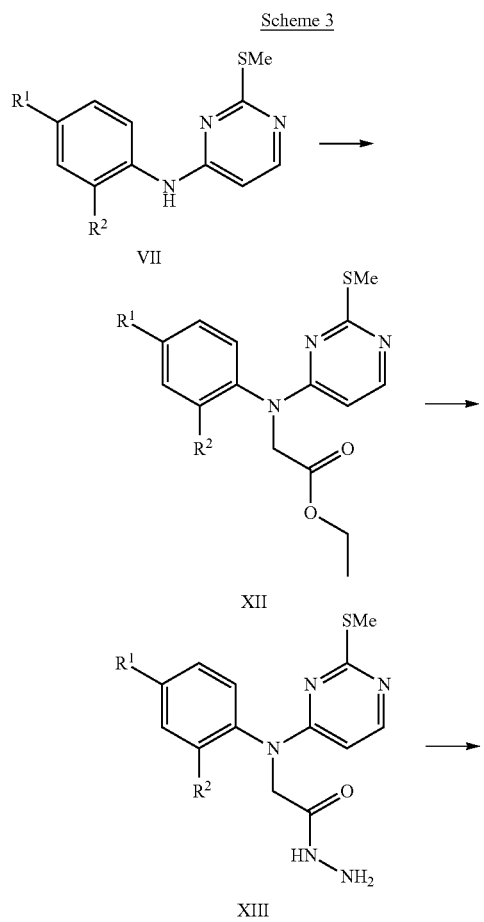

ent compounds by HPLC using a gradient mobile phase of 5% ACN in H₂O (containing 0.05% TFA) to 95% ACN in H₂O (containing 0.05% TFA), over 8 minutes using a 30 mm×100 mm InertSil ODS-3 column, which was kept at 46° C. with 80 ml/min flow rate.

Scheme 5

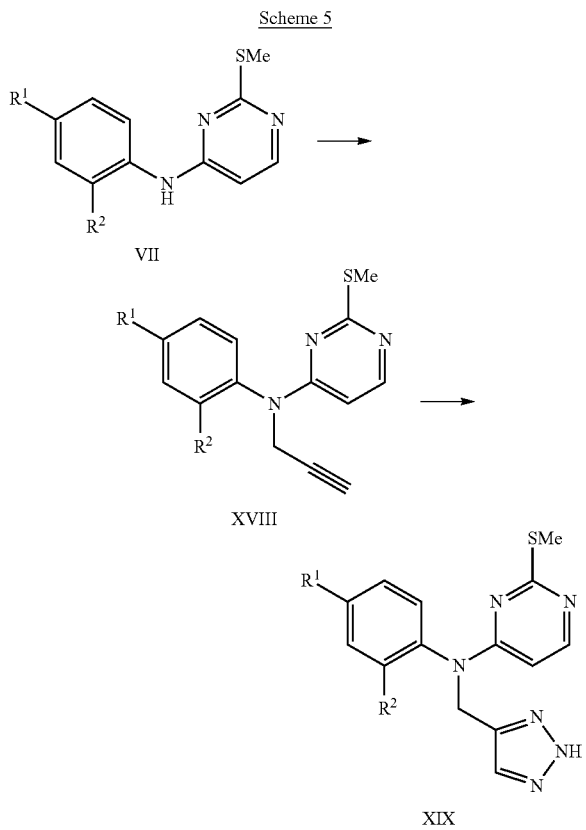

Compound VII is converted to compound XVIII by treating it with NaH in DMF at a temperature starting at 10 C, followed by addition of 3-bromoprop-1-yne wherein the temperature is raised to rt for about 2 h. Compound XVIII is converted to compound XIX by treating it with formalin, acetic acid, CuSO₄, L-ascorbic acid sodium salt and NaN₃ in a solvent such as dioxane at a temperature of about 0° C. to rt. Compound XIX then is converted to compound of formula I by using the conditions described to convert compound VIII to compound of formula I in Scheme 1.

Scheme 6

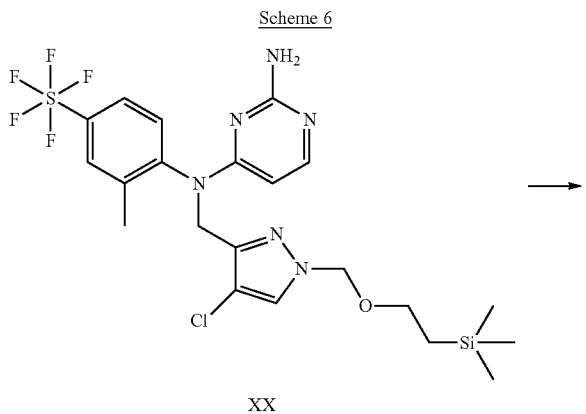

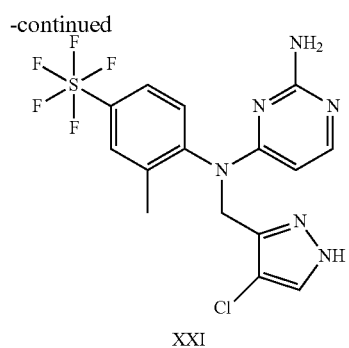

Compound XX is converted to compound XXI by treating it with concentrated HCl in a solvent such as MeOH at a temperature of about 45° C. for a time period of about 15 h. Compound XXI is a compound of formula I.

EXAMPLES

In obtaining the compounds described in the examples below and the corresponding analytical data, the following experimental and analytical protocols were followed unless otherwise indicated.

Reaction mixtures were magnetically stirred at room temperature. Where solutions are characterized as "dried," they were generally dried over a drying agent such as Na₂SO₄ or MgSO₄. Where mixtures, solutions, and extracts were "concentrated", they were typically concentrated on a rotary evaporator under reduced pressure.

Thin-layer chromatography was performed using Merck silica gel 60 F254 2.5 cm×7.5 cm, 250 μm or 5.0 cm×10.0 cm, 250 μm pre-coated silica gel plates.

Normal-phase flash column chromatography (FCC) was performed on silica gel (SiO₂) eluting with 2M NH₃ in MeOH/CH₂Cl₂, unless otherwise noted.

Mass spectra (MS) were obtained on an Agilent series 1100 MSD using electrospray ionization (ESI) in positive mode unless otherwise indicated. Calculated (calcd.) mass corresponds to the exact mass.

Compound purification was made in some cases by acidic HPLC that entailed purification on a reverse phase HPLC system using different mobile phases that started initially with a mobile phase of 5% ACN in H₂O (both with 0.05% TFA) that was held for 1 min, then changed to a gradient of 5-99% ACN over 6 min, which was held at 99% ACN for 3 min, with a flow rate of 80 mL/min. Columns that were used include: Inertsil ODS-3 column (3 μm, 30×100 mm, T=45° C.), XBridge C18 OBD column (5 μm, 50×100 mm), and Phenomenex Luna C18 column (5 μm, 100×30 mm).

Nuclear magnetic resonance (NMR) spectra were obtained on Bruker model DRX spectrometers. The format of the 1H NMR data below is: chemical shift in ppm downfield of the tetramethylsilane reference (multiplicity, coupling constant J in Hz, integration).

Chemical names were generated by either using Chem-Draw (CambridgeSoft, Cambridge, Mass.) or ACD/Name Version 9 (Advanced Chemistry Development, Toronto, Ontario, Canada).

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Whenever a yield is given as a percentage, such yield refers to a mass of the entity for which the yield is given with respect to the maximum amount of the same entity that could be obtained under the particular stoichiometric conditions. Reagent concentrations that are given as percentages refer to mass ratios, unless indicated differently.

The following examples are provided to further illustrate aspects of the invention and various embodiments.

Intermediate 1: 2-propyl-4-(trifluoromethoxy)aniline

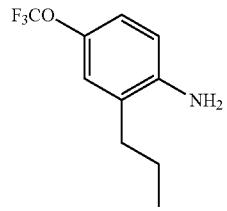

A solution of 2-bromo-4-(trifluoromethoxy)aniline (256 mg, 1.00 mmol), [(E)-prop-1-enyl]boronic acid (172 mg, 2.00 mmol), 1,1'-bis(diphenylphosphino)ferrocene-palladium(II)dichloride dichloromethane complex (29.0 mg, 0.0400 mmol), and $K_2CO_{3(aq)}$ (1M, 2 equiv) in MeOH (0.5 mL)/toluene (0.5 mL) was stirred at 125° C. for 4 h. The organic layer was separated, concentrated to dryness, and purified by FCC ($SiO_2$) to give (E)-2-(prop-1-en-1-yl)-4-(trifluoromethoxy)aniline. (E)-2-(Prop-1-en-1-yl)-4-(trifluoromethoxy)aniline and Pd/C (10% on carbon, 30 mg) in MeOH (10 mL) was stirred under $H_2$ (1 atm) for 3 h. After filtration on diatomaceous earth such as Celite®, the filtrate was collected and concentrated to dryness to give 2-propyl-4-(trifluoromethoxy)aniline. MS (ESI): mass calcd. for $C_{10}H_{12}F_3NO$, 219.1; m/z found, 220.1 $[M+H]^+$.

Intermediate 2: 2-Ethoxy-4-fluoro-1-nitrobenzene

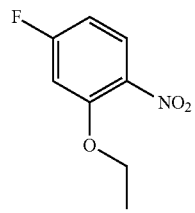

To a 100 mL round-bottomed flask were added a mixture of 5-fluoro-2-nitrophenol (3.14 g, 20.0 mmol), iodoethane (3.43 g, 22.0 mmol), $K_2CO_3$ (5.52 g, 40.0 mmol), and acetone (30.0 mL). The mixture was heated at reflux for 15 h, and then concentrated under vacuum to dryness. Water (30 mL) was added to the residue and the resulting mixture was extracted with EtOAc (3×20 mL). The combined organic phases were washed with saturated $NaCl_{(aq)}$ (30 mL), dried over anhydrous $Na_2SO_4$, and concentrated to dryness to give the title compound (3.7 g, 100%) as a yellow oil. $^1H$ NMR (300 MHz, $CDCl_3$): δ 7.92 (dd, J=9.0, 6.0 Hz, 1H), 6.80-6.65 (m, 2H), 4.17 (q, J=7.0 Hz, 2H), 1.51 (t, J=7.0 Hz, 3H).

Intermediate 3: 2-Ethoxy-4-fluorobenzenamine

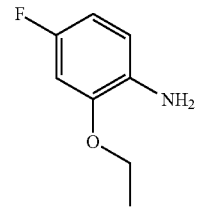

To a 250 mL round-bottomed flask were added 2-ethoxy-4-fluoro-1-nitrobenzene (3.70 g, 20.0 mmol) and 10% Pd/C (370 mg) in MeOH (80.0 mL). The mixture was stirred at rt for 3 h under a $H_2$ atmosphere. The mixture was filtered and the filtrate was concentrated to dryness to give the title product (2.8 g, crude, 90%) as a dark oil. MS (ESI): mass calcd. for $C_8H_{10}FNO$ 155.07, m/z found 156.2 $[M+H]^+$.

Intermediate 4: 4-Fluoro-1-nitro-2-(2,2,2-trifluoroethoxy)benzene

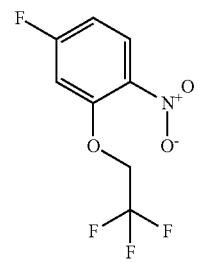

To a 100 mL round-bottomed flask were added 2,4-difluoro-1-nitrobenzene (1.6 g, 10 mmol), 2,2,2-trifluoroethanol (1.4 g, 14 mmol), and toluene (20 mL) and the mixture cooled to 0° C. The reaction was treated with NaH (60% in mineral oil, 0.48 g, 12 mmol) in four portions over 5 min and was stirred at 45° C. for 15 h. The mixture was cooled to rt, diluted with water (30 mL), and extracted with EtOAc (3×20 mL). The combined organic phases were washed with saturated aqueous NaCl, dried over anhydrous $Na_2SO_4$, filtered, and concentrated to dryness to give the title compound (1.2 g, 50%) as a red oil, which was used in the next reaction without any further purification. $^1H$ NMR (300 MHz, $CDCl_3$): δ 8.00 (dd, J=9.3 Hz, 6.0 Hz, 1H), 6.92-6.86 (m, 1H), 6.82 (dd, J=9.3 Hz, 2.4 Hz, 1H), 4.48 (q, J=7.8 Hz, 2H).

Intermediates 5, 6 and 10-16, whose characterization is provided in Table 2, were made in a manner analogous to the procedure described below for intermediate 17, substituting the appropriate reagents where necessary.

2-Cyclobutyl-4-(methylsulfonyl)aniline (Intermediate 17)

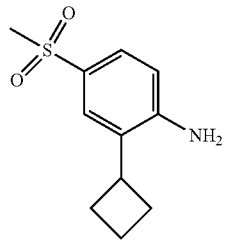

To a 500 mL round-bottomed flask were added 2-bromo-4-methanesulfonylaniline (10 g, 40 mmol) and 1,1'-bis(diphenylphosphino)ferrocene-palladium(II)dichloride dichloromethane complex (820 mg, 1.0 mmol) as solids. The round-bottomed flask was equipped with a 125 mL addition funnel and the system was evacuated, then backfilled with $N_2$ (3x). The addition funnel was removed briefly to add THF (80 mL, 0.50M, 40 mmol) and the round-bottomed flask was placed into an ice/water bath to cool with stirring to ~0° C. To the addition funnel was added cyclobutylzinc bromide (0.12 L, 0.50M, 60 mmol) via cannula transfer. After cooling the reaction for ~15 min, cyclobutylzinc bromide was added dropwise at a rate of ~20 mL/5 min. After the reaction began to turn to a dark brown color, the addition rate was increased to add the remainder of material over 5 min. The round-bottomed flask was removed from the cold bath, and placed into a preheated 60° C. heating block. The reaction was stirred under a blanket of $N_2$ at 60° C. for 30 minutes than cooled to room temperature. The reaction mixture was then poured onto saturated aqueous $NH_4Cl$ (200 mL) and EtOAc (200 mL). The aqueous layer was found to contain a small amount of insoluble solids, therefore water (100 mL) was added to afford two distinct layers. The aqueous layer was extracted further with EtOAc (100 mL). The combine organics were washed with brine (100 mL), dried over anhydrous $MgSO_4$, and concentrated to dryness. The residue was purified by FCC (330 g $SiO_2$, 5-50% EtOAc/hexane). Fractions were combined and concentrated to dryness to give the title compound (6.90 g, 75.8% yield) as an off-white powder. $^1H$ NMR (400 MHz, $CDCl_3$): δ 7.63-7.53 (m, 2H), 6.67 (d, J=8.2 Hz, 1H), 4.11 (s, 2H), 3.53-3.33 (m, 1H), 3.01 (s, 3H), 2.49-2.30 (m, 2H), 2.26-2.01 (m, 3H), 1.94-1.80 (m, 1H).

TABLE 2

| Intermediate # | Chemical name | Structure | MS data |
|---|---|---|---|
| 5 | 2-cyclobutyl-4-(trifluoromethoxy)aniline | 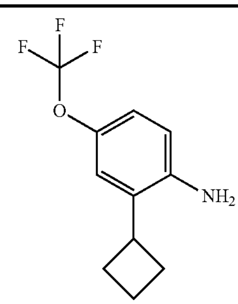 | MS (ESI): mass calcd. for $C_{11}H_{12}F_3NO$ 231.1, m/z found 232.1 $[M + H]^+$. |
| 6 | 2-isobutyl-4-(trifluoromethoxy)aniline | 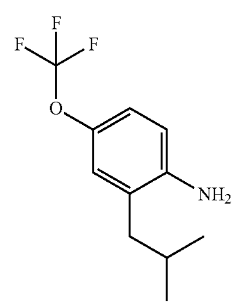 [SMILES: CC(C)Cc1cc(OC(F)(F)F)ccc1N] | MS (ESI): mass calcd. for $C_{11}H_{14}F_3NO$ 233.1, m/z found 234.1 $[M + H]^+$. |
| 10 | 2-cyclobutyl-4-((trifluoromethyl)sulfonyl)aniline | 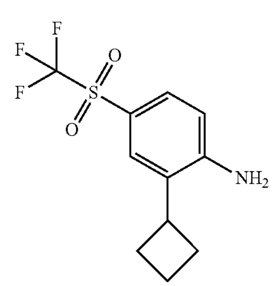 [SMILES: Nc1ccc(S(=O)(=O)C(F)(F)F)cc1C1CCC1] | MS (ESI): mass calcd. for $C_{11}H_{12}F_3NO_2S$ 279.1, m/z found 279.9 $[M + H]^+$. 1H NMR (500 MHz, CDCl3) d 7.70-7.61 (m, 2H), 6.78-6.64 (m, 1H), 4.40 (s, 2H), 3.53-3.25 (m, 1H), 2.51-2.34 (m, 2H), 2.30-2.03 (m, 3H), 1.99-1.85 (m, 1H). |

TABLE 2-continued

| Intermediate # | Chemical name | Structure | MS data |
| --- | --- | --- | --- |
| 11 | 2-cyclobutyl-4-(ethylsulfonyl)aniline | 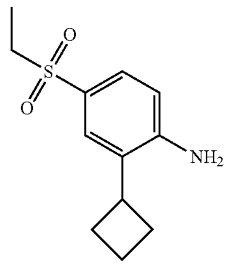 [SMILES: CCS(=O)(=O)c1ccc(N)c(C2CCC2)c1] | 1H NMR (400 MHz, Chloroform-d) d 7.59-7.47 (m, 2H), 6.74-6.61 (m, 1H), 4.10 (s, 2H), 3.52 -3.33 (m, 1H), 3.07 (q, J = 7.4 Hz, 2H), 2.46-2.31 (m, 2H), 2.27-2.00 (m, 3H), 1.96-1.81 (m, 1H), 1.26 (t, J = 7.4 Hz, 3H). |
| 12 | 2-cyclopropyl-4-(ethylsulfonyl)aniline | 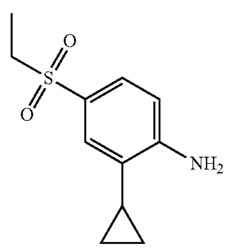 | 1H NMR (400 MHz, Chloroform-d) d 7.58-7.49 (m, 2H), 6.74-6.66 (m, 1H), 4.48 (s, 2H), 3.04 (q, J = 7.4 Hz, 2H), 1.70-1.59 (m, 1H), 1.25 (t, J = 7.4 Hz, 3H), 1.01-0.91 (m, 2H), 0.68-0.59 (m, 2H). |
| 13 | 2-cyclopropyl-4-(methylsulfonyl)aniline | 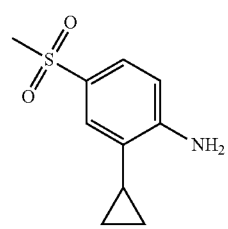 | 1H NMR (400 MHz, Chloroform-d) d 7.63-7.53 (m, 2H), 6.71 (d, J = 9.0 Hz, 1H), 4.49 (s, 2H), 2.99 (s, 3H), 1.69-1.61 (m, 1H), 1.00-0.92 (m, 2H), 0.70-0.59 (m, 2H). |
| 14 | 2-isobutyl-4-(methylsulfonyl)aniline | 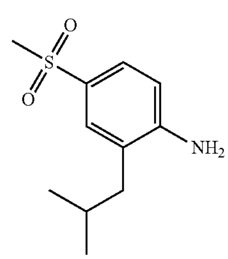 | 1H NMR (500 MHz, Chloroform-d) d 7.56-7.49 (m, 2H), 6.72 (d, J = 8.3 Hz, 1H), 4.35 (s, 2H), 3.00 (s, 3H), 2.38 (d, J = 7.2 Hz, 2H), 1.94 (dq, J = 13.5, 6.8 Hz, 1H), 0.94 (d, J = 6.6 Hz, 6H). MS (ESI): mass calcd. for $C_{11}H_{17}NO_2S$ 227.1, m/z found 228.1 [M + H]$^+$. |

TABLE 2-continued

| Intermediate # | Chemical name | Structure | MS data |
|---|---|---|---|
| 15 | 4-amino-3-cyclobutyl-N-methylbenzenesulfonamide | 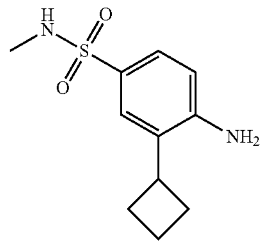 [SMILES: CNS(=O)(=O)c1ccc(N)c(C2CCC2)c1] | MS (ESI): mass calcd. for $C_{11}H_{16}N_2O_2S$ 240.1, m/z found 241.0 $[M + H]^+$. |
| 16 | 4-amino-3-propylbenzonitrile | 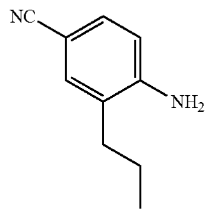 | 1H NMR (600 MHz, Chloroform-d) d 7.27 (dq, J = 3.9, 2.0 Hz, 2H), 6.64 (d, J = 8.8 Hz, 1H), 4.20-4.08 (m, 2H), 2.46-2.36 (m, 2H), 1.69-1.58 (m, 2H), 0.99 (t, J = 7.4 Hz, 3H). |

Intermediates 9 and 15, whose characterization is provided in Table 3, were made in a manner analogous to the procedure described below for intermediate 7, substituting the appropriate reagents where necessary.

2-ethyl-4-((trifluoromethyl)sulfonyl)aniline (Intermediate 7)

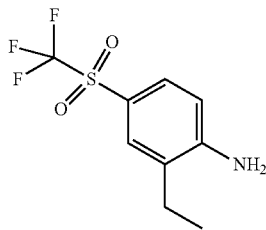 [SMILES: CCc1cc(S(=O)(=O)C(F)(F)F)ccc1N]

A 20 mL vial was charged 2-bromo-4-((trifluoromethyl)sulfonyl)aniline (505 mg, 1.66 mmol), 1,1'-bis(diphenylphosphino)ferrocene-palladium(ii)dichloride dichloromethane complex (100 mg, 0.122 mmol), $Cs_2CO_3$ (3.16 g, 9.70 mmol), and DMF (10 mL). The vial was capped and the resulting mixture was sparged with $N_2$ for 15 min. Triethylborane (1M in hexanes) (4.57 mL, 4.57 mmol) was then added via syringe to the vial and the contents again sparged with $N_2$ for 15 min. The vial was placed into a preheated 50° C. heating block. At 18 h, the contents were cooled to room temperature, filter cake was rinsed with ethyl acetate and the resulting filtrate was washed with water then brine. The organics were dried using $MgSO_4$ and then concentrated to dryness. Purification by FCC (40 g $SiO_2$, 30% EA/hexanes) afforded 331 mg of 2-ethyl-4-((trifluoromethyl)sulfonyl)aniline. 1H NMR (400 MHz, Chloroform-d) δ 7.72-7.59 (m, 2H), 6.81-6.63 (m, 1H), 4.46 (s, 2H), 2.53 (q, J=7.5 Hz, 2H), 1.30 (t, J=7.5 Hz, 3H).

TABLE 3

| Intermediate # | Chemical name | Structure | MS data |
|---|---|---|---|
| 9 | 2-ethyl-4-(methylsulfonyl)aniline | 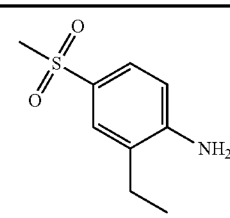 | MS (ESI): mass calcd. for $C_9H_{13}NO_2S$ 199.1, m/z found 200.1 $[M + H]^+$. |
| 15 | 4-((difluoromethyl)sulfonyl)-2-ethylaniline | 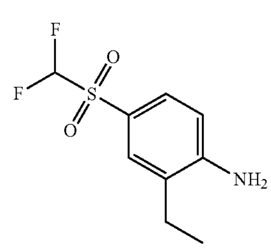 | MS (ESI): mass calcd. for $C_9H_{11}F_2NO_2S$ 235.1, m/z found 235.9 $[M + H]^+$. |

Example 1: (2-Ethoxy-4-fluorophenyl)-N⁴-isopropylpyrimidine-2,4-diamine

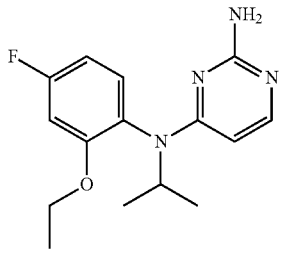 [SMILES: CCOc1cc(F)ccc1N(c1ccnc(N)n1)C(C)C]

Step A: 2-Ethoxy-4-fluoro-N-isopropylaniline

To a 100 mL round-bottomed flask were added 2-ethoxy-4-fluoroaniline (Intermediate 3, 1.0 g, 6.1 mmol), 2-methoxypropene (0.70 mL, 7.3 mmol) and 1,2-dichloroethane (20 mL). To the resulting solution was added acetic acid (0.35 mL, 6.1 mmol) and NaBH(OAc)$_3$ (2.7 g, 12 mmol). The mixture was stirred at rt for 16 h. The mixture was diluted with water (30 mL) and extracted with CH$_2$Cl$_2$ (30 mL). The organic layer was separated then dried over anhydrous Na$_2$SO$_4$, filtered, and concentrated under vacuum to dryness. The residue was purified by FCC to give the title compound (680 g, 56%) as a yellow oil. MS (ESI): mass calcd. for C$_{11}$H$_{16}$FNO 197.1, m/z found 198.1 [M+H]$^+$.

Step B: N⁴-(2-Ethoxy-4-fluorophenyl)-N⁴-isopropylpyrimidine-2,4-diamine

To a 10 mL microwave vial were added 2-ethoxy-4-fluoro-N-isopropylaniline (200 mg, 1.0 mmol), 4-chloropyrimidin-2-amine (260 mg, 2.0 mmol), 1,4-dioxane (0.66 mL) and water (0.33 mL). p-Toluenesulfonic acid monohydrate (190 mg, 1.0 mmol) was added to the mixture and the resulting mixture was heated at 150° C. using microwave heating for 90 min. Additional 4-chloropyrimidin-2-amine (130 mg, 1.0 mmol) was added and heated further using microwave heating at 150° C. for 30 min. After cooling to rt, the mixture was neutralized with a saturated aqueous NaHCO$_3$ solution and extracted with DCM (2×). The organic phase was dried over anhydrous Na$_2$SO$_4$, and concentrated under vacuum to dryness. The residue was purified by FCC (4 g SiO$_2$ column: 100% hexane for 5 min, then 0 to 100% EtOAc/hexane with 10 min gradient) to give the title compound (78 mg, 27%) as a yellow solid. MS (ESI): mass calcd. for C$_{15}$H$_{19}$FN$_4$O, 290.3; m/z found, 291.1 [M+H]$^+$. $^1$H NMR (500 MHz, CD$_3$OD): δ 7.58-7.46 (m, 1H), 7.15-7.10 (m, 1H), 6.93 (dd, J=10.8, 2.7 Hz, 1H), 6.81-6.74 (m, 1H), 5.39-5.00 (m, 2H), 4.08-3.96 (m, 2H), 1.28 (t, J=7.0 Hz, 3H), 1.20 (d, J=6.6 Hz, 3H), 1.05 (d, J=6.7 Hz, 3H).

Example 2: N⁴-((1H-Pyrazol-5-yl)methyl)-N⁴-(4-fluoro-2-methylphenyl)pyrimidine-2,4-diamine

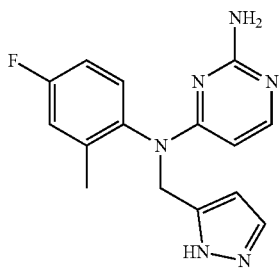 [SMILES: Cc1cc(F)ccc1N(Cc1ccn[nH]1)c1ccnc(N)n1]

The title compound was prepared using analogous conditions described in Example 1 and using 1H-pyrazole-5-carbaldehyde and 4-fluoro-2-methylbenzenamine in place of 2-methoxypropene and 2-ethoxy-4-fluoroaniline, respectively, in step A. MS (ESI): mass calcd. for C$_{15}$H$_{15}$FN$_6$ 298.1, m/z found 299.1 [M+H]$^+$. $^1$H NMR (400 MHz, DMSO-d$_6$): δ 8.39 (d, J=2.6 Hz, 1H), 8.32 (d, J=5.4 Hz, 1H), 7.00 (d, J=5.4 Hz, 1H), 6.89-6.84 (m, 3H), 6.81-6.75 (m, 1H), 6.52 (dd, J=8.8, 4.9 Hz, 1H), 6.47 (d, J=2.6 Hz, 1H), 5.41 (t, J=6.0 Hz, 1H), 4.34 (d, J=6.0 Hz, 2H), 2.15 (s, 3H).

Example 3: N⁴-(2-Ethoxy-4-fluorophenyl)-N⁴-(isoxazol-4-ylmethyl)pyrimidine-2,4-diamine

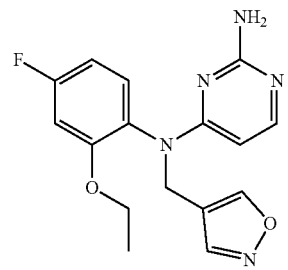 [SMILES: CCOc1cc(F)ccc1N(Cc1cnoc1)c1ccnc(N)n1]

The title compound was prepared using analogous conditions described in Example 1, using isoxazole-4-carbaldehyde in place of 2-methoxypropene in step A. MS (ESI): mass calcd. for C$_{16}$H$_{16}$FN$_5$O$_2$, 329.3; m/z found, m/z=330.1 [M+H]$^+$. $^1$H NMR (400 MHz, CDCl$_3$): δ 8.25 (d, J=4.6 Hz, 2H), 7.72 (d, J=6.0 Hz, 1H), 6.95 (dd, J=8.4, 6.3 Hz, 1H), 6.71-6.61 (m, 2H), 5.42 (d, J=6.0 Hz, 1H), 5.07-4.58 (m, 4H), 3.93 (q, J=7.0 Hz, 2H), 1.24 (t, J=7.0 Hz, 3H).

Example 4: N⁴-Benzyl-N⁴-(2-ethoxy-4-fluorophenyl)pyrimidine-2,4-diamine

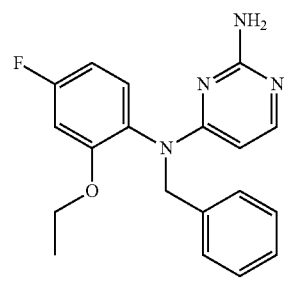 [SMILES: CCOc1cc(F)ccc1N(Cc1ccccc1)c1ccnc(N)n1]

The title compound was prepared using analogous conditions described in Example 1 using benzaldehyde in place of 2-methoxypropene in Step A. MS (ESI): mass calcd. for C$_{19}$H$_{19}$FN$_4$O, 338.4; m/z found, 339.1 [M+H]$^+$. $^1$H NMR (500 MHz, CD$_3$OD): δ 7.56 (d, J=7.4 Hz, 1H), 7.28-7.19 (m, 5H), 7.03 (dd, J=8.7, 6.1 Hz, 1H), 6.92 (dd, J=10.7, 2.7 Hz, 1H), 6.73-6.67 (m 1H), 5.67 (d, J=7.4 Hz, 1H), 5.34 (d, J=14.4 Hz, 1H), 4.99 (d, J=14.3 Hz, 1H), 4.04-3.96 (m, 1H), 3.91-3.83 (m, 1H), 1.21 (t, J=7.0 Hz, 3H).

Example 5: N⁴-(Oxazol-4-ylmethyl)-N⁴-(2-propyl-4-(trifluoromethoxy)phenyl)pyrimidine-2,4-diamine

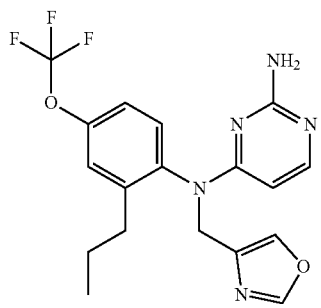 [SMILES: CCCc1cc(OC(F)(F)F)ccc1N(Cc1cocn1)c1ccnc(N)n1]

The title compound was prepared using analogous conditions described in Example 1, using 2-propyl-4-(trifluoromethoxy)aniline (Intermediate 1) and oxazole-4-carbaldehyde in place of 2-ethoxy-4-fluoroaniline and 2-methoxypropene, respectively, in step A. MS (ESI): mass calcd. for $C_{18}H_{18}F_3N_5O_2$, 393.4; m/z found, 394.1 [M+H]⁺. ¹H NMR (500 MHz, CD₃OD): δ 8.11 (s, 1H), 7.92 (s, 1H), 7.63 (d, J=6.0 Hz, 1H), 7.28 (d, J=2.5 Hz, 1H), 7.25-7.01 (m, 2H), 5.36-5.22 (m, 2H), 4.64-4.51 (m, 1H), 2.55-2.25 (m, 2H), 1.70-1.38 (m, 2H), 0.88 (t, J=7.3 Hz, 3H).

Example 6: N⁴-(2-Cyclobutyl-4-(trifluoromethoxy)phenyl)-N⁴-(oxazol-4-ylmethyl)pyrimidine-2,4-diamine

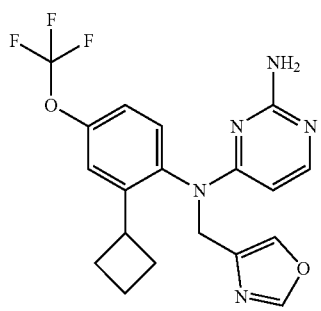 [SMILES: Nc1nccc(N(Cc2cocn2)c2ccc(OC(F)(F)F)cc2C2CCC2)n1]

The title compound was prepared using analogous conditions described in Example 1 using 2-cyclobutyl-4-(trifluoromethoxy)aniline (Intermediate 5) in place of 2-ethoxy-4-fluoroaniline and oxazole-4-carbaldehyde in place of 2-methoxypropene in Step A. MS (ESI): mass calcd. for $C_{19}H_{18}F_3N_5O_2$, 405.4; m/z found, 406.1 [M+H]⁺. ¹H NMR (600 MHz, CD₃OD): δ 8.11 (s, 1H), 7.91 (s, 1H), 7.63 (d, J=6.3 Hz, 1H), 7.45-7.32 (m, 1H), 7.26-7.10 (m, 2H), 5.51-5.05 (m, 2H), 4.53 (d, J=15.3 Hz, 1H), 3.55-3.40 (m, 1H), 2.30-1.68 (m, 6H).

Example 7: N⁴-(2-Methyl-4-(trifluoromethoxy)phenyl)-N⁴-(oxazol-4-ylmethyl)pyrimidine-2,4-diamine

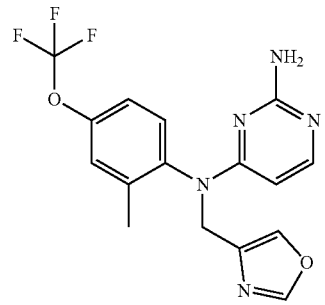 [SMILES: Cc1cc(OC(F)(F)F)ccc1N(Cc1cocn1)c1ccnc(N)n1]

The title compound was prepared using analogous conditions described in Example 1 using 2-methyl-4-(trifluoromethoxy)aniline and oxazole-4-carbaldehyde in place of 2-ethoxy-4-fluoroaniline and 2-methoxypropene in Step A, respectively. MS (ESI): mass calcd. for $C_{16}H_{14}F_3N_5O_2$, 365.3; m/z found, 366.1 [M+H]⁺. ¹H NMR (500 MHz, CD₃OD): δ 8.19-8.06 (m, 1H), 7.93 (s, 1H), 7.66 (d, J=5.9 Hz, 1H), 7.32-7.12 (m, 3H), 5.56-5.08 (m, 2H), 4.73 (d, J=15.2 Hz, 1H), 2.10 (s, 3H).

Example 8: N⁴-(2-Isobutyl-4-(trifluoromethoxy)phenyl)-N⁴-(oxazol-4-ylmethyl)pyrimidine-2,4-diamine

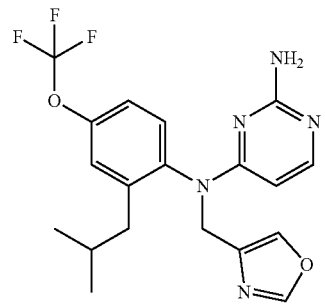 [SMILES: CC(C)Cc1cc(OC(F)(F)F)ccc1N(Cc1cocn1)c1ccnc(N)n1]

The title compound was prepared using analogous conditions described in Example 1 using 2-isobutyl-4-(trifluoromethoxy)aniline and oxazole-4-carbaldehyde in place of 2-ethoxy-4-fluoroaniline and 2-methoxypropene, respectively in Step A. MS (ESI): mass calcd. for $C_{19}H_{20}F_3N_5O_2$, 407.4; m/z found, 408.1 [M+H]⁺. ¹H NMR (500 MHz, CD₃OD): δ 8.12 (d, J=0.7 Hz, 1H), 7.95 (s, 1H), 7.70-7.56 (m, 1H), 7.29 (s, 1H), 7.25-7.11 (m, 2H), 5.56-5.12 (m, 2H), 4.43 (d, J=15.2 Hz, 1H), 2.51-2.22 (m, 2H), 1.90 (m, 1H), 0.86 (d, J=6.6, 6H).

Example 9: 2-(4-((2-Aminopyrimidin-4-yl)(oxazol-4-ylmethyl)amino)-3-ethylphenyl)-1,1,1,3,3,3-hexafluoropropan-2-ol

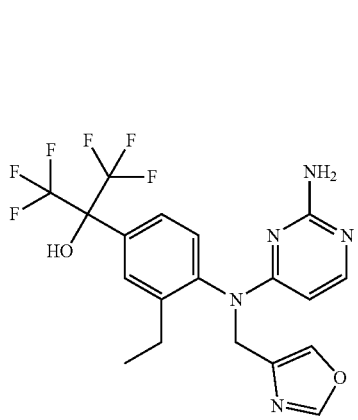 [SMILES: CCc1cc(C(O)(C(F)(F)F)C(F)(F)F)ccc1N(Cc1cocn1)c1ccnc(N)n1]

The title compound was prepared using analogous conditions described in Example 1 using 2-(4-amino-3-ethylphenyl)-1,1,1,3,3,3-hexafluoropropan-2-ol and oxazole-4-carbaldehyde in place of 2-ethoxy-4-fluoroaniline and 2-methoxypropene, respectively. MS (ESI): mass calcd. for $C_{19}H_{17}F_6N_5O_2$, 461.4; m/z found, 462.1 $[M+H]^+$. $^1H$ NMR (500 MHz, CDCl$_3$): δ 7.84-7.44 (m, 4H), 6.97 (d, J=8.4 Hz, 1H), 6.80-6.49 (m, 1H), 5.46-5.14 (m, 1H), 5.01-4.70 (m, 3H), 4.43 (d, J=15.2 Hz, 1H), 2.45-2.14 (m, 2H), 1.04-0.80 (m, 3H).

Example 10: $N^4$-(2-Ethoxy-4-fluorophenyl)-$N^4$-(oxazol-2-ylmethyl)pyrimidine-2,4-diamine

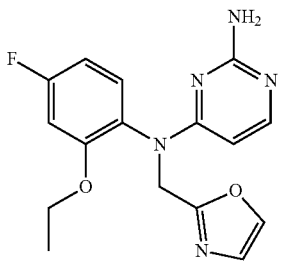 [SMILES: CCOc1cc(F)ccc1N(Cc1ncco1)c1ccnc(N)n1]

The title compound was prepared using analogous conditions described in Example 1 using oxazole-2-carbaldehyde in place of 2-methoxypropene in step A. MS (ESI): mass calcd. for $C_{16}H_{16}FN_5O_2$, 329.1; m/z found, 330.1 $[M+H]^+$. $^1H$ NMR (400 MHz, CDCl$_3$): δ 7.74 (d, J=6.0 Hz, 1H), 7.57 (s, 1H), 7.17 (dd, J=8.6, 6.3 Hz, 1H), 7.02 (s, 1H), 6.69 (dd, J=10.4, 2.7 Hz, 1H), 6.66-6.59 (m, 1H), 5.80-5.60 (m, 1H), 5.51 (d, J=5.4 Hz, 1H), 4.8 (br s, 2H), 4.66-4.52 (m, 1H), 3.99 (q, J=7.0 Hz, 2H), 1.31 (t, J=7.0 Hz, 3H).

Example 11: $N^4$-((1H-Pyrazol-3-yl)methyl)-$N^4$-(2-ethoxy-4-fluorophenyl)pyrimidine-2,4-diamine

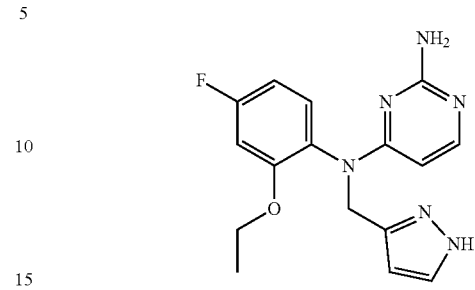

Step A: N-((1H-Pyrazol-3-yl)methyl)-2-ethoxy-4-fluorobenzenamine

The title compound was prepared using analogous conditions described in Example 1, Step A, using 1H-pyrazole-3-carbaldehyde in place of 2-methoxypropene to give the title compound as a yellow oil. MS (ESI): mass calcd. for $C_{12}H_{14}FN_3O$, 235.11, m/z found 236.2 $[M+H]^+$.

Step B: $N^4$-((1H-Pyrazol-3-yl)methyl)-$N^4$-(2-ethoxy-4-fluorophenyl)pyrimidine-2,4-diamine The title compound was prepared using analogous conditions described in Example 1, Step B using N-((1H-pyrazol-3-yl)methyl)-2-ethoxy-4-fluorobenzenamine in place of 2-ethoxy-4-fluoro-N-isopropylaniline in step B, to give the title compound as a yellow solid. MS (ESI): mass calcd. for $C_{16}H_{17}FN_6O$, 328.14, m/z found 329.1 $[M+H]^+$. $^1H$ NMR (400 MHz, CDCl$_3$): δ 10.98 (br s, 1H), 7.68 (d, J=6.2 Hz, 1H), 7.45 (d, J=1.7 Hz, 1H), 6.94 (dd, J=8.6, 6.2 Hz, 1H), 6.69 (dd, J=10.4, 2.7 Hz, 1H), 6.66-6.59 (m, 1H), 6.06 (s, 1H), 5.52-5.05 (m, 4H), 4.72 (s, 1H), 3.95 (q, J=6.9 Hz, 2H), 1.27 (t, J=7.0 Hz, 3H).

Example 12: $N^4$-(2-Ethoxy-4-fluorophenyl)-$N^4$-(oxazol-4-ylmethyl)pyrimidine-2,4-diamine

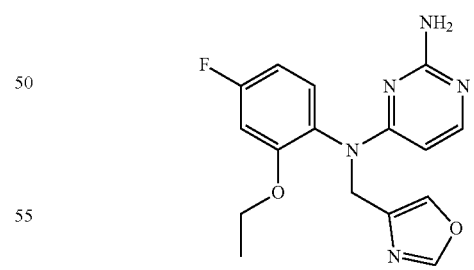

The title compound was prepared using analogous conditions described in Example 1 using oxazole-4-carbaldehyde in place of 1H-pyrazole-3-carbaldehyde. MS (ESI): mass calcd. for $C_{16}H_{16}FN_5O_2$, 329.1; m/z found, m/z=330.1 $[M+H]^+$. $^1H$ NMR (400 MHz, CDCl$_3$): δ 7.80 (s, 1H), 7.73 (d, J=6.1 Hz, 1H), 7.60 (s, 1H), 7.08 (dd, J=8.6, 6.3 Hz, 1H), 6.71 (dd, J=10.4, 2.6 Hz, 1H), 6.68-6.61 (m, 1H), 5.57-5.28 (m, 2H), 4.84 (br s, 2H), 4.66-4.46 (m, 1H), 4.01 (q, J=6.9 Hz, 2H), 1.31 (t, J=7.0 Hz, 3H).

Example 13: N⁴-((4-Chloro-1H-pyrazol-3-yl)methyl)-N⁴-(2-ethoxy-4-fluorophenyl)pyrimidine-2,4-diamine

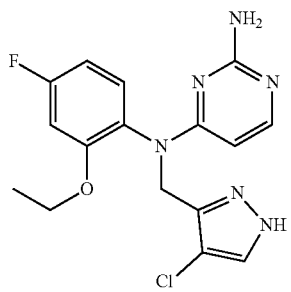 [SMILES: CCOc1cc(F)ccc1N(Cc1n[nH]cc1Cl)c1ccnc(N)n1]

The title compound was prepared using analogous conditions described in Example 11 using 4-chloro-1H-pyrazole-3-carbaldehyde in place of 2-methoxypropene in step A and using concentrated $H_2SO_4$ in place of p-toluenesulfonic acid monohydrate in step B to give the title compound. MS (ESI): mass calcd. for $C_{16}H_{16}ClFN_6O$, 362.1; m/z found, 363.0 [M+H]⁺. ¹H NMR (400 MHz, CDCl₃): δ 11.28 (br s, 1H), 7.72 (d, J=6.1 Hz, 1H), 7.41 (s, 1H), 7.01 (dd, J=8.5, 6.2 Hz, 1H), 6.72-6.63 (m, 2H), 5.48 (d, J=6.1 Hz, 1H), 5.14 (br s, 2H), 5.02-4.80 (m, 2H), 3.95 (q, J=7.0 Hz, 2H), 1.24 (t, J=7.0 Hz, 3H).

Example 14: N⁴-(2-Ethoxy-4-fluorophenyl)-N⁴-(isoxazol-3-ylmethyl)pyrimidine-2,4-diamine

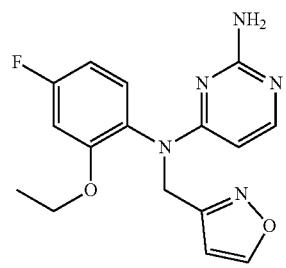 [SMILES: CCOc1cc(F)ccc1N(Cc1ccon1)c1ccnc(N)n1]

The title compound was prepared using analogous conditions described in Example 11 using isoxazole-3-carbaldehyde in place of 2-methoxypropene in step A and using concentrated $H_2SO_4$ in place of p-toluenesulfonic acid monohydrate in step B to give the title compound. MS (ESI): mass calcd. for $C_{16}H_{16}FN_5O_2$, 329.1; m/z found, 330.1 [M+H]⁺. ¹H NMR (400 MHz, CDCl₃): δ 8.30 (d, J=1.1 Hz, 1H), 7.74 (d, J=6.0 Hz, 1H), 6.98 (dd, J=8.6, 6.3 Hz, 1H), 6.68 (dd, J=10.4, 2.6 Hz, 1H), 6.64-6.58 (m, 1H), 6.44 (d, J=1.4 Hz, 1H), 5.52-5.36 (m, 2H), 4.90-4.75 (m, 3H), 3.96 (q, J=7.0 Hz, 2H), 1.28 (t, J=7.0 Hz, 3H).

Example 15: N⁴-(2-Ethoxy-4-fluorophenyl)-N⁴-(thiazol-5-ylmethyl)pyrimidine-2,4-diamine

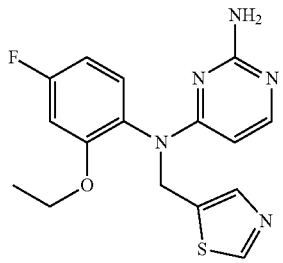 [SMILES: CCOc1cc(F)ccc1N(Cc1cncs1)c1ccnc(N)n1]

The title compound was prepared using analogous conditions described in Example 11 using thiazole-5-carbaldehyde in place of 2-methoxypropene in step A and using concentrated $H_2SO_4$ in place of p-toluenesulfonic acid monohydrate in Step B to give the title compound. MS (ESI): mass calcd. for $C_{16}H_{16}FN_5OS$, 345.1; m/z found, 346.1 [M+H]⁺. ¹H NMR (400 MHz, CD₃OD): δ 8.89 (s, 1H), 7.66-7.61 (m, 2H), 7.04 (dd, J=8.6, 6.3 Hz, 1H), 6.91 (dd, J=10.7, 2.7 Hz, 1H), 6.75-6.69 (m, 1H), 5.50-5.29 (m, 2H), 5.08 (d, J=14.7 Hz, 1H), 4.00-3.91 (m, 2H), 1.19 (t, J=7.0 Hz, 3H).

Example 16: N⁴-(2-Ethoxy-4-fluorophenyl)-N⁴-(oxazol-5-ylmethyl)pyrimidine-2,4-diamine

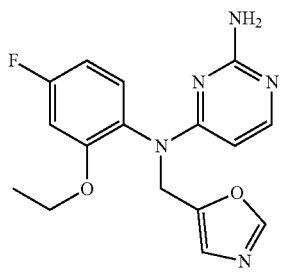 [SMILES: CCOc1cc(F)ccc1N(Cc1cnco1)c1ccnc(N)n1]

The title compound was prepared using analogous conditions described in Example 1 using oxazole-5-carbaldehyde in place of 2-methoxypropene in step A and using concentrated $H_2SO_4$ in place of p-toluenesulfonic acid monohydrate in Step B to give the title compound. MS (ESI): mass calcd. for $C_{16}H_{16}FN_5OS$, 329.1; m/z found, 330.1 [M+H]⁺. ¹H NMR (400 MHz, CDCl₃): 7.75 (s, 1H), 7.72 (d, J=6.1 Hz, 1H), 6.97 (dd, J=8.5, 6.3 Hz, 1H), 6.90 (s, 1H), 6.69 (dd, J=10.4, 2.6 Hz, 1H), 6.66-6.59 (m, 1H), 5.52-5.40 (m, 2H), 4.88 (br s, 2H), 4.76-4.60 (m, 1H), 3.97 (q, J=7.0 Hz, 2H), 1.28 (t, J=7.0 Hz, 3H)

Example 17: N⁴-(2-Ethoxy-4-fluorophenyl)-N⁴-(thiazol-4-ylmethyl)pyrimidine-2,4-diamine

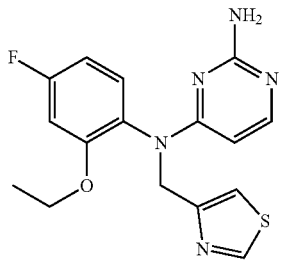 [SMILES: CCOc1cc(F)ccc1N(Cc1cscn1)c1ccnc(N)n1]

The title compound was prepared using analogous conditions described in Example 1 using thiazole-4-carbaldehyde in place of 2-methoxypropene in step A and using concentrated $H_2SO_{04}$ in place of p-toluenesulfonic acid monohydrate in Step B to give the title compound. MS (ESI): mass calcd. for $C_{16}H_{16}FN_5OS$, 345.1; m/z found, 346.1 [M+H]⁺. ¹H NMR (400 MHz, CDCl₃): 8.71 (d, J=1.9 Hz, 1H), 7.72 (d, J=6.0 Hz, 1H), 7.25 (d, J=1.6 Hz, 1H), 7.02 (dd, J=8.6, 6.4 Hz, 1H), 6.68 (dd, J=10.5, 2.7 Hz, 1H), 6.63-6.57 (m, 1H), 5.67-5.43 (m, 2H), 4.92-4.76 (m, 3H), 3.98 (q, J=7.0 Hz, 2H), 1.29 (t, J=7.0 Hz, 3H).

Example 18: N⁴-((1H-Pyrazol-3-yl)methyl)-N⁴-(4-fluoro-2-(2,2,2-trifluoroethoxy)phenyl)pyrimidine-2,4-diamine

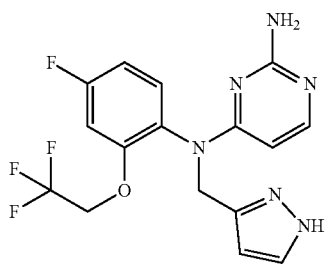 [SMILES: Nc1nccc(N(Cc2cc[nH]n2)c2ccc(F)cc2OCC(F)(F)F)n1]

The title compound was prepared using analogous conditions described in Example 1 using N-((1H-pyrazol-3-yl)methyl)-4-fluoro-2-(2,2,2-trifluoroethoxy)aniline derived from 4-fluoro-1-nitro-2-(2,2,2-trifluoroethoxy)benzene (Intermediate 4) in place of 2-ethoxy-4-fluoronitrobenzene in step B and using concentrated $H_2SO_4$ in place of p-toluenesulfonic acid monohydrate in Step B to give the title compound. MS (ESI): mass calcd. for $C_{16}H_{14}F_4N_6O$ 382.12, m/z found 383.1 [M+H]⁺. ¹H NMR (400 MHz, CDCl₃): δ 11.00 (br s, 1H), 7.74 (d, J=6.1 Hz, 1H), 7.45 (d, J=1.8 Hz, 1H), 6.99 (dd, J=8.4, 6.2 Hz, 1H), 6.79-6.70 (m, 2H), 6.08 (s, 1H), 5.50-5.23 (m, 2H), 5.09 (s, 2H), 4.65-4.45 (m, 1H), 4.25 (q, J=7.9 Hz, 2H).

Example 19: N⁴-(2-Methyl-4-(pentafluorosulfanyl)phenyl)-N⁴-(oxazol-4-ylmethyl)pyrimidine-2,4-diamine

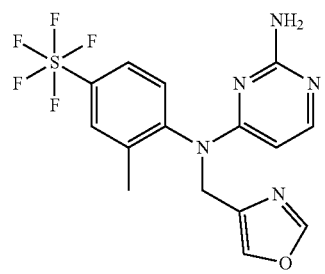 [SMILES: Cc1cc(S(F)(F)(F)(F)F)ccc1N(Cc1cocn1)c1ccnc(N)n1]

Step A: 2-Bromo-4-(pentafluorosulfanyl)aniline

To a 500 mL round-bottomed flask were added 4-aminophenylsulfur pentafluoride (4.4 g, 20 mmol) and dichloromethane (120 mL). The solution was cooled to 0° C., then 1,3-dibromo-5,5-dimethylhydantoin (2.8 g, 9.8 mmol) was added. The mixture was stirred at 0° C. for 1 h, then warmed to rt and stirred for 1 h. The mixture was filtered through a pad of diatomaceous earth such as Celite®. The filtrate was concentrated to dryness and the residue was purified by FCC to give the title compound (5.8 g, 97% yield) as yellow oil. MS (ESI): mass calcd. for $C_6H_5BrF_5NS$, 296.92, m/z found 297.9 [M+H]⁺.

Step B: 2-Methyl-4-(pentafluorosulfanyl)benzenamine

To a 1 L round-bottomed flask were added 2-bromo-4-(pentafluorosulfanyl)aniline (13.4 g, 44.9 mmol), 2,4,6-trimethyl-1,3,5,2,4,6-trioxatriborinane (6.80 g, 53.9 mmol), $Cs_2CO_3$ (29.2 g, 89.8 mmol), Pd(dppf)Cl₂ (3.30 g, 4.50 mmol), $H_2O$ (50.0 mL), and toluene (200 mL). The mixture was degassed and refilled with Ar. The reaction mixture was heated at 95° C. for 15 h, and then allowed to cool to rt. The reaction was extracted with EtOAc (2×250 mL) and the combined organic layers were washed with saturated aqueous NaCl solution (250 mL), dried over anhydrous $Na_2SO_4$, concentrated to dryness, and purified by FCC to give the title compound (6.5 g, 62% yield) as yellow oil. MS (ESI): mass calcd. for $C_7H_8F_5NS$, 233.03, m/z found 234.0 [M+H]⁺.

Step C: N-(2-Methyl-4-(pentafluorosulfanyl)phenyl)-2-(methylthio)pyrimidin-4-amine To a 500 mL round-bottomed flask were added 2-methyl-4-(pentafluorosulfanyl)benzenamine (4.6 g, 20 mmol), 4-chloro-2-(methylthio)pyrimidine (4.8 g, 30 mmol), i-PrOH (45 mL), and concentrated HCl (3.0 mL). The mixture was stirred at 85° C. for 15 h. The mixture was cooled and concentrated to dryness. The residue was dissolved in dichloromethane (500 mL) and washed with saturated NaHCO₃ aqueous solution (100 mL), saturated NaCl aqueous solution (100 mL), dried over anhydrous $Na_2SO_4$, filtered, and concentrated to dryness. The residue was purified by FCC to give the title compound (5.8 g, 54% yield) as yellow oil. MS (ESI): mass calcd. for $C_{12}H_{12}F_5N_3S_2$ 357.04, m/z found 358.0 [M+H]⁺.

Step D: N-(2-Methyl-4-(pentafluorosulfanyl)phenyl)-2-(methylthio)-N-(oxazol-4-ylmethyl)pyrimidin-4-amine To a 100 mL round-bottomed flask were added N-(2-methyl-4-(pentafluorosulfanyl)phenyl)-2-(methylthio)pyrimidin-4-amine (1.43 g, 4.00 mmol) and DMF (25.0 mL). The solution was cooled to 0° C., then NaH (60% in mineral oil, 480 mg, 12.0 mmol) was added. The mixture was stirred at 0° C. for 0.5 h, then 4-(bromomethyl)oxazole (HBr salt, 1.45 g, 6.0 mmol) was added to the reaction mixture and stirred at rt for 15 h. The mixture was diluted with brine (60 mL) and extracted with EtOAc (2×200 mL). The organic layers were combined, washed with saturated NaCl (100 mL), filtered, and concentrated to dryness. The residue was purified by FCC to give the title compound (1.45 g, 83% yield) as colorless oil. MS (ESI): mass calcd. for $C_{16}H_{15}F_5N_4OS_2$, 438.06, m/z found 439.0 [M+H]$^+$.

Step E: N-(2-Methyl-4-(pentafluorosulfanyl)phenyl)-2-(methylsulfonyl)-N-(oxazol-4-ylmethyl)pyrimidin-4-amine To a 1 L round-bottomed flask were added N-(2-methyl-4-(pentafluorosulfanyl)phenyl)-2-(methylthio)-N-(oxazol-4-ylmethyl)pyrimidin-4-amine (1.45 g, 3.31 mmol), dichloromethane (100 mL), and m-CPBA (85%, 1.95 g, 9.91 mmol), in sequence at 0° C. The reaction mixture was stirred at 0° C. for 3 h. The mixture was diluted with dichloromethane (300 mL), washed with saturated aqueous NaHCO$_3$ solution (80.0 mL), saturated aqueous NaCl solution (80.0 mL), and concentrated to dryness. The residue was purified by FCC to give the title compound (1.25 g, 81.0% yield) as a yellow solid. MS (ESI): mass calcd. for $C_{16}H_{15}F_5N_4O_3S_2$, 470.05, m/z found 470.9 [M+H]$^+$.

Step F: N$^4$-(2-Methyl-4-(pentafluorosulfanyl)phenyl)-N$^4$-(oxazol-4-ylmethyl)pyrimidine-2,4-diamine To a 100 mL sealed vessel were added N-(2-methyl-4-(pentafluorosulfanyl)phenyl)-2-(methylsulfonyl)-N-(oxazol-4-ylmethyl)pyrimidin-4-amine (1.25 g, 2.65 mmol), NH$_4$OH (25 wt %, 6.00 mL), and i-PrOH (4.00 mL). The mixture was stirred at 100° C. for 4 h. The mixture was cooled to rt and concentrated to dryness and the residue was purified by FCC to give the title compound as a white solid (582 mg, 52.3%). MS (ESI): mass calcd. for $C_{15}H_{14}F_5N_5OS$, 407.08, m/z found 408.0 [M+H]$^+$. $^1$H NMR (400 MHz, CD$_3$OD) δ 8.13 (s, 1H), 7.96 (s, 1H), 7.84 (d, J=2.2 Hz, 1H), 7.75 (dd, J=8.7, 2.5 Hz, 1H), 7.70 (d, J=5.9 Hz, 1H), 7.38 (d, J=8.7 Hz, 1H), 5.54-5.30 (m, 1H), 5.28-5.10 (m, 1H), 4.85-4.70 (m, 1H), 2.17 (s, 3H).

Example 20: N$^4$-(4-Bromo-2-(trifluoromethyl)phenyl)-N$^4$-isopropylpyrimidine-2,4-diamine

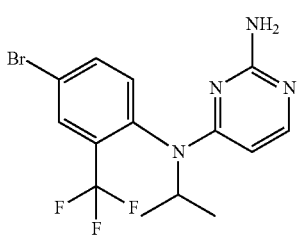 [SMILES: CC(C)N(c1ccnc(N)n1)c1ccc(Br)cc1C(F)(F)F]

The title compound was prepared using analogous conditions described in Example 19, Steps C-F starting with 2-amino-5-bromobenzotrifluoride in place of 2-methyl-4-(pentafluorosulfanyl)benzenamine in step C and 2-iodopropane in place of 4-(bromomethyl)oxazole hydrobromide in step D. MS (ESI): mass calcd. for $C_{14}H_{14}BrF_3N_4$, 375.19; m/z found, 374.8 [M+H]$^+$. $^1$H NMR (500 MHz, CDCl$_3$): δ 7.91 (d, J=2.3 Hz, 1H), 7.76 (dd, J=8.4, 2.3 Hz, 1H), 7.71 (d, J=6.1 Hz, 1H), 7.11 (d, J=8.4 Hz, 1H), 5.22 (d, J=6.1 Hz, 1H), 4.86 (s, 2H), 4.75 (hept, J=6.7 Hz, 1H), 1.33 (d, J=6.5 Hz, 3H), 1.06 (d, J=6.9 Hz, 3H).

Example 21: N$^4$-(2-Cyclobutyl-4-(methylsulfonyl)phenyl)-N$^4$-ethylpyrimidine-2,4-diamine

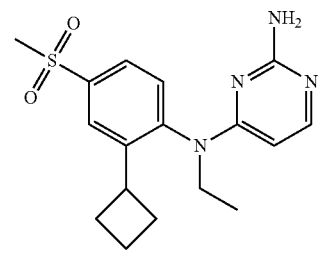 [SMILES: CCN(c1ccnc(N)n1)c1ccc(S(C)(=O)=O)cc1C1CCC1]

Step A: N-(2-Cyclobutyl-4-(methylsulfonyl)phenyl)-2-(methylthio)pyrimidin-4-amine To a 1 L round-bottomed flask were added 4-chloro-2-(methylthio)pyrimidine (30.2 g, 188 mmol), 2-cyclobutyl-4-(methylsulfonyl)aniline (Intermediate 17, 26.4 g, 117 mmol) and i-PrOH (300 mL) under nitrogen, followed by the addition of pTsOH.H$_2$O (1.20 g, 6.31 mmol). The contents were warmed gradually to 70° C. over 40 min and allowed to react at 70° C. for approximately 22 hours, then stirred at room temperature overnight. The reaction was cooled to 0° C. and saturated aqueous sodium bicarbonate (200 mL) and deionized water (400 mL) were added and stirred for approximately 30 minutes. The precipitate was collected via vacuum filtration and rinsed with deionized water (~150 mL) and dried under reduced pressure to yield the title compound (40.5 g, 99.0% yield). MS (ESI): mass calcd. for $C_{16}H_{19}N_3O_2S_2$, 349.48, m/z found 349.9 [M+H]$^+$.

Step B: N-(2-Cyclobutyl-4-(methylsulfonyl)phenyl)-N-ethyl-2-(methylthio)pyrimidin-4-amine Step B: To a 2 L, 3-neck round-bottomed flask containing a stir bar, condenser, and septa with N$_2$ inlet were added N-(2-cyclobutyl-4-(methylsulfonyl)phenyl)-2-(methylthio) pyrimidin-4-amine (68.1 g, 195 mmol), ACN (1.00 L), Cs$_2$CO$_3$ (159 g, 487 mmol) and 1-iodoethane (24.0 mL, 295 mmol) under a nitrogen atmosphere and was immersed in an oil bath 70° C. for one hour, then cooled to room temperature. The reaction mixture was diluted with deionized water (300 mL) and ethyl acetate (300 mL), the layers were separated and the aqueous layer extracted twice with ethyl acetate. The combined organics were dried over anhydrous magnesium sulfate, filtered, and concentrated to dryness. The crude product was filtered prior to purification by FCC (silica gel, 30-40% hexanes/ethyl acetate) to yield the title compound (57.2 g, 77.8% yield). MS (ESI): mass calcd. for $C_{18}H_{23}N_3O_2S_2$, 377.53, m/z found 377.9 [M+H]$^+$. $^1$H NMR (400 MHz, CD$_3$OD): δ 8.10 (d, J=2.2 Hz, 1H), 7.92-7.83 (m, 2H), 7.29 (d, J=8.2 Hz, 1H), 5.48 (s, 1H), 4.30 (s, 1H), 3.57-3.44 (m, 2H), 3.14 (s, 3H), 2.54 (s, 3H), 2.33-2.24 (m, 1H), 2.25-2.11 (m, 2H), 2.11-2.03 (m, 1H), 2.03-1.92 (m, 1H), 1.90-1.79 (m, 1H), 1.23 (t, J=7.0 Hz, 3H).

Step C: N-(2-Cyclobutyl-4-(methylsulfonyl)phenyl)-N-ethyl-2-(methylsulfonyl)pyrimidin-4-amine To a 1 L round-bottomed flask were added N-(2-cyclobutyl-4-(methylsulfonyl)phenyl)-N-ethyl-2-(methylthio)pyrimidin-4-amine (28.3 g, 74.8 mmol) followed by DCM (600 mL). The reaction mixture was cooled to 0° C. then treated with m-CPBA (43.4 g, 176 mmol) in small portions over 0.5 h. The reaction mixture was removed from the ice bath and the reaction was stirred an additional 45 min. The reaction mixture was poured onto a stirred solution of 0.5M Na$_2$S$_2$O$_3$ (500 mL) then treated with saturated aqueous sodium bicarbonate (500 mL). DCM (250 mL) was added, the mixture was extracted, and the organic layer was separated. The aqueous layer was extracted again with DCM (400 mL). The combined organic layers were dried over anhydrous MgSO$_4$ and concentrated to dryness to give a yellow oil/foam. The residue was dissolved in isopropanol (100 mL) and water (100 mL). The resulting emulsion was stirred vigorously at rt. After about 20 minutes, a solid began to form. The mixture was stirred for an additional 15 minutes, filtered, dried under reduced pressure for 16 h, and then dried for an additional 2 h under high vacuum while being heated at 60° C. to give the title compound (21.8 g, 71.1% yield) as an off-white solid. MS (ESI): mass calcd. for $C_{18}H_{23}N_3O_4S_2$, 409.52; m/z found, 410.1 [M+H]$^+$. $^1$H NMR (500 MHz, CDCl$_3$): δ 8.17 (s, 1H), 8.12 (d, J=6.2 Hz, 1H), 7.92 (dd, J=8.4, 2.2 Hz, 1H), 7.29 (d, J=8.1 Hz, 1H), 5.90 (d, J=6.1 Hz, 1H), 4.45-4.33 (m, 1H), 3.64-3.53 (m, 1H), 3.53-3.45 (m, 1H), 3.35 (s, 3H), 3.15 (s, 3H), 2.31 (s, 1H), 2.26-2.17 (m, 1H), 2.15-1.97 (m, 3H), 1.93-1.82 (m, 1H), 1.26 (t, J=7.1 Hz, 3H).

Step D: N$^4$-(2-Cyclobutyl-4-(methylsulfonyl)phenyl)-N$^4$-ethylpyrimidine-2,4-diamine N-(2-Cyclobutyl-4-(methylsulfonyl)phenyl)-N-ethyl-2-(methylsulfonyl)pyrimidin-4-amine (1.77 g, 4.33 mmol) was added to a 25 mL microwave vial and then NH$_4$OH (1.0M in i-PrOH, 8.00 mL, 4.50 mmol) was added. The vial was capped and heated at 130° C. for 1.25 h in the microwave. The contents of the reaction vessel were transferred to a round bottom flask, evaporated to dryness, dissolved in DCM, and purified by FCC (SiO$_2$, EtOAc with 0.1% Et$_3$N) to give the title compound (986 mg, 65.7% yield) as a white solid. MS (ESI): mass calcd. for $C_{17}H_{22}N_4O_2S$, 346.45; m/z found, 347.1 [M+H]$^+$. $^1$H NMR (600 MHz, CDCl$_3$): δ 8.07 (d, J=2.3 Hz, 1H), 7.84 (dd, J=8.2, 2.2 Hz, 1H), 7.72 (br s, 1H), 7.29 (d, J=8.2 Hz, 1H), 5.21 (br s, 1H), 4.84 (s, 2H), 4.22 (br s, 1H), 3.53 (p, J=8.9 Hz, 1H), 3.46-3.38 (m, 1H), 3.15 (s, 3H), 2.32-2.23 (m, 1H), 2.21-2.12 (m, 2H), 2.11-2.03 (m, 1H), 2.02-1.92 (m, 1H), 1.86-1.79 (m, 1H), 1.18 (t, J=7.1 Hz, 3H).

Example 22: N$^4$-Ethyl-N$^4$-(2-methyl-4-(pentafluorosulfanyl)phenyl)pyrimidine-2,4-diamine

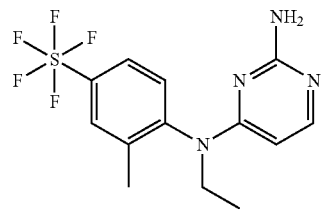 [SMILES: CCN(c1ccnc(N)n1)c1ccc(S(F)(F)(F)(F)F)cc1C]

The title compound was prepared using analogous conditions described in Example 19 using iodoethane in place of 4-(bromomethyl)oxazole hydrobromide in step D. MS (ESI): mass calcd. for $C_{13}H_{15}F_5N_4S$, 354.1; m/z found, m/z=355.1 [M+H]$^+$. $^1$H NMR (400 MHz, CDCl$_3$): δ 7.73 (d, J=2.7 Hz, 2H), 7.69-7.64 (m, 1H), 7.22 (d, J=8.6 Hz, 1H), 5.41-5.18 (m, 1H), 4.88 (br s, 2H), 4.20-4.00 (m, 1H), 3.75-3.53 (m, 1H), 2.21 (s, 3H), 1.19 (t, J=7.1 Hz, 3H).

Example 23: N$^4$-[2-Ethyl-4-(pentafluorosulfanyl)phenyl]-N$^4$-(oxazol-4-ylmethyl)pyrimidine-2,4-diamine

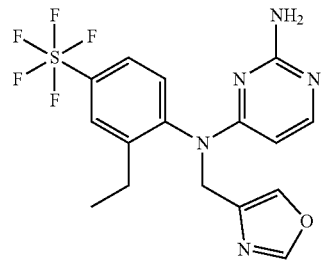 [SMILES: CCc1cc(S(F)(F)(F)(F)F)ccc1N(Cc1cocn1)c1ccnc(N)n1]

The title compound was prepared using analogous conditions described in Example 19 using 2-ethyl-4-(pentafluorothio)aniline in place of 2-methyl-4-(pentafluorosulfanyl)benzenamine in step C. MS (ESI): mass calcd. for $C_{16}H_{16}F_5N_5OS$, 421.4; m/z found, 422.0 [M+H]$^+$. $^1$H NMR (500 MHz, CD$_3$OD): δ 8.11 (s, 1H), 7.94 (s, 1H), 7.83 (d, J=2.5 Hz, 1H), 7.72 (dd, J=8.7, 2.7 Hz, 1H), 7.66 (d, J=5.8 Hz, 1H), 7.33 (d, J=8.6 Hz, 1H), 5.43-5.04 (m, 2H), 4.67 (d, J=15.5 Hz, 1H), 2.52 (q, J=7.6 Hz, 2H), 1.14 (t, J=7.6 Hz, 3H).

Example 24: N$^4$-(2-Methyl-4-(pentafluorosulfanyl)phenyl)-N$^4$-(pyridazin-3-ylmethyl)pyrimidine-2,4-diamine

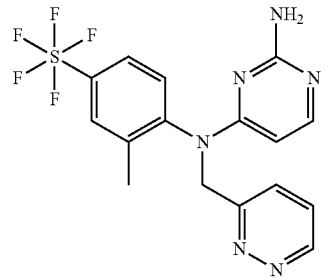 [SMILES: Cc1cc(S(F)(F)(F)(F)F)ccc1N(Cc1cccnn1)c1ccnc(N)n1]

The title compound was prepared using analogous conditions described in Example 19 employing 3-(bromomethyl)pyridazine in place of 4-bromomethyloxazole hydrobromide salt in step D. MS (ESI): mass calcd. for $C_{16}H_{15}F_5N_6S$, 418.1, m/z found 419.0 [M+H]$^+$. $^1$H NMR (400 MHz, CDCl$_3$): δ 9.13 (dd, J=4.9, 1.6 Hz, 1H), 7.77 (d, J=6.1 Hz, 1H), 7.74 (dd, J=8.5, 1.5 Hz, 1H), 7.72 (d, J=2.5 Hz, 1H), 7.61 (dd, J=8.7, 2.5 Hz, 1H), 7.49 (dd, J=8.5, 4.9 Hz, 1H), 7.23 (d, J=8.7 Hz, 1H), 5.71 (br s, 1H), 5.43 (d, J=6.0 Hz, 1H), 5.09 (br s, 2H), 4.99 (br s, 1H), 2.18 (s, 3H).

Example 25: $N^4$-[2-Ethyl-4-(pentafluorosulfanyl)phenyl]-$N^4$-(1H-pyrazol-5-ylmethyl)pyrimidine-2,4-diamine

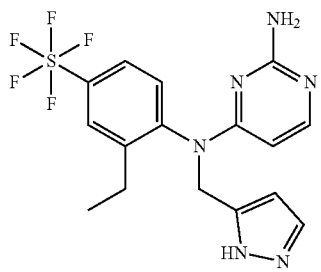 [SMILES: CCc1cc(S(F)(F)(F)(F)F)ccc1N(Cc1ccn[nH]1)c1ccnc(N)n1]

The title compound was prepared using analogous conditions described in Example 19 using 2-ethyl-4-(pentafluorothio)aniline in place of 2-methyl-4-(pentafluorosulfanyl)benzenamine in step C and 5-(chloromethyl)-1H-pyrazole hydrochloride in place of 4-(bromomethyl)oxazole hydrobromide in step D. MS (ESI): mass calcd. for $C_{16}H_{17}F_5N_6S$, 420.4; m/z found, 420.9 [M+H]$^+$. $^1$H NMR (500 MHz, CD$_3$OD): δ 7.81 (s, 1H), 7.75-7.62 (m, 2H), 7.54 (s, 1H), 7.16 (d, J=8.6 Hz, 1H), 6.32 (s, 1H), 5.48-5.07 (m, 2H), 4.82 (d, J=15.6 Hz, 1H), 2.54-2.35 (m, 2H), 1.08 (t, J=7.6 Hz, 3H).

Example 26: $N^4$-[2-Ethyl-4-(pentafluorosulfanyl)phenyl]-$N^4$-(1,3,4-oxadiazol-2-ylmethyl)pyrimidine-2,4-diamine

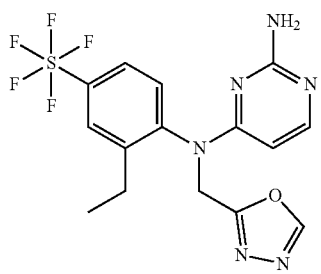 [SMILES: CCc1cc(S(F)(F)(F)(F)F)ccc1N(Cc1nnco1)c1ccnc(N)n1]

The title compound was prepared using analogous conditions described in Example 19 using 2-ethyl-4-(pentafluorothio)aniline in place of 2-methyl-4-(pentafluorosulfanyl)benzenamine in step C and 2-(chloromethyl)-1,3,4-oxadiazole in place of 4-(bromomethyl)oxazole hydrobromide in step D. MS (ESI): mass calcd. for $C_{15}H_{15}F_5N_6OS$, 422.4; m/z found, 422.9 [M+H]$^+$. $^1$H NMR (400 MHz, CD$_3$OD): δ 8.91 (s, 1H), 7.89 (d, J=2.5 Hz, 1H), 7.78 (dd, J=8.7, 2.6 Hz, 1H), 7.72 (d, J=6.0 Hz, 1H), 7.57 (d, J=8.7 Hz, 1H), 5.63 (d, J=16.4 Hz, 1H), 5.54-5.39 (m, 1H), 4.98 (d, J=16.4 Hz, 1H), 2.62 (q, J=7.5 Hz, 2H), 1.20 (t, J=7.6 Hz, 3H).

Example 27: $N^4$-Isopropyl-$N^4$-(2-(2-methylprop-1-en-1-yl)-4-(pyrrolidin-1-ylsulfonyl)phenyl)pyrimidine-2,4-diamine

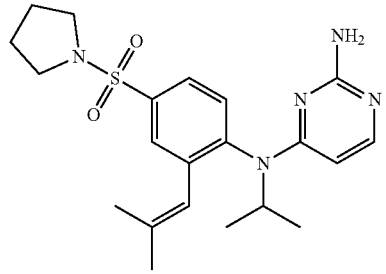 [SMILES: CC(C)=Cc1cc(S(=O)(=O)N2CCCC2)ccc1N(c1ccnc(N)n1)C(C)C]

Step A. 2-chloro-4-(pyrrolidin-1-ylsulfonyl)aniline

The title compound was prepared as described in Example 29, step A, MS (ESI): mass calcd. for $C_{10}H_{13}ClN_2O_2S$, 260.0; m/z found, 260.9 [M+H]$^+$. $^1$H NMR (400 MHz, Methanol-d4) δ 7.62 (d, J=2.1 Hz, 1H), 7.46 (dd, J=8.6, 2.1 Hz, 1H), 6.88 (d, J=8.5 Hz, 1H), 3.21-3.13 (m, 4H), 1.79-1.71 (m, 4H).

Step B: N-(2-chloro-4-(pyrrolidin-1-ylsulfonyl)phenyl)-2-(methylthio)pyrimidin-4-amine The title compound was prepared using analogous conditions described in Example 19. MS (ESI): mass calcd. for $C_{15}H_{17}ClN_4O_2S_2$, 384.0 z; m/z found, 384.9 [M+H]$^+$. $^1$H NMR (500 MHz, Methanol-d4) b 8.40 (d, J=8.7 Hz, 1H), 8.14 (d, J=5.9 Hz, 1H), 7.90 (d, J=2.1 Hz, 1H), 7.77 (dd, J=8.7, 2.1 Hz, 1H), 6.71 (d, J=5.9 Hz, 1H), 3.29-3.23 (m, 4H), 2.47 (s, 3H), 1.81-1.75 (m, 4H).

Step C: N4-(2-chloro-4-(pyrrolidin-1-ylsulfonyl)phenyl)-N4-isopropylpyrimidine-2,4-diamine 2-Iodopropane (0.55 mL, 5.5 mmol) was added to a stirring mixture of N-(2-chloro-4-(pyrrolidin-1-ylsulfonyl)phenyl)-2-(methylthio)pyrimidin-4-amine (1.16 g, 2.8 mmol) and cesium carbonate (2.7 g, 8.3 mmol) in acetonitrile (9 mL, 2.8 mmol). The mixture was heated at 85° C. for 1 hr then worked-up with DCM and water. The separated organic layer was dried over Na$_2$SO$_4$, filtered, and concentrated. The crude material was dissolved in DCM (18.4 mL, 2.8 mmol) and submerged in an ice bath. 3-Chloroperoxybenzoic acid (1.90 g, 11.0 mmol) was added to the mixture and allowed to stir for 1 hr. The reaction was quenched with sodium thiosulfate (500 mg) and water (10 mL), then extracted with DCM/sat'd NaHCO$_3$. Separated the crude material into 4 separate sealed tubes (for safety reasons), then added 2 mL IPA and 2 mL 33% ammonia in H$_2$O in each vial. Heated all 4 vials at 120° C. for 16 hr, then carefully released the pressure for each. A batch work-up with DCM/brine was performed after combining the 4 vials in a separatory funnel. Purified crude over silica gel (0 to 100% EtOAc in hexane) to yield the title product (715. mg, 66% yield). MS (ESI): mass calcd. for $C_{17}H_{22}ClN_5O_2S$, 395.1; m/z found, 395.9 [M+H]$^+$. 1H NMR (400 MHz, Chloroform-d) δ 8.00 (d, J=2.1 Hz, 1H), 7.80 (dd, J=8.2, 2.1 Hz, 1H), 7.75 (d, J=6.0 Hz, 1H), 7.39 (d, J=8.2 Hz, 1H), 5.20 (d, J=5.9 Hz, 1H), 5.15-5.04 (m, 1H), 4.73 (s, 2H), 3.42-3.28 (m, 4H), 1.89-1.82 (m, 4H), 1.33-0.97 (m, 6H).

Step D. N$^4$-Isopropyl-N$^4$-(2-(2-methylprop-1-en-1-yl)-4-(pyrrolidin-1-ylsulfonyl)phenyl)pyrimidine-2,4-diamine This title compound was prepared using analogous conditions described in Example 98, step B, using 2,2-dimethylethenylboronic acid. MS (ESI): mass calcd. for C$_{21}$H$_{29}$N$_5$O$_2$S, 415.6; m/z found, 416.0 [M+H]$^+$. $^1$H NMR (400 MHz, CDCl$_3$): δ 7.82 (d, J=2.1 Hz, 1H), 7.74 (dd, J=8.2, 2.2 Hz, 1H), 7.67 (d, J=6.1 Hz, 1H), 7.24 (d, J=8.2 Hz, 1H), 6.00 (s, 1H), 5.10 (d, J=5.9 Hz, 1H), 5.07-4.97 (m, 1H), 4.78 (s, 2H), 3.36-3.29 (m, 4H), 2.08-1.89 (m, 1H), 1.85-1.77 (m, 10H), 1.24-1.00 (m, 5H).

Example 28: N$^4$-(2-Cyclobutyl-4-(pyrrolidin-1-ylsulfonyl)phenyl)-N$^4$-isopropylpyrimidine-2,4-diamine

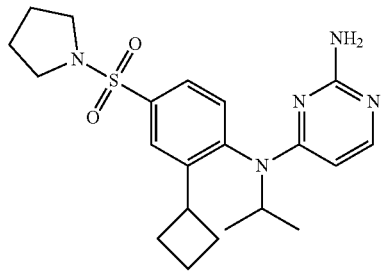 [SMILES: CC(C)N(c1ccnc(N)n1)c1ccc(S(=O)(=O)N2CCCC2)cc1C1CCC1]

The title compound was prepared using analogous conditions described in Example 21 using 2-cyclobutyl-4-(pyrrolidine-1-sulfonyl)phenylamine in place of 2-cyclobutyl-4-(methylsulfonyl)aniline (Intermediate 17) in step A and 2-iodopropane in place of 1-iodoethane in step C. MS (ESI): mass calcd. for C$_{21}$H$_{29}$N$_5$O$_2$S, 415.6; m/z found, 416.1 [M+H]$^+$. $^1$H NMR (400 MHz, CD$_3$OD): δ 8.07 (d, J=2.1 Hz, 1H), 7.77 (dd, J=8.2, 2.2 Hz, 1H), 7.57 (d, J=6.2 Hz, 1H), 7.33 (d, J=8.2 Hz, 1H), 5.30-4.99 (m, 2H), 3.67-3.52 (m, 1H), 2.32-1.85 (m, 8H), 1.84-1.72 (m, 4H), 1.39-1.20 (m, 5H), 0.94 (d, J=6.9 Hz, 3H).

Example 29: N$^4$-(4-((Difluoromethyl)sulfonyl)-2-ethylphenyl)-N$^4$-(oxazol-4-ylmethyl)pyrimidine-2,4-diamine

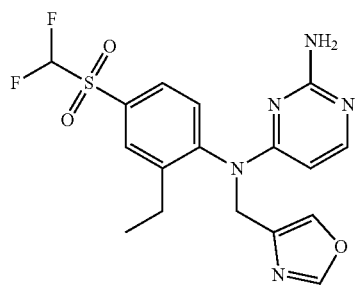 [SMILES: CCc1cc(S(=O)(=O)C(F)F)ccc1N(Cc1cocn1)c1ccnc(N)n1]

Step A:
2-Chloro-4-((difluoromethyl)sulfonyl)aniline

To a round-bottomed flask were added 4-((difluoromethyl)sulfonyl)aniline (1.98 g, 9.54 mmol) and ACN (25.0 mL) and was stirred to dissolve at 50° C. To this mixture was added NCS (1.26 g, 9.22 mmol) and was stirred for 3 h at 50° C. The reaction temperature was increased to 75° C. and stirred overnight. The reaction mixture was cooled to rt, washed with DCM, H$_2$O, and saturated NaHCO$_3$, and collecting the organic phase. The aqueous phase was extracted again with DCM. The combined organics were dried over anhydrous Na$_2$SO$_4$, filtered, and concentrated to dryness. The residue was purified by FCC (120 g SiO$_2$ column, eluent=0-30% ethyl acetate/hexanes) to give the title compound (740 mg, 32.0% yield) of an off-white solid.

Step B: N$^4$-(4-((Difluoromethyl)sulfonyl)-2-ethylphenyl)-N$^4$-(oxazol-4-ylmethyl)pyrimidine-2,4-diamine The title compound was prepared using analogous conditions described in Example 21 using 2-chloro-4-(trifluoromethylsulfonyl)aniline in place of 2-bromo-4-(pentafluorosulfanyl)aniline and triethylborane in place of cyclobutylzinc bromide in step A. MS (ESI): mass calcd. for C$_{17}$H$_{17}$F$_2$N$_5$O$_3$S, 409.4; m/z found, 410.1 [M+H]$^+$. $^1$H NMR (400 MHz, CDCl$_3$): δ 7.97 (d, J=2.2 Hz, 1H), 7.86 (dd, J=8.3, 2.2 Hz, 1H), 7.85-7.74 (m, 2H), 7.69-7.60 (m, 1H), 7.44 (d, J=8.3 Hz, 1H), 6.23 (t, J=53.4 Hz, 1H), 5.51-5.18 (m, 2H), 4.98 (s, 2H), 4.59 (s, 1H), 2.56 (q, J=7.5 Hz, 2H), 1.19 (t, J=7.6 Hz, 3H).

Example 30: N$^4$-Isopropyl-N$^4$-(2-methyl-4-(pentafluorosulfanyl)phenyl)pyrimidine-2,4-diamine

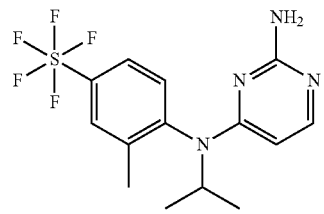 [SMILES: Cc1cc(S(F)(F)(F)(F)F)ccc1N(c1ccnc(N)n1)C(C)C]

The title compound was prepared using analogous conditions described in Example 19 using 2-iodopropane in place of 4-(bromomethyl)oxazole in step D. MS (ESI): mass calcd. for C$_{14}$H$_{17}$F$_5$N$_4$S, 368.1; m/z found, m/z=369.1 [M+H]$^+$. $^1$H NMR (400 MHz, CDCl$_3$): δ 7.73 (d, J=2.4 Hz, 1H), 7.70 (d, J=6.1 Hz, 1H), 7.66 (dd, J=8.6, 2.5 Hz, 1H), 7.19 (d, J=8.6 Hz, 1H), 5.26-5.02 (m, 2H), 4.82 (br s, 2H), 2.21 (s, 3H), 1.38-1.27 (m, 3H), 1.06-0.97 (m, 3H).

Example 31: N$^4$-(2-Methyl-4-(pentafluorosulfanyl)phenyl)-N$^4$-(2-methoxyethyl)pyrimidine-2,4-diamine

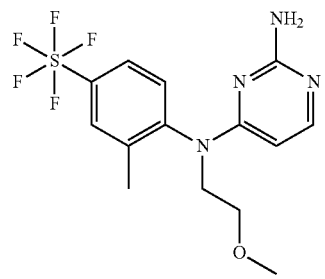 [SMILES: COCCN(c1ccnc(N)n1)c1ccc(S(F)(F)(F)(F)F)cc1C]

The title compound was prepared using analogous conditions described in Example 19 using 1-bromo-2-methoxyethane in place of 4-(bromomethyl)oxazole in step D. MS (ESI): mass calcd. for $C_{14}H_{17}F_5N_4OS$, 384.1; m/z found, m/z=385.1 [M+H]+. 1H NMR (400 MHz, CDCl3): δ 7.74 (d, J=6.0 Hz, 1H), 7.70 (d, J=2.2 Hz, 1H), 7.66 (dd, J=8.6, 2.4 Hz, 1H), 7.31 (d, J=8.6 Hz, 1H), 5.38-5.24 (m, 1H), 4.88 (br s, 2H), 4.28-4.14 (m, 1H), 3.88-3.72 (m, 1H), 3.68-3.54 (m, 2H), 3.31 (s, 3H), 2.20 (s, 3H).

Example 32: N4-(2-Methyl-4-(pentafluorosulfanyl)phenyl)-N4-(pyrimidin-2-ylmethyl)pyrimidine-2,4-diamine

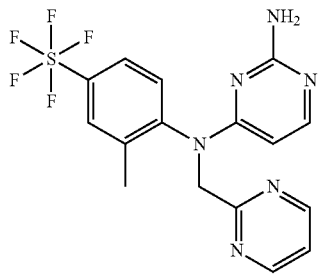 [SMILES: Cc1cc(S(F)(F)(F)(F)F)ccc1N(Cc1ncccn1)c1ccnc(N)n1]

The title compound was prepared using analogous conditions described in Example 19 using 2-(chloromethyl)pyrimidine in place of 4-(bromomethyl)oxazole in step D. MS (ESI): mass calcd. for $C_{16}H_{15}F_5N_6S$, 418.1; m/z found, m/z=419.1 [M+H]+. 1H NMR (400 MHz, CDCl3): δ 8.70 (d, J=4.9 Hz, 2H), 7.82-7.68 (m, 3H), 7.63 (dd, J=8.7, 2.5 Hz, 1H), 7.20 (t, J=4.9 Hz, 1H), 5.82-5.64 (m, 1H), 5.58-5.45 (m, 1H), 5.30 (br s, 2H), 4.67 (d, J=14.7 Hz, 1H), 2.33 (s, 3H).

Example 33: N4-[(5-Methyloxazol-4-yl)methyl]-N4-[2-methyl-4-(pentafluorosulfanyl)phenyl]pyrimidine-2,4-diamine

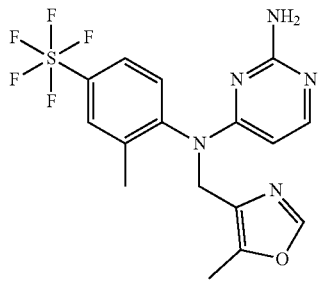 [SMILES: Cc1cc(S(F)(F)(F)(F)F)ccc1N(Cc1ncoc1C)c1ccnc(N)n1]

The title compound was prepared using analogous conditions described in Example 19 using 4-(chloromethyl)-5-methyloxazole in place of 4-(bromomethyl)oxazole in step D. MS (ESI): mass calcd. for $C_{16}H_{16}F_5N_5OS$, 421.1; m/z found, m/z=422.0 [M+H]+. 1H NMR (400 MHz, CDCl3): δ 7.78-7.60 (m, 4H), 7.31 (d, J=8.6 Hz, 1H), 5.40-5.08 (m, 4H), 4.63 (d, J=13.6 Hz, 1H), 2.28 (s, 3H), 2.14 (s, 3H).

Example 34: N4-(Isoxazol-3-ylmethyl)-N4-(2-methyl-4-(pentafluorosulfanyl)phenyl)pyrimidine-2,4-diamine

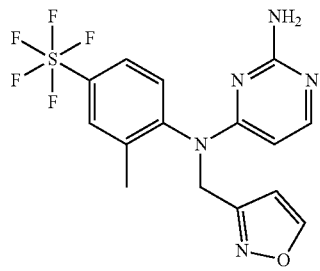 [SMILES: Cc1cc(S(F)(F)(F)(F)F)ccc1N(Cc1ccon1)c1ccnc(N)n1]

The title compound was prepared using analogous conditions described in Example 19 using 3-(chloromethyl)isoxazole (which was prepared according to Hughes, L. R., et al., Eur. Pat. Appl., EP373891A2) in place of 4-(bromomethyl)oxazole in step D. MS (ESI): mass calcd. for $C_{15}H_{14}F_5N_5OS$, 407.1; m/z found, m/z=408.1 [M+H]+. 1H NMR (400 MHz, CD3OD): δ 8.62 (d, J=1.1 Hz, 1H), 7.87 (d, J=2.3 Hz, 1H), 7.79-7.68 (m, 2H), 7.34 (d, J=8.6 Hz, 1H), 6.63 (s, 1H), 5.48-5.30 (m, 2H), 5.01-4.91 (m, 1H), 2.17 (s, 3H).

Example 35: N4-(2-Methyl-4-(pentafluorosulfanyl)phenyl)-N4-(oxazol-5-ylmethyl)pyrimidine-2,4-diamine

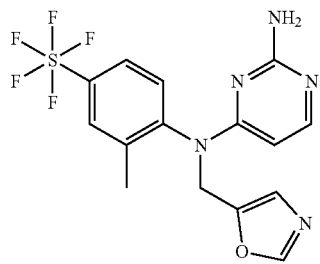 [SMILES: Cc1cc(S(F)(F)(F)(F)F)ccc1N(Cc1cnco1)c1ccnc(N)n1]

The title compound was prepared using analogous conditions described in Example 19 using 5-(chloromethyl)oxazole, (which was prepared according to Bull, J. A.; et al., Chemistry—A European Journal, 2007, 13(19), 5515-5538) in place of 4-(bromomethyl)oxazole in step D. MS (ESI): mass calcd. for $C_{15}H_{14}FsN_5OS$, 407.1; m/z found, m/z=408.1 [M+H]+. 1H NMR (400 MHz, CD3OD): δ 8.15 (s, 1H), 7.87 (d, J=2.4 Hz, 1H), 7.77 (dd, J=8.7, 2.6 Hz, 1H), 7.72 (d, J=5.9 Hz, 1H), 7.33 (d, J=8.6 Hz, 1H), 7.14 (s, 1H), 5.50-5.23 (m, 2H), 5.12-5.00 (m, 1H), 2.13 (s, 3H).

Example 36: N⁴-(2-Methyl-4-(pentafluorosulfanyl) phenyl)-N⁴-(oxazol-2-ylmethyl)pyrimidine-2,4-diamine

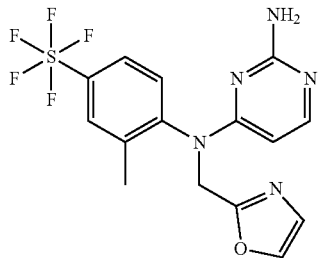 [SMILES: Cc1cc(S(F)(F)(F)(F)F)ccc1N(Cc1ncco1)c1ccnc(N)n1]

The title compound was prepared using analogous conditions described in Example 19 using 2-(chloromethyl) oxazole in place of 4-(bromomethyl)oxazole in step D. MS (ESI): mass calcd. for $C_{15}H_{14}F_5N_5OS$, 407.1; m/z found, m/z=408.0 [M+H]⁺. ¹H NMR (400 MHz, CD₃OD): δ 7.89 (d, J=0.7 Hz, 1H), 7.87 (d, J=2.3 Hz, 1H), 7.81-7.70 (m, 2H), 7.49 (d, J=8.8 Hz, 1H), 7.14 (d, J=0.6 Hz, 1H), 5.57-5.35 (m, 2H), 5.06-4.92 (m, 1H), 2.21 (s, 3H).

Example 37: N⁴-[(3-Chloro-2-pyridyl)methyl]-N⁴-[2-methyl-4-(pentafluorosulfanyl)phenyl]pyrimidine-2,4-diamine

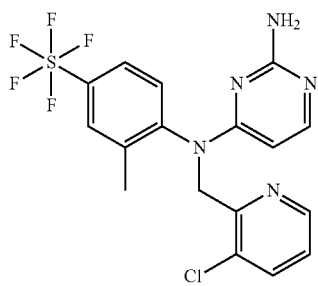 [SMILES: Cc1cc(S(F)(F)(F)(F)F)ccc1N(Cc1ncccc1Cl)c1ccnc(N)n1]

The title compound was prepared using analogous conditions described in Example 19 using 2-(bromomethyl)-3-chloropyridine in place of 4-(bromomethyl)oxazole in step D. MS (ESI): mass calcd. for $C_{17}H_{15}ClF_5N_5S$, 451.1; m/z found, m/z=452.0 [M+H]⁺. ¹H NMR (400 MHz, CDCl₃): δ 8.42 (dd, J=4.7, 1.4 Hz, 1H), 7.76 (d, J=6.0 Hz, 1H), 7.70-7.62 (m, 3H), 7.59 (dd, J=8.8, 2.5 Hz, 1H), 7.14 (dd, J=8.0, 4.7 Hz, 1H), 5.76 (d, J=10.4 Hz, 1H), 5.44 (d, J=4.6 Hz, 1H), 4.77 (br s, 2H), 4.68 (d, J=15.2 Hz, 1H), 2.30 (s, 3H).

Example 38: N⁴-(2-Methyl-4-(pentafluorosulfanyl) phenyl)-N⁴-(thiazol-4-ylmethyl)pyrimidine-2,4-diamine

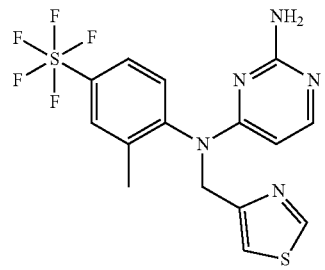

The title compound was prepared using analogous conditions described in Example 19 using 4-(chloromethyl) thiazole in place of 4-(bromomethyl)oxazole in step D. MS (ESI): mass calcd. for $C_{15}H_{14}F_5N_5S_2$, 423.1; m/z found, m/z=424.0 [M+H]⁺. ¹H NMR (400 MHz, CD₃OD): δ 8.93 (d, J=1.8 Hz, 1H), 7.82 (d, J=2.1 Hz, 1H), 7.74-7.68 (m, 2H), 7.61 (s, 1H), 7.33 (d, J=8.7 Hz, 1H), 5.50-5.30 (m, 2H), 5.15-5.00 (m, 1H), 2.10 (s, 3H).

Example 39: N⁴-[(4-Fluoro-1H-pyrazol-3-yl) methyl]-N⁴-[2-methyl-4-(pentafluorosulfanyl)phenyl]pyrimidine-2,4-diamine

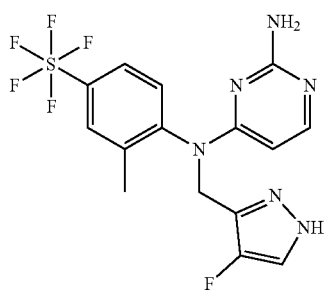 [SMILES: Cc1cc(S(F)(F)(F)(F)F)ccc1N(Cc1n[nH]cc1F)c1ccnc(N)n1]

The title compound was prepared using analogous conditions described in Example 19 using 3-(chloromethyl)-4-fluoro-1H-pyrazole in place of 4-(bromomethyl)oxazole in step D. MS (ESI): mass calcd. for $C_{15}H_{14}F_6N_6S$, 424.1; m/z found, m/z=425.1 [M+H]⁺. ¹H NMR (400 MHz, CDCl₃): δ 10.94 (br s, 1H), 7.80-7.71 (m, 2H), 7.66 (dd, J=8.6, 2.4 Hz, 1H), 7.36 (d, J=4.6 Hz, 1H), 7.15 (d, J=8.8 Hz, 1H), 5.67 (br s, 2H), 5.41-5.32 (m, 1H), 5.23-5.10 (m, 1H), 4.78-4.65 (m, 1H), 2.13 (s, 3H).

Example 40: N⁴-((4-Chloro-1H-pyrazol-3-yl)methyl)-N⁴-(2-methyl-4-(pentafluorosulfanyl)phenyl)pyrimidine-2,4-diamine

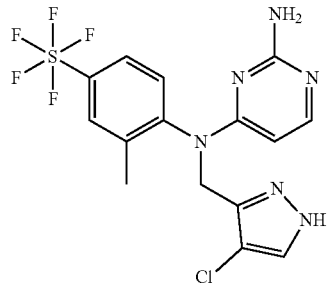 [SMILES: Cc1cc(S(F)(F)(F)(F)F)ccc1N(Cc1n[nH]cc1Cl)c1ccnc(N)n1]

Step A. N⁴-((4-Chloro-1-((2-(trimethylsilyl)ethoxy)methyl)-1H-pyrazol-3-yl)methyl)-N⁴-(2-methyl-4-(pentafluorosulfanyl)phenyl)pyrimidine-2,4-diamine The title compound was prepared using analogous conditions described in Example 19 using 4-chloro-3-(chloromethyl)-1-((2-(trimethylsilyl)ethoxy)methyl)-1H-pyrazole in place of 4-(bromomethyl)oxazole in step D. MS (ESI): mass calcd. for $C_{21}H_{28}ClF_5N_6OSSi$, 570.14, m/z found 571.0 [M+H]⁺.

Step B. N⁴-((4-Chloro-1H-pyrazol-3-yl)methyl)-N⁴-(2-methyl-4-(pentafluorosulfanyl)phenyl)pyrimidine-2,4-diamine To a 100 mL round-bottomed flask were added N⁴-((4-chloro-1-((2-(trimethylsilyl)ethoxy)methyl)-1H-pyrazol-3-yl)methyl)-N⁴-(2-methyl-4-(pentafluorosulfanyl)phenyl)pyrimidine-2,4-diamine (260 mg, 0.45 mmol), MeOH (20 mL), and concentrated HCl (2 mL). The reaction mixture was stirred at 45° C. for 15 h, and then concentrated to dryness. The residue was dissolved in DCM (150 mL), washed with saturated aqueous NaHCO₃ solution (30 mL), water (30 mL), and concentrated to dryness. The residue was purified by FCC to give the title compound as a white solid (95 mg). MS (ESI): mass calcd. for $C_{15}H_{14}ClF_5N_6S$, 440.06, m/z found 441.0 [M+H]⁺. ¹H NMR (400 MHz, CDCl₃): δ 11.38 (br s, 1H), 7.78 (d, J=6.0 Hz, 1H), 7.71 (d, J=2.3 Hz, 1H), 7.63 (dd, J=8.7, 2.4 Hz, 1H), 7.46 (s, 1H), 7.11 (d, J=8.6 Hz, 1H), 5.34 (d, J=5.8 Hz, 1H), 5.28-5.06 (m, 3H), 4.75 (br s, 1H), 2.09 (s, 3H).

Example 41: N⁴-[2-Methyl-4-(pentafluorosulfanyl)phenyl]-N⁴-(1H-pyrazol-3-ylmethyl)pyrimidine-2,4-diamine

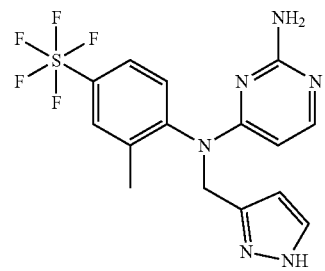 [SMILES: Cc1cc(S(F)(F)(F)(F)F)ccc1N(Cc1cc[nH]n1)c1ccnc(N)n1]

The title compound was prepared using analogous conditions described in Example 40 steps A-D, using 3-(chloromethyl)-1-((2-(trimethylsilyl)ethoxy)methyl)-1H-pyrazole. MS (ESI): mass calcd. for $C_{15}H_{15}F_5N_6S$, 406.1; m/z found, m/z=407.1 [M+H]⁺. ¹H NMR (400 MHz, CDCl₃): δ 11.03 (br s, 1H), 7.78 (d, J=6.0 Hz, 1H), 7.69 (d, J=2.4 Hz, 1H), 7.60 (dd, J=8.6, 2.4 Hz, 1H), 7.49 (d, J=1.8 Hz, 1H), 7.05 (d, J=8.6 Hz, 1H), 6.14 (s, 1H), 5.25 (m, 2H), 5.02 (br s, 2H), 4.79-4.64 (m, 1H), 2.05 (s, 3H).

Example 42: N⁴-Ethyl-N⁴-(2-ethyl-4-((trifluoromethyl)sulfonyl)phenyl)pyrimidine-2,4-diamine

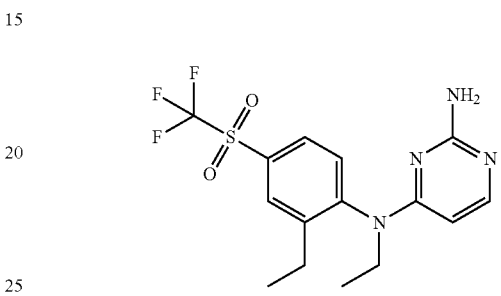

The title compound was prepared using analogous conditions described in Example 19 starting with 4-((trifluoromethyl)sulfonyl)aniline in step A, and 2,4,6-triethyl-1,3,5,2,4,6-trioxatriborinane in place of 2,4,6-trimethyl-1,3,5,2,4,6-trioxatriborinane in step B, and iodoethane in place of 4-(bromomethyl)oxazole in step D. MS (ESI): mass calcd. for $C_{15}H_{14}F_6N_6S$, 424.1; m/z found, m/z=425.1 [M+H]⁺. ¹H NMR (400 MHz, CDCl₃): δ 10.94 (br s, 1H), 7.80-7.71 (m, 2H), 7.66 (dd, J=8.6, 2.4 Hz, 1H), 7.36 (d, J=4.6 Hz, 1H), 7.15 (d, J=8.8 Hz, 1H), 5.67 (br s, 2H), 5.41-5.32 (m, 1H), 5.23-5.10 (m, 1H), 4.78-4.65 (m, 1H), 2.13 (s, 3H).

Example 43: N⁴-(2-Cyclobutyl-4-((trifluoromethyl)sulfonyl)phenyl)-N⁴-ethylpyrimidine-2,4-diamine

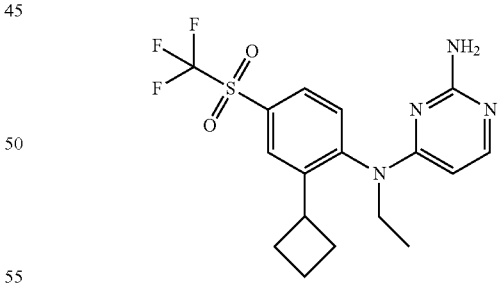

The title compound was prepared using analogous conditions described in Example 21 starting with 2-cyclobutyl-(4-(trifluoromethyl)sulfonyl)aniline in place of 2-cyclobutyl-4-(methylsulfonyl)aniline (Intermediate 17) MS (ESI): mass calcd. for $C_{17}H_{19}F_3N_4O_2S$, 400.4; m/z found, 401.1 [M+H]⁺. ¹H NMR (400 MHz, CDCl₃): δ 8.12 (d, J=2.4 Hz, 1H), 7.93 (dd, J=8.2, 2.2 Hz, 1H), 7.77 (d, J=6.0 Hz, 1H), 7.38 (d, J=8.3 Hz, 1H), 5.32 (s, 1H), 4.91 (s, 2H), 4.19 (s, 1H), 3.63-3.39 (m, 2H), 2.38-1.80 (m, 6H), 1.20 (t, J=7.0 Hz, 3H).

Example 44: N⁴-(2-Cyclobutyl-4-((trifluoromethyl)sulfonyl)phenyl)-N⁴-(oxazol-4-ylmethyl)pyrimidine-2,4-diamine

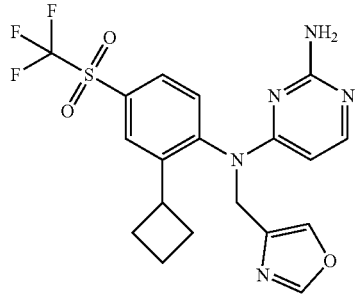 [SMILES: Nc1nccc(N(Cc2cocn2)c2ccc(S(=O)(=O)C(F)(F)F)cc2C2CCC2)n1]

The title compound was prepared using analogous conditions described in Example 21 starting with 2-cyclobutyl-(4-(trifluoromethyl)sulfonyl)aniline in place of 2-cyclobutyl-4-(methylsulfonyl)aniline (Intermediate 17) and using 4-bromomethyloxazole in place of 1-iodoethane in Step C. MS (ESI): mass calcd. for $C_{19}H_{18}F_3N_5O_3S$, 453.4; m/z found, 453.9 [M+H]⁺. ¹H NMR (500 MHz, CDCl₃): δ 8.09-8.02 (m, 1H), 7.90 (dd, J=8.3, 2.2 Hz, 1H), 7.84-7.77 (m, 2H), 7.65 (s, 1H), 7.52 (d, J=8.3 Hz, 1H), 5.53-5.21 (m, 2H), 4.83 (s, 2H), 4.49-4.29 (m, 1H), 3.51 (p, J=8.9 Hz, 1H), 2.28-2.16 (m, 2H), 2.16-2.03 (m, 2H), 2.03-1.92 (m, 1H), 1.90-1.77 (m, 1H).

Example 45: N⁴-(2-Cyclobutyl-4-(methylsulfonyl)phenyl)-N⁴-isopropylpyrimidine-2,4-diamine

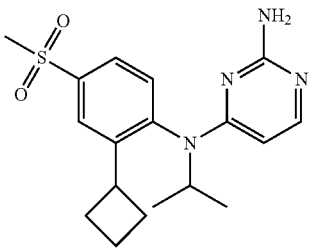 [SMILES: CC(C)N(c1ccnc(N)n1)c1ccc(S(C)(=O)=O)cc1C1CCC1]

The title compound was prepared using analogous conditions described in Example 21 employing 2-iodopropane in place of 1-iodoethane in step C. MS (ESI): mass calcd. for $C_{18}H_{24}N_4O_2S$, 360.5; m/z found, 361.0 [M+H]⁺. ¹H NMR (400 MHz, CDCl₃): δ 8.20 (d, J=2.2 Hz, 1H), 7.82 (dd, J=8.2, 2.3 Hz, 1H), 7.66 (d, J=6.1 Hz, 1H), 7.23 (d, J=8.2 Hz, 1H), 5.23-4.87 (m, 2H), 4.81 (s, 2H), 3.62-3.50 (m, 1H), 3.16 (s, 3H), 2.27-2.14 (m, 2H), 2.14-1.99 (m, 2H), 1.99-1.78 (m, 2H), 1.28 (d, J=6.6 Hz, 3H), 0.89 (d, J=6.9 Hz, 3H).

Example 46: N⁴-(2-Ethyl-4-((trifluoromethyl)sulfonyl)phenyl)-N⁴-(oxazol-2-ylmethyl)pyrimidine-2,4-diamine

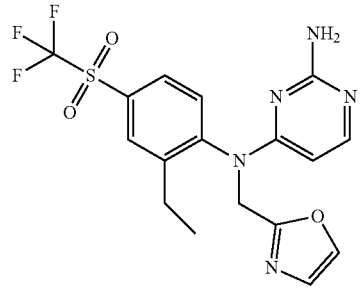 [SMILES: CCc1cc(S(=O)(=O)C(F)(F)F)ccc1N(Cc1ncco1)c1ccnc(N)n1]

The title compound was prepared using analogous conditions described in Example 21 starting at Step A using 4-amino-3-ethylphenyl trifluoromethanesulfonate (Intermediate 7) and 2-(bromomethyl)oxazole in place of 1-iodoethane in Step C. MS (ESI): mass calcd. for $C_{17}H_{16}F_3N_5O_3S$, 427.4; m/z found, 427.9 [M+H]⁺. ¹H NMR (500 MHz, CDCl₃): δ 8.03 (d, J=2.1 Hz, 1H), 7.93 (dd, J=8.3, 2.2 Hz, 1H), 7.84 (d, J=6.0 Hz, 1H), 7.65 (d, J=8.3 Hz, 1H), 7.61 (d, J=0.8 Hz, 1H), 7.06 (d, J=0.8 Hz, 1H), 5.81-5.20 (m, 2H), 4.98-4.51 (m, 3H), 2.62 (q, J=7.5 Hz, 2H), 1.22 (t, J=7.5 Hz, 3H).

Example 47: N⁴-(2-Ethyl-4-((trifluoromethyl)sulfonyl)phenyl)-N⁴-((3-fluoropyridin-4-yl)methyl)pyrimidine-2,4-diamine

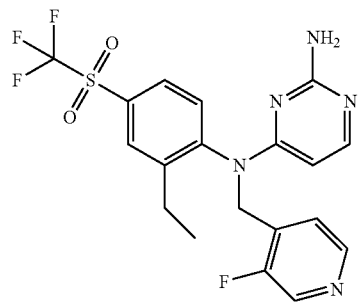 [SMILES: CCc1cc(S(=O)(=O)C(F)(F)F)ccc1N(Cc1ccncc1F)c1ccnc(N)n1]

The title compound was prepared using analogous conditions described in Example 21 starting at Step A using 4-amino-3-ethylphenyl trifluoromethanesulfonate (Intermediate 7) and 4-(bromomethyl)-3-fluoropyridine in place of 1-iodoethane in Step C. MS (ESI): mass calcd. for $C_{19}H_{17}F_4N_5O_2S$, 455.4; m/z found, 455.9 [M+H]⁺. ¹H NMR (400 MHz, CDCl₃): δ 8.45-8.30 (m, 2H), 8.04 (d, J=2.1 Hz, 1H), 7.89 (dd, J=8.4, 2.2 Hz, 1H), 7.85 (d, J=5.9 Hz, 1H), 7.47-7.38 (m, 1H), 7.32 (d, J=8.3 Hz, 1H), 5.81-5.09 (m, 2H), 5.08-4.48 (m, 3H), 2.57 (q, J=7.5 Hz, 2H), 1.19 (t, J=7.6 Hz, 3H).

Example 48: N⁴-(2-Cyclobutyl-4-(methylsulfonyl)phenyl)-N⁴-((6-(trifluoromethyl)pyridin-2-yl)methyl)pyrimidine-2,4-diamine

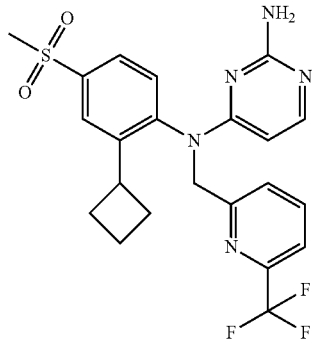 [SMILES: CS(=O)(=O)c1ccc(N(Cc2cccc(C(F)(F)F)n2)c2ccnc(N)n2)c(C2CCC2)c1]

The title compound was prepared using analogous conditions described in Example 21 employing 2-(chloromethyl)-6-(trifluoromethyl)pyridine in place of 1-iodoethane. MS (ESI): mass calcd. for $C_{22}H_{22}F_3N_5O_2S$, 477.5; m/z found, 478.15 [M+H]⁺. ¹H NMR (500 MHz, CDCl₃): δ 8.03 (d, J=2.2 Hz, 1H), 7.86 (t, J=7.8 Hz, 1H), 7.83-7.74 (m, 2H), 7.66 (d, J=7.9 Hz, 1H), 7.57 (dd, J=7.7, 1.0 Hz, 1H), 7.44 (d, J=8.2 Hz, 1H), 5.70 (d, J=15.6 Hz, 1H), 5.37 (s, 1H), 5.02 (s, 2H), 4.53 (d, J=15.9 Hz, 1H), 3.62-3.50 (m, 1H), 3.11 (s, 3H), 2.29-1.90 (m, 5H), 1.88-1.77 (m, 1H).

Example 49: N⁴-((3,5-Dimethylisoxazol-4-yl)methyl)-N⁴-(2-ethyl-4-((trifluoromethyl)sulfonyl)phenyl)pyrimidine-2,4-diamine

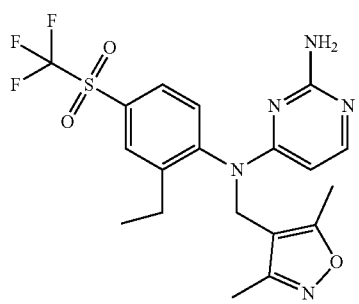 [SMILES: CCc1cc(S(=O)(=O)C(F)(F)F)ccc1N(Cc1c(C)noc1C)c1ccnc(N)n1]

The title compound was prepared using analogous conditions described in Example 21 starting at Step A using 4-amino-3-ethylphenyl trifluoromethanesulfonate (Intermediate 7) and subsequently using 4-(chloromethyl)-3,5-dimethylisoxazole in place of 1-iodoethane in Step C. MS (ESI): mass calcd. for $C_{19}H_{20}F_3N_5O_3S$, 455.5; m/z found, 456.0 [M+H]⁺. ¹H NMR (400 MHz, CDCl₃): δ 8.05 (d, J=2.1 Hz, 1H), 7.93 (dd, J=8.3, 2.2 Hz, 1H), 7.79 (d, J=5.7 Hz, 1H), 7.22 (d, J=8.3 Hz, 1H), 5.19 (d, J=5.9 Hz, 1H), 5.10 (s, 1H), 4.96-4.72 (m, 3H), 2.57-2.28 (m, 2H), 2.00 (s, 3H), 1.98 (s, 3H), 1.13 (t, J=7.6 Hz, 3H).

Example 50: N⁴-(2-Ethyl-4-((trifluoromethyl)sulfonyl)phenyl)-N⁴-(pyrimidin-2-ylmethyl)pyrimidine-2,4-diamine

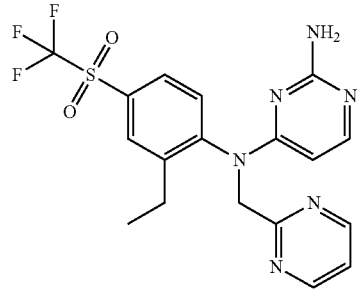 [SMILES: CCc1cc(S(=O)(=O)C(F)(F)F)ccc1N(Cc1ncccn1)c1ccnc(N)n1]

The title compound was prepared using analogous conditions described in Example 21 starting at Step A using 4-amino-3-ethylphenyl trifluoromethanesulfonate (Intermediate 7) and subsequently using 2-(chloromethyl)pyrimidine in place of 1-iodoethane. MS (ESI): mass calcd. for $C_{18}H_{17}F_3N_6O_2S$, 438.4; m/z found, 438.9 [M+H]⁺. 1H NMR (400 MHz, CDCl₃): δ 8.69 (d, J=4.9 Hz, 2H), 8.02 (dd, J=5.3, 3.1 Hz, 2H), 7.91 (dd, J=8.4, 2.2 Hz, 1H), 7.82 (s, 1H), 7.19 (t, J=4.9 Hz, 1H), 6.07-5.35 (m, 2H), 5.16-4.30 (m, 3H), 2.72 (q, J=7.4 Hz, 2H), 1.26 (t, J=7.6 Hz, 3H).

Example 51: N⁴-(2-Cyclobutyl-4-((trifluoromethyl)sulfonyl)phenyl)-N⁴-isopropylpyrimidine-2,4-diamine

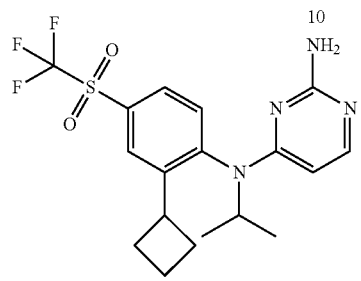 [SMILES: CC(C)N(c1ccnc(N)n1)c1ccc(S(=O)(=O)C(F)(F)F)cc1C1CCC1]

The title compound was prepared using analogous conditions described in Example 21 starting with 2-bromo-4-(trifluoromethylsulfonyl)aniline in place of 2-bromo-4-(pentafluorosulfanyl)aniline and 2-iodopropane in place of 1-iodoethane. MS (ESI): mass calcd. for $C_{18}H_{21}F_3N_4O_2S$, 414.5; m/z found, 415.0 [M+H]⁺. ¹H NMR (400 MHz, CDCl₃): δ 8.25 (d, J=2.2 Hz, 1H), 7.93 (dd, J=8.3, 2.3 Hz, 1H), 7.72 (d, J=6.0 Hz, 1H), 7.34 (d, J=8.3 Hz, 1H), 5.14-4.97 (m, 2H), 4.76 (s, 2H), 3.58 (p, J=8.9 Hz, 1H), 2.19 (s, 3H), 2.08-1.83 (m, 3H), 1.32 (s, 3H), 0.94 (s, 3H).

Example 52: N⁴-Isopropyl-N⁴-(2-methyl-4-(trifluoromethoxy)phenyl)pyrimidine-2,4-diamine

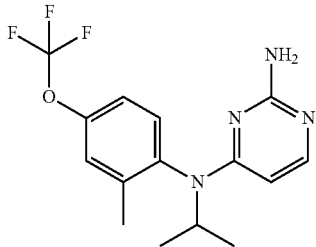 [SMILES: Cc1cc(OC(F)(F)F)ccc1N(c1ccnc(N)n1)C(C)C]

The title compound was prepared using analogous conditions described in Example 19 starting with 2-methyl-4-(trifluoromethoxy)aniline in place of 2-methyl-4-(pentafluorosulfanyl)aniline in step C and 2-iodopropane in place of 1-iodoethane in step D. MS (ESI): mass calcd. for $C_{15}H_{17}F_3N_4O$, 326.3; m/z found, 327.1 [M+H]⁺. ¹H NMR (500 MHz, CD₃OD): δ 7.58 (d, J=6.3 Hz, 1H), 7.37-7.25 (m, 1H), 7.24 (d, J=1.1 Hz, 2H), 5.35-4.96 (m, 2H), 2.17 (s, 3H), 1.31 (d, J=6.6 Hz, 3H), 1.00 (d, J=6.9 Hz, 3H).

Example 53: N⁴-(2-Ethyl-4-(trifluoromethoxy)phenyl)-N⁴-(oxazol-4-ylmethyl)pyrimidine-2,4-diamine

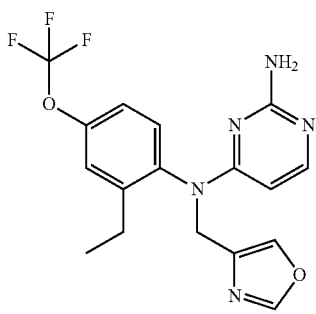 [SMILES: CCc1cc(OC(F)(F)F)ccc1N(Cc1cocn1)c1ccnc(N)n1]

N⁴-(2-bromo-4-(trifluoromethoxy)phenyl)-N⁴-(oxazol-4-ylmethyl)pyrimidine-2,4-diamine (structure not shown) was prepared using analogous conditions described in Example 21. N⁴-(2-bromo-4-(trifluoromethoxy)phenyl)-N⁴-(oxazol-4-ylmethyl)pyrimidine-2,4-diamine was then converted to the title compound using conditions analogous to those described in the synthesis of 2-cyclobutyl-4-(methylsulfonyl)aniline (Intermediate 17). MS (ESI): mass calcd. for $C_{17}H_{16}F_3N_5O_2$, 379.3; m/z found, 380.1 [M+H]⁺. ¹H NMR (400 MHz, CD₃OD): δ 8.11 (d, J=1.0 Hz, 1H), 7.92 (d, J=1.0 Hz, 1H), 7.63 (d, J=6.1 Hz, 1H), 7.33-7.27 (m, 1H), 7.23-7.15 (m, 2H), 5.33-5.24 (broad, 2H), 4.61 (d, J=15.2 Hz, 1H), 2.46 (q, J=7.6 Hz, 2H), 1.12 (t, J=7.6 Hz, 3H).

Example 54: N⁴-(2-Cyclobutyl-4-(methylsulfonyl)phenyl)-N⁴-propylpyrimidine-2,4-diamine

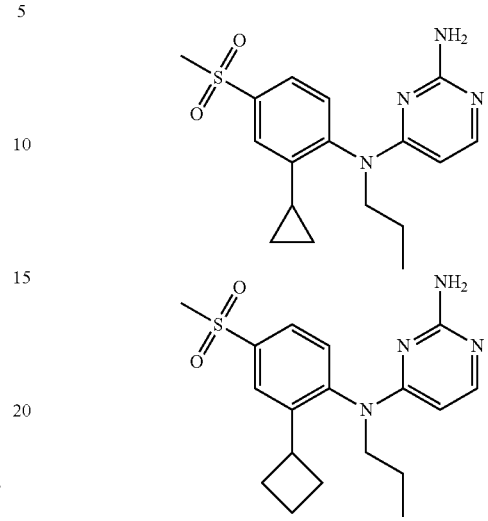

The title compound was prepared using analogous conditions described in Example 21 employing 1-iodopropane in place of 1-iodoethane. MS (ESI): mass calcd. for $C_{18}H_{24}N_4O_2S$, 360.5; m/z found, 361.2 [M+H]⁺. ¹H NMR (500 MHz, CD₃OD): δ 8.10 (s, 1H), 7.89 (dd, J=8.2, 1.7 Hz, 1H), 7.62 (s, 1H), 7.40 (d, J=8.2 Hz, 1H), 5.34 (br s, 1H), 4.13 (s, 1H), 3.68-3.52 (m, 1H), 3.40-3.32 (m, 1H), 3.19 (s, 3H), 2.36-2.26 (m, 1H), 2.25-2.18 (m, 1H), 2.17-2.04 (m, 2H), 2.03-1.94 (m, 1H), 1.91-1.81 (m, 1H), 1.76-1.66 (m, 1H), 1.65-1.57 (m, 1H), 0.92 (t, J=7.4 Hz, 3H).

Example 55: N⁴-(2-Cyclopropyl-4-(methylsulfonyl)phenyl)-N⁴-ethylpyrimidine-2,4-diamine

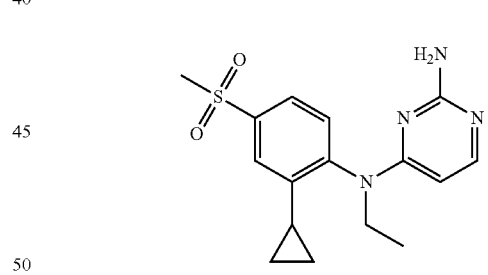

The title compound was prepared using analogous conditions described in Example 21 starting at Step A using 2-cyclopropyl-4-(ethylsulfonyl)aniline (Intermediate 12). MS (ESI): mass calcd. for $C_{16}H_{20}N_4O_2S$, 332.4; m/z found, 333.0 [M+H]⁺. ¹H NMR (400 MHz, CDCl₃): δ 7.78 (dd, J=8.2, 2.2 Hz, 1H), 7.74 (d, J=5.9 Hz, 1H), 7.46 (d, J=2.2 Hz, 1H), 7.31 (d, J=8.2 Hz, 1H), 5.37 (s, 1H), 4.78 (s, 2H), 4.16 (s, 1H), 3.72 (s, 1H), 3.09 (s, 3H), 1.94-1.81 (m, 1H), 1.21 (t, J=7.1 Hz, 3H), 1.09-0.95 (m, 2H), 0.87-0.68 (m, 2H).

Example 56: N⁴-(2-Cyclopropyl-4-(methylsulfonyl)phenyl)-N⁴-propylpyrimidine-2,4-diamine The title compound was prepared using analogous conditions described in Example 21 starting at Step A using 2-cyclopropyl-4-(ethylsulfonyl)aniline (Intermediate 13) and 1-iodopropane in place of 1-iodoethane in Step C. MS (ESI): mass calcd. for $C_{17}H_{22}N_4O_2S$, 346.5; m/z found, 347.0 [M+H]+. $^1H$ NMR (400 MHz, CDCl$_3$): δ 7.77 (dd, J=8.2, 2.2 Hz, 1H), 7.74 (d, J=6.1 Hz, 1H), 7.45 (d, J=2.2 Hz, 1H), 7.31 (d, J=8.2 Hz, 1H), 5.36 (s, 1H), 4.76 (s, 2H), 4.05 (s, 1H), 3.58 (s, 1H), 3.09 (s, 3H), 1.92-1.77 (m, 1H), 1.78-1.53 (m, 2H), 1.12-0.96 (m, 2H), 0.92 (t, J=7.4 Hz, 3H), 0.86-0.67 (m, 2H).

Example 57: N$^4$-(2-Cyclopropyl-4-(ethylsulfonyl)phenyl)-N$^4$-ethylpyrimidine-2,4-diamine

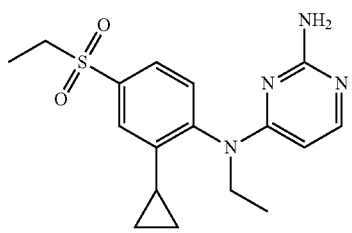 [SMILES: CCN(c1ccnc(N)n1)c1ccc(S(=O)(=O)CC)cc1C1CC1]

The title compound was prepared using analogous conditions described in Example 21 starting at Step A using 2-cyclopropyl-4-(ethylsulfonyl)aniline (Intermediate 12). MS (ESI): mass calcd. for $C_{17}H_{22}N_4O_2S$, 346.5; m/z found, 347.0 [M+H]+. $^1H$ NMR (400 MHz, CDCl$_3$): δ 7.80-7.67 (m, 2H), 7.42 (d, J=2.1 Hz, 1H), 7.30 (d, J=8.2 Hz, 1H), 5.34 (s, 1H), 4.77 (s, 2H), 4.16 (s, 1H), 3.73 (s, 1H), 3.14 (q, J=7.4 Hz, 2H), 1.93-1.80 (m, 1H), 1.32 (t, J=7.4 Hz, 3H), 1.20 (t, J=7.1 Hz, 3H), 1.09-0.94 (m, 2H), 0.86-0.65 (m, 2H).

Example 58: N$^4$-Ethyl-N$^4$-(2-isobutyl-4-(methylsulfonyl)phenyl)pyrimidine-2,4-diamine

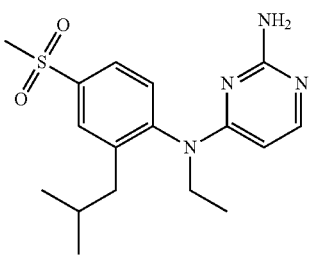 [SMILES: CCN(c1ccnc(N)n1)c1ccc(S(C)(=O)=O)cc1CC(C)C]

The title compound was prepared using analogous conditions described in Example 21 starting at Step A using 2-isobutyl-4-(methylsulfonyl)aniline (Intermediate 14). MS (ESI): mass calcd. for $C_{17}H_{24}N_4O_2S$, 348.5; m/z found, 349.2 [M+H]+. $^1H$ NMR (500 MHz, CDCl$_3$): δ 7.94 (d, J=2.2 Hz, 1H), 7.84 (dd, J=8.2, 2.3 Hz, 1H), 7.73 (d, J=6.0 Hz, 1H), 7.32 (d, J=8.2 Hz, 1H), 4.94 (s, 2H), 4.32 (s, 1H), 3.34 (s, 1H), 3.12 (s, 3H), 2.48-2.38 (m, 3H), 1.99 (dq, J=13.6, 6.8 Hz, 1H), 1.21 (t, J=7.0 Hz, 3H), 0.87 (s, 6H).

Example 59: N$^4$-(2-Cyclobutyl-4-methylsulfonylphenyl)-N$^4$-(oxazol-4-ylmethyl)pyrimidine-2,4-diamine

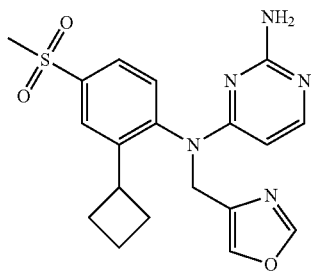 [SMILES: CS(=O)(=O)c1ccc(N(Cc2cocn2)c2ccnc(N)n2)c(C2CCC2)c1]

The title compound was prepared using analogous conditions described in Example 21 using 4-bromomethyloxazole in place of 1-iodoethane, in Step C. MS (ESI): mass calcd. for $C_{19}H_{21}N_5O_3S$, 399.5; m/z found, 400.2 [M+H]+. $^1H$ NMR (500 MHz, CDCl$_3$): δ 8.03 (d, J=2.2 Hz, 1H), 7.88-7.72 (m, 3H), 7.67 (s, 1H), 7.42-7.31 (m, 1H), 5.41 (d, J=15.6 Hz, 1H), 5.33-5.27 (m, 1H), 5.09 (s, 2H), 4.38 (d, J=15.3 Hz, 1H), 3.56-3.44 (m, 2H), 3.13 (s, 3H), 2.48 (s, 1H), 2.25-2.04 (m, 2H), 2.02-1.89 (m, 1H), 1.87-1.76 (m, 1H).

Example 60: N$^4$-(2-Cyclobutyl-4-methylsulfonylphenyl)-N$^4$-(2-methoxyethyl)pyrimidine-2,4-diamine

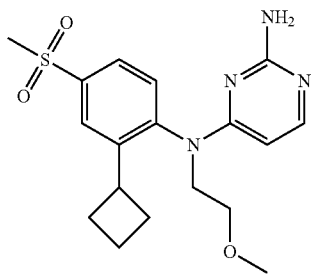 [SMILES: COCCN(c1ccnc(N)n1)c1ccc(S(C)(=O)=O)cc1C1CCC1]

The title compound was prepared using analogous conditions described in Example 21 using 2-bromoethyl methyl ether in place of 1-iodoethane in step C. MS (ESI): mass calcd. for $C_{18}H_{24}N_4O_3S$, 376.5; m/z found, 377.05 [M+H]+. $^1H$ NMR (500 MHz, CDCl$_3$): δ 8.04 (d, J=2.2 Hz, 1H), 7.84 (dd, J=8.2, 2.2 Hz, 1H), 7.72 (d, J=5.9 Hz, 1H), 7.42 (d, J=8.2 Hz, 1H), 5.24 (s, 1H), 4.94 (s, 2H), 4.39 (s, 1H), 3.72-3.66 (m, 1H), 3.61-3.44 (m, 4H), 3.31 (s, 3H), 3.13 (s, 3H), 2.32-2.23 (m, 2H), 2.21-1.91 (m, 4H), 1.88-1.78 (m, 1H).

Example 61: $N^4$-Ethyl-$N^4$-(2-ethyl-4-(methylsulfonyl)phenyl)pyrimidine-2,4-diamine

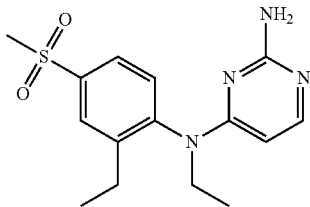 [SMILES: CCc1cc(S(C)(=O)=O)ccc1N(CC)c1ccnc(N)n1]

The title compound was prepared using analogous conditions described in Example 21 starting at Step A using 2-ethyl-4-(methylsulfonyl)aniline (Intermediate 9). MS (ESI): mass calcd. for $C_{15}H_{20}N_4O_2S$, 320.4; m/z found, 320.95 [M+H]$^+$. $^1$H NMR (400 MHz, CDCl$_3$): δ 7.98 (d, J=2.2 Hz, 1H), 7.87 (dd, J=8.3, 2.2 Hz, 1H), 7.73 (d, J=6.0 Hz, 1H), 7.33 (d, J=8.2 Hz, 1H), 5.31 (s, 1H), 5.20 (s, 2H), 4.18 (s, 1H), 3.55 (s, 1H), 3.15 (s, 3H), 2.58 (q, J=7.6 Hz, 2H), 1.21 (q, J=7.5 Hz, 6H).

Example 62: $N^4$-(2-Isobutyl-4-((trifluoromethyl)sulfonyl)phenyl)-$N^4$-(oxazol-4-ylmethyl)pyrimidine-2,4-diamine

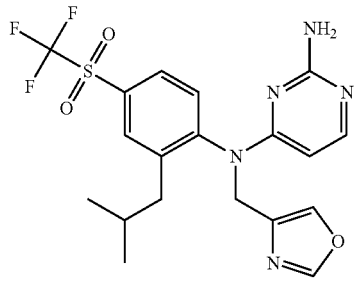 [SMILES: CC(C)Cc1cc(S(=O)(=O)C(F)(F)F)ccc1N(Cc1cocn1)c1ccnc(N)n1]

Step A. $N^4$-(2-(2-methylprop-1-en-1-yl)-4-((trifluoromethyl)sulfonyl)phenyl)-$N^4$-(oxazol-4-ylmethyl)pyrimidine-2,4-diamine The title compound was prepared using analogous conditions described in Example 19 starting with 4-((trifluoromethyl)sulfonyl)aniline in place of 4-(pentafluorosulfanyl)aniline in step A and 2,2-dimethylenylboronic acid pinacol ester in place of 2,4,6-trimethyl-1,3,5,2,4,6-trioxatriborinane in step B. MS (ESI): mass calcd. for $C_{19}H_{18}F_3N_5O_3$, 453.11; m/z found, 453.9 [M+H]$^+$.

Step B: $N^4$-(2-Isobutyl-4-((trifluoromethyl)sulfonyl)phenyl)-$N^4$-(oxazol-4-ylmethyl)pyrimidine-2,4-diamine To a 10 mL microwave vial was charged a solution of N4-(2-(2-methylprop-1-en-1-yl)-4-((trifluoromethyl)sulfonyl)phenyl)-N4-(oxazol-4-ylmethyl)pyrimidine-2,4-diamine (31 mg, 0.068 mmol) in ethanol (1.4 mL). Resulting solution was sparged with nitrogen for 15 min then 10% Pd/C was added. The resulting mixture was gain sparged with nitrogen for 15 min, then hydrogen gas (1 atm) was introduced by sparging mixture for 15 min then maintain under a static 1 atm. The mixture was heated to 50° C. After 3 h, the mixture was sparged with nitrogen to remove the hydrogen gas and the mixture was filtered through a pad of diatomaceous earth such as Celite®. The filter cake was rinsed with copious amount of ethanol and ethyl acetate. The filtrate was concentrated to dryness. Purification by acidic HPLC afforded 13 mg of $N^4$-(2-Isobutyl-4-((trifluoromethyl)sulfonyl)phenyl)-$N^4$-(oxazol-4-ylmethyl)pyrimidine-2,4-diamine. MS (ESI): mass calcd. for $C_{19}H_{20}F_3N_5O_3S$, 455.5; m/z found, 456.0 [M+H]$^+$. $^1$H NMR (400 MHz, CDCl$_3$): δ 7.98 (d, J=2.2 Hz, 1H), 7.91 (dd, J=8.4, 2.3 Hz, 1H), 7.82 (d, J=1.0 Hz, 1H), 7.79 (d, J=6.0 Hz, 1H), 7.68 (d, J=1.0 Hz, 1H), 7.52 (d, J=8.3 Hz, 1H), 5.62-5.21 (m, 2H), 4.91 (s, 2H), 4.57-4.18 (m, 1H), 2.44 (d, J=7.2 Hz, 2H), 1.93 (dp, J=13.6, 6.9 Hz, 1H), 0.84 (d, J=6.6 Hz, 6H).

Example 63: $N^4$-(2-Ethyl-4-((trifluoromethyl)sulfonyl)phenyl)-$N^4$-isopropylpyrimidine-2,4-diamine

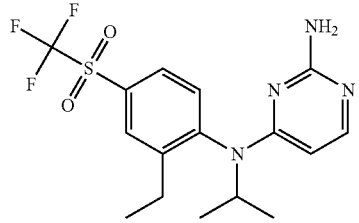 [SMILES: CCc1cc(S(=O)(=O)C(F)(F)F)ccc1N(c1ccnc(N)n1)C(C)C]

The title compound was prepared using analogous conditions described in Example 21 starting at Step A using 4-amino-3-ethylphenyl trifluoromethanesulfonate (Intermediate 7) and 2-iodopropane in place of 1-iodoethane. MS (ESI): mass calcd. for $C_{16}H_{19}F_3N_4O_2S$, 388.4; m/z found, 388.9 [M+H]$^+$. $^1$H NMR (400 MHz, CDCl$_3$): δ 8.06 (d, J=2.2 Hz, 1H), 7.94 (dd, J=8.3, 2.2 Hz, 1H), 7.74 (d, J=6.0 Hz, 1H), 7.39 (d, J=8.3 Hz, 1H), 5.15 (d, J=6.0 Hz, 1H), 5.11-4.96 (m, 1H), 4.81 (s, 2H), 2.60 (q, J=7.6 Hz, 2H), 1.51-0.80 (m, 9H).

Example 64: $N^4$-(2-Ethyl-4-((trifluoromethyl)sulfonyl)phenyl)-$N^4$-(oxazol-4-ylmethyl)pyrimidine-2,4-diamine

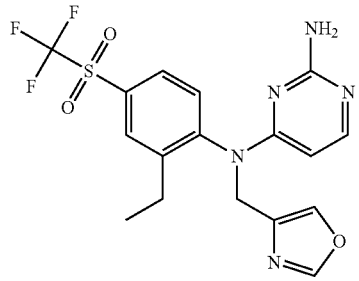 [SMILES: CCc1cc(S(=O)(=O)C(F)(F)F)ccc1N(Cc1cocn1)c1ccnc(N)n1]

The title compound was prepared using analogous conditions described in Example 21 starting at Step A using 4-amino-3-ethylphenyl trifluoromethanesulfonate (Intermediate 7) and 4-bromomethyloxazole in place of 1-iodoethane. MS (ESI): mass calcd. for $C_{17}H_{16}F_3N_5O_3S$, 427.4; m/z found, 427.9 [M+H]$^+$. $^1$H NMR (400 MHz, CDCl$_3$): δ 8.01 (d, J=2.1 Hz, 1H), 7.96-7.88 (m, 1H), 7.84-7.77 (m, 2H), 7.69-7.62 (m, 1H), 7.49 (d, J=8.3 Hz, 1H), 5.34 (s, 1H), 4.83 (s, 2H), 2.57 (q, J=7.6 Hz, 2H), 1.19 (t, J=7.5 Hz, 3H).

Example 65: N$^4$-(2-Ethyl-4-(methylsulfonyl)phenyl)-N$^4$-((6-(trifluoromethyl)pyridin-2-yl)methyl)pyrimidine-2,4-diamine

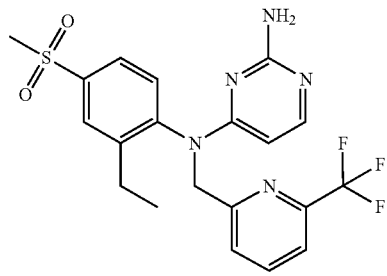 [SMILES: CCc1cc(S(C)(=O)=O)ccc1N(Cc1cccc(C(F)(F)F)n1)c1ccnc(N)n1]

The title compound was prepared using analogous conditions described in Example 21 starting at Step A using 2-ethyl-4-(methylsulfonyl)aniline (Intermediate 9) and 2-(chloromethyl)-6-(trifluoromethyl)pyridine in place of 1-iodoethane. MS (ESI): mass calcd. for $C_{20}H_{20}F_3N_5O_2S$, 451.5; m/z found, 452.2 [M+H]$^+$. $^1$H NMR (500 MHz, CDCl$_3$): δ 7.96 (d, J=2.2 Hz, 1H), 7.90-7.74 (m, 3H), 7.70 (d, J=7.9 Hz, 1H), 7.57 (d, J=7.7 Hz, 1H), 7.45 (d, J=8.3 Hz, 1H), 5.63 (d, J=14.0 Hz, 1H), 5.38 (s, 1H), 5.14 (d, J=3.5 Hz, 2H), 4.70 (d, J=15.7 Hz, 1H), 3.10 (s, 3H), 2.58 (q, J=7.5 Hz, 2H), 1.19 (t, J=7.5 Hz, 3H).

Example 66: N$^4$-(2-Ethyl-4-(methylsulfonyl)phenyl)-N$^4$-(2-methoxyethyl)pyrimidine-2,4-diamine

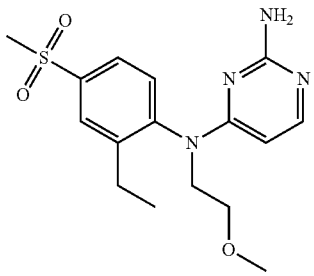 [SMILES: CCc1cc(S(C)(=O)=O)ccc1N(CCOC)c1ccnc(N)n1]

The title compound was prepared using analogous conditions described in Example 21 starting at Step A using 2-ethyl-4-(methylsulfonyl)aniline (Intermediate 9) and 2-bromoethyl methyl ether in place of 1-iodoethane. MS (ESI): mass calcd. for $C_{16}H_{22}N_4O_3S$, 350.4; m/z found, 351.0 [M+H]$^+$. $^1$H NMR (400 MHz, CDCl$_3$): δ 7.95 (d, J=2.2 Hz, 1H), 7.85 (dd, J=8.2, 2.3 Hz, 1H), 7.76-7.68 (m, 1H), 7.43 (d, J=8.2 Hz, 1H), 5.28 (s, 1H), 5.11 (s, 2H), 4.32 (s, 1H), 3.71-3.56 (m, 3H), 3.30 (s, 3H), 3.13 (s, 3H), 2.57 (p, J=7.6 Hz, 2H), 1.22 (t, J=7.6 Hz, 3H).

Example 67: N$^4$-(2-Ethyl-4-(methylsulfonyl)phenyl)-N$^4$-(pyrimidin-4-ylmethyl)pyrimidine-2,4-diamine

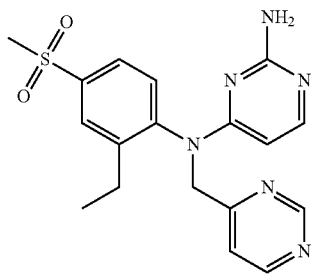 [SMILES: CCc1cc(S(C)(=O)=O)ccc1N(Cc1ccncn1)c1ccnc(N)n1]

The title compound was prepared using analogous conditions described in Example 21 employing starting at Step A using 2-ethyl-4-(methylsulfonyl)aniline (Intermediate 9) and 4-(bromomethyl)pyrimidine hydrobromide in place of 1-iodoethane. MS (ESI): mass calcd. for $C_{18}H_{20}N_6O_2S$, 384.5; m/z found, 385.0 [M+H]$^+$. $^1$H NMR (400 MHz, CDCl$_3$): δ 9.12 (d, J=1.4 Hz, 1H), 8.70 (d, J=5.2 Hz, 1H), 7.97 (d, J=2.2 Hz, 1H), 7.85-7.73 (m, 2H), 7.52-7.43 (m, 2H), 5.57 (d, J=16.8 Hz, 1H), 5.40 (d, J=6.0 Hz, 1H), 5.01 (s, 2H), 4.56 (d, J=17.0 Hz, 1H), 3.10 (d, J=7.1 Hz, 3H), 2.60 (q, J=7.6 Hz, 2H), 1.22 (t, J=7.5 Hz, 3H).

Example 68: N$^4$-(2-Ethyl-4-(methylsulfonyl)phenyl)-N$^4$-(oxazol-4-ylmethyl)pyrimidine-2,4-diamine

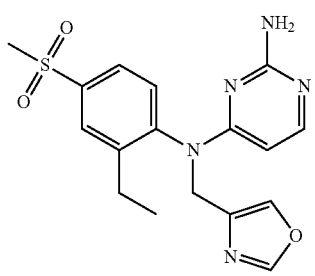 [SMILES: CCc1cc(S(C)(=O)=O)ccc1N(Cc1cocn1)c1ccnc(N)n1]

The title compound was prepared using analogous conditions described in Example 21 starting at Step A using 2-ethyl-4-(methylsulfonyl)aniline (Intermediate 9) and 4-(bromomethyl)oxazole in place of 1-iodoethane. MS (ESI): mass calcd. for $C_{17}H_{19}N_5O_3S$, 373.4; m/z found, 374.0 [M+H]$^+$. $^1$H NMR (500 MHz, CDCl$_3$): δ 7.95 (d, J=2.2 Hz, 1H), 7.87-7.79 (m, 2H), 7.75 (d, J=6.0 Hz, 1H), 7.69 (d, J=1.1 Hz, 1H), 7.34 (d, J=8.2 Hz, 1H), 5.32 (d, J=11.2 Hz, 2H), 5.22 (s, 2H), 4.55 (d, J=15.3 Hz, 1H), 3.12 (s, 3H), 2.54 (q, J=7.6 Hz, 2H), 1.18 (q, J=7.4 Hz, 3H).

Example 69: N⁴-((1H-Pyrazol-5-yl)methyl)-N⁴-(2-cyclobutyl-4-(methylsulfonyl)phenyl)pyrimidine-2,4-diamine

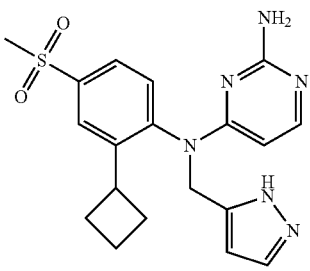 [SMILES: CS(=O)(=O)c1ccc(N(Cc2ccn[nH]2)c2ccnc(N)n2)c(C2CCC2)c1]

The title compound was prepared using analogous conditions described in Example 21 employing 5-(chloromethyl)-1H-pyrazole hydrochloride in place of 1-iodoethane. MS (ESI): mass calcd. for $C_{19}H_{22}N_6O_2S$, 398.5; m/z found, 399.1 [M+H]⁺. ¹H NMR (500 MHz, CDCl₃): δ 8.04 (d, J=2.2 Hz, 1H), 7.80-7.70 (m, 2H), 7.51-7.46 (m, 1H), 7.09-7.03 (m, 1H), 6.14 (s, 1H), 5.42 (d, J=14.5 Hz, 1H), 5.23 (s, 1H), 5.14 (s, 2H), 4.46 (d, J=15.2 Hz, 1H), 3.50-3.39 (m, 1H), 3.12 (s, 3H), 2.21-1.99 (m, 4H), 2.00-1.87 (m, 1H), 1.86-1.75 (m, 1H).

Example 70: N⁴-(2-Cyclobutyl-4-(methylsulfonyl)phenyl)-N⁴-(pyrimidin-4-ylmethyl)pyrimidine-2,4-diamine

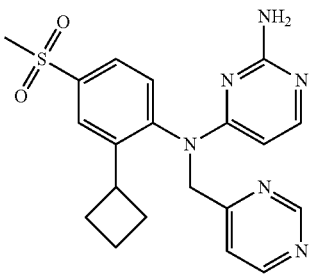 [SMILES: CS(=O)(=O)c1ccc(N(Cc2ccncn2)c2ccnc(N)n2)c(C2CCC2)c1]

The title compound was prepared using analogous conditions described in Example 21 employing 4-(bromomethyl)pyrimidine hydrobromide in place of 1-iodoethane. MS (ESI): mass calcd. for $C_{20}H_{22}N_6O_2S$, 410.5; m/z found, 411.2 [M+H]⁺. ¹H NMR (500 MHz, CDCl₃): δ 9.12 (d, J=1.5 Hz, 1H), 8.70 (d, J=5.2 Hz, 1H), 8.07-7.98 (m, 1H), 7.83-7.74 (m, 2H), 7.50-7.40 (m, 2H), 5.62 (d, J=16.1 Hz, 1H), 5.41-5.37 (m, 1H), 4.91 (s, 2H), 4.42 (d, J=16.5 Hz, 1H), 3.68-3.50 (m, 1H), 3.09 (d, J=18.4 Hz, 3H), 2.28-2.06 (m, 4H), 2.07-1.79 (m, 2H).

Example 71: N⁴-(2-Ethyl-4-(methylsulfonyl)phenyl)-N⁴-isopropylpyrimidine-2,4-diamine

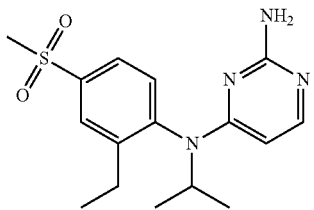 [SMILES: CCc1cc(S(C)(=O)=O)ccc1N(c1ccnc(N)n1)C(C)C]

The title compound was prepared using analogous conditions described in Example 21 starting at Step A using 2-ethyl-4-(methylsulfonyl)aniline (Intermediate 9) and 2-iodopropane in place of 1-iodoethane. MS (ESI): mass calcd. for $C_{16}H_{22}N_4O_2S$, 334.4; m/z found, 335.1 [M+H]⁺. ¹H NMR (500 MHz, CDCl₃): δ 8.00 (d, J=2.2 Hz, 1H), 7.86 (dd, J=8.2, 2.2 Hz, 1H), 7.67-7.62 (m, 1H), 7.30 (d, J=8.2 Hz, 1H), 5.16 (s, 1H), 5.05 (d, J=21.0 Hz, 2H), 3.36 (s, 1H), 3.16 (s, 3H), 2.58 (qd, J=7.6, 4.0 Hz, 2H), 1.33 (d, J=6.6 Hz, 3H), 1.23 (t, J=7.6 Hz, 3H), 0.99 (d, J=6.9 Hz, 3H).

Example 72: N⁴-(2-Isobutyl-4-(methylsulfonyl)phenyl)-N⁴-propylpyrimidine-2,4-diamine

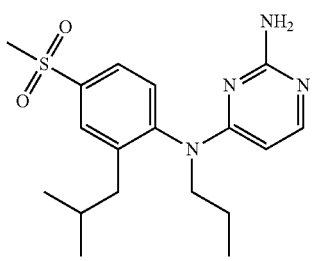 [SMILES: CCCN(c1ccnc(N)n1)c1ccc(S(C)(=O)=O)cc1CC(C)C]

The title compound was prepared using analogous conditions described in Example 21 starting at Step A using 2-isobutyl-4-(methylsulfonyl)aniline (Intermediate 14) and 1-iodopropane in place of 1-iodoethane. MS (ESI): mass calcd. for $C_{18}H_{26}N_4O_2S$, 362.5; m/z found, 363.0 [M+H]⁺. ¹H NMR (400 MHz, CDCl₃): δ 7.94 (d, J=2.2 Hz, 1H), 7.84 (dd, J=8.2, 2.2 Hz, 1H), 7.73 (d, J=6.1 Hz, 1H), 7.33 (d, J=8.2 Hz, 1H), 5.34-5.28 (m, 1H), 5.05 (s, 2H), 4.21 (s, 1H), 3.13 (s, 4H), 2.43 (dd, J=15.5, 7.6 Hz, 2H), 2.05-1.92 (m, 1H), 1.58 (d, J=9.7 Hz, 2H), 0.94-0.83 (m, 9H).

Example 73: N⁴-(2-Ethyl-4-((trifluoromethyl)sulfonyl)phenyl)-N⁴-((6-(trifluoromethyl)pyridin-2-yl)methyl)pyrimidine-2,4-diamine

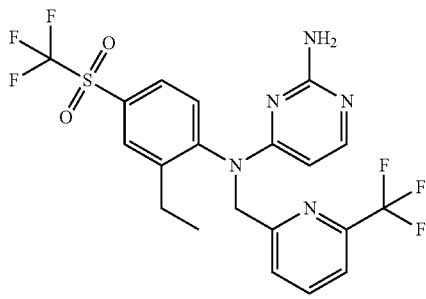 [SMILES: CCc1cc(S(=O)(=O)C(F)(F)F)ccc1N(Cc1cccc(C(F)(F)F)n1)c1ccnc(N)n1]

The title compound was prepared using analogous conditions described in Example 21 starting at Step A using 4-amino-3-ethylphenyl trifluoromethanesulfonate (Intermediate 7) and 2-(chloromethyl)-6-(trifluoromethyl)pyridine in place of 1-iodoethane. MS (ESI): mass calcd. for $C_{20}H_{17}F_6N_5O_2S$, 505.4; m/z found, 505.9 [M+H]⁺. ¹H NMR (400 MHz, CDCl₃): δ 8.02 (d, J=2.2 Hz, 1H), 7.94-7.89 (m, 1H), 7.89-7.83 (m, 1H), 7.83-7.77 (m, 1H), 7.69-7.55 (m, 3H), 5.77-5.23 (m, 2H), 5.00-4.53 (m, 3H), 2.62 (q, J=7.5 Hz, 2H), 1.21 (t, J=7.6 Hz, 3H).

Example 74: N⁴-(2-Ethyl-4-((trifluoromethyl)sulfonyl)phenyl)-N⁴-(pyrimidin-4-ylmethyl)pyrimidine-2,4-diamine

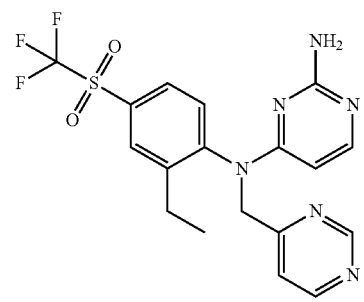 [SMILES: CCc1cc(S(=O)(=O)C(F)(F)F)ccc1N(Cc1ccncn1)c1ccnc(N)n1]

The title compound was prepared using analogous conditions described in Example 21 starting at Step A using 4-amino-3-ethylphenyl trifluoromethanesulfonate (Intermediate 7) and 4-(bromomethyl)pyridine hydrobromide in place of 1-iodoethane. MS (ESI): mass calcd. for $C_{18}H_{17}F_3N_6O_2S$, 438.4; m/z found, 438.9 [M+H]⁺. ¹H NMR (400 MHz, CDCl₃): δ 9.13 (d, J=1.4 Hz, 1H), 8.71 (d, J=5.2 Hz, 1H), 8.04 (d, J=2.1 Hz, 1H), 7.93 (dd, J=8.3, 2.2 Hz, 1H), 7.84 (d, J=5.9 Hz, 1H), 7.66 (d, J=8.3 Hz, 1H), 7.43 (dd, J=5.2, 1.4 Hz, 1H), 5.81-5.18 (m, 2H), 5.07-4.34 (m, 3H), 2.64 (q, J=7.5 Hz, 2H), 1.23 (t, J=7.6 Hz, 3H).

Example 75: N⁴-(2-Ethyl-4-((trifluoromethyl)sulfonyl)phenyl)-N⁴-(2-methoxyethyl)pyrimidine-2,4-diamine

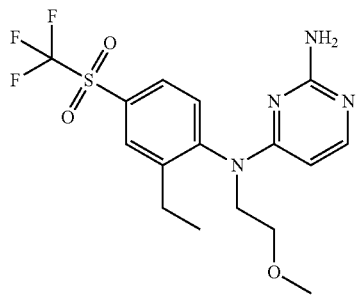 [SMILES: CCc1cc(S(=O)(=O)C(F)(F)F)ccc1N(CCOC)c1ccnc(N)n1]

The title compound was prepared using analogous conditions described in Example 21 starting at Step A using 4-amino-3-ethylphenyl trifluoromethanesulfonate (Intermediate 7) and 2-bromoethyl methyl ether in place of 1-iodoethane. MS (ESI): mass calcd. for $C_{16}H_{19}F_3N_4O_3S$, 404.4; m/z found, 405.0 [M+H]⁺. ¹H NMR (400 MHz, CDCl₃): δ 8.02 (d, J=2.1 Hz, 1H), 7.94 (dd, J=8.2, 2.2 Hz, 1H), 7.77 (d, J=6.0 Hz, 1H), 7.54 (d, J=8.3 Hz, 1H), 5.30 (s, 1H), 4.87 (s, 2H), 4.26 (s, 1H), 3.64 (s, 3H), 3.29 (s, 3H), 2.58 (q, J=7.5 Hz, 2H), 1.22 (t, J=7.4 Hz, 3H).

Example 76: N⁴-(4-((Difluoromethyl)sulfonyl)-2-ethylphenyl)-N⁴-ethylpyrimidine-2,4-diamine

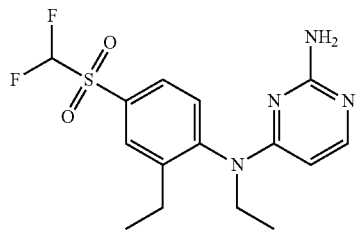 [SMILES: CCc1cc(S(=O)(=O)C(F)F)ccc1N(CC)c1ccnc(N)n1]

The title compound was prepared using analogous conditions described in Example 21 starting at Step A using 4-((difluoromethyl)sulfonyl)-2-ethylaniline (Intermediate 15). MS (ESI): mass calcd. for $C_{15}H_{18}F_2N_4O_2S$, 356.4; m/z found, 357.0 [M+H]⁺. ¹H NMR (400 MHz, CDCl₃): δ 7.99 (d, J=2.2 Hz, 1H), 7.90 (dd, J=8.3, 2.2 Hz, 1H), 7.77 (d, J=6.0 Hz, 1H), 7.39 (d, J=8.3 Hz, 1H), 6.24 (t, J=53.4 Hz, 1H), 5.32 (s, 1H), 4.77 (s, 2H), 4.47-3.38 (m, 2H), 2.59 (q, J=7.6 Hz, 2H), 1.30-1.14 (m, 6H).

Example 77: N⁴-(2-Cyclobutyl-4-(ethylsulfonyl) phenyl)-N⁴-ethylpyrimidine-2,4-diamine

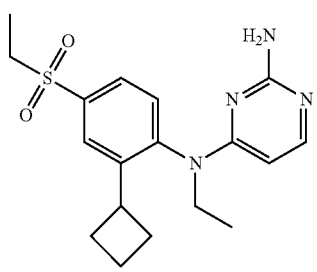 [SMILES: CCN(c1ccnc(N)n1)c1ccc(S(=O)(=O)CC)cc1C1CCC1]

The title compound was prepared using analogous conditions described in Example 21 starting at Step A using 2-cyclobutyl-4-(ethylsulfonyl)aniline (Intermediate 11). MS (ESI): mass calcd. for $C_{18}H_{24}N_4O_2S$, 360.5; m/z found, 361.0 [M+H]⁺. ¹H NMR (400 MHz, CDCl₃): δ 8.03 (d, J=2.2 Hz, 1H), 7.80 (dd, J=8.2, 2.2 Hz, 1H), 7.70 (s, 1H), 7.27 (d, J=8.2 Hz, 1H), 5.23 (s, 1H), 4.90 (s, 2H), 4.37-4.07 (m, 1H), 3.64-3.31 (m, 2H), 3.19 (q, J=7.4 Hz, 2H), 2.41-1.88 (m, 5H), 1.88-1.74 (m, 1H), 1.36 (t, J=7.4 Hz, 3H), 1.17 (t, J=7.1 Hz, 3H).

Example 78: N⁴-(2-Ethoxy-4-fluorophenyl)-N⁴-(imidazo[1,2-a]pyridin-2-ylmethyl)pyrimidine-2,4-diamine

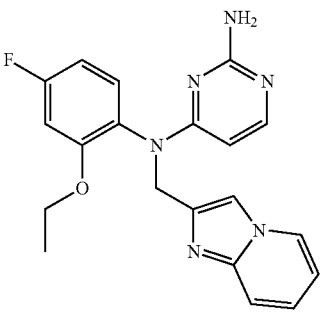 [SMILES: CCOc1cc(F)ccc1N(Cc1cn2ccccc2n1)c1ccnc(N)n1]

MS (ESI): mass calcd. for $C_{20}H_{19}FN_6O$, 378.2; m/z found, 379.1 [M+H]⁺. ¹H NMR (400 MHz, CD₃OD): δ 8.35-8.32 (m, 1H), 7.79 (s, 1H), 7.63 (d, J=6.0 Hz, 1H), 7.50-7.39 (m, 1H), 7.29-7.23 (m, 1H), 7.12 (dd, J=8.5, 6.4 Hz, 1H), 6.93-6.84 (m, 2H), 6.68-6.62 (m, 1H), 5.68-5.38 (m, 2H), 4.78 (d, J=14.9 Hz, 1H), 4.02 (q, J=7.0 Hz, 2H), 1.24 (t, J=7.0 Hz, 3H).

Example 79: N⁴-(2-Ethoxy-4-fluorophenyl)-N⁴-((2-methyloxazol-4-yl)methyl)pyrimidine-2,4-diamine

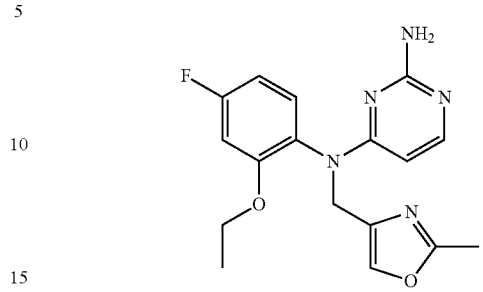

Step A: N-(2-Ethoxy-4-fluorophenyl)-2-(methylthio)pyrimidin-4-amine

The title compound was prepared using analogous conditions described in Example 19 starting with 2-ethoxy-4-fluoroaniline in place of 2-methyl-4-(pentafluorosulfanyl)benzenamine in step C.

Step B: N⁴-(2-Ethoxy-4-fluorophenyl)-N⁴-((2-methyloxazol-4-yl)methyl)pyrimidine-2,4-diamine The title compound was prepared using analogous conditions described in step D of example 102 using N-(2-ethoxy-4-fluorophenyl)-2-(methylthio)pyrimidin-4-amine and 4-(chloromethyl)-2-methyloxazole instead of N-(4-bromo-2-cyclobutylphenyl)-2-methylsulfanylpyrimidin-4-amine and 2-iodopropane, respectively.

Step C: N⁴-(2-Ethoxy-4-fluorophenyl)-N⁴-((2-methyloxazol-4-yl)methyl)pyrimidine-2,4-diamine The title compound was prepared using analogous conditions described in step F-G in example of 102. MS (ESI): mass calcd. for $C_{17}H_{18}FN_5O_2$, 343.1; m/z found, 344.1 [M+H]⁺. ¹H NMR (400 MHz, CDCl₃): δ 7.70 (d, J=6.0 Hz, 1H), 7.40 (s, 1H), 7.06 (dd, J=8.6, 6.3 Hz, 1H), 6.68 (dd, J=10.5, 2.7 Hz, 1H), 6.66-6.59 (m, 1H), 5.52-5.42 (m, 1H), 5.39-5.21 (m, 1H), 4.83 (br s, 2H), 4.46 (d, J=12.9 Hz, 1H), 3.98 (q, J=7.0 Hz, 2H), 2.40 (s, 3H), 1.29 (t, J=7.0 Hz, 3H).

Example 80: 4-((2-Aminopyrimidin-4-yl)(ethyl)amino)-3-cyclobutyl-N-ethyl-N-methylbenzenesulfonamide

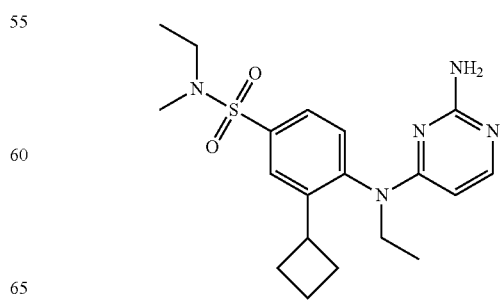

Step A: 3-cyclobutyl-N-methyl-4-((2-(methylthio) pyrimidin-4-yl)amino)benzenesulfonamide The title compound was prepared using analogous conditions described in Example 21, step A starting with 4-amino-3-cyclobutyl-N-methylbenzenesulfonamide (Intermediate 15) in place of 2-cyclobutyl-4-(methylsulfonyl) aniline (Intermediate 17). MS (ESI): mass calcd. for $C_{16}H_{20}N_4O_2S_2$, 364.1; m/z found, 364.9 $[M+H]^+$.

Step B: 3-cyclobutyl-N-ethyl-4-(ethyl(2-(methylsulfonyl)pyrimidin-4-yl)amino)-N-methylbenzenesulfonamide To a 100 mL round bottom flask was charged a solution of 3-cyclobutyl-N-methyl-4-((2-(methylthio)pyrimidin-4-yl)amino)benzenesulfonamide (350 mg, 0.96 mmol) in CAN (48 mL). 1-iodoethane (0.12 mL, 1.44 mmol) and $Cs_2CO_3$ (0.78 g, 2.4 mmol) were added, then the reaction vessel was flushed with $N_2$. The reaction mixture was heated to 70° C. The reaction was run for a total of 1 h, then cooled to room temperature. The reaction mixture was diluted with water, and an oil collected at the bottom of the flask. EtOAc was added and the mixture was extracted, then the organic layer was separated. The aqueous layer was extracted again with EtOAc, and the combined organic layers were dried ($MgSO_4$) and concentrated to dryness. The residue was purified (FCC, 120 g column, 30-40% EtOAc/hexanes), to afford the title compound. MS (ESI): mass calcd. for $C_{19}H_{27}N_5O_2S$, 389.5; m/z found, 390.0 $[M+H]^+$. $^1H$ NMR (500 MHz, $CDCl_3$): δ 7.90 (d, J=2.2 Hz, 1H), 7.76-7.64 (m, 2H), 7.22 (d, J=8.2 Hz, 1H), 6.44 (s, 1H), 5.20 (s, 1H), 4.95 (s, 2H), 4.20 (s, 1H), 3.57-3.37 (m, 2H), 3.19 (q, J=7.1 Hz, 2H), 2.82 (s, 3H), 2.32-2.23 (m, 1H), 2.21-1.89 (m, 4H), 1.22-1.15 (m, 6H).

Example 81: 4-((2-Aminopyrimidin-4-yl)(propyl)amino)-3-cyclobutyl-N-methyl-N-propylbenzenesulfonamide

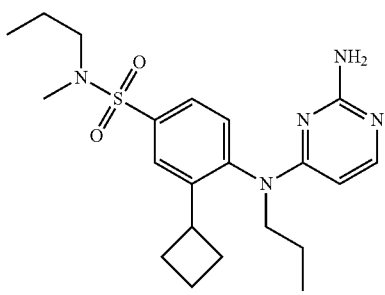 [SMILES: CCCN(c1ccnc(N)n1)c1ccc(S(=O)(=O)N(C)CCC)cc1C1CCC1]

The title compound was prepared using analogous conditions described in Example 80 using 1-iodopropane in place of 1-iodoethane. MS (ESI): mass calcd. for $C_{21}H_{31}N_5O_2S$, 417.6; m/z found, 418.1 $[M+H]^+$. $^1H$ NMR (500 MHz, $CDCl_3$): δ 7.90 (d, J=2.2 Hz, 1H), 7.74-7.65 (m, 2H), 5.25 (s, 2H), 4.14-4.08 (m, 1H), 3.58-3.42 (m, 2H), 3.34-3.25 (m, 1H), 3.07 (t, J=7.2 Hz, 2H), 2.81 (s, 3H), 2.33-2.24 (m, 1H), 2.21-1.90 (m, 4H), 1.87-1.78 (m, 1H), 1.74-1.52 (m, 4H), 0.96 (t, J=7.4 Hz, 1H), 0.90 (t, J=7.4 Hz, 1H).

Example 82: $N^4$-(4-Bromo-2-(trifluoromethoxy)phenyl)-$N^4$-(oxazol-4-ylmethyl)pyrimidine-2,4-diamine

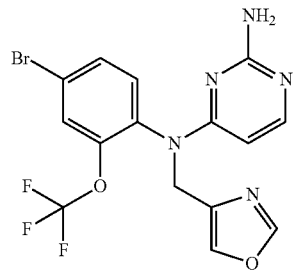 [SMILES: Nc1nccc(N(Cc2cocn2)c2ccc(Br)cc2OC(F)(F)F)n1]

The title compound was prepared using analogous conditions described in Example 19 starting with 4-bromo-2-(trifluoromethoxy)aniline in place of 2-methyl-4-(pentafluorosulfanyl)benzenamine in step C. MS (ESI): mass calcd. for $C_{15}H_{11}BrF_3N_5O_2$, 430.2; m/z found, 429.7 $[M+H]^+$. $^1H$ NMR (600 MHz, DMSO-d6): δ 8.27 (d, J=1.0 Hz, 1H), 8.08 (d, J=0.9 Hz, 1H), 7.76-7.71 (m, 2H), 7.68 (dd, J=8.5, 2.2 Hz, 1H), 7.49 (d, J=8.5 Hz, 1H), 6.20 (s, 2H), 5.51 (br s, 1H), 4.84 (br s, 2H).

Example 83: $N^4$-Ethyl-$N^4$-(4-(methylsulfonyl)-2-(prop-1-en-2-yl)phenyl)pyrimidine-2,4-diamine

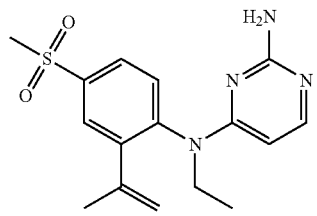 [SMILES: C=C(C)c1cc(S(C)(=O)=O)ccc1N(CC)c1ccnc(N)n1]

Step A: $N^4$-(2-Bromo-4-(methylsulfonyl)phenyl)-$N^4$-ethylpyrimidine-2,4-diamine The title compound was prepared using analogous conditions described in Example 19 starting with 2-bromo-4-(methylsulfonyl)aniline in place of 2-methyl-4-(pentafluorosulfanyl)benzenamine in step C and iodoethane in place of 4-(bromomethyl)oxazole hydrobromide in step D. MS (ESI): mass calcd. for $C_{13}H_{15}BrN_4O_2S$, 371.25; m/z found, 371.0 $[M+H]^+$. $^1H$ NMR (500 MHz, $CDCl_3$): δ 8.29 (d, J=2.1 Hz, 1H), 7.97 (dd, J=8.2, 2.1 Hz, 1H), 7.81 (d, J=6.0 Hz, 1H), 7.45 (d, J=8.2 Hz, 1H), 5.43 (br s, 1H), 4.76 (br s, 2H), 4.26-3.58 (m, 2H), 3.14 (s, 3H), 1.21 (t, J=7.1 Hz, 3H).

Step B: $N^4$-Ethyl-$N^4$-(4-(methylsulfonyl)-2-(prop-1-en-2-yl)phenyl)pyrimidine-2,4-diamine $N^4$-(2-Bromo-4-(methylsulfonyl)phenyl)-$N^4$-ethylpyrimidine-2,4-diamine (200 mg, 0.539 mmol), 2-dicyclohexylphosphino-2',4',6'-triisopropylbiphenyl (10.0 mg, 0.0140 mmol), and 2-isopropenyl-4,4,5,5-tetramethyl-1,3,2-dioxaborolane (453 mg, 2.69 mmol) were added to a microwave vial. The vial was evacuated and purged with $N_2$. THF (2.00 mL) was added via syringe, followed by $K_3PO_4$ (0.5M, 4.00 mL, 2.00 mmol). The entire reaction mixture was evacuated for 30 seconds, then purged with N₂. The mixture was heated at 130° C. for 1 h. The reaction mixture was poured onto saturated aqueous NaHCO₃ (50 mL) then extracted with DCM (2×50 mL). The combined organic layers were dried over anhydrous MgSO₄, filtered, and concentrated to dryness. The residue was purified by FCC to give the title compound (167 mg, 93% yield) as a clear oil. MS (ESI): mass calcd. for $C_{16}H_{20}N_4O_2S$, 332.4; m/z found, 333.1 [M+H]⁺. ¹H NMR (500 MHz, DMSO): δ 7.91 (dd, J=2.31, 8.22 Hz, 1H), 7.87 (d, J=2.29 Hz, 1H), 7.70 (d, J=5.92 Hz, 1H), 7.46 (d, J=8.26 Hz, 1H), 6.12 (s, 2H), 5.45 (s, 1H), 5.21 (s, 1H), 5.05 (s, 1H), 4.67-3.46 (m, 2H), 3.30 (s, 3H), 1.94 (s, 3H), 1.11-1.07 (m, 3H).

Example 84: N⁴-Ethyl-N⁴-(2-isopropyl-4-(methylsulfonyl)phenyl)pyrimidine-2,4-diamine

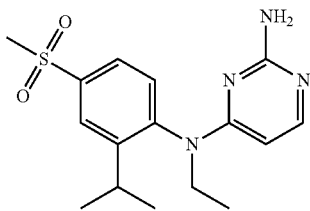 [SMILES: CCN(c1ccnc(N)n1)c1ccc(S(C)(=O)=O)cc1C(C)C]

A solution of N⁴-ethyl-N⁴-(4-(methylsulfonyl)-2-(prop-1-en-2-yl)phenyl)pyrimidine-2,4-diamine (as prepared in Example 83, 150 mg, 0.451 mmol) in MeOH (5 mL) was treated with Pd/C (15 mg) then evacuated and backfilled with hydrogen using a balloon which was attached to the reaction flask. The reaction mixture was stirred for 48 h at room temperature. The mixture was filtered and rinsed with additional MeOH (3 mL). The solution was concentrated to dryness and the residue was purified by FCC to give a clear oil. The oil was dissolved in DCM (1 mL) and treated with hexanes (10 mL). The resulting precipitate was isolated by filtration to give the title compound (26 mg, 17% yield) as a white solid. MS (ESI): mass calcd. for $C_{16}H_{22}N_4O_2S$, 334.4; m/z found, 335.1 [M+H]. ¹H NMR (500 MHz, CDCl₃): δ 8.00 (d, J=2.2 Hz, 1H), 7.82 (dd, J=8.2, 2.2 Hz, 1H), 7.73 (d, J=6.0 Hz, 1H), 7.29 (d, J=8.2 Hz, 1H), 5.29 (br s, 1H), 4.74 (s, 2H), 4.24 (br s, 1H), 3.50-3.38 (m, 1H), 3.12 (s, 3H), 3.08-2.99 (m, 1H), 1.25 (d, J=6.9 Hz, 3H), 1.21 (t, J=7.1 Hz, 3H), 1.15 (d, J=6.8 Hz, 3H).

Example 85: N⁴-(4-Bromo-2-(trifluoromethoxy)phenyl)-N⁴-isopropylpyrimidine-2,4-diamine

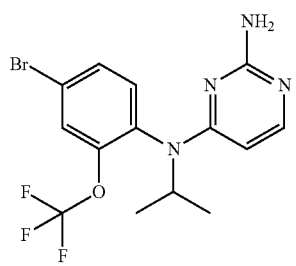 [SMILES: CC(C)N(c1ccnc(N)n1)c1ccc(Br)cc1OC(F)(F)F]

The title compound was prepared using analogous conditions described in Example 19 starting with 4-bromo-2-(trifluoromethoxy)aniline in place of 2-methyl-4-(pentafluorosulfanyl)benzenamine in step C and using 2-iodopropane in place of 4-(bromomethyl)oxazole hydrobromide in step D. MS (ESI): mass calcd. for $C_{14}H_{14}BrF_3N_4O$, 391.2; m/z found, 390.0 [M+H]⁺. ¹H NMR (500 MHz, CDCl₃): δ 7.72 (d, J=6.1 Hz, 1H), 7.58-7.52 (m, 1H), 7.48 (dd, J=8.4, 2.1 Hz, 1H), 7.09 (d, J=8.4 Hz, 1H), 5.28 (d, J=6.0 Hz, 1H), 5.13-4.99 (m, 1H), 4.72 (s, 2H), 1.13 (d, J=6.4 Hz, 6H).

Example 86: N⁴-(4-Bromo-2-isopropoxyphenyl)-N⁴-isopropylpyrimidine-2,4-diamine

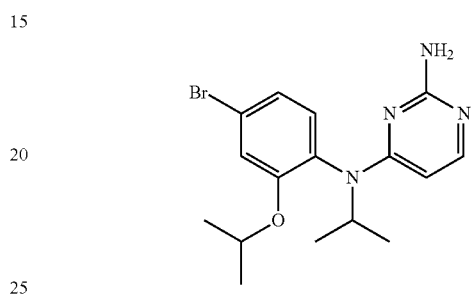

Step A: 4-Bromo-2-isopropoxyaniline

To a 100 mL round-bottomed flask was added NaH (60% in mineral oil, 215 mg, 5.38 mmol) and DMF (55 mL) affording a white suspension. The round-bottomed flask was placed into an ice/water bath and cooled for 10 min. 2-Amino-5-bromophenol (1.00 g, 5.30 mmol) was dissolved in DMF (6 mL) and was added dropwise over 10 min. After 35 min, 2-iodopropane (0.537 mL, 5.32 mmol) was added dropwise slowly to the reaction. After 1.5 h, the reaction was concentrated to remove most of the DMF. The resulting brown solution was diluted with EtOAc (150 mL) and poured onto saturated NaHCO₃ (50 mL). The aqueous layer was removed and the organic layer was washed sequentially with water (50 mL), brine (50 mL), and then dried over anhydrous MgSO₄. The organics were concentrated to dryness to afford a dark brown solid/oil mixture. The residue was purified by FCC (120 g silica gel, eluent=0-15% ethyl acetate/hexanes) to give the title compound (660 mg, 53% yield) as a light brown/red oil.

Step B: N⁴-(4-Bromo-2-isopropoxyphenyl)-N⁴-isopropylpyrimidine-2,4-diamine

The title compound was prepared using analogous conditions described in Example 19 starting with 4-bromo-2-isopropoxyaniline in place of 2-methyl-4-(pentafluorosulfanyl)benzenamine in step C and using 2-iodopropane in place of 4-(bromomethyl)oxazole hydrobromide in step D. MS (ESI): mass calcd. for $C_{16}H_{21}BrN_4O$, 365.3; m/z found, 364.9 [M+H]⁺. ¹H NMR (500 MHz, CDCl₃): δ 7.62 (d, J=6.1 Hz, 1H), 7.11-7.03 (m, 2H), 6.96-6.88 (m, 1H), 5.22 (s, 1H), 5.12 (s, 1H), 4.68 (s, 2H), 4.48 (hept, J=6.0 Hz, 1H), 1.36-0.92 (m, 12H).

Example 87: N⁴-(4-Bromo-2-(2,2,2-trifluoroethoxy)phenyl)-N⁴-isopropylpyrimidine-2,4-diamine

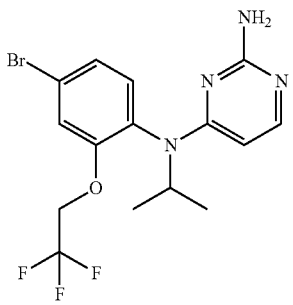 [SMILES: CC(C)N(c1ccnc(N)n1)c1ccc(Br)cc1OCC(F)(F)F]

Step A: 4-Bromo-2-(2,2,2-trifluoroethoxy)aniline

The title compound (343 mg, 24%) was prepared using the method for Example 86, step A, and using 2-iodo-1,1,1-trifluoroethane in place of 2-iodopropane. MS (ESI): mass calcd. for $C_8H_7BrF_3NO$, 270.05; m/z found, 269.8 $[M+H]^+$. ¹H NMR (500 MHz, CDCl₃): δ 7.00 (dd, J=8.4, 2.0 Hz, 1H), 6.89 (d, J=2.1 Hz, 1H), 6.62 (d, J=8.4 Hz, 1H), 4.35 (q, J=8.0 Hz, 2H), 3.91-3.77 (m, 2H).

Step B: N⁴-(4-Bromo-2-(2,2,2-trifluoroethoxy)phenyl)-N⁴-isopropylpyrimidine-2,4-diamine The title compound was prepared using analogous conditions described in Example 19 starting with 4-bromo-2-(2,2,2-trifluoroethoxy)aniline in place of 2-methyl-4-(pentafluorosulfanyl)benzenamine in step C and using 2-iodopropane in place of 4-(bromomethyl)oxazole hydrobromide in step D. MS (ESI): mass calcd. for $C_{15}H_{16}BrF_3N_4O$, 405.2; m/z found, 404.8 $[M+H]^+$. ¹H NMR (500 MHz, CDCl₃): δ 7.68 (d, J=6.1 Hz, 1H), 7.31-7.23 (m, 1H), 7.13 (d, J=2.1 Hz, 1H), 7.01 (d, J=8.3 Hz, 1H), 5.25 (s, 1H), 5.10 (s, 1H), 4.68 (s, 2H), 4.26 (d, J=8.8 Hz, 2H), 1.11 (s, 6H).

Example 88: N⁴-(4-Bromo-2-methylphenyl)-N⁴-isopropylpyrimidine-2,4-diamine

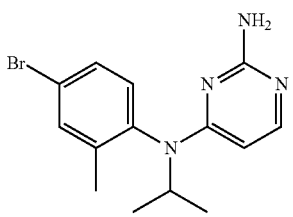 [SMILES: Cc1cc(Br)ccc1N(c1ccnc(N)n1)C(C)C]

The title compound was prepared using analogous conditions described in Example 19 starting with 4-bromo-2-methylaniline in place of 2-methyl-4-(pentafluorosulfanyl)benzenamine in step C and using 2-iodopropane in place of 4-(bromomethyl)oxazole hydrobromide in step D. MS (ESI): mass calcd. for $C_{14}H_{17}BrN_4$, 321.2; m/z found, 321.0 $[M+H]^+$. ¹H NMR (500 MHz, CDCl₃): δ 7.66 (d, J=6.0 Hz, 1H), 7.48 (dd, J=2.2, 0.9 Hz, 1H), 7.42-7.35 (m, 1H), 6.95 (d, J=8.4 Hz, 1H), 5.20-5.00 (m, 2H), 4.70 (s, 2H), 2.10 (s, 3H), 1.26 (d, J=6.6 Hz, 3H), 0.97 (d, J=6.9 Hz, 3H).

Example 89: 4-((2-Aminopyrimidin-4-yl)(isopropyl)amino)-3-(trifluoromethoxy)benzonitrile

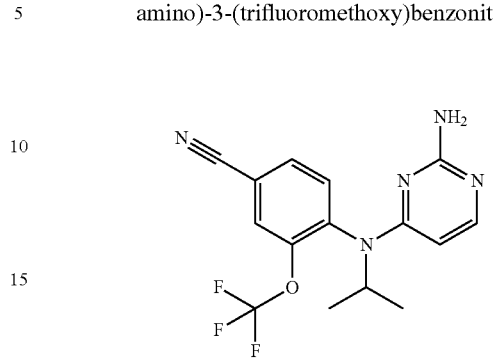

Step A: N-(4-Bromo-2-(trifluoromethoxy)phenyl)-N-isopropyl-2-(methylthio)pyrimidin-4-amine The title compound was prepared using analogous conditions described in Example 19 starting with 4-bromo-2-(trifluoromethoxy)aniline in place of 2-methyl-4-(pentafluorosulfanyl)benzenamine in step C and using 2-iodopropane in place of 4-(bromomethyl)oxazole hydrobromide in step D. MS (ESI): mass calcd. for $C_{15}H_{15}BrF_3N_3OS$, 422.26; m/z found, 422.8 $[M+H]^+$.

Step B: 4-(Isopropyl(2-(methylthio)pyrimidin-4-yl)amino)-3-(trifluoromethoxy)benzonitrile To a 20 mL vial were added N-(4-bromo-2-(trifluoromethoxy)phenyl)-N-isopropyl-2-(methylthio)pyrimidin-4-amine (302 mg, 0.715 mmol), zinc cyanide (190 mg, 1.62 mmol), 2-dicyclohexylphosphino-2',4',6'-triisopropylbiphenyl (81.0 mg, 0.170 mmol), zinc powder (11.0 mg, 0.17 mmol), and Pd₂(dba)₃ (105 mg, 0.115 mmol) as solids. The reaction vessel was then evacuated and backfilled with N₂ twice. DMA (7 mL) was added in one portion and the reaction mixture was heated at 120° C. in a heating block for 1 h. The vial was removed from the heat and allowed to cool to rt. The reaction was diluted with EtOAc (15 mL) and filtered through a pad of diatomaceous earth such as Celite® to remove the insoluble particulates. The cake was rinsed with EtOAc (2×5 mL). The filtrate was washed with saturated NaHCO₃ (20 mL), water (20 mL), brine (20 mL), and dried over anhydrous MgSO₄, filtered and concentrated to dryness. The residue was purified by FCC to give the title compound (221 mg, 84% yield) as a colorless residue. MS (ESI): mass calcd. for $C_{16}H_{15}F_3N_4OS$, 368.38; m/z found, 369.0 $[M+H]^+$.

Step C: 4-((2-Aminopyrimidin-4-yl)(isopropyl)amino)-3-(trifluoromethoxy)benzonitrile The title compound (222 mg) was prepared using analogous conditions described in Example 19, step E starting with 4-(isopropyl(2-(methylthio)pyrimidin-4-yl)amino)-3-(trifluoromethoxy)benzonitrile in place of N-(2-methyl-4-(pentafluorosulfanyl)phenyl)-2-(methylthio)-N-(oxazol-4-ylmethyl)pyrimidin-4-amine. MS (ESI): mass calcd. for $C_{15}H_{14}F_3N_5O$, 337.3; m/z found, 337.9 $[M+H]^+$. ¹H NMR (500 MHz, CDCl₃): δ 7.79 (d, J=6.0 Hz, 1H), 7.70-7.66 (m, 1H), 7.65 (dd, J=8.1, 1.8 Hz, 1H), 7.37 (d, J=8.1 Hz, 1H), 5.37 (d, J=6.0 Hz, 1H), 4.96 (hept, J=6.9 Hz, 1H), 4.72 (s, 2H), 1.17 (d, J=6.7 Hz, 6H).

Example 90: N⁴-(4-(Ethylsulfonyl)-2-(trifluoromethoxy)phenyl)-N⁴-isopropylpyrimidine-2,4-diamine

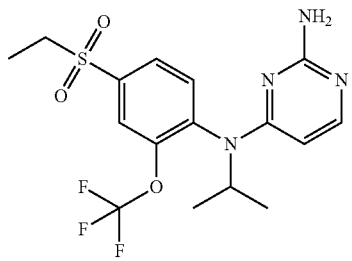 [SMILES: CCS(=O)(=O)c1ccc(N(c2ccnc(N)n2)C(C)C)c(OC(F)(F)F)c1]

To a 20 mL vial were added N⁴-(4-bromo-2-(trifluoromethoxy)phenyl)-N⁴-isopropylpyrimidine-2,4-diamine (Example 20, 194 mg, 0.496 mmol), ethanesulfinic acid, sodium salt (154 mg, 1.33 mmol), and CuI (230 mg, 1.21 mmol). The vial was sealed, evacuated, and backfilled with N₂ (2×). DMSO (5.5 mL), which was degassed using argon for 30 min, was added. The vial was heated at 130° C. on a heating block for 22 h. The reaction was cooled to rt and diluted with EtOAc (50 mL) and poured into water resulting in an inseparable emulsion. The emulsion was filtered through a pad of diatomaceous earth, such as diatomaceous earth such as Celite®, and the biphasic mixture was separated. The aqueous layer was extracted further with EtOAc (50 mL). The combined organics were washed with water (50 mL) and brine (50 mL), dried over anhydrous MgSO₄, and concentrated to dryness. The residue was purified by acidic HPLC to give the title compound (56 mg, 28% yield) as a colorless powder. MS (ESI): mass calcd. for C₁₆H₁₉F₃N₄O₃S, 404.4; m/z found, 405.1 [M+H]⁺. ¹H NMR (500 MHz, CDCl₃): δ 7.93-7.90 (m, 1H), 7.88 (dd, J=8.2, 2.0 Hz, 1H), 7.78 (s, 1H), 7.45 (d, J=8.2 Hz, 1H), 5.36 (d, J=5.9 Hz, 1H), 5.07-4.92 (m, 1H), 4.78 (s, 2H), 3.21 (q, J=7.4 Hz, 2H), 1.37 (t, J=7.4 Hz, 3H), 1.18 (d, J=6.8 Hz, 6H).

Example 91: N⁴-(4-Bromo-2-methylphenyl)-N⁴-(oxazol-4-ylmethyl)pyrimidine-2,4-diamine

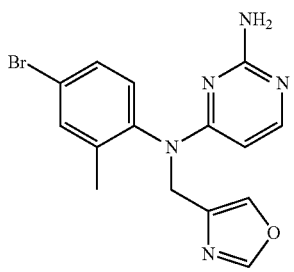 [SMILES: Cc1cc(Br)ccc1N(Cc1cocn1)c1ccnc(N)n1]

The title compound was prepared using analogous conditions described in Example 19 starting with 4-bromo-2-(trifluoromethoxy)aniline in place of 2-methyl-4-(pentafluorosulfanyl)benzenamine in step C. MS (ESI): mass calcd. for C₁₅H₁₄BrN₅O, 360.2; m/z found, 360.1 [M+H]⁺. ¹H NMR (500 MHz, CDCl₃): δ 7.82-7.79 (m, 1H), 7.74 (d, J=6.0 Hz, 1H), 7.63-7.57 (m, 1H), 7.48-7.41 (m, 1H), 7.37-7.31 (m, 1H), 6.95 (d, J=8.4 Hz, 1H), 5.34 (s, 1H), 5.26 (d, J=15.1 Hz, 1H), 4.77 (s, 2H), 4.59 (d, J=15.1 Hz, 1H), 2.05 (s, 3H).

Example 92: N⁴-(4-(Ethylsulfonyl)-2-methylphenyl)-N⁴-(oxazol-4-ylmethyl)pyrimidine-2,4-diamine

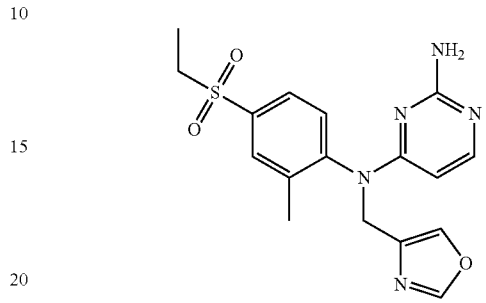

The title compound was prepared using analogous conditions described in Example 90, using N⁴-(4-(ethylsulfonyl)-2-methylphenyl)-N⁴-(oxazol-4-ylmethyl)pyrimidine-2,4-diamine (Example 91) instead of N⁴-(4-bromo-2-(trifluoromethoxy)phenyl)-N⁴-isopropylpyrimidine-2,4-diamine. MS (ESI): mass calcd. for C₁₇H₁₉N₅O₃S, 373.4; m/z found, 373.9 [M+H]⁺. ¹H NMR (500 MHz, CDCl₃): δ 7.84 (d, J=2.1 Hz, 1H), 7.82-7.80 (m, 1H), 7.80-7.73 (m, 2H), 7.64 (s, 1H), 7.35 (d, J=8.2 Hz, 1H), 5.44-5.20 (m, 2H), 4.92 (s, 2H), 4.79-4.52 (m, 1H), 3.15 (q, J=7.4 Hz, 2H), 2.18 (s, 3H), 1.33 (t, J=7.4 Hz, 3H).

Example 93: N⁴-Isopropyl-N⁴-(4-(methylsulfonyl)-2-(trifluoromethyl)phenyl)pyrimidine-2,4-diamine

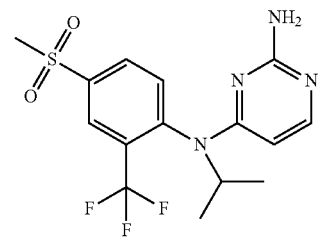 [SMILES: CC(C)N(c1ccnc(N)n1)c1ccc(S(C)(=O)=O)cc1C(F)(F)F]

To a 10 mL vial were added N⁴-(4-bromo-2-(trifluoromethyl)phenyl)-N⁴-isopropylpyrimidine-2,4-diamine (Example 20, 108 mg, 0.288 mmol), sodium methanesulfinate (85.0 mg, 0.710 mmol), and DMSO (0.58 mL). The vial was sealed and heated to 130° C. using a heating block. After 20 h, an additional 2.5 equivalents of sodium methanesulfinate (85.0 mg, 0.710 mmol) was added and the heat was increased to 150° C. for 2 d. The reaction was poured into water (20 mL) and extracted with EtOAc (50 mL). The layers were separated and the organic layer was washed with water, brine, dried over anhydrous MgSO₄, and concentrated to dryness. The residue was purified by acidic HPLC to give the title compound (48 mg, 44% yield) as a white powder. MS (ESI): mass calcd. for C₁₅H₁₇F₃N₄O₂S, 374.4; m/z found, 375.0 [M+H]⁺. ¹H NMR (500 MHz, CDCl₃): δ 8.35 (d, J=2.2 Hz, 1H), 8.21 (dd, J=8.3, 2.2 Hz, 1H), 7.88-7.70 (m, 1H), 7.47 (d, J=8.2 Hz, 1H), 5.32 (d, J=6.0 Hz, 1H), 4.78-4.63 (m, 3H), 3.18 (s, 3H), 1.50-0.99 (m, 6H).

Example 94: $N^4$-Isopropyl-$N^4$-(4-(isopropylsulfonyl)-2-(trifluoromethyl)phenyl)pyrimidine-2,4-diamine

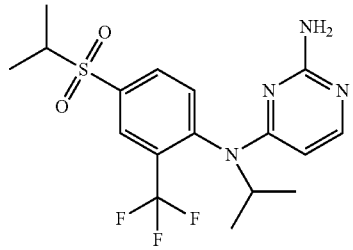 [SMILES: CC(C)N(c1ccnc(N)n1)c1ccc(S(=O)(=O)C(C)C)cc1C(F)(F)F]

To a 10 mL vial were added $N^4$-(4-bromo-2-(trifluoromethyl)phenyl)-$N^4$-isopropylpyrimidine-2,4-diamine (Example 20, 150 mg, 0.40 mmol), the sodium salt of isopropylsulfinic acid (81 mg, 0.62 mmol), and copper(I) trifluoromethanesulfonate benzene complex (45 mg, 0.080 mmol) as solids. The vial was sealed, evacuated, and back-filled with $N_2$ (3×). N,N'-Dimethylethylenediamine (16 mg, 0.18 mmol) was dissolved in degassed DMSO (1.0 mL) and the solution was added to the vial. The vial was heated to 120° C. in a microwave for 2.5 h. The reaction mixture was poured into water (20 mL) and extracted with EtOAc (30 mL). The layers were separated and the aqueous phase was back extracted with EtOAc (25 mL). The combined organics were washed with water (20 mL), brine (20 mL), dried over anhydrous $MgSO_4$, filtered, and concentrated to dryness. The residue was purified by FCC (24 g silica gel, 0-5% 2N $NH_3$-MeOH/DCM as eluent) and by acidic HPLC to give the title compound (42 mg, 26% yield) as a white powder. MS (ESI): mass calcd. for $C_{17}H_{21}F_3N_4O_2S$, 402.4; m/z found, 403.0 $[M+H]^+$. $^1H$ NMR (400 MHz, $CDCl_3$): δ 8.29 (d, J=2.2 Hz, 1H), 8.15 (dd, J=8.2, 2.2 Hz, 1H), 7.77 (d, J=6.0 Hz, 1H), 7.46 (d, J=8.2 Hz, 1H), 5.27 (d, J=6.0 Hz, 1H), 4.81-4.62 (m, 3H), 3.38-3.19 (m, 1H), 1.44-1.32 (m, 9H), 1.16 (d, J=41.0 Hz, 3H).

Example 95: $N^4$-(2-Ethoxy-4-fluorophenyl)-$N^4$-(isoxazol-5-ylmethyl)pyrimidine-2,4-diamine

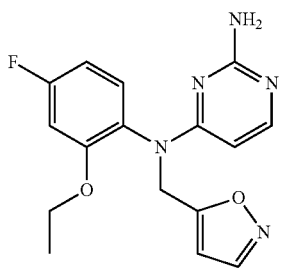 [SMILES: CCOc1cc(F)ccc1N(Cc1ccno1)c1ccnc(N)n1]

Step A: N-(2-Ethoxy-4-fluorophenyl)isoxazole-5-carboxamide

To a 100 mL round-bottomed flask was added, in sequence, isoxazole-5-carboxylic acid (0.34 g, 3.0 mmol), HATU (1.4 g, 3.6 mmol), TEA (0.92 g, 9.1 mmol), DCM (40 mL), and 2-ethoxy-4-fluoroanaline (0.60 g, 3.9 mmol) at 0° C. The reaction mixture was warmed to rt and stirred for 15 h. The reaction mixture was concentrated to dryness and the residue was purified by FCC to give the title compound (0.32 g, 43% yield) as a yellow solid. MS (ESI): mass calcd. for $C_{12}H_{11}FN_2O_3$ 250.1, m/z found 251.1 $[M+H]^+$.

Step B: 2-Ethoxy-4-fluoro-N-(isoxazol-5-ylmethyl)aniline

To a 100 mL round-bottomed flask were added N-(2-ethoxy-4-fluorophenyl)isoxazole-5-carboxamide (0.47 g, 1.9 mmol), $BH_3$ (1M in THF, 30 mL), and THF (30 mL). The reaction was heated at 40° C. for 4 h, and then concentrated to dryness. The residue was dissolved in MeOH (30 mL) and stirred for 5 min. The mixture was concentrated to dryness and the residue was purified by FCC to give the title compound (0.37 g, 83% yield) as a colorless oil. MS (ESI): mass calcd. for $C_{12}H_{13}FN_2O_2$ 236.1, m/z found 237.1 $[M+H]^+$.

Step C: $N^4$-(2-Ethoxy-4-fluorophenyl)-$N^4$-(isoxazol-5-ylmethyl)pyrimidine-2,4-diamine To a 50 mL round-bottomed flask were added 2-ethoxy-4-fluoro-N-(isoxazol-5-ylmethyl)aniline (1.3 mmol), 4-chloropyrimidin-2-amine (200 mg, 1.5 mmol), and i-PrOH (10 mL). Concentrated $H_2SO_4$ (2 drops) was added to the mixture and heated at 60° C. for 15 h. After cooling to rt, the mixture was diluted with water (20 mL), neutralized with a saturated aqueous $NaHCO_3$ (10 mL), and extracted with EtOAc (50 mL). The organic phase was washed with saturated aqueous NaCl (20 mL), dried over anhydrous $Na_2SO_4$, and concentrated under vacuum to dryness. The residue was purified by FCC to give the title compound. MS (ESI): mass calcd. for $C_{16}H_{16}FN_5O_2$ 329.1, m/z found 330.1 $[M+H]^+$. $^1H$ NMR (400 MHz, $CDCl_3$): δ 8.14 (s, 1H), 7.75 (d, J=6.0 Hz, 1H), 7.07 (dd, J=8.6, 6.3 Hz, 1H), 6.70 (dd, J=10.4, 2.6 Hz, 1H), 6.67-6.61 (m, 1H), 6.19 (s, 1H), 5.55-5.40 (m, 2H), 4.88-4.72 (m, 3H), 3.98 (q, J=6.9 Hz, 2H), 1.29 (t, J=7.0 Hz, 3H).

Example 96: $N^4$-((1,3,4-Oxadiazol-2-yl)methyl)-$N^4$-(2-ethoxy-4-fluorophenyl)pyrimidine-2,4-diamine

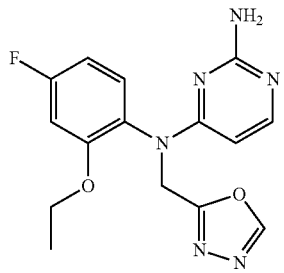 [SMILES: CCOc1cc(F)ccc1N(Cc1nnco1)c1ccnc(N)n1]

Step A: N-(2-Ethoxy-4-fluorophenyl)-2-(methylthio)pyrimidin-4-amine

To a 100 mL round-bottomed flask were added in sequence 2-ethoxy-4-fluoroaniline (0.50 g, 3.2 mmol), 4-chloro-2-(methylthio)pyrimidine (1.2 g, 7.5 mmol), i-PrOH (20 mL), and concentrated HCl (2 drops). The reaction was heated at 80° C. for 4 h then cooled to rt. The reaction mixture was diluted with water (20 mL), neutralized with saturated aqueous NaHCO$_3$, and extracted with EtOAc (3×20 mL). The combined organic phase was washed with saturated aqueous NaCl, dried over anhydrous Na$_2$SO$_4$, and concentrated to dryness under vacuum. The residue was purified by FCC to give the title compound (0.83 g, 93% yield) as a yellow oil. MS (ESI): mass calcd. for C$_{13}$H$_{14}$FN$_3$OS 279.1, m/z found 280.1 [M+H]$^+$.

Step B: Ethyl 2-((2-ethoxy-4-fluorophenyl)(2-(methylthio)pyrimidin-4-yl)amino)acetate To a 50 mL round-bottomed flask were added N-(2-ethoxy-4-fluorophenyl)-2-(methylthio)pyrimidin-4-amine (1.05 g, 3.70 mmol) and DMF (10 mL). The reaction was cooled to 0° C. and NaH (60% in mineral oil, 0.180 g, 4.50 mmol) was added. The reaction was stirred at 0° C. for 10 min, and then 2-bromoacetate (1.00 g, 5.90 mmol) was added and was stirred at rt for 15 h. The reaction was diluted with EtOAc (60 mL), washed with water (2×30 mL) and saturated aqueous NaCl (30 mL), dried over anhydrous Na$_2$SO$_4$, filtered, and concentrated to dryness to give the title compound (1.5 g) as a yellow solid, which was used directly in the next step without further purification. MS (ESI): mass calcd. for C$_{17}$H$_{20}$FN$_3$O$_3$S 365.1, m/z found 366.1 [M+H]$^+$.

Step C: 2-((2-Ethoxy-4-fluorophenyl)(2-(methylthio)pyrimidin-4-yl)amino)acetohydrazide To a 100 mL round-bottomed flask were added ethyl 2-((2-ethoxy-4-fluorophenyl)(2-(methylthio)pyrimidin-4-yl)amino)acetate (1.5 g), NH$_2$NH$_2$·H$_2$O (80%, 5.0 mL), and EtOH (30 mL). The reaction was heated at 80° C. for 15 h, and then cooled to rt. The reaction was concentrated to dryness, diluted with DCM (50 mL), washed with water (2×20 mL) and saturated aqueous NaCl, dried over anhydrous Na$_2$SO$_4$, filtered, and concentrated to dryness under vacuum to give the title compound (1.5 g) as a yellow solid. MS (ESI): mass calcd. for C$_{15}$H$_{18}$FN$_5$O$_2$S 351.12, m/z found 352.1 [M+H]$^+$.

Step D: N-((1,3,4-Oxadiazol-2-yl)methyl)-N-(2-ethoxy-4-fluorophenyl)-2-(methylthio)pyrimidin-4-amine To a 100 mL round-bottomed flask were added 2-((2-ethoxy-4-fluorophenyl)(2-(methylthio)pyrimidin-4-yl)amino)acetohydrazide (1.5 g), TsOH (100 mg, 0.60 mmol), and trimethoxymethane (30 mL). The reaction was heated at reflux for 6 h and then cooled to rt. The reaction was concentrated to dryness, diluted with DCM (60 mL), washed with saturated K$_2$CO$_3$ (30 mL) and saturated aqueous NaCl, dried over anhydrous Na$_2$SO$_4$, filtered, and concentrated to dryness under vacuum. The residue was purified by FCC to give the title compound (0.50 g, 37% yield over 3 steps) as a yellow solid. MS (ESI): mass calcd. for C$_{16}$H$_{16}$FN$_5$O$_2$S 361.1, m/z found 362.1 [M+H]$^+$.

Step E: N$^4$-((1,3,4-Oxadiazol-2-yl)methyl)-N$^4$-(2-ethoxy-4-fluorophenyl)pyrimidine-2,4-diamine The title compound was prepared using analogous conditions described in Example 19, steps E and F, and using N-((1,3,4-oxadiazol-2-yl)methyl)-N-(2-ethoxy-4-fluorophenyl)-2-(methylthio)pyrimidin-4-amine in place of N-(2-methyl-4-(pentafluorosulfanyl)phenyl)-2-(methylthio)-N-(oxazol-4-ylmethyl)pyrimidin-4-amine. MS (ESI): mass calcd. for C$_{16}$H$_{16}$FN$_5$O$_2$ 330.1, m/z found 331.1 [M+H]$^+$. $^1$H NMR (400 MHz, CDCl$_3$): δ 8.35 (s, 1H), 7.76 (d, J=6.0 Hz, 1H), 7.23 (dd, J=8.4, 6.5 Hz, 1H), 6.74-6.63 (m, 2H), 5.70 (d, J=15.5 Hz, 1H), 5.55 (d, J=5.9 Hz, 1H), 4.93-4.80 (m, 3H), 3.99 (dd, J=13.7, 6.8 Hz, 2H), 1.30 (t, J=6.9 Hz, 3H).

Example 97: 4-((2-Aminopyrimidin-4-yl)(isopropyl)amino)-3-propylbenzonitrile

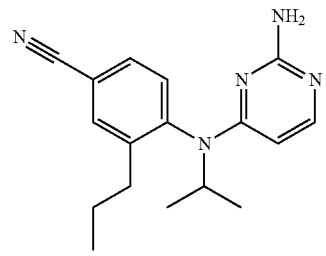 [SMILES: CCCc1cc(C#N)ccc1N(c1ccnc(N)n1)C(C)C]

The title compound was prepared using analogous conditions described in Example 19, beginning at step C using with 4-amino-3-propylbenzonitrile (Intermediate 16) in place of 2-methyl-4-(pentafluorosulfanyl)benzenamine and 2-iodopropane in place of 4-bromomethyloxazole in step D. MS (ESI): mass calcd. for C$_{17}$H$_{21}$N$_5$, 295.4; m/z found, 296.1 [M+H]$^+$. $^1$H NMR (600 MHz, CDCl$_3$): δ 7.69 (d, J=6.0 Hz, 2H), 7.57 (dd, J=8.2, 2.0 Hz, 1H), 7.20 (d, J=8.1 Hz, 1H), 5.14-5.10 (m, 1H), 5.03 (h, J=6.8, 6.3 Hz, 1H), 4.95 (s, 2H), 2.47 (td, J=8.0, 2.8 Hz, 2H), 1.61 (td, J=16.5, 15.0, 7.6 Hz, 2H), 1.32-1.28 (m, 3H), 0.99 (d, J=7.0 Hz, 3H), 0.92 (t, J=7.3 Hz, 3H).

Example 98: (E)-4-((2-Aminopyrimidin-4-yl)(oxazol-4-ylmethyl)amino)-3-(prop-1-en-1-yl)benzamide

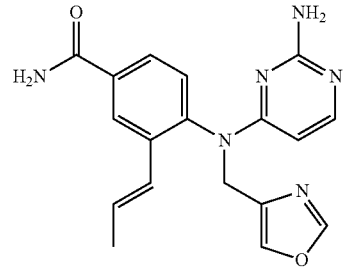 [SMILES: C/C=C/c1cc(C(N)=O)ccc1N(Cc1cocn1)c1ccnc(N)n1]

Step A: 4-((2-Aminopyrimidin-4-yl)(oxazol-4-ylmethyl)amino)-3-chlorobenzonitrile The title compound was prepared using analogous conditions described in Example 19 starting with 4-amino-3-chlorobenzonitrile in place of 2-methyl-4-(pentafluorosulfanyl)aniline in step C. MS (ESI): mass calcd. for C$_{15}$H$_{11}$ClN$_6$O, 326.74; m/z found, 327.0 [M+H]$^+$. $^1$H NMR (500 MHz, CDCl$_3$): δ 7.86-7.79 (m, 4H), 7.66 (d, J=1.1 Hz, 1H), 7.61 (dd, J=8.2, 1.9 Hz, 1H), 7.46 (d, J=8.2 Hz, 1H), 5.45 (s, 1H), 5.13 (d, J=4.1 Hz, 3H).

Step B: (E)-4-((2-Aminopyrimidin-4-yl)(oxazol-4-ylmethyl)amino)-3-(prop-1-en-1-yl)benzamide To a 25 mL vial were added 4-((2-aminopyrimidin-4-yl)(oxazol-4-ylmethyl)amino)-3-chlorobenzonitrile (200 mg, 0.612 mmol), [(E)-prop-1-enyl]boronic acid (131 mg, 1.53 mmol), and 2-dicyclohexylphosphino-2',6'-diisopropoxybiphenyl, palladium(II) phenethylamine chloride (13.0 mg, 0.0180 mmol). The vial was sealed and evacuated and backfilled with $N_2$ (2×). Dioxane (2.08 mL) and degassed phosphate solution (0.5M, 3.67 mL, 1.84 mmol) were added. The resulting mixture was heated to 120° C. in a microwave reactor for 30 min. The reaction was cooled to rt, then diluted with EtOAc (30 mL). The mixture was poured into water (20 mL) and the layers separated. The aqueous layer was extracted with EtOAc (30 mL). The combined organics were washed with brine (20 mL), dried over anhydrous $MgSO_4$, and concentrated to dryness. The residue was purified by HPLC to give the title compound (95 mg, 44% yield). MS (ESI): mass calcd. for $C_{18}H_{18}N_6O_2$, 350.4; m/z found, 351.0 [M+H]$^+$. $^1$H NMR (400 MHz, CDCl$_3$): δ 8.09 (d, J=2.0 Hz, 1H), 7.83 (d, J=1.0 Hz, 1H), 7.66 (dd, J=8.1, 2.1 Hz, 1H), 7.59 (s, 1H), 7.49-7.42 (m, 1H), 7.14 (d, J=8.2 Hz, 1H), 6.40 (dq, J=15.7, 6.6 Hz, 1H), 6.12 (dq, J=15.6, 1.6 Hz, 1H), 5.80 (s, 1H), 5.41 (d, J=17.1 Hz, 2H), 4.65 (d, J=14.9 Hz, 1H), 3.49 (s, 1H), 1.87 (dd, J=6.6, 1.7 Hz, 3H).

Example 99: (E)-4-((2-Aminopyrimidin-4-yl)(isopropyl)amino)-3-(prop-1-en-1-yl)benzonitrile

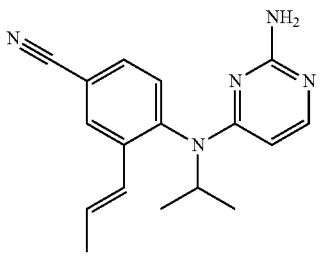 [SMILES: C/C=C/c1cc(C#N)ccc1N(c1ccnc(N)n1)C(C)C]

The title compound was prepared using the method for Example 98 employing 4-((2-aminopyrimidin-4-yl)(isopropyl)amino)-3-bromobenzonitrile in place of 4-((2-aminopyrimidin-4-yl)(oxazol-4-ylmethyl)amino)-3-chlorobenzonitrile. A second compound was also isolated: (E)-4-((2-Aminopyrimidin-4-yl)(isopropyl)amino)-3-(prop-1-en-1-yl)benzamide (Example 100). MS (ESI): mass calcd. for $C_{17}H_{19}N_5$, 293.4; m/z found, 294.2 [M+H]$^+$. $^1$H NMR (400 MHz, CDCl$_3$): δ 7.95 (d, J=1.9 Hz, 1H), 7.70-7.48 (m, 2H), 7.37-7.06 (m, 1H), 6.58-6.09 (m, 4H), 5.39-4.96 (m, 2H), 1.88 (dd, J=6.7, 1.6 Hz, 3H), 1.30 (s, 3H), 0.99 (s, 3H).

Example 100: (E)-4-((2-Aminopyrimidin-4-yl)(isopropyl)amino)-3-(prop-1-en-1-yl)benzamide

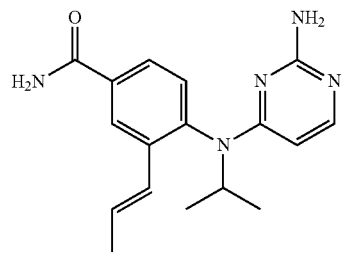 [SMILES: C/C=C/c1cc(C(N)=O)ccc1N(c1ccnc(N)n1)C(C)C]

The title compound was isolated in combination with Example 99. MS (ESI): mass calcd. for $C_{17}H_{21}N_5O$, 311.4; m/z found, 312.0 [M+H]$^+$. $^1$H NMR (500 MHz, CDCl$_3$): δ 8.14 (d, J=2.1 Hz, 1H), 7.72 (dd, J=8.1, 2.1 Hz, 1H), 7.49 (d, J=6.6 Hz, 1H), 7.20-7.09 (m, 1H), 6.54-6.48 (m, 1H), 6.38 (dq, J=15.7, 6.6 Hz, 2H), 6.23 (dq, J=15.8, 1.7 Hz, 1H), 6.14 (d, J=13.9 Hz, 2H), 5.14 (dt, J=20.8, 6.3 Hz, 2H), 1.90-1.81 (m, 3H), 1.29 (d, J=6.5 Hz, 3H), 0.98 (d, J=6.9 Hz, 3H).

Example 101: (E)-N$^4$-(4-Chloro-2-(prop-1-en-1-yl)phenyl)-N$^4$-(oxazol-4-ylmethyl)pyrimidine-2,4-diamine

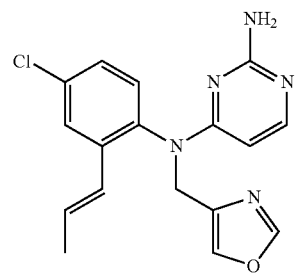 [SMILES: C/C=C/c1cc(Cl)ccc1N(Cc1cocn1)c1ccnc(N)n1]

Step A: N-(4-Chloro-2-iodophenyl)-2-(methylthio)pyrimidin-4-amine

The title compound was prepared using analogous conditions described in Example 19, Step C and D starting with 4-chloro-2-iodoaniline in place of 2-methyl-4-(pentafluorosulfanyl)aniline in step C. MS (ESI): mass calcd. for $C_{11}H_9ClIN_3S$, 377.63; m/z found, 377.8 [M+H]$^+$. $^1$H NMR (400 MHz, CDCl$_3$): δ 8.16 (d, J=5.8 Hz, 1H), 7.87-7.78 (m, 2H), 7.35 (dd, J=8.7, 2.4 Hz, 1H), 6.72 (s, 1H), 6.30 (d, J=5.8 Hz, 1H), 2.53 (s, 3H).

Step B: (E)-N-(4-Chloro-2-(prop-1-en-1-yl)phenyl)-2-(methylthio)pyrimidin-4-amine To a 25 mL vial were added N-(4-chloro-2-iodophenyl)-2-(methylthio)pyrimidin-4-amine (1.0 g, 2.6 mmol), [(E)-prop-1-enyl]boronic acid (210 mg, 2.4 mmol), and chloro-(2-dicyclohexylphosphino-2',6'-diisopropoxy-1,1'-biphenyl)[2-(2-aminoethyl)phenyl]palladium(II)-methyl-t-butyl ether adduct (56.0 mg, 0.077 mmol). The vial was sealed then evacuated and backfilled with $N_2$ (2×). Dioxane (9.0 mL) and degassed phosphate solution (0.5M, 16 mL, 7.9 mmol) were added. The resulting mixture was heated to 120° C. in a microwave reactor for 60 min. The reaction was cooled to rt, then diluted with EtOAc (30 mL). The mixture was poured into water (20 mL) and the layers separated. The aqueous layer was extracted further with EtOAc (30 mL). The combined organics were washed with brine (20 mL), dried over anhydrous $MgSO_4$, and concentrated to dryness. The residue was purified by FCC to give the title compound (500 mg, 65% yield). MS (ESI): mass calcd. for $C_{14}H_{14}ClN_3S$, 291.80; m/z found, 292.0 [M+H]$^+$. $^1$H NMR (500 MHz, CDCl$_3$): δ 8.06 (d, J=5.9 Hz, 1H), 7.47 (d, J=2.4 Hz, 1H), 7.37-7.26 (m, 1H), 7.20 (ddd, J=8.4, 3.7, 2.3 Hz, 1H), 6.75 (s, 1H), 6.41 (dq, J=15.6, 1.7 Hz, 1H), 6.31-6.16 (m, 1H), 6.08 (d, J=5.9 Hz, 1H), 2.52 (d, J=5.7 Hz, 3H), 1.86 (dd, J=6.6, 1.7 Hz, 3H).

Step C: (E)-N⁴-(4-Chloro-2-(prop-1-en-1-yl)phenyl)-N⁴-(oxazol-4-ylmethyl)pyrimidine-2,4-diamine The title compound was prepared using the method for Example 19, steps E-F, and using (E)-N-(4-chloro-2-(prop-1-en-1-yl)phenyl)-2-(methylthio)pyrimidin-4-amine in place of N-(2-methyl-4-(pentafluorosulfanyl)phenyl)-2-(methylsulfonyl)-N-(oxazol-4-ylmethyl) pyrimidin-4-amine in step E. MS (ESI): mass calcd. for $C_{17}H_{16}ClN_5O$, 341.8; m/z found, 342.1 [M+H]⁺. ¹H NMR (500 MHz, CDCl₃): δ 7.79 (d, J=1.0 Hz, 1H), 7.72 (d, J=6.0 Hz, 1H), 7.60-7.52 (m, 2H), 7.17 (dd, J=8.4, 2.5 Hz, 1H), 6.96 (d, J=8.4 Hz, 1H), 6.31-6.10 (m, 2H), 5.39-5.28 (m, 2H), 5.02 (s, 2H), 4.53 (d, J=15.3 Hz, 1H), 1.81 (dd, J=6.4, 1.5 Hz, 3H).

Example 102: N⁴-(2-Cyclobutyl-4-(isopropylsulfonyl)phenyl)-N⁴-isopropylpyrimidine-2,4-diamine

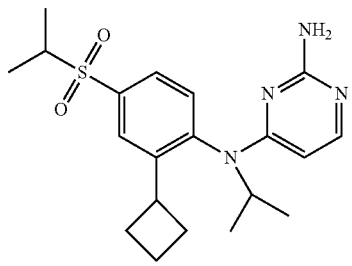 [SMILES: CC(C)N(c1ccnc(N)n1)c1ccc(S(=O)(=O)C(C)C)cc1C1CCC1]

Step A: 2-Cyclobutylaniline

To a round-bottomed flask were added 2-bromoaniline (10.3 g, 58.4 mmol), bis(tri-tert-butylphosphine)palladium (0) (1.79 g, 52.6 mmol), and THF (195 mL). The reaction was stirred and purged with N₂ gas for 30 min. Cyclobutylzinc bromide (105 mL, 52.6 mmol) was added by syringe to the reaction mixture and heated at 50° C. for 20 h. After cooling to room temperature, the reaction was then poured onto saturated aqueous NH₄Cl and EtOAc. The layers were separated and aqueous layer was extracted further with EtOAc. The combined organic layers were washed with brine, dried over MgSO₄, filtered, and concentrated to dryness. The residue was purified by FCC to yield the title compound as a brown oil (3.28 g, 38% yield).

Step B: 4-Bromo-2-cyclobutylaniline

To a round-bottomed flask was added 2-cyclobutylaniline (4.75 g, 32.3 mmol), followed by ammonium acetate (250 mg, 3.23 mmol) and ACN (160 mL). The reaction mixture was stirred in an ice bath. Next, N-bromosuccinimide (5.80 g, 32.3 mmol) was added slowly and stirred for 15 min at 0° C. The reaction was quenched by the addition of water and concentrated to dryness. The aqueous layer was extracted with DCM (2×). The combined organic layers were dried over anhydrous Na₂SO₄, filtered, and concentrated to dryness. The residue was purified by FCC to yield the title compound as a red oil (5.76 g, 78.9% yield).

Step C: N-(4-Bromo-2-cyclobutylphenyl)-2-methylsulfanylpyrimidin-4-amine

To a round-bottomed flask were added 4-bromo-2-cyclobutylaniline (5.76 g, 25.5 mmol), p-toluenesulfonic acid monohydrate (0.984 g, 5.09 mmol), and i-PrOH (25.5 mL) with stirring. The reaction was heated to 50° C. to dissolve all reagents, then 4-chloro-2-(methylthio)pyrimidine (3.17 mL, 26.7 mmol) was added. The reaction was stirred at 50° C. overnight. The reaction was quenched by the addition of water and extracted with DCM (2×), separating the organic layers. The combined organic phases were dried over anhydrous Na₂SO₄, filtered, and concentrated to dryness to yield the title compound as a brown oil (10.2 g, 114% yield).

Step D: N-(4-Bromo-2-cyclobutylphenyl)-N-isopropyl-2-methylsulfanylpyrimidin-4-amine To a round-bottomed flask were added N-(4-bromo-2-cyclobutylphenyl)-2-methylsulfanylpyrimidin-4-amine (5.34 g, 15.2 mmol), cesium carbonate (15.0 g, 45.7 mmol), 2-iodopropane (3.00 mL, 30.5 mmol), and ACN (50.0 mL) and the resulting reaction mixture was heated at 50° C. for 2 h. After 2 h, additional 2-iodopropane (1.00 mL, 10.2 mmol) was added and the resulting reaction mixture heated at 65° C. for an additional 40 min. The reaction mixture was quenched by the addition of water and extracted with DCM (2×). The combined organic layers were dried over anhydrous Na₂SO₄, filtered, and concentrated to dryness. The residue was purified by FCC to yield the title compound as an amber oil (5.81 g, 97.2% yield).

Step E: N-(2-Cyclobutyl-4-isopropylsulfanylphenyl)-N-isopropyl-2-methylsulfanylpyrimidin-4-amine To a 20 mL microwave reaction vial were added N-(4-bromo-2-cyclobutylphenyl)-N-isopropyl-2-methylsulfanylpyrimidin-4-amine (270 mg, 0.70 mmol) and THF (2.3 mL). The reaction vial was placed into a dry ice/i-PrOH bath and cooled to ~−73° C. for 15 min. With stirring, n-butyllithium (2.5M in hexanes, 0.30 mL, 0.77 mmol) was then added dropwise over 5 min and stirred at −73° C. for an additional 10 min, then isopropyl disulfide (0.12 mL, 0.77 mmol) was added in one portion. The reaction was allowed to warm slowly to rt. The reaction was stirred at room temperature for 3 h, then quenched by pouring into a solution of water and extracted with EtOAc (2×). The combined organic layer was washed with brine, dried over anhydrous MgSO₄, filtered and concentrated to dryness. The residue was purified by FCC to yield the title compound as a colorless oil (135 mg, 49.9% yield).

Step F: N⁴-(2-Cyclobutyl-4-(isopropylsulfonyl)phenyl)-N⁴-isopropylpyrimidine-2,4-diamine The title compound was prepared using analogous conditions described in Example 19 using N-(2-cyclobutyl-4-isopropylsulfanylphenyl)-N-isopropyl-2-methylsulfanylpyrimidin-4-amine in place of N-(2-methyl-4-(pentafluorosulfanyl)phenyl)-2-(methylsulfonyl)-N-(oxazol-4-ylmethyl)pyrimidin-4-amine in step E and an increased amount of mCPBA (418 mg, 2.42 mmol, 7 eq). MS (ESI): mass calcd. for $C_{20}H_{28}N_4O_2S$, 388.5; m/z found, 389.0 [M+H]⁺. ¹H NMR (500 MHz, CDCl₃): δ 8.13 (d, J=2.2 Hz, 1H), 7.77 (dd, J=8.1, 2.2 Hz, 1H), 7.67 (d, J=6.0 Hz, 1H), 7.22 (d, J=8.2 Hz, 1H), 5.23-4.91 (m, 2H), 4.74 (s, 2H), 3.65-3.51 (m, 1H), 3.32-3.19 (m, 1H), 2.27-2.07 (m, 3H), 2.07-1.79 (m, 3H), 1.36 (d, J=6.7 Hz, 6H), 1.29 (d, J=6.5 Hz, 3H), 0.91 (d, J=6.9 Hz, 3H).

Example 103: N⁴-(4-Fluoro-2-(trifluoromethoxy)phenyl)-N⁴-isopropylpyrimidine-2,4-diamine

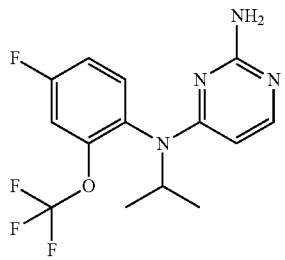 [SMILES: CC(C)N(c1ccnc(N)n1)c1ccc(F)cc1OC(F)(F)F]

Step A: 4-Fluoro-1-nitro-2-(trifluoromethoxy)benzene

To a 100 mL round-bottomed flask were added concentrated H₂SO₄ (25 mL), fuming HNO₃ (25 mL), and 1-fluoro-3-(trifluoromethoxy)benzene (9.0 g, 50 mmol) at −10° C. in sequence. The mixture was stirred at rt for 30 min then poured onto ice and extracted with EtOAc (3×20 mL). The combined organic layers were washed with saturated aqueous NaHCO₃ solution (30 mL), brine (30 mL), dried over anhydrous Na₂SO₄, concentrated to dryness, and purified by FCC to give the title compound as a pale-yellow oil (0.50 g). ¹H NMR (300 MHz, CDCl₃): δ 8.21-8.14 (m, 1H), 7.21-7.12 (m, 2H).

Step B: 4-Fluoro-2-(trifluoromethoxy)benzenamine

The title compound was prepared using analogous conditions described in the preparation of Intermediate 3 using 4-fluoro-1-nitro-2-(trifluoromethoxy)benzene in place of 2-ethoxy-4-fluoro-1-nitrobenzene. MS (ESI): mass calcd. for C₇H₅F₄NO, 195.03, m/z found 196.1 [M+H]⁺.

Step C: N-(4-Fluoro-2-(trifluoromethoxy)phenyl)-2-(methylthio)pyrimidin-4-amine To a 50 mL round-bottomed flask were added 4-fluoro-2-(trifluoromethoxy)benzenamine (0.39 g, 2.0 mmol), 2-chloro-4-(methylthio)pyrimidine (0.39 g, 2.4 mmol), concentrated HCl (0.25 mL), and i-PrOH (10 mL). The mixture was heated at 80° C. for 15 h, then neutralized with saturated aqueous NaHCO₃ solution (5 mL) and concentrated to dryness. The residue was diluted with water (10 mL) and extracted with EtOAc (3×10 mL). The combined organic layers were washed with brine (10 mL), dried over anhydrous Na₂SO₄, concentrated to dryness, and purified by FCC to give the title compound as a pale-yellow oil (0.59 g). MS (ESI): mass calcd. for C₁₂H₉F₄N₃OS, 319.04, m/z found 320.0 [M+H]⁺.

Step D: N-(4-Fluoro-2-(trifluoromethoxy)phenyl)-N-isopropyl-2-(methylthio)pyrimidin-4-amine To a 50 mL round-bottomed flask were added N-(4-fluoro-2-(trifluoromethoxy)phenyl)-2-(methylthio)pyrimidin-4-amine (0.59 g, 1.8 mmol) and DMF (10 mL). To the mixture was added NaH (60% in mineral oil, 0.14 g, 3.6 mmol) at 0° C. The mixture was stirred at 0° C. for 30 min, then 2-iodopropane (0.46 g, 2.7 mmol) was added. The mixture was stirred at rt for 15 h. The mixture was quenched with water (20 mL) and extracted with EtOAc (3×20 mL). The combined organic layers were washed with water (20 mL) and saturated aqueous NaCl solution (20 mL), dried over anhydrous Na₂SO₄, and concentrated to dryness. The residue was purified by FCC to give the title compound as an off-white solid (0.54 g). MS (ESI): mass calcd. for C₁₅H₁₅F₄N₃OS, 361.09, m/z found 362.0 [M+H]⁺.

Step E: N-(4-Fluoro-2-(trifluoromethoxy)phenyl)-N-isopropyl-2-(methylsulfonyl)pyrimidin-4-amine To a 50 mL round-bottomed flask were added N-(4-fluoro-2-(trifluoromethoxy)phenyl)-N-isopropyl-2-(methylthio)pyrimidin-4-amine (0.54 g, 1.5 mmol), MeOH (5 mL), and water (5 mL). The mixture was cooled to 0° C., and then Oxone (1.8 g, 3.0 mmol) was added. The mixture was stirred at rt for 3 h, then saturated aqueous NaHCO₃ solution (5.0 mL) was added and the mixture extracted with EtOAc (3×10 mL). The combined organic layers were washed with saturated aqueous NaCl solution (10 mL), dried over anhydrous Na₂SO₄, and concentrated to dryness. The residue was purified by FCC to give the title compound as a pale-yellow oil (0.28 g). MS (ESI): mass calcd. for C₁₅H₁₅F₄N₃O₃S, 393.08, m/z found 394.1 [M+H]⁺.

Step F: N⁴-(4-Fluoro-2-(trifluoromethoxy)phenyl)-N⁴-isopropylpyrimidine-2,4-diamine To a 25 mL microwave tube were added N-(4-fluoro-2-(trifluoromethoxy)phenyl)-N-isopropyl-2-(methylsulfonyl)pyrimidin-4-amine (0.28 g, 0.71 mmol), i-PrOH (4.0 mL), and NH₄OH (6.0 mL). The mixture was heated at 140° C. for 40 min in a microwave reactor. After cooling to rt, the reaction mixture was concentrated to dryness and the residue was purified by FCC to give the title compound as a yellow solid (0.12 g). MS (ESI): mass calcd. for C₁₄H₁₄F₄N₄O, 330.28, m/z found 331.1 [M+H]⁺. ¹H NMR (400 MHz, CDCl₃): δ 7.72 (d, J=6.1 Hz, 1H), 7.21 (t, J=8.6 Hz, 1H), 7.12 (d, J=9.5 Hz, 2H), 5.31 (d, J=5.9 Hz, 1H), 5.25-5.11 (m, 1H), 4.83 (brs, 2H), 1.13 (d, J=6.7 Hz, 6H).

Example 104: N⁴-((2H-1,2,3-Triazol-4-yl)methyl)-N⁴-(2-ethoxy-4-fluorophenyl)pyrimidine-2,4-diamine

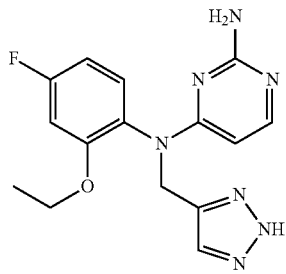 [SMILES: CCOc1cc(F)ccc1N(Cc1cn[nH]n1)c1ccnc(N)n1]

Step A: N-(2-Ethoxy-4-fluorophenyl)-2-(methylthio)-N-(prop-2-ynyl)pyrimidin-4-amine To a 50 mL round-bottomed flask were added N-(2-ethoxy-4-fluorophenyl)-2-(methylthio)pyrimidin-4-amine (as prepared in Example 96, step A) 1.0 g, 3.6 mmol) and DMF (10 mL). The mixture was cooled to 0° C. and NaH (60% in mineral oil, 170 mg, 4.3 mmol) was added. The mixture was stirred at 0° C. for 10 min and then 3-bromoprop-1-yne (650 mg, 5.4 mmol) was added dropwise and the resulting reaction mixture was stirred at rt for 2 h. The mixture was diluted with EtOAc (50 mL), washed with water (3×30 mL) and brine (30 mL), dried over anhydrous Na$_2$SO$_4$, filtered, and concentrated to dryness. The residue was purified by FCC to give the title compound (1.0 g, 87% yield) as a brown oil. MS (ESI): mass calcd. for C$_{16}$H$_{16}$FN$_3$OS 317.10, m/z found 318.0 [M+H]$^+$.

Step B: N-((2H-1,2,3-Triazol-4-yl)methyl)-N-(2-ethoxy-4-fluorophenyl)-2-(methylthio)pyrimidin-4-amine To a 100 mL round-bottomed flask were added formalin (25%, 5.0 mL), AcOH (0.92 g, 15 mmol), and dioxane (30 mL). The solution was cooled to 0° C. and NaN$_3$ (1.0 g, 15 mmol) was added. The mixture was stirred at 0° C. for 15 min and then N-(2-ethoxy-4-fluorophenyl)-2-(methylthio)-N-(prop-2-ynyl)pyrimidin-4-amine (1.1 g, 3.5 mmol) was added and was stirred at 0° C. for another 20 min. CuSO$_4$ (100 mg, 0.63 mmol) and L-ascorbic acid sodium salt (500 mg, 2.7 mmol) were added and stirred at rt for 15 h. The reaction mixture was filtered and concentrated to dryness. The residue was purified by FCC to give title compound (0.60 g, 47% yield) as a colorless oil. MS (ESI): mass calcd. for C$_{16}$H$_{17}$FN$_6$OS 360.12, m/z found 361.1 [M+H]$^+$.

Step C: N$^4$-((2H-1,2,3-Triazol-4-yl)methyl)-N$^4$-(2-ethoxy-4-fluorophenyl)pyrimidine-2,4-diamine The title compound was prepared using analogous conditions described in Example 19, step E and F starting with N-((2H-1,2,3-triazol-4-yl)methyl)-N-(2-ethoxy-4-fluorophenyl)-2-(methylthio)pyrimidin-4-amine in place of N-(2-methyl-4-(pentafluorosulfanyl)phenyl)-2-(methylthio)-N-(oxazol-4-ylmethyl)pyrimidin-4-amine. MS (ESI): mass calcd. for C$_{15}$H$_{16}$FN$_7$O, 329.1, m/z found 330.1 [M+H]$^+$. $^1$H NMR (400 MHz, CD$_3$OD): δ 7.76 (s, 1H), 7.62 (d, J=6.2 Hz, 1H), 7.08 (dd, J=8.7, 6.2 Hz, 1H), 6.90 (dd, J=10.8, 2.8 Hz, 1H), 6.71 (td, J=8.4, 2.7 Hz, 1H), 5.43 (s, 1H), 5.31 (d, J=15.5 Hz, 1H), 4.98-4.87 (m, 1H), 3.98 (q, J=7.0 Hz, 2H), 1.23 (t, J=7.0 Hz, 3H).

Example 105: N$^4$-Ethyl-N$^4$-(4-(methylsulfonyl)-2-propylphenyl)pyrimidine-2,4-diamine

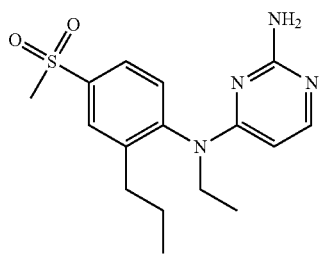 [SMILES: CCCc1cc(S(C)(=O)=O)ccc1N(CC)c1ccnc(N)n1]

Step A: N$^4$-Ethyl-N$^4$-(4-(methylsulfonyl)-2-(prop-1-enyl)phenyl)pyrimidine-2,4-diamine To a 100 mL round-bottomed flask were added N$^4$-(2-bromo-4-(methylsulfonyl)phenyl)-N$^4$-ethylpyrimidine-2,4-diamine hydrochloride (as prepared in Example 83, step A, 160 mg, 0.392 mmol), prop-1-enylboronic acid (50.0 mg, 0.580 mmol), Cs$_2$CO$_3$ (350 mg, 1.07 mmol), Pd(PPh$_3$)$_4$ (50.0 mg, 0.0430 mmol), dioxane (30 mL), and water (10 mL). The reaction mixture was degassed, back filled with Argon and heated at 100° C. for 15 h. After cooling to rt, the reaction mixture was diluted with EtOAc (30 mL), washed with saturated aqueous NaCl (30 mL), dried over anhydrous Na$_2$SO$_4$, filtered, and concentrated to dryness. The residue was purified by FCC to give title compound (100 mg, 76.0% yield) as a white solid. MS (ESI): mass calcd. for C$_{16}$H$_{20}$N$_4$O$_2$S, 332.13, m/z found 332.9 [M+H]+.

Step B: N$^4$-Ethyl-N$^4$-(4-(methylsulfonyl)-2-propylphenyl)pyrimidine-2,4-diamine To a 100 mL round-bottomed flask were added N$^4$-ethyl-N$^4$-(4-(methylsulfonyl)-2-(prop-1-enyl)phenyl)pyrimidine-2,4-diamine (130 mg, 0.301 mmol), MeOH (30 mL), and Pd/C (10% w/w, 30 mg). The reaction was degassed under vacuum and back filled with H$_2$ using a balloon and was stirred for 15 h. The reaction mixture was filtered and concentrated to dryness and the residue was purified by FCC to give title compound (70 mg, 69% yield) as a white solid. MS (ESI): mass calcd. for C$_{16}$H$_{22}$N$_4$O$_2$S, 334.2, m/z found 334.9 [M+H]$^+$. $^1$H NMR (400 MHz, CD$_3$OD): δ 8.02 (d, J=2.0 Hz, 1H), 7.91 (dd, J=8.2, 2.2 Hz, 1H), 7.66 (s, 1H), 7.45 (d, J=8.2 Hz, 1H), 5.36 (br s, 1H), 4.27 (br s, 1H), 3.55 (br s, 1H), 3.19 (s, 3H), 2.56 (dd, J=8.8, 7.0 Hz, 2H), 1.77-1.58 (m, 2H), 1.24 (t, J=7.1 Hz, 3H), 0.95 (t, J=7.3 Hz, 3H).

Example 106: N$^4$-(2-Cyclobutyl-4-(cyclopropylsulfonyl)phenyl)-N$^4$-ethylpyrimidine-2,4-diamine

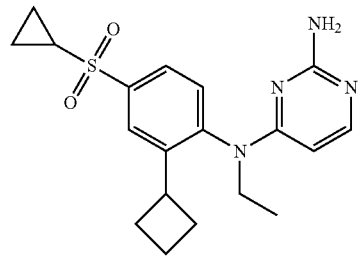 [SMILES: CCN(c1ccnc(N)n1)c1ccc(S(=O)(=O)C2CC2)cc1C1CCC1]

Step A: 4-(Cyclopropylsulfonyl)aniline

To a 50 mL sealed vessel were added 4-iodoaniline (2.19 g, 10.0 mmol), sodium cyclopropanesulfinate (1.54 g, 12.0 mmol), trifluoromethanesulfonate benzene complex (251 mg, 0.500 mmol), dimethylethylenediamine (88.0 mg, 1.00 mmol), and DMSO (50 mL). The reaction vessel was heated at 120° C. for 16 h. The reaction was then poured into a mixture of H$_2$O (50 mL) and EtOAc (500 mL). The organic layer was washed with water (3×30 mL) and saturated aqueous NaCl (20 mL), dried over anhydrous Na$_2$SO$_4$, filtered, and concentrated to dryness. The residue was purified by FCC to give the title compound (1.80 g, 91.0%) as yellow solid. MS (ESI): mass calcd. for C$_9$H$_{11}$NO$_2$S, 197.05, m/z found 198.0 [M+H]$^+$.

Step B: N$^4$-(2-Cyclobutyl-4-(cyclopropylsulfonyl)phenyl)-N$^4$-ethylpyrimidine-2,4-diamine The title compound was prepared using analogous conditions described in Example 21 starting with 4-(cyclopropylsulfonyl)aniline in place of 4-(methylsulfonyl)aniline. MS (ESI): mass calcd. for $C_{19}H_{24}N_4O_2S$, 372.2, m/z found 372.9 [M+H]$^+$. $^1$H NMR (400 MHz, CDCl$_3$): δ 8.03 (d, J=2.1 Hz, 1H), 7.79 (dd, J=8.2, 2.2 Hz, 1H), 7.74-7.67 (m, 1H), 7.27-7.24 (m, 1H), 5.26 (br s, 1H), 4.85 (br s, 2H), 4.22 (br s, 1H), 3.59-3.36 (m, 2H), 2.58-2.50 (m, 1H), 2.35-2.23 (m, 1H), 2.18-1.91 (m, 4H), 1.88-1.78 (m, 1H), 1.45-1.39 (m, 2H), 1.18 (t, J=7.1 Hz, 3H), 1.14-1.07 (m, 2H).

Example 107: N$^4$-(2-Cyclobutyl-4-(cyclopropylsulfonyl)phenyl)-N$^4$-propylpyrimidine-2,4-diamine

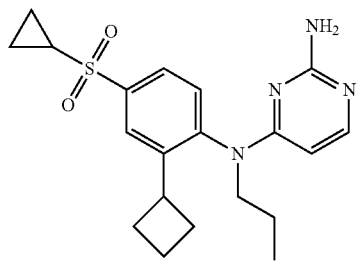 [SMILES: CCCN(c1ccnc(N)n1)c1ccc(S(=O)(=O)C2CC2)cc1C1CCC1]

The title compound was prepared using analogous conditions described in Example 21 employing 4-(cyclopropylsulfonyl)aniline in place of 4-(methylsulfonyl)aniline and 1-iodopropane in place of 1-iodoethane. MS (ESI): mass calcd. for $C_{20}H_{26}N_4O_2S$, 386.2, m/z found 386.9 [M+H]$^+$. $^1$H NMR (400 MHz, CDCl$_3$): δ 8.03 (d, J=2.0 Hz, 1H), 7.78 (dd, J=8.2, 2.2 Hz, 1H), 7.75-7.68 (m, 1H), 7.29 (s, 1H), 5.26 (br s, 1H), 5.18-4.51 (m, 2H), 4.11 (br s, 1H), 3.56-3.45 (m, 1H), 3.31-3.22 (m, 1H), 2.58-2.50 (m, 1H), 2.33-2.24 (m, 1H), 2.22-1.92 (m, 4H), 1.87-1.77 (m, 1H), 1.73-1.51 (m, 2H), 1.45-1.39 (m, 2H), 1.14-1.08 (m, 2H), 0.91 (t, J=7.4 Hz, 3H).

Example 108: N$^4$-((4H-1,2,4-Triazol-3-yl)methyl)-N$^4$-(2-ethoxy-4-fluorophenyl)pyrimidine-2,4-diamine

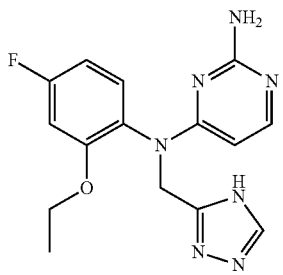 [SMILES: CCOc1cc(F)ccc1N(Cc1nnc[nH]1)c1ccnc(N)n1]

The title compound was prepared using analogous conditions described in Example 19 starting with 2-ethoxy-4-fluoroaniline in place of 2-methyl-4-(pentafluorosulfanyl)benzenamine in step C, and 3-(chloromethyl)-4H-1,2,4-triazole in place of 4-bromomethyloxazole hydrobromide salt in step D. MS (ESI): mass calcd. for $C_{15}H_{16}FN_7O$, 329.1, m/z found 330.1 [M+H]$^+$. $^1$H NMR (400 MHz, CD$_3$OD): δ 8.86 (s, 1H), 7.92 (s, 1H), 7.71 (d, J=6.1 Hz, 1H), 7.22 (dd, J=8.7, 6.2 Hz, 1H), 6.92 (dd, J=10.7, 2.7 Hz, 1H), 6.81-6.75 (m, 1H), 6.22 (d, J=13.9 Hz, 1H), 6.09 (d, J=13.6 Hz, 1H), 5.46 (d, J=5.9 Hz, 1H), 3.93 (q, J=7.0 Hz, 2H), 1.16 (t, J=7.0 Hz, 3H).

Example 109: N$^4$-(2-Ethyl-4-(trifluoromethyl)phenyl)-N$^4$-(oxazol-4-ylmethyl)pyrimidine-2,4-diamine

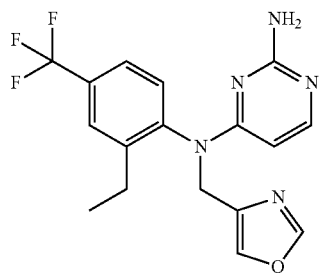 [SMILES: CCc1cc(C(F)(F)F)ccc1N(Cc1cocn1)c1ccnc(N)n1]

Step A: N$^4$-(2-Bromo-4-(trifluoromethyl)phenyl)-N$^4$-(oxazol-4-ylmethyl)pyrimidine-2,4-diamine The title compound was prepared using analogous conditions described in Example 102, steps C-D, and F-G, and using 2-bromo-4-(trifluoromethyl)aniline in place of 4-bromo-2-cyclobutylaniline in step C, and using 4-bromomethyloxazole in place of 2-iodopropane in step D.

Step B: N$^4$-(Oxazol-4-ylmethyl)-N$^4$-(4-(trifluoromethyl)-2-vinylphenyl)pyrimidine-2,4-diamine To a 35 mL microwave vial were added N$^4$-(2-bromo-4-(trifluoromethyl)phenyl)-N$^4$-(oxazol-4-ylmethyl)pyrimidine-2,4-diamine (207 mg, 0.500 mmol), chloro-(2-dicyclohexylphosphino-2',6'-diisopropoxy-1,1'-biphenyl)[2-(2-aminoethyl)phenyl]palladium(II)-methyl-t-butyl ether adduct (20 mg, cat.), K$_3$PO$_4$ (0.5M in H$_2$O, 2.00 mL, 1.00 mmol), 4,4,5,5-tetramethyl-2-vinyl-1,3,2-dioxaborolane (308 mg, 2.00 mmol), and dioxane (10.0 mL) under N$_2$. The reaction was heated at 120° C. for 1 h in a microwave reactor. The mixture was cooled to rt and diluted with EtOAc (50 mL), washed with water (3×30 mL) and saturated aqueous NaCl (20 mL), dried over anhydrous Na$_2$SO$_4$, filtered, and concentrated to dryness. The residue was purified by FCC to give the title compound (160 mg, 89% yield) as a yellow oil. MS (ESI): mass calcd. for $C_{17}H_{14}F_3N_5O$, 361.12, m/z found 362.1 [M+H]$^+$.

Step C: N$^4$-(2-Ethyl-4-(trifluoromethyl)phenyl)-N$^4$-(oxazol-4-ylmethyl)pyrimidine-2,4-diamine To a 100-mL round-bottomed flask were added N$^4$-(oxazol-4-ylmethyl)-N$^4$-(4-(trifluoromethyl)-2-vinylphenyl)pyrimidine-2,4-diamine (160 mg, 0.443 mmol), Pd/C (10% on activated carbon, 20 mg), and MeOH (20 mL). The flask was degassed under vacuum and refilled with hydrogen gas using a balloon. The reaction mixture was stirred at rt for 14 h under a H$_2$ atmosphere. The mixture was filtered through a pad of diatomaceous earth such as Celite® and the filtrate was concentrated to dryness. The residue was purified by FCC to give the title compound (112 mg, 70% yield) as a yellow solid. MS (ESI): mass calcd. for $C_{17}H_{16}F_3N_5O$, 363.1, m/z found 364.1 [M+H]$^+$. $^1$H NMR (400 MHz, CDCl$_3$): δ 7.81 (s, 1H), 7.73 (d, J=5.4 Hz, 1H), 7.63 (d, J=8.7 Hz, 2H), 7.50 (d, J=8.1 Hz, 1H), 7.20 (d, J=8.2 Hz, 1H), 5.44-5.24 (m, 2H), 4.96 (br s, 2H), 4.53 (d, J=15.2 Hz, 1H), 2.50 (q, J=7.5 Hz, 2H), 1.16 (t, J=7.6 Hz, 3H).

Example 110: N⁴-(Oxazol-4-ylmethyl)-N⁴-(4-(trifluoromethyl)phenyl)pyrimidine-2,4-diamine

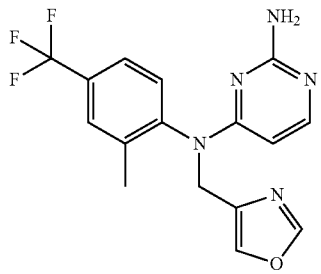 [SMILES: Cc1cc(C(F)(F)F)ccc1N(Cc1cocn1)c1ccnc(N)n1]

The title compound was prepared using analogous conditions described in Example 102, steps C-D, and F-G, and using 2-methyl-4-(trifluoromethyl)aniline in place of 4-bromo-2-cyclobutylaniline in step C, and using 4-bromomethyloxazole in place of 2-iodopropane in step D. MS (ESI): mass calcd. for $C_{16}H_{14}F_3N_5O$, 349.1, m/z found 350.1 [M+H]⁺. ¹H NMR (400 MHz, CDCl₃): δ 7.82 (s, 1H), 7.73 (d, J=6.1 Hz, 1H), 7.64 (s, 1H), 7.57 (s, 1H), 7.51 (d, J=8.2 Hz, 1H), 7.24 (d, J=8.2 Hz, 1H), 5.42-5.20 (m, 2H), 5.07 (br s, 2H), 4.64 (d, J=14.9 Hz, 1H), 2.15 (s, 3H).

Example 111: 4-((2-Aminopyrimidin-4-yl)(ethyl)amino)-3-cyclobutylbenzamide

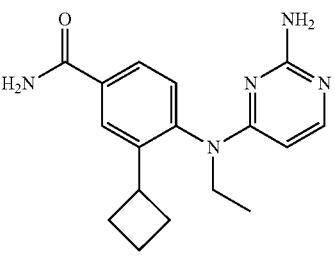 [SMILES: CCN(c1ccnc(N)n1)c1ccc(C(N)=O)cc1C1CCC1]

The title compound was prepared using analogues conditions as described in example 113, steps A-E wherein, methyl 4-amino-3-cyclobutylbenzoate was used in place of methyl 4-amino-3-bromobenzoate in step A. Purification by column chromatography (DCM: MeOH, 20:1) afforded the title compound. MS (ESI): mass calcd. for $C_{17}H_{21}N_5O$, 311.2, m/z found 312.0 [M+H]⁺. ¹H NMR (400 MHz, CDCl₃): δ 8.01 (d, J=1.9 Hz, 1H), 7.71-7.59 (m, 2H), 7.15 (d, J=8.1 Hz, 1H), 6.15 (br s, 1H), 5.79 (br s, 1H), 5.23 (br s, 1H), 4.94 (br s, 2H), 4.22 (br s, 1H), 3.55-3.38 (m, 2H), 2.25-2.07 (m, 4H), 2.02-1.89 (m, 1H), 1.87-1.77 (m, 1H), 1.17 (t, J=7.1 Hz, 3H).

Example 112: 4-((2-Aminopyrimidin-4-yl)(isopropyl)amino)-3-cyclobutylbenzamide

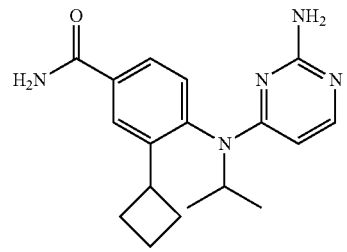 [SMILES: CC(C)N(c1ccnc(N)n1)c1ccc(C(N)=O)cc1C1CCC1]

The title compound was prepared using analogous conditions described in Example 102, steps A, C-D, and F-G, and using methyl 4-amino-3-bromobenzoate in place of 2-bromoaniline in step A, and using methyl 4-amino-3-cyclobutylbenzoate in place of 4-bromo-2-cyclobutylaniline in step C. MS (ESI): mass calcd. for $C_{18}H_{23}N_5O$, 325.4, m/z found 326.0 [M+H]⁺. ¹H NMR (400 MHz, CDCl₃): δ 8.14 (d, J=2.1 Hz, 1H), 7.66 (dd, J=8.1, 2.1 Hz, 1H), 7.59 (d, J=6.2 Hz, 1H), 7.10 (d, J=8.1 Hz, 1H), 6.20 (br s, 1H), 5.89 (br s, 1H), 5.17-4.93 (m, 4H), 3.57-3.46 (m, 1H), 2.29-2.16 (m, 2H), 2.14-1.97 (m, 2H), 1.96-1.80 (m, 2H), 1.28 (d, J=6.5 Hz, 3H), 0.92 (d, J=6.9 Hz, 3H).

Example 113: 4-((2-Aminopyrimidin-4-yl)(ethyl)amino)-3-isobutylbenzamide

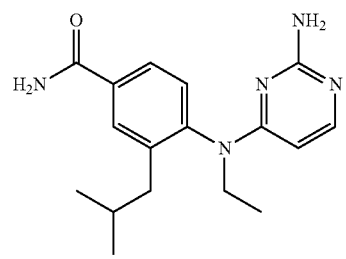 [SMILES: CCN(c1ccnc(N)n1)c1ccc(C(N)=O)cc1CC(C)C]

Step A: Methyl 3-bromo-4-((2-(methylthio)pyrimidin-4-yl)amino)benzoate

To a solution of methyl 4-amino-3-bromobenzoate (920 mg, 4.00 mmol) and 4-chloro-2-(methylthio)pyrimidine (964 mg, 6.00 mmol) in isopropanol (20 mL) was added p-toluene sulphonic acid (100 mg, 0.580 mmol) at rt. The mixture was stirred for 2 h at 100° C. using microwave irradiation in a microwave reactor. The mixture was concentrated in vacuo and purified by a column chromatography (DCM:CH₃OH=20:1) to afford 1.1 g of the title compound. MS (ESI): mass calcd. for $C_{13}H_{12}BrN_3O_2S$, 354.2; m/z found, 355.1 [M+H]⁺.

Step B: Methyl 3-bromo-4-(ethyl(2-(methylthio)pyrimidin-4-yl)amino)benzoate To a 50 mL sealed tube was added methyl 3-bromo-4-((2-(methylthio)pyrimidin-4-yl)amino)benzoate (1.1 g, 3.1 mmol), iodoethane (0.97 g, 6.2 mmol) and cesium carbonate (2.0 g, 6.2 mmol) in acetonitrile (100 mL). The vessel was heated to 65° C. for 3 h, then cooled to rt and filtered. The reaction mixture was concentrated in vacuo and purified by column chromatography (DCM:CH₃OH=20:1) to afford 1.0 g of the title compound. MS (ESI): mass calcd. for $C_{15}H_{16}BrN_3O_2S$, 382.3; m/z found, 383.1 [M+H]⁺.

Step C: Methyl 3-bromo-4-(ethyl(2-(methylsulfonyl)pyrimidin-4-yl)amino)benzoate

To a 200 mL round-bottomed flask was added methyl 3-bromo-4-(ethyl(2-(methylthio)pyrimidin-4-yl)amino)benzoate (1.0 g, 2.6 mmol) in dichloromethane (100 mL), then m-CPBA (1.5 g, 8.5 mmol) was added to the solution. The mixture was stirred at 0° C. for 3 h, then NaHCO₃/H₂O and DCM were added and the layers separated. The organic layer was dried and concentrated in vacuo, then purified by column chromatography (DCM:CH₃OH=50:1) to afford 900 mg of the title compound. MS (ESI): mass calcd. for $C_{15}H_{16}BrN_3O_4S$, 414.2; m/z found, 415.7 [M+H]⁺.

Step D: 4-((2-aminopyrimidin-4-yl)(ethyl)amino)-3-bromobenzamide

To a round-bottomed flask was charged methyl 3-bromo-4-(ethyl(2-(methylsulfonyl)pyrimidin-4-yl)amino)benzoate (900 mg, 2.17 mg) which was dissolved into 1,4-dioxane (10 mL) then ammonium hydroxide (5 mL) was added. The resulting mixture was stirred for 14 h at 105° C., then DCM and water were added. The layers were separated and the organic layers were dried and concentrated. Purification by column chromatography (DCM:CH₃OH=15:1) afforded 150 mg of the title compound. MS (ESI): mass calcd. for $C_{13}H_{14}BrN_5O$, 336.2; m/z found, 336.0 [M+H]⁺.

Step E: 4-((2-aminopyrimidin-4-yl)(ethyl)amino)-3-(2-methylprop-1-en-1-yl)benzamide To a 15 mL reaction vessel was added 4-((2-aminopyrimidin-4-yl)(ethyl)amino)-3-bromobenzamide (150 mg, 0.446 mmol), 4,4,5,5-tetramethyl-2-(2-methylprop-1-en-1-yl)-1,3,2-dioxaborolane (255 mg, 1.40 mmol), chloro-(2-dicyclohexylphosphino-2',6'-diisopropoxy-1,1'-biphenyl)[2-(2-aminoethyl)phenyl]palladium(II)-methyl-t-butyl ether adduct (50 mg) and 0.5M K₃PO₄ (aq.) (1.84 mL, 0.920 mmol) in 1,4-dioxane (10 mL) under N₂. The resulting mixture was stirred at 120° C. for 1 h. The mixture was filtered, concentrated in vacuo. and purified by column chromatography (petroleum ether:ethyl acetate=100:1) to afford 110 mg of the title compound. MS (ESI): mass calcd. for $C_{17}H_{21}N_5O$, 311.4; m/z found, 312.0 [M+H]⁺.

Step F: 4-((2-aminopyrimidin-4-yl)(ethyl)amino)-3-isobutylbenzamide

To a 100 mL round-bottomed flask was added 4-((2-aminopyrimidin-4-yl)(ethyl)amino)-3-(2-methylprop-1-en-1-yl)benzamide (110 mg, 0.35 mmol) and palladium on carbon (10 mg) in methanol (20 mL). The resulting mixture was stirred for 14 hours under 2 atm of H₂, filtered and concentrated in vacuo. Purification by preparative HPLC afforded 29 mg of the title compound. MS (ESI): mass calcd. for $C_{17}H_{23}N_5O$, 313.2; m/z found, 313.9 [M+H]⁺. ¹H NMR (400 MHz, CDCl₃): δ 7.85 (d, J=2.0 Hz, 1H), 7.71-7.60 (m, 2H), 7.18 (d, J=8.1 Hz, 1H), 6.11 (br s, 1H), 5.77 (br s, 1H), 5.29 (br s, 1H), 4.94 (br s, 1H), 4.36 (br s, 1H), 3.37-3.25 (m, 1H), 2.47-2.30 (m, 2H), 2.07-1.89 (m, 1H), 1.21 (t, J=7.1 Hz, 3H), 0.86 (dd, J=8.3, 6.8 Hz, 6H).

Example 114: (E)-N⁴-Isopropyl-N⁴-(2-(prop-1-en-1-yl)-4-(trifluoromethyl)phenyl)pyrimidine-2,4-diamine

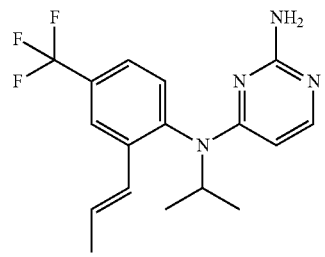 [SMILES: C/C=C/c1cc(C(F)(F)F)ccc1N(c1ccnc(N)n1)C(C)C]

Step A: N⁴-(2-Chloro-4-(trifluoromethyl)phenyl)-N⁴-isopropylpyrimidine-2,4-diamine The title compound was prepared using the method for Example 102, steps C-D and F-G, and using 2-chloro-4-(trifluoromethyl)aniline in place of 4-bromo-2-cyclobutylaniline in step C, to give the title compound. MS (ESI): mass calcd. for $C_{14}H_{14}ClF_3N_4$, 330.74; m/z found, 331.0 [M+H]⁺. ¹H NMR (500 MHz, CDCl₃): δ 7.81 (d, J=2.1 Hz, 1H), 7.74 (d, J=6.0 Hz, 1H), 7.62 (dd, J=8.3, 2.1 Hz, 1H), 7.37 (dd, J=8.2, 1.0 Hz, 1H), 5.24-5.18 (m, 1H), 5.12 (p, J=6.9 Hz, 1H), 4.89 (s, 2H), 1.10 (s, 6H).

Step B: (E)-N⁴-isopropyl-N⁴-(2-(prop-1-en-1-yl)-4-(trifluoromethyl)phenyl)pyrimidine-2,4-diamine To a microwave vial were added N⁴-(2-chloro-4-(trifluoromethyl)phenyl)-N⁴-isopropylpyrimidine-2,4-diamine (590 mg, 3.57 mmol), 4,4,5,5-tetramethyl-2-[(E)-prop-1-enyl]-1,3,2-dioxaborolane (600 mg, 3.57 mmol), chloro-(2-dicyclohexylphosphino-2',6'-diisopropoxy-1,1'-biphenyl)[2-(2-aminoethyl)phenyl]palladium(II)-methyl-t-butyl ether adduct (260 mg, 0.357 mmol), potassium phosphate tribasic solution (0.5M, 10.0 mL), and dioxane (5.4 mL). The mixture was degassed with N₂ for 15 min, then heated in a microwave reactor at 110° C. for 60 min. The reaction was purified by acidic HPLC (0-100% acetonitrile/water using trifluoroacetic acid as modifier) to give the title compound (570 mg, 95.0% yield). MS (ESI): mass calcd. for $C_{17}H_{19}F_3N_4$, 336.35; m/z found, 337.2 [M+H]⁺. ¹H NMR (500 MHz, CDCl₃): δ 7.89 (d, J=2.2 Hz, 1H), 7.67 (d, J=6.0 Hz, 1H), 7.52 (dd, J=8.2, 2.1 Hz, 1H), 7.18 (d, J=8.1 Hz, 1H), 6.33 (d, J=4.0 Hz, 2H), 5.14 (dt, J=21.0, 6.8 Hz, 2H), 4.91 (s, 2H), 1.84 (d, J=4.4 Hz, 3H), 1.27 (d, J=6.6 Hz, 3H), 0.97 (d, J=7.0 Hz, 3H).

Example 115: N⁴-Isopropyl-N⁴-(2-propyl-4-(trifluoromethyl)phenyl)pyrimidine-2,4-diamine

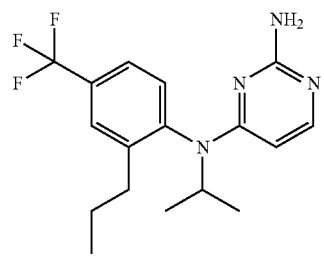 [SMILES: CCCc1cc(C(F)(F)F)ccc1N(c1ccnc(N)n1)C(C)C]

A solution of (E)-N⁴-isopropyl-N⁴-(2-(prop-1-en-1-yl)-4-(trifluoromethyl)phenyl)pyrimidine-2,4-diamine (Example 114, 500 mg, 1.49 mmol) in MeOH (30 mL) was subjected to atmospheric H₂ at rt for 5 h. The reaction was concentrated to dryness and the residue was purified by acidic HPLC to give the title compound. MS (ESI): mass calcd. for $C_{17}H_{21}F_3N_4$, 338.1; m/z found, 339.0 [M+H]⁺. ¹H NMR (500 MHz, CDCl₃): δ 7.71 (dd, J=2.0, 1.0 Hz, 1H), 7.59 (dd, J=8.2, 2.1 Hz, 1H), 7.42 (d, J=7.4 Hz, 1H), 7.20 (d, J=8.2 Hz, 1H), 5.49-4.86 (m, 2H), 2.56-2.36 (m, 2H), 1.76-1.58 (m, 2H), 1.35 (d, J=6.6 Hz, 3H), 1.04 (d, J=6.9 Hz, 3H), 0.98 (t, J=7.3 Hz, 3H).

Example 116: N⁴-Isopropyl-N⁴-(2-methyl-4-(trifluoromethyl)phenyl)pyrimidine-2,4-diamine

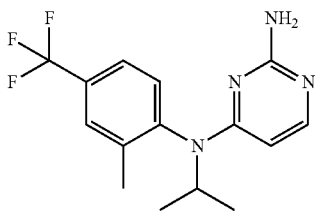 [SMILES: Cc1cc(C(F)(F)F)ccc1N(c1ccnc(N)n1)C(C)C]

N⁴-Isopropyl-N⁴-(2-methyl-4-(trifluoromethyl)phenyl)pyrimidine-2,4-diamine. To a 25 mL vial were added N⁴-(2-chloro-4-(trifluoromethyl)phenyl)-N⁴-isopropylpyrimidine-2,4-diamine (as prepared in Example 114, step A, 250 mg, 0.756 mmol), 2,4,6-trimethyl-1,3,5,2,4,6-trioxatriborinane (82.0 mg, 0.660 mmol), and 1,1'-bis(diphenylphosphino)ferrocene-palladium(II)dichloride dichloromethane complex (55.0 mg, 0.0760 mmol). The vial was sealed then evacuated and backfilled with N₂ (2×). Dioxane (10.0 mL) and degassed phosphate solution (0.5M, 16.0 mL, 7.90 mmol) were added. The resulting mixture was heated to 140° C. in a microwave reactor for 30 min. The reaction was cooled to rt, then diluted with EtOAc (30 mL) and poured into water (20 mL). The aqueous layer was extracted further with EtOAc (30 mL). The combined organics were washed with brine (20 mL), dried over anhydrous MgSO₄, and concentrated to dryness. The residue was purified by FCC to give the title compound (80 mg, 34% yield). MS (ESI): mass calcd. for $C_{15}H_{17}F_3N_4$, 310.1; m/z found, 311.0 [M+H]⁺. ¹H NMR (400 MHz, CDCl₃): δ 7.71-7.56 (m, 2H), 7.45 (d, J=7.1 Hz, 1H), 7.23 (d, J=8.2 Hz, 2H), 5.30 (s, 1H), 5.21 (dd, J=23.2, 7.4 Hz, 2H), 2.22 (s, 3H), 1.35 (d, J=6.6 Hz, 3H), 1.03 (d, J=6.9 Hz, 3H).

Example 117: 4-((2-Aminopyrimidin-4-yl)(oxazol-4-ylmethyl)amino)-3-propylbenzonitrile

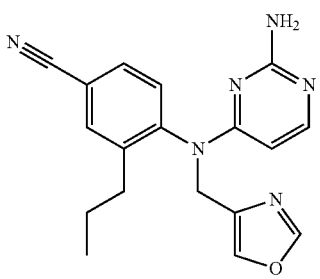 [SMILES: CCCc1cc(C#N)ccc1N(Cc1cocn1)c1ccnc(N)n1]

Step A: (E)-4-((2-Aminopyrimidin-4-yl)(oxazol-4-ylmethyl)amino)-3-(prop-1-en-1-yl)benzonitrile To a 20 mL microwave vial were added (E)-N⁴-(4-chloro-2-(prop-1-en-1-yl)phenyl)-N⁴-(oxazol-4-ylmethyl)pyrimidine-2,4-diamine (Example 101, 500 mg, 1.46 mmol), zinc cyanide (388 mg, 3.31 mmol), X-Phos (166 mg, 0.348 mmol), Zn powder (22 mg, 0.34 mmol), and Pd₂(dba)₃ (215 mg, 0.235 mmol). The reaction vessel was then evacuated and backfilled with N₂ (2×). DMA (15 mL) was added in one portion and the resulting brown mixture was placed into a preheated 120° C. heating block and heated for 1 h. The vial was removed from the heat and cooled to rt. The reaction was diluted with EtOAc (15 mL) and was filtered through a pad of diatomaceous earth such as Celite® to remove the insoluble particulates. The cake was rinsed with EtOAc (2×5 mL). The filtrate was transferred to a 125 mL separatory funnel and washed with saturated NaHCO₃ (20 mL), water (20 mL), and brine (20 mL), then dried over anhydrous MgSO₄. The organics were concentrated to dryness to afford a yellow semi solid. The residue was purified by FCC to give the title compound as a colorless residue (370 mg, 76% yield). MS (ESI): mass calcd. for $C_{18}H_{16}N_6O$, 332.36; m/z found, 333.1 [M+H]⁺. ¹H NMR (500 MHz, CDCl₃): δ 7.79 (d, J=1.0 Hz, 1H), 7.72 (d, J=6.0 Hz, 1H), 7.60-7.52 (m, 2H), 7.17 (dd, J=8.4, 2.5 Hz, 1H), 6.96 (d, J=8.4 Hz, 1H), 6.31-6.10 (m, 2H), 5.39-5.28 (m, 2H), 5.02 (s, 2H), 4.53 (d, J=15.3 Hz, 1H), 1.81 (dd, J=6.4, 1.5 Hz, 3H).

Step B: 4-((2-Aminopyrimidin-4-yl)(oxazol-4-ylmethyl)amino)-3-propylbenzonitrile A solution of (E)-4-((2-aminopyrimidin-4-yl)(oxazol-4-ylmethyl)amino)-3-(prop-1-en-1-yl)benzonitrile (300 mg, 0.903 mmol) in MeOH (18 mL) was hydrogenated using a H₂ balloon at rt for 5 h. The reaction was concentrated to dryness and the residue was purified by HPLC (0-100% acetonitrile/water using trifluoroacetic acid as modifier) to give the title compound (90 mg, 30% yield). MS (ESI): mass calcd. for $C_{18}H_{18}N_6O$, 334.4; m/z found, 335.1 [M+H]⁺. ¹H NMR (500 MHz, CDCl₃): δ 9.71 (s, 1H), 7.85 (s, 1H), 7.77 (s, 1H), 7.72 (d, J=1.9 Hz, 1H), 7.61 (dd, J=8.2, 1.9 Hz, 1H), 7.50 (d, J=7.2 Hz, 1H), 7.32 (d, J=8.2 Hz, 1H), 6.48 (s, 1H), 5.50 (d, J=14.8 Hz, 1H), 5.39 (d, J=7.2 Hz, 1H), 4.50 (d, J=14.8 Hz, 1H), 2.49-2.39 (m, 2H), 1.70-1.53 (m, 2H), 0.94 (t, J=7.3 Hz, 3H).

Example 118: (E)-N⁴-(4-Fluoro-2-(prop-1-en-1-yl)phenyl)-N⁴-isopropylpyrimidine-2,4-diamine

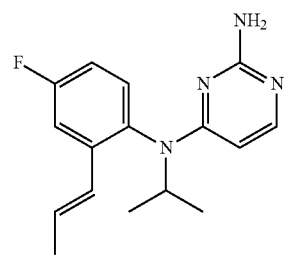 [SMILES: C/C=C/c1cc(F)ccc1N(c1ccnc(N)n1)C(C)C]

Step A: N⁴-(2-Chloro-4-fluorophenyl)-N⁴-isopropylpyrimidine-2,4-diamine

The title compound was prepared using the method for Example 102 steps C-D and F-G, and using 2-chloro-4- fluoroaniline in place of 4-bromo-2-cyclobutylaniline in step C (2300 mg). 1H NMR (400 MHz, Methanol-d4) δ 7.63-7.56 (m, 1H), 7.48-7.40 (m, 1H), 7.40-7.31 (m, 1H), 7.28-7.17 (m, 1H), 5.38-5.03 (m, 2H), 1.28 (d, J=6.5 Hz, 3H), 1.05 (d, J=6.8 Hz, 3H). MS (ESI): mass calcd. for $C_{13}H_{14}ClFN_4$, 280.7; m/z found, 281.1 [M+H]$^+$.

Step B: (E)-N$^4$-(4-Fluoro-2-(prop-1-en-1-yl)phenyl)-N$^4$-isopropylpyrimidine-2,4-diamine A microwave vial containing N$^4$-(2-chloro-4-fluorophenyl)-N$^4$-isopropylpyrimidine-2,4-diamine (112 mg, 0.399 mmol), 2-dicyclohexylphosphino-2',6'-diisopropoxybiphenyl, palladium(II) phenethylamine chloride (7.3 mg, 0.010 mmol), K$_3$PO$_4$ solution (0.5M 2.39 mL), dioxane (1.21 mL), and trans-1-propen-1-ylboronic acid (103 mg, 1.20 mmol) was stirred and degassed with N$_2$ for 15 min, and then the reaction was heated in a microwave for 20 min at 140° C. The reaction mixture was filtered, added DCM and H$_2$O, collected the organic layer, and extracted the aqueous layer again with DCM. The combined organic fractions were dried over anhydrous Na$_2$SO$_4$, filtered, and concentrated to dryness. The residue was purified by FCC to give the title compound (57.9 mg). MS (ESI): mass calcd. for $C_{16}H_{19}FN_4$, 286.4; m/z found, 287.1 [M+H]$^+$. $^1$H NMR (500 MHz, CDCl$_3$): δ 7.65 (d, J=6.1 Hz, 1H), 7.31 (dd, J=10.0, 2.8 Hz, 1H), 7.04-6.93 (m, 2H), 6.26-6.22 (m, 2H), 5.19-5.05 (m, 2H), 4.72 (s, 2H), 1.84-1.81 (m, 3H), 1.23 (d, J=6.6 Hz, 3H), 0.95 (d, J=6.9 Hz, 3H).

Example 119: N$^4$-(4-Fluoro-2-propylphenyl)-N$^4$-isopropylpyrimidine-2,4-diamine

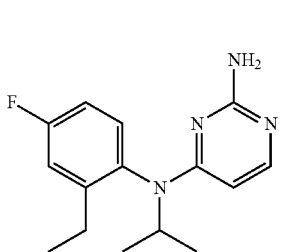

A solution of (E)-N$^4$-(4-fluoro-2-(prop-1-en-1-yl)phenyl)-N$^4$-isopropylpyrimidine-2,4-diamine (Example 118, 108 mg, 0.377 mmol) in MeOH (7.5 mL) was hydrogentated (H$_2$, 1 atm, 80° C.) over 10% Pd/C for 2 h. The reaction was concentrated to dryness and the residue was purified by FCC to give the title compound (87.7 mg, 80.6% yield). MS (ESI): mass calcd. for $C_{16}H_{21}FN_4$, 288.4; m/z found, 289.2 [M+H]$^+$. $^1$H NMR (400 MHz, CD$_3$OD): δ 7.56-7.51 (m, 1H), 7.26 (dd, J=9.8, 2.8 Hz, 1H), 7.22-7.16 (m, 1H), 7.13-7.07 (m, 1H), 5.36 (s, 1H), 5.12 (s, 1H), 2.52-2.35 (m, 2H), 1.72-1.59 (m, 2H), 1.33 (d, J=6.6 Hz, 3H), 1.04 (d, J=6.8 Hz, 3H), 0.95 (t, J=7.3 Hz, 3H).

Example 120: N$^4$-(4-Fluoro-2-(prop-1-en-2-yl)phenyl)-N$^4$-isopropylpyrimidine-2,4-diamine

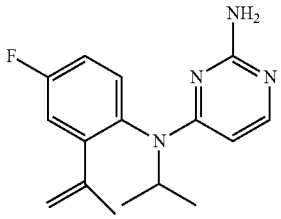 [SMILES: C=C(C)c1cc(F)ccc1N(c1ccnc(N)n1)C(C)C]

The title compound was prepared using the method for Example 118, steps A-B, and using isopropenylboronic acid pinacol ester in place of trans-1-propen-1-ylboronic acid in step B (65.3 mg). MS (ESI): mass calcd. for $C_{16}H_{19}FN_4$, 286.4; m/z found, 287.3 [M+H]$^+$. $^1$H NMR (500 MHz, CDCl$_3$): δ 7.68 (d, J=6.1 Hz, 1H), 7.09 (dd, J=9.5, 2.7 Hz, 1H), 7.04-6.95 (m, 2H), 5.28 (d, J=6.0 Hz, 1H), 5.12-5.08 (m, 1H), 5.01-4.97 (m, 1H), 4.91-4.82 (m, 1H), 4.69 (s, 2H), 1.95 (s, 3H), 1.19 (d, J=6.6 Hz, 3H), 1.06 (d, J=6.9 Hz, 3H).

Example 121: N$^4$-(4-Fluoro-2-isopropylphenyl)-N$^4$-isopropylpyrimidine-2,4-diamine

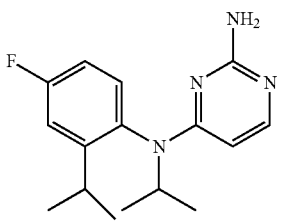 [SMILES: CC(C)c1cc(F)ccc1N(c1ccnc(N)n1)C(C)C]

A solution of N$^4$-(4-fluoro-2-(prop-1-en-2-yl)phenyl)-N$^4$-isopropylpyrimidine-2,4-diamine (Example 120, 60 mg, 0.21 mmol) in MeOH (4.2 mL) was hydrogenated (H$_2$, 1 atm) using an H-Cube machine and a 10% Pd/C cartridge for 2 h. The reaction mixture was concentrated to dryness and the residue purified by HPLC. The HPLC fractions were washed with saturated NaHCO$_3$ and DCM, collected the organic phase, and extracted the aqueous phase again with DCM. The pooled organic layers were dried over anhydrous Na$_2$SO$_4$, filtered, and concentrated to dryness to give the title compound (38.7 mg, 64% yield). MS (ESI): mass calcd. for $C_{16}H_{21}FN_4$, 288.4; m/z found, 289.1 [M+H]$^+$. $^1$H NMR (400 MHz, CD$_3$OD): δ 7.54 (d, J=6.2 Hz, 1H), 7.20 (dd, J=10.0, 2.9 Hz, 1H), 7.13-7.08 (m, 1H), 7.06-6.99 (m, 1H), 5.23-5.01 (m, 2H), 3.03-2.91 (m, 1H), 1.26 (d, J=6.6 Hz, 3H), 1.22 (d, J=6.9 Hz, 3H), 1.09 (d, J=6.8 Hz, 3H), 1.02 (d, J=6.9 Hz, 3H).

Example 122: (E)-4-((2-Aminopyrimidin-4-yl)(oxazol-4-ylmethyl)amino)-3-(prop-1-en-1-yl)benzonitrile

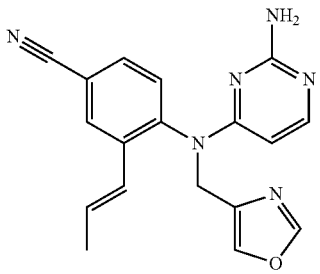 [SMILES: C/C=C/c1cc(C#N)ccc1N(Cc1cocn1)c1ccnc(N)n1]

The title compound was prepared using the method for Example 117, steps A-B (370 mg). MS (ESI): mass calcd. for $C_{18}H_{16}N_6O$, 332.4; m/z found, 333.10 $[M+H]^+$. $^1H$ NMR (500 MHz, $CDCl_3$): δ 7.79 (d, J=1.0 Hz, 1H), 7.72 (d, J=6.0 Hz, 1H), 7.60-7.52 (m, 2H), 7.17 (dd, J=8.4, 2.5 Hz, 1H), 6.96 (d, J=8.4 Hz, 1H), 6.31-6.10 (m, 2H), 5.39-5.28 (m, 2H), 5.02 (s, 2H), 4.53 (d, J=15.3 Hz, 1H), 1.81 (dd, J=6.4, 1.5 Hz, 3H).

Binding Assay on Recombinant Human Histamine $H_4$ Receptor.

Receptor binding was assessed using isolated plasma membranes from SKNMC neuroblastoma cell lines stably expressing recombinant human $H_4$ receptor. To isolate plasma membrane enriched in recombinant human $H_4$ receptor, cells were collected from 100 culture dishes (150 mm) in PBS-EDTA. The cells were pellet by centrifugation (800 g) and resuspended in 5×TE buffer (50 mM Tris/5 mM EDTA). The cells were then homogenized and centrifuged at 1000 g for 10 min. The supernatant was collected and centrifuged for an additional 26000 g for 30 min. The supernatant was removed and the pellet was gently resuspended in 30 ml of 5×TE buffer. Protein concentration was then determined using Bradford protein assay (Bradford, M. M., Anal. Biochem., 1976, 72: 248-254). Isolated cell membranes were incubated with $2×K_D$ (10 nM), [$^3H$] histamine (Specific activity: 23 $C_i$/mmol), with or without test compounds for 45 min at 25° C. Nonspecific binding was defined with 100 μM cold histamine. $K_i$ values were calculated based on an experimentally determined appropriate $K_D$ values according to Cheng and Prusoff (*Biochem. Pharmacol.* 1973, 22(23):3099-3108). Membranes were harvested by rapid filtration using the 96 well Brandel system or a cell harvester using a Whatman GF/C filter or filter plates treated with 0.5% polyethylenimine (PEI), and washed 4 times with ice-cold 50 mM Tris/5 mM EDTA buffer. Filters were then dried, mixed with scintillant and radioactive counts were determined. Results for the compounds tested in theses assays are presented in Table 4 as an average of results obtained.

TABLE 4

| Example # | Avg (hH4 binding Ki) (nM) |
|---|---|
| 1 | 6 |
| 2 | >2000 |
| 3 | 492 |
| 4 | 12 |
| 5 | 14 |
| 6 | 9 |
| 7 | 29 |
| 8 | 12 |
| 9 | 31 |
| 10 | 54 |
| 11 | 31 |
| 12 | 24 |
| 13 | 24 |
| 14 | 24 |
| 15 | 75 |
| 16 | 27 |
| 17 | 29 |
| 18 | 62 |
| 19 | 9 |
| 20 | 30 |
| 21 | 39 |
| 22 | 26 |
| 23 | 8 |
| 24 | 334 |
| 25 | 9 |
| 26 | 46 |
| 27 | 46 |
| 28 | 30 |
| 29 | 71 |
| 30 | 7 |
| 31 | 37 |
| 32 | 22 |
| 33 | 9 |
| 34 | 14 |
| 35 | 14 |
| 36 | 15 |
| 37 | 12 |
| 38 | 7 |
| 39 | 14 |
| 40 | 16 |
| 41 | 16 |
| 42 | 65 |
| 43 | 8 |
| 44 | 13 |
| 45 | 35 |
| 46 | 38 |
| 47 | 39 |
| 48 | 37 |
| 49 | 53 |
| 50 | 81 |
| 51 | 10 |
| 52 | 30 |
| 53 | 16 |
| 54 | 32 |
| 55 | 60 |
| 56 | 44 |
| 57 | 134 |
| 58 | 42 |
| 59 | 170 |
| 60 | 133 |
| 61 | 179 |
| 62 | 16 |
| 63 | 21 |
| 64 | 29 |
| 65 | 351 |
| 66 | 717 |
| 67 | 1003 |
| 68 | 243 |
| 69 | 162 |
| 70 | 628 |
| 71 | 71 |
| 72 | 23 |
| 73 | 101 |
| 74 | 155 |
| 75 | 96 |
| 76 | 26 |
| 77 | 34 |
| 78 | 1242 |
| 79 | 1021 |
| 80 | 65 |

TABLE 4-continued

| Example # | Avg (hH4 binding Ki) (nM) |
|---|---|
| 81 | 31 |
| 82 | 41 |
| 83 | 120 |
| 84 | 84 |
| 85 | 8 |
| 86 | 3 |
| 87 | 11 |
| 88 | 35 |
| 89 | 91 |
| 90 | 111 |
| 91 | 34 |
| 92 | 425 |
| 93 | 326 |
| 94 | 981 |
| 95 | 160 |
| 96 | 249 |
| 97 | 15 |
| 98 | 176 |
| 99 | 19 |
| 100 | 66 |
| 101 | 28 |
| 102 | 30 |
| 103 | 175 |
| 104 | 294 |
| 105 | 60 |
| 106 | 25 |
| 107 | 32 |
| 108 | 1466 |
| 109 | 9 |
| 110 | 23 |
| 111 | 59 |
| 112 | 69 |
| 113 | 45 |
| 114 | 7 |
| 115 | 4 |
| 116 | 17 |
| 117 | 99 |
| 118 | 11 |
| 119 | 7 |
| 120 | 40 |
| 121 | 21 |
| 122 | 134 |

What is claimed is:

1. A compound of Formula I, or a pharmaceutically acceptable salt thereof,

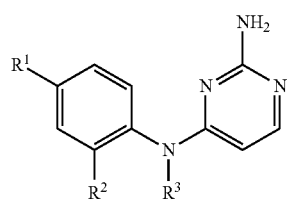

Formula I wherein
$R^1$ is $S(O)_nR^4$ or $SF_5$;
n is 1 or 2;
$R^4$ is selected from the group consisting of $C_1$-$C_4$ alkyl, $C_1$-$C_2$ perhaloalkyl, $C_3$-$C_4$ cycloalkyl and $NR^5R^6$; each of $R^5$ and $R^6$ is independently $C_1$-$C_4$ alkyl, or $R^5$ and $R^6$ together with the nitrogen to which they are attached form a 5-6 membered heterocyclic ring;
or
$R^1$ is selected from the group consisting of halo, $CF_3$, $OCF_3$, $C(OH)(CF_3)_2$, $CN$, and $C(O)NH_2$;

$R^2$ is selected from the group consisting of $C_1$-$C_5$ alkyl, $C_2$-$C_5$ alkenyl, $C_3$-$C_5$ cycloalkyl, $C_1$-$C_2$ perhaloalkyl, $OC_1$-$C_4$ alkyl, and $OC_1$-$C_3$ perhaloalkyl;

$R^3$ is selected from the group consisting of

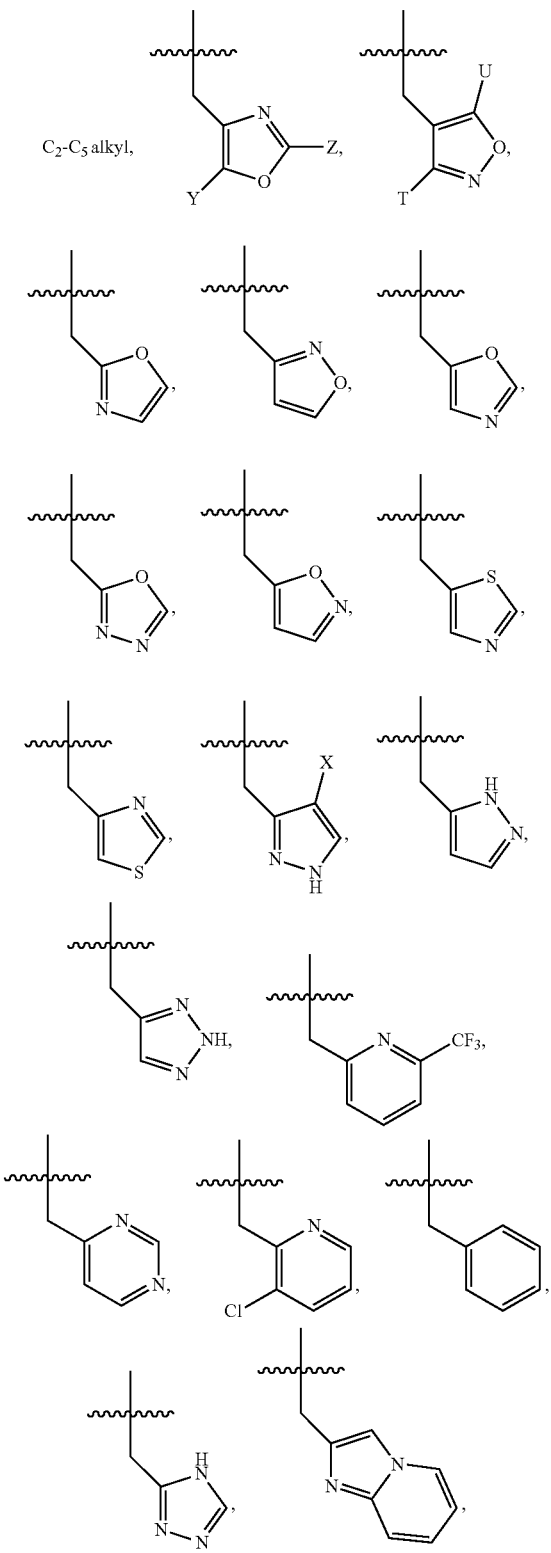

-continued

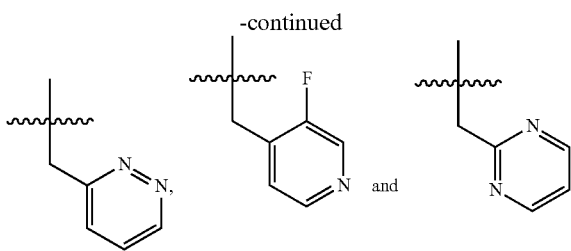

wherein
said $C_2$-$C_5$ alkyl is optionally substituted with one $OCH_3$ group;
each of Y, U, T and Z are independently H or $CH_3$; and
X is selected from the group consisting of H, Cl, and F.

2. A compound as claimed in claim 1, wherein $R^1$ is $S(O)_nR^4$ or $SF_5$.

3. A compound as claimed in claim 1, wherein $R^1$ is $S(O)_nR^4$, $R^4$ is $C_1$-$C_4$ alkyl, and n is 2.

4. A compound as claimed in claim 1, wherein $R^1$ is selected from the group consisting of $SO_2CH_3$, $SO_2CF_3$, $SF_5$, F, and $OCF_3$.

5. A compound as claimed in claim 1, wherein $R^1$ is halo.

6. A compound as claimed in claim 1, wherein $R^1$ is $SO_2CH_3$, $R^2$ is cyclobutyl, and $R^3$ is ethyl.

7. A compound as claimed in claim 1, wherein $R^1$ is $SF_5$, $R^2$ is $CH_3$, and $R^3$ is

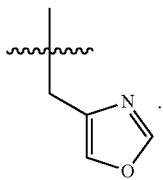 [SMILES: *Cc1cocn1]

8. A compound as claimed in claim 1, wherein $R^1$ is $SO_2CF_3$, $R^2$ is cyclobutyl, and $R^3$ is

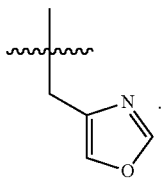 [SMILES: *Cc1cocn1]

9. A compound as claimed in claim 1, wherein $R^1$ is F, $R^2$ is $OCH_2CH_3$, and $R^3$ is isopropyl.

10. A compound or a pharmaceutically acceptable salt thereof, wherein said compound is selected from the group consisting of
(2-Ethoxy-4-fluorophenyl)-$N^4$-isopropylpyrimidine-2,4-diamine;
$N^4$-((1H-Pyrazol-5-yl)methyl)-$N^4$-(4-fluoro-2-methylphenyl)pyrimidine-2,4-diamine;
$N^4$-(2-Ethoxy-4-fluorophenyl)-$N^4$-(isoxazol-4-ylmethyl)pyrimidine-2,4-diamine;
$N^4$-Benzyl-$N^4$-(2-ethoxy-4-fluorophenyl)pyrimidine-2,4-diamine;
$N^4$-(Oxazol-4-ylmethyl)-$N^4$-(2-propyl-4-(trifluoromethoxy)phenyl)pyrimidine-2,4-diamine;
$N^4$-(2-Cyclobutyl-4-(trifluoromethoxy)phenyl)-$N^4$-(oxazol-4-ylmethyl)pyrimidine-2,4-diamine;
$N^4$-(2-Methyl-4-(trifluoromethoxy)phenyl)-$N^4$-(oxazol-4-ylmethyl)pyrimidine-2,4-diamine;
$N^4$-(2-Isobutyl-4-(trifluoromethoxy)phenyl)-$N^4$-(oxazol-4-ylmethyl)pyrimidine-2,4-diamine;
2-(4-((2-Aminopyrimidin-4-yl)(oxazol-4-ylmethyl)amino)-3-ethylphenyl)-1,1,1,3,3,3-hexafluoropropan-2-ol;
$N^4$-(2-Ethoxy-4-fluorophenyl)-$N^4$-(oxazol-2-ylmethyl)pyrimidine-2,4-diamine;
$N^4$-((1H-Pyrazol-3-yl)methyl)-$N^4$-(2-ethoxy-4-fluorophenyl)pyrimidine-2,4-diamine;
$N^4$-(2-Ethoxy-4-fluorophenyl)-$N^4$-(oxazol-4-ylmethyl)pyrimidine-2,4-diamine;
$N^4$-((4-Chloro-1H-pyrazol-3-yl)methyl)-$N^4$-(2-ethoxy-4-fluorophenyl)pyrimidine-2,4-diamine;
$N^4$-(2-Ethoxy-4-fluorophenyl)-$N^4$-(isoxazol-3-ylmethyl)pyrimidine-2,4-diamine;
$N^4$-(2-Ethoxy-4-fluorophenyl)-$N^4$-(thiazol-5-ylmethyl)pyrimidine-2,4-diamine;
$N^4$-(2-Ethoxy-4-fluorophenyl)-$N^4$-(oxazol-5-ylmethyl)pyrimidine-2,4-diamine;
$N^4$-(2-Ethoxy-4-fluorophenyl)-$N^4$-(thiazol-4-ylmethyl)pyrimidine-2,4-diamine;
$N^4$-((1H-Pyrazol-3-yl)methyl)-$N^4$-(4-fluoro-2-(2,2,2-trifluoroethoxy)phenyl)pyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(4-Bromo-2-(trifluoromethyl)phenyl)-$N^4$-isopropylpyrimidine-2,4-diamine;
$N^4$-(2-Cyclobutyl-4-(methylsulfonyl)phenyl)-$N^4$-ethylpyrimidine-2,4-diamine;
$N^4$-Ethyl-$N^4$-(2-methyl-4-(pentafluorosulfanyl)phenyl)pyrimidine-2,4-diamine;
$N^4$-[2-Ethyl-4-(pentafluorosulfanyl)phenyl]-$N^4$-(oxazol-4-ylmethyl)pyrimidine-2,4-diamine;
$N^4$-(2-Methyl-4-(pentafluorosulfanyl)phenyl)-$N^4$-(pyridazin-3-ylmethyl)pyrimidine-2,4-diamine;
$N^4$-[2-Ethyl-4-(pentafluorosulfanyl)phenyl]-$N^4$-(1H-pyrazol-5-ylmethyl)pyrimidine-2,4-diamine;
$N^4$-[2-Ethyl-4-(pentafluorosulfanyl)phenyl]-$N^4$-(1,3,4-oxadiazol-2-ylmethyl)pyrimidine-2,4-diamine;
$N^4$-Isopropyl-$N^4$-(2-(2-methylprop-1-en-1-yl)-4-(pyrrolidin-1-ylsulfonyl)phenyl)pyrimidine-2,4-diamine;
$N^4$-(2-Cyclobutyl-4-(pyrrolidin-1-ylsulfonyl)phenyl)-$N^4$-isopropylpyrimidine-2,4-diamine;
$N^4$-(4-((Difluoromethyl)sulfonyl)-2-ethylphenyl)-$N^4$-(oxazol-4-ylmethyl)pyrimidine-2,4-diamine;
$N^4$-Isopropyl-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(2-methoxyethyl)pyrimidine-2,4-diamine;
$N^4$-(2-Methyl-4-(pentafluorosulfanyl)phenyl)-$N^4$-(pyrimidin-2-ylmethyl)pyrimidine-2,4-diamine;
$N^4$-[(5-Methyloxazol-4-yl)methyl]-$N^4$-[2-methyl-4-(pentafluorosulfanyl)phenyl]pyrimidine-2,4-diamine;
$N^4$-(Isoxazol-3-ylmethyl)-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(oxazol-5-ylmethyl)pyrimidine-2,4-diamine;
$N^4$-(2-Methyl-4-(pentafluorosulfanyl)phenyl)-$N^4$-(oxazol-2-ylmethyl)pyrimidine-2,4-diamine;
$N^4$-[(3-Chloro-2-pyridyl)methyl]-$N^4$-[2-methyl-4-(pentafluorosulfanyl)phenyl]pyrimidine-2,4-diamine;
$N^4$-(2-Methyl-4-(pentafluorosulfanyl)phenyl)-$N^4$-(thiazol-4-ylmethyl)pyrimidine-2,4-diamine;
$N^4$-[(4-Fluoro-1H-pyrazol-3-yl)methyl]-$N^4$-[2-methyl-4-(pentafluorosulfanyl)phenyl]pyrimidine-2,4-diamine;

$N^4$-((4-Chloro-1H-pyrazol-3-yl)methyl)-$N^4$-(2-methyl-4-(pentafluorosulfanyl)phenyl)pyrimidine-2,4-diamine;
$N^4$-[2-Methyl-4-(pentafluorosulfanyl)phenyl]-$N^4$-(1H-pyrazol-3-ylmethyl)pyrimidine-2,4-diamine;
$N^4$-Ethyl-$N^4$-(2-ethyl-4-((trifluoromethyl)sulfonyl)phenyl)pyrimidine-2,4-diamine;
$N^4$-(2-Cyclobutyl-4-((trifluoromethyl)sulfonyl)phenyl)-$N^4$-ethylpyrimidine-2,4-diamine;
$N^4$-(2-Cyclobutyl-4-((trifluoromethyl)sulfonyl)phenyl)-$N^4$-(oxazol-4-ylmethyl)pyrimidine-2,4-diamine;
$N^4$-(2-Cyclobutyl-4-(methylsulfonyl)phenyl)-$N^4$-isopropylpyrimidine-2,4-diamine;
$N^4$-(2-Ethyl-4-((trifluoromethyl)sulfonyl)phenyl)-$N^4$-(oxazol-2-ylmethyl)pyrimidine-2,4-diamine;
$N^4$-(2-Ethyl-4-((trifluoromethyl)sulfonyl)phenyl)-$N^4$-((3-fluoropyridin-4-yl)methyl)pyrimidine-2,4-diamine;
$N^4$-(2-Cyclobutyl-4-(methylsulfonyl)phenyl)-$N^4$-((6-(trifluoromethyl)pyridin-2-yl)methyl)pyrimidine-2,4-diamine;
$N^4$-((3,5-Dimethylisoxazol-4-yl)methyl)-$N^4$-(2-ethyl-4-((trifluoromethyl)sulfonyl)phenyl)pyrimidine-2,4-diamine;
$N^4$-(2-Ethyl-4-((trifluoromethyl)sulfonyl)phenyl)-$N^4$-(pyrimidin-2-ylmethyl)pyrimidine-2,4-diamine;
$N^4$-(2-Cyclobutyl-4-((trifluoromethyl)sulfonyl)phenyl)-$N^4$-isopropylpyrimidine-2,4-diamine;
$N^4$-Isopropyl-$N^4$-(2-methyl-4-(trifluoromethoxy)phenyl)pyrimidine-2,4-diamine;
$N^4$-(2-Ethyl-4-(trifluoromethoxy)phenyl)-$N^4$-(oxazol-4-ylmethyl)pyrimidine-2,4-diamine;
$N^4$-(2-Cyclobutyl-4-(methylsulfonyl)phenyl)-$N^4$-propylpyrimidine-2,4-diamine;
$N^4$-(2-Cyclopropyl-4-(methylsulfonyl)phenyl)-$N^4$-ethylpyrimidine-2,4-diamine;
$N^4$-(2-Cyclopropyl-4-(methylsulfonyl)phenyl)-$N^4$-propylpyrimidine-2,4-diamine;
$N^4$-(2-Cyclopropyl-4-(ethylsulfonyl)phenyl)-$N^4$-ethylpyrimidine-2,4-diamine;
$N^4$-Ethyl-$N^4$-(2-isobutyl-4-(methylsulfonyl)phenyl)pyrimidine-2,4-diamine;
$N^4$-(2-Cyclobutyl-4-methylsulfonylphenyl)-$N^4$-(oxazol-4-ylmethyl)pyrimidine-2,4-diamine;
$N^4$-(2-Cyclobutyl-4-methylsulfonylphenyl)-$N^4$-(2-methoxyethyl)pyrimidine-2,4-diamine;
$N^4$-Ethyl-$N^4$-(2-ethyl-4-(methylsulfonyl)phenyl)pyrimidine-2,4-diamine;
$N^4$-(2-Isobutyl-4-((trifluoromethyl)sulfonyl)phenyl)-$N^4$-(oxazol-4-ylmethyl)pyrimidine-2,4-diamine;
$N^4$-(2-Ethyl-4-((trifluoromethyl)sulfonyl)phenyl)-$N^4$-isopropylpyrimidine-2,4-diamine;
$N^4$-(2-Ethyl-4-((trifluoromethyl)sulfonyl)phenyl)-$N^4$-(oxazol-4-ylmethyl)pyrimidine-2,4-diamine;
$N^4$-(2-Ethyl-4-(methylsulfonyl)phenyl)-$N^4$-((6-(trifluoromethyl)pyridin-2-yl)methyl)pyrimidine-2,4-diamine;
$N^4$-(2-Ethyl-4-(methylsulfonyl)phenyl)-$N^4$-(2-methoxyethyl)pyrimidine-2,4-diamine;
$N^4$-(2-Ethyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-(oxazol-4-ylmethyl)pyrimidine-2,4-diamine;
$N^4$-((1H-Pyrazol-5-yl)methyl)-$N^4$-(2-cyclobutyl-4-(methylsulfonyl)phenyl)pyrimidine-2,4-diamine;
$N^4$-(2-Cyclobutyl-4-(methylsulfonyl)phenyl)-$N^4$-(pyrimidin-4-ylmethyl)pyrimidine-2,4-diamine;
$N^4$-(2-Ethyl-4-(methylsulfonyl)phenyl)-$N^4$-isopropylpyrimidine-2,4-diamine;
$N^4$-(2-Isobutyl-4-(methylsulfonyl)phenyl)-$N^4$-propylpyrimidine-2,4-diamine;
$N^4$-(2-Ethyl-4-((trifluoromethyl)sulfonyl)phenyl)-$N^4$-((6-(trifluoromethyl)pyridin-2-yl)methyl)pyrimidine-2,4-diamine;
$N^4$-(2-Ethyl-4-((trifluoromethyl)sulfonyl)phenyl)-$N^4$-(pyrimidin-4-ylmethyl)pyrimidine-2,4-diamine;
$N^4$-(2-Ethyl-4-((trifluoromethyl)sulfonyl)phenyl)-$N^4$-(2-methoxyethyl)pyrimidine-2,4-diamine;
$N^4$-(4-((Difluoromethyl)sulfonyl)-2-ethylphenyl)-$N^4$-ethylpyrimidine-2,4-diamine;
$N^4$-(2-Cyclobutyl-4-(ethylsulfonyl)phenyl)-$N^4$-ethylpyrimidine-2,4-diamine;
$N^4$-(2-Ethoxy-4-fluorophenyl)-$N^4$-(imidazo[1,2-a]pyridin-2-ylmethyl)pyrimidine-2,4-diamine;
$N^4$-(2-Ethoxy-4-fluorophenyl)-$N^4$-((2-methyloxazol-4-yl)methyl)pyrimidine-2,4-diamine;
4-((2-Aminopyrimidin-4-yl)(ethyl)amino)-3-cyclobutyl-N-ethyl-N-methylbenzenesulfonamide;
4-((2-Aminopyrimidin-4-yl)(propyl)amino)-3-cyclobutyl-N-methyl-N-propylbenzenesulfonamide;
$N^4$-(4-Bromo-2-(trifluoromethoxy)phenyl)-$N^4$-(oxazol-4-ylmethyl)pyrimidine-2,4-diamine;
$N^4$-Ethyl-$N^4$-(4-(methylsulfonyl)-2-(prop-1-en-2-yl)phenyl)pyrimidine-2,4-diamine;
$N^4$-Ethyl-$N^4$-(2-isopropyl-4-(methylsulfonyl)phenyl)pyrimidine-2,4-diamine;
$N^4$-(4-Bromo-2-(trifluoromethoxy)phenyl)-$N^4$-isopropylpyrimidine-2,4-diamine;
$N^4$-(4-Bromo-2-isopropoxyphenyl)-$N^4$-isopropylpyrimidine-2,4-diamine;
$N^4$-(4-Bromo-2-(2,2,2-trifluoroethoxy)phenyl)-$N^4$-isopropylpyrimidine-2,4-diamine;
$N^4$-(4-Bromo-2-methylphenyl)-$N^4$-isopropylpyrimidine-2,4-diamine;
4-((2-Aminopyrimidin-4-yl)(isopropyl)amino)-3-(trifluoromethoxy)benzonitrile;
$N^4$-(4-(Ethylsulfonyl)-2-(trifluoromethoxy)phenyl)-$N^4$-isopropylpyrimidine-2,4-diamine;
$N^4$-(4-Bromo-2-methylphenyl)-$N^4$-(oxazol-4-ylmethyl)pyrimidine-2,4-diamine;
$N^4$-(4-(Ethylsulfonyl)-2-methylphenyl)-$N^4$-(oxazol-4-ylmethyl)pyrimidine-2,4-diamine;
$N^4$-Isopropyl-$N^4$-(4-(methylsulfonyl)-2-(trifluoromethyl)phenyl)pyrimidine-2,4-diamine;
$N^4$-Isopropyl-$N^4$-(4-(isopropylsulfonyl)-2-(trifluoromethyl)phenyl)pyrimidine-2,4-diamine;
$N^4$-(2-Ethoxy-4-fluorophenyl)-$N^4$-(isoxazol-5-ylmethyl)pyrimidine-2,4-diamine;
$N^4$-((1,3,4-Oxadiazol-2-yl)methyl)-$N^4$-(2-ethoxy-4-fluorophenyl)pyrimidine-2,4-diamine;
4-((2-Aminopyrimidin-4-yl)(isopropyl)amino)-3-propylbenzonitrile;
(E)-4-((2-Aminopyrimidin-4-yl)(oxazol-4-ylmethyl)amino)-3-(prop-1-en-1-yl)benzamide;
(E)-4-((2-Aminopyrimidin-4-yl)(isopropyl)amino)-3-(prop-1-en-1-yl)benzonitrile;
(E)-4-((2-Aminopyrimidin-4-yl)(isopropyl)amino)-3-(prop-1-en-1-yl)benzamide;
(E)-$N^4$-(4-Chloro-2-(prop-1-en-1-yl)phenyl)-$N^4$-(oxazol-4-ylmethyl)pyrimidine-2,4-diamine;
$N^4$-(2-Cyclobutyl-4-(isopropylsulfonyl)phenyl)-$N^4$-isopropylpyrimidine-2,4-diamine;
$N^4$-(4-Fluoro-2-(trifluoromethoxy)phenyl)-$N^4$-isopropylpyrimidine-2,4-diamine;
$N^4$-((2H-1,2,3-Triazol-4-yl)methyl)-$N^4$-(2-ethoxy-4-fluorophenyl)pyrimidine-2,4-diamine;

N$^4$-Ethyl-N$^4$-(4-(methylsulfonyl)-2-propylphenyl)pyrimidine-2,4-diamine;
N$^4$-(2-Cyclobutyl-4-(cyclopropylsulfonyl)phenyl)-N$^4$-ethylpyrimidine-2,4-diamine;
N$^4$-(2-Cyclobutyl-4-(cyclopropylsulfonyl)phenyl)-N$^4$-propylpyrimidine-2,4-diamine;
N$^4$-((4H-1,2,4-Triazol-3-yl)methyl)-N$^4$-(2-ethoxy-4-fluorophenyl)pyrimidine-2,4-diamine;
N$^4$-(2-Ethyl-4-(trifluoromethyl)phenyl)-N$^4$-(oxazol-4-ylmethyl)pyrimidine-2,4-diamine;
N$^4$-(Oxazol-4-ylmethyl)-N$^4$-(4-(trifluoromethyl)phenyl)pyrimidine-2,4-diamine;
4-((2-Aminopyrimidin-4-yl)(ethyl)amino)-3-cyclobutylbenzamide;
4-((2-Aminopyrimidin-4-yl)(isopropyl)amino)-3-cyclobutylbenzamide;
4-((2-Aminopyrimidin-4-yl)(ethyl)amino)-3-isobutylbenzamide;
(E)-N$^4$-Isopropyl-N$^4$-(2-(prop-1-en-1-yl)-4-(trifluoromethyl)phenyl)pyrimidine-2,4-diamine;
N$^4$-Isopropyl-N$^4$-(2-propyl-4-(trifluoromethyl)phenyl)pyrimidine-2,4-diamine;
N$^4$-Isopropyl-N$^4$-(2-methyl-4-(trifluoromethyl)phenyl)pyrimidine-2,4-diamine;
4-((2-Aminopyrimidin-4-yl)(oxazol-4-ylmethyl)amino)-3-propylbenzonitrile;
(E)-N$^4$-(4-Fluoro-2-(prop-1-en-1-yl)phenyl)-N$^4$-isopropylpyrimidine-2,4-diamine;
N$^4$-(4-Fluoro-2-propylphenyl)-N$^4$-isopropylpyrimidine-2,4-diamine;
N$^4$-(4-Fluoro-2-(prop-1-en-2-yl)phenyl)-N$^4$-isopropylpyrimidine-2,4-diamine;
N$^4$-(4-Fluoro-2-isopropylphenyl)-N$^4$-isopropylpyrimidine-2,4-diamine; and
(E)-4-((2-Aminopyrimidin-4-yl)(oxazol-4-ylmethyl)amino)-3-(prop-1-en-1-yl)benzonitrile.

11. A compound or a pharmaceutically acceptable salt thereof as claimed in claim 10, wherein said compound is selected from the group consisting of
N$^4$-(2-Cyclobutyl-4-(methylsulfonyl)phenyl)-N$^4$-ethylpyrimidine-2,4-diamine;
N$^4$-Isopropyl-N$^4$-(2-(2-methylprop-1-en-1-yl)-4-(pyrrolidin-1-ylsulfonyl)phenyl)pyrimidine-2,4-diamine;
N$^4$-(2-Cyclobutyl-4-(pyrrolidin-1-ylsulfonyl)phenyl)-N$^4$-isopropylpyrimidine-2,4-diamine;
N$^4$-(4-((Difluoromethyl)sulfonyl)-2-ethylphenyl)-N$^4$-(oxazol-4-ylmethyl)pyrimidine-2,4-diamine;
N$^4$-Ethyl-N$^4$-(2-ethyl-4-((trifluoromethyl)sulfonyl)phenyl)pyrimidine-2,4-diamine;
N$^4$-(2-Cyclobutyl-4-((trifluoromethyl)sulfonyl)phenyl)-N$^4$-ethylpyrimidine-2,4-diamine;
N$^4$-(2-Cyclobutyl-4-((trifluoromethyl)sulfonyl)phenyl)-N$^4$-(oxazol-4-ylmethyl)pyrimidine-2,4-diamine;
N$^4$-(2-Cyclobutyl-4-(methylsulfonyl)phenyl)-N$^4$-isopropylpyrimidine-2,4-diamine;
N$^4$-(2-Ethyl-4-((trifluoromethyl)sulfonyl)phenyl)-N$^4$-(oxazol-2-ylmethyl)pyrimidine-2,4-diamine;
N$^4$-(2-Ethyl-4-((trifluoromethyl)sulfonyl)phenyl)-N$^4$-((3-fluoropyridin-4-yl)methyl)pyrimidine-2,4-diamine;
N$^4$-(2-Cyclobutyl-4-(methylsulfonyl)phenyl)-N$^4$-((6-(trifluoromethyl)pyridin-2-yl)methyl)pyrimidine-2,4-diamine;
N$^4$-((3,5-Dimethylisoxazol-4-yl)methyl)-N$^4$-(2-ethyl-4-((trifluoromethyl)sulfonyl)phenyl)pyrimidine-2,4-diamine;
N$^4$-(2-Ethyl-4-((trifluoromethyl)sulfonyl)phenyl)-N$^4$-(pyrimidin-2-ylmethyl)pyrimidine-2,4-diamine;
N$^4$-(2-Cyclobutyl-4-((trifluoromethyl)sulfonyl)phenyl)-N$^4$-isopropylpyrimidine-2,4-diamine;
N$^4$-(2-Cyclobutyl-4-(methylsulfonyl)phenyl)-N$^4$-propylpyrimidine-2,4-diamine;
N$^4$-(2-Cyclopropyl-4-(methylsulfonyl)phenyl)-N$^4$-ethylpyrimidine-2,4-diamine;
N$^4$-(2-Cyclopropyl-4-(methylsulfonyl)phenyl)-N$^4$-propylpyrimidine-2,4-diamine;
N$^4$-(2-Cyclopropyl-4-(ethylsulfonyl)phenyl)-N$^4$-ethylpyrimidine-2,4-diamine;
N$^4$-Ethyl-N$^4$-(2-isobutyl-4-(methylsulfonyl)phenyl)pyrimidine-2,4-diamine;
N$^4$-(2-Cyclobutyl-4-methylsulfonylphenyl)-N$^4$-(oxazol-4-ylmethyl)pyrimidine-2,4-diamine;
N$^4$-(2-Cyclobutyl-4-methylsulfonylphenyl)-N$^4$-(2-methoxyethyl)pyrimidine-2,4-diamine;
N$^4$-Ethyl-N$^4$-(2-ethyl-4-(methylsulfonyl)phenyl)pyrimidine-2,4-diamine;
N$^4$-(2-Isobutyl-4-((trifluoromethyl)sulfonyl)phenyl)-N$^4$-(oxazol-4-ylmethyl)pyrimidine-2,4-diamine;
N$^4$-(2-Ethyl-4-((trifluoromethyl)sulfonyl)phenyl)-N$^4$-isopropylpyrimidine-2,4-diamine;
N$^4$-(2-Ethyl-4-((trifluoromethyl)sulfonyl)phenyl)-N$^4$-(oxazol-4-ylmethyl)pyrimidine-2,4-diamine;
N$^4$-(2-Ethyl-4-(methylsulfonyl)phenyl)-N$^4$-((6-(trifluoromethyl)pyridin-2-yl)methyl)pyrimidine-2,4-diamine;
N$^4$-(2-Ethyl-4-(methylsulfonyl)phenyl)-N$^4$-(2-methoxyethyl)pyrimidine-2,4-diamine;
N$^4$-(2-Ethyl-4-(methylsulfonyl)phenyl)-N$^4$-(pyrimidin-4-ylmethyl)pyrimidine-2,4-diamine;
N$^4$-(2-Ethyl-4-(methylsulfonyl)phenyl)-N$^4$-(oxazol-4-ylmethyl)pyrimidine-2,4-diamine;
N$^4$-((1H-Pyrazol-5-yl)methyl)-N$^4$-(2-cyclobutyl-4-(methylsulfonyl)phenyl)pyrimidine-2,4-diamine;
N$^4$-(2-Cyclobutyl-4-(methylsulfonyl)phenyl)-N$^4$-(pyrimidin-4-ylmethyl)pyrimidine-2,4-diamine;
N$^4$-(2-Ethyl-4-(methylsulfonyl)phenyl)-N$^4$-isopropylpyrimidine-2,4-diamine;
N$^4$-(2-Isobutyl-4-(methylsulfonyl)phenyl)-N$^4$-propylpyrimidine-2,4-diamine;
N$^4$-(2-Ethyl-4-((trifluoromethyl)sulfonyl)phenyl)-N$^4$-((6-(trifluoromethyl)pyridin-2-yl)methyl)pyrimidine-2,4-diamine;
N$^4$-(2-Ethyl-4-((trifluoromethyl)sulfonyl)phenyl)-N$^4$-(pyrimidin-4-ylmethyl)pyrimidine-2,4-diamine;
N$^4$-(2-Ethyl-4-((trifluoromethyl)sulfonyl)phenyl)-N$^4$-(2-methoxyethyl)pyrimidine-2,4-diamine;
N$^4$-(4-((Difluoromethyl)sulfonyl)-2-ethylphenyl)-N$^4$-ethylpyrimidine-2,4-diamine;
N$^4$-(2-Cyclobutyl-4-(ethylsulfonyl)phenyl)-N$^4$-ethylpyrimidine-2,4-diamine;
4-((2-Aminopyrimidin-4-yl)(ethyl)amino)-3-cyclobutyl-N-ethyl-N-methylbenzenesulfonamide;
4-((2-Aminopyrimidin-4-yl)(propyl)amino)-3-cyclobutyl-N-methyl-N-propylbenzenesulfonamide;
N$^4$-Ethyl-N$^4$-(4-(methylsulfonyl)-2-(prop-1-en-2-yl)phenyl)pyrimidine-2,4-diamine;
N$^4$-Ethyl-N$^4$-(2-isopropyl-4-(methylsulfonyl)phenyl)pyrimidine-2,4-diamine;
N$^4$-(4-(Ethylsulfonyl)-2-(trifluoromethoxy)phenyl)-N$^4$-isopropylpyrimidine-2,4-diamine;
N$^4$-(4-(Ethylsulfonyl)-2-methylphenyl)-N$^4$-(oxazol-4-ylmethyl)pyrimidine-2,4-diamine;
N$^4$-Isopropyl-N$^4$-(4-(methylsulfonyl)-2-(trifluoromethyl)phenyl)pyrimidine-2,4-diamine;

$N^4$-Isopropyl-$N^4$-(4-(isopropylsulfonyl)-2-(trifluoromethyl)phenyl)pyrimidine-2,4-diamine;
$N^4$-(2-Cyclobutyl-4-(isopropylsulfonyl)phenyl)-$N^4$-isopropylpyrimidine-2,4-diamine;
$N^4$-Ethyl-$N^4$-(4-(methylsulfonyl)-2-propylphenyl)pyrimidine-2,4-diamine;
$N^4$-(2-Cyclobutyl-4-(cyclopropylsulfonyl)phenyl)-$N^4$-ethylpyrimidine-2,4-diamine; and
$N^4$-(2-Cyclobutyl-4-(cyclopropylsulfonyl)phenyl)-$N^4$-propylpyrimidine-2,4-diamine.

12. A compound or a pharmaceutically acceptable salt thereof as claimed in claim 10, wherein said compound is selected from the group consisting of
$N^4$-(2-Methyl-4-(pentafluorosulfanyl)phenyl)-$N^4$-(oxazol-4-ylmethyl)pyrimidine-2,4-diamine;
$N^4$-Ethyl-$N^4$-(2-methyl-4-(pentafluorosulfanyl)phenyl)pyrimidine-2,4-diamine;
$N^4$-[2-Ethyl-4-(pentafluorosulfanyl)phenyl]-$N^4$-(oxazol-4-ylmethyl)pyrimidine-2,4-diamine;
$N^4$-(2-Methyl-4-(pentafluorosulfanyl)phenyl)-$N^4$-(pyridazin-3-ylmethyl)pyrimidine-2,4-diamine;
$N^4$-[2-Ethyl-4-(pentafluorosulfanyl)phenyl]-$N^4$-(1H-pyrazol-5-ylmethyl)pyrimidine-2,4-diamine;
$N^4$-[2-Ethyl-4-(pentafluorosulfanyl)phenyl]-$N^4$-(1,3,4-oxadiazol-2-ylmethyl)pyrimidine-2,4-diamine;
$N^4$-Isopropyl-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(2-methoxyethyl)pyrimidine-2,4-diamine;
$N^4$-(2-Methyl-4-(pentafluorosulfanyl)phenyl)-$N^4$-(pyrimidin-2-ylmethyl)pyrimidine-2,4-diamine;
$N^4$-[(5-Methyloxazol-4-yl)methyl]-$N^4$-[2-methyl-4-(pentafluorosulfanyl)phenyl]pyrimidine-2,4-diamine;
$N^4$-(Isoxazol-3-ylmethyl)-$N^4$-(2-methyl-4-(pentafluorosulfanyl)phenyl)pyrimidine-2,4-diamine;
$N^4$-(2-Methyl-4-(pentafluorosulfanyl)phenyl)-$N^4$-(oxazol-5-ylmethyl)pyrimidine-2,4-diamine;
$N^4$-(2-Methyl-4-(pentafluorosulfanyl)phenyl)-$N^4$-(oxazol-2-ylmethyl)pyrimidine-2,4-diamine;
$N^4$-[(3-Chloro-2-pyridyl)methyl]-$N^4$-[2-methyl-4-(pentafluorosulfanyl)phenyl]pyrimidine-2,4-diamine;
$N^4$-(2-Methyl-4-(pentafluorosulfanyl)phenyl)-$N^4$-(thiazol-4-ylmethyl)pyrimidine-2,4-diamine;
$N^4$-[(4-Fluoro-1H-pyrazol-3-yl)methyl]-$N^4$-[2-methyl-4-(pentafluorosulfanyl)phenyl]pyrimidine-2,4-diamine;
$N^4$-((4-Chloro-1H-pyrazol-3-yl)methyl)-$N^4$-(2-methyl-4-(pentafluorosulfanyl)phenyl)pyrimidine-2,4-diamine; and
$N^4$-[2-Methyl-4-(pentafluorosulfanyl)phenyl]-$N^4$-(1H-pyrazol-3-ylmethyl)pyrimidine-2,4-diamine.

13. A compound or a pharmaceutically acceptable salt thereof as claimed in claim 10, wherein said compound is selected from the group consisting of
(2-Ethoxy-4-fluorophenyl)-$N^4$-isopropylpyrimidine-2,4-diamine;
$N^4$-(2-Cyclobutyl-4-(trifluoromethoxy)phenyl)-$N^4$-(oxazol-4-ylmethyl)pyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(2-Cyclobutyl-4-((trifluoromethyl)sulfonyl)phenyl)-$N^4$-(oxazol-4-ylmethyl)pyrimidine-2,4-diamine; and
$N^4$-(2-Cyclobutyl-4-(methylsulfonyl)phenyl)-$N^4$-ethylpyrimidine-2,4-diamine.

14. A compound or a pharmaceutically acceptable salt thereof as claimed in claim 10, wherein said compound is selected from the group consisting of
$N^4$-(2-Cyclobutyl-4-(methylsulfonyl)phenyl)-$N^4$-ethylpyrimidine-2,4-diamine;
$N^4$-(2-Methyl-4-(pentafluorosulfanyl)phenyl)-$N^4$-(oxazol-4-ylmethyl)pyrimidine-2,4-diamine;
$N^4$-(2-Cyclobutyl-4-((trifluoromethyl)sulfonyl)phenyl)-$N^4$-(oxazol-4-ylmethyl)pyrimidine-2,4-diamine;
$N^4$-(2-Cyclobutyl-4-(trifluoromethoxy)phenyl)-$N^4$-(oxazol-4-ylmethyl)pyrimidine-2,4-diamine; and
(2-Ethoxy-4-fluorophenyl)-$N^4$-isopropylpyrimidine-2,4-diamine.

15. A pharmaceutical composition comprising a compound or a pharmaceutically acceptable salt thereof as claimed in claim 10.

16. A pharmaceutical composition comprising a compound or a pharmaceutically acceptable salt thereof as claimed in claim 11.

17. A pharmaceutical composition comprising a compound or a pharmaceutically acceptable salt thereof as claimed in claim 12.

18. A pharmaceutical composition comprising a compound or a pharmaceutically acceptable salt thereof as claimed in claim 13.

19. A pharmaceutical composition comprising a compound or a pharmaceutically acceptable salt thereof as claimed in claim 14.

20. A method of treating a subject suffering from or diagnosed with a disease, disorder, or medical condition mediated by histamine $H_4$ receptor activity, comprising administering to a subject in need of such treatment an effective amount of at least one compound of formula I or a pharmaceutically acceptable salt thereof as claimed in claim 1, wherein the disease, disorder, or medical condition is selected from the group consisting of inflammatory disorders, allergic disorders, dermatological disorders, autoimmune disease, lymphatic disorders, and immunodeficiency disorders.

21. A method of treating a subject suffering from or diagnosed with a disease, disorder, or medical condition mediated by histamine $H_4$ receptor activity, comprising administering to a subject in need of such treatment an effective amount of at least one compound of formula I or a pharmaceutically acceptable salt thereof as claimed in claim 1, wherein the disease, disorder, or medical condition is selected from: allergy, asthma, eosinophilic asthma, dry eye, chronic obstructive pulmonary disease (COPD), atherosclerosis, rheumatoid arthritis, multiple sclerosis, inflammatory bowel disease, psoriasis, pruritus, itchy skin, atopic dermatitis, urticaria, ocular inflammation, conjunctivitis, nasal polyps, allergic rhinitis, nasal itch, parasitic or fungal infection, hidradenitis suppurativa, malignancy, jaundice, polycythemia, punctate palmoplantar keratoderma, thyroid illness/hyperparathyroidism, diabetes, chicken pox, iron deficiency anemia, psychiatric diseases, medication-induced itch, cholestasis, pregnancy-related itch, xerosis, sunburn, dandruff, scab/scars, insect bites, poison ivy, poison oak, hemorrhoids, contact dermatitis, age associated itch, itch associated with dialysis, scleroderma, autoimmune disease, immune-mediated diabetes mellitus, lupus, myasthenia gravis, pernicious anemia, temporal arteritis, anti-phospholipid syndrome, vasculitides, Behcet's disease, dermatitis herpetiformis, pemphigus vulgaris, vitiligio, primary biliary cirrhosis, autoimmune hepatitis, orchitis, polymyositis, dermatomyositis, spondyloarthropathy, Sjogren's syndrome, and pruritus, wherein said autoimmune disease is at least one of autoimmune thyroid disease, autoimmune neuropathy, autoimmune uveitis, autoimmune hemolytic anemia, autoimmune thrombocytopenia, autoimmune hepatitis, autoimmune oophoritis, and autoimmune disease of the adrenal gland.

22. A method as claimed in claim 21, wherein said inflammatory bowel disease is one of colitis, Crohn's disease, and ulcerative colitis.

* * * * *